(12) United States Patent
Adams et al.

(10) Patent No.: US 9,108,923 B2
(45) Date of Patent: Aug. 18, 2015

(54) COMPOUNDS, COMPOSITIONS, AND METHODS FOR CANCER THERAPY

(71) Applicant: The Broad Institute, Inc., Cambridge, MA (US)

(72) Inventors: Drew Adams, Cambridge, MA (US); Mingji Dai, West Lafayette, IN (US); Stuart Schreiber, Boston, MA (US); Mahmud Mustaqim Hussain, Cambridge, MA (US); Zarko Boskovic, Cambridge, MA (US)

(73) Assignees: Howard Hughes Medical Institute, Chevy Chase, MD (US); The Broad Institute, Cambridge, MA (US); The President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 13/946,959

(22) Filed: Jul. 19, 2013

(65) Prior Publication Data
US 2014/0024639 A1  Jan. 23, 2014

Related U.S. Application Data

(60) Provisional application No. 61/779,434, filed on Mar. 13, 2013, provisional application No. 61/674,100, filed on Jul. 20, 2012.

(51) Int. Cl.

| | |
|---|---|
| *A61K 33/44* | (2006.01) |
| *C07D 213/62* | (2006.01) |
| *C07D 213/78* | (2006.01) |
| *C07D 211/86* | (2006.01) |
| *C07D 225/02* | (2006.01) |
| *C07D 211/74* | (2006.01) |
| *C07D 409/06* | (2006.01) |
| *C07D 409/04* | (2006.01) |
| *C07D 401/04* | (2006.01) |
| *C07D 405/06* | (2006.01) |
| *C07C 233/91* | (2006.01) |
| *A61K 31/4412* | (2006.01) |
| *A61K 31/55* | (2006.01) |
| *A61K 31/45* | (2006.01) |
| *A61K 31/4015* | (2006.01) |
| *A61K 45/06* | (2006.01) |
| *C07D 223/10* | (2006.01) |
| *C07D 207/38* | (2006.01) |
| *A61K 31/4436* | (2006.01) |
| *A61K 31/444* | (2006.01) |

(52) U.S. Cl.
CPC .......... *C07D 211/86* (2013.01); *A61K 31/4015* (2013.01); *A61K 31/444* (2013.01); *A61K 31/4412* (2013.01); *A61K 31/4436* (2013.01); *A61K 31/45* (2013.01); *A61K 31/55* (2013.01); *A61K 45/06* (2013.01); *C07C 233/91* (2013.01); *C07D 207/38* (2013.01); *C07D 211/74* (2013.01); *C07D 223/10* (2013.01); *C07D 225/02* (2013.01); *C07D 401/04* (2013.01); *C07D 405/06* (2013.01); *C07D 409/04* (2013.01); *C07D 409/06* (2013.01)

(58) Field of Classification Search
None
See application file for complete search history.

(56) References Cited

U.S. PATENT DOCUMENTS

| 8,349,832 B2 * | 1/2013 | Foley et al. ............... 514/235.5 |
|---|---|---|
| 2009/0157455 A1 | 6/2009 | Kuo et al. |
| 2009/0312373 A1 | 12/2009 | Lee et al. |
| 2011/0053938 A1 | 3/2011 | Foley et al. |
| 2011/0224141 A1 | 9/2011 | Thompson et al. |
| 2012/0059004 A1 | 3/2012 | Elliott et al. |

FOREIGN PATENT DOCUMENTS

| CN | 101774875 A * | 7/2010 |
|---|---|---|
| CN | 102125552 A | 7/2011 |
| CN | 102146054 A | 8/2011 |

OTHER PUBLICATIONS

Pineschi, M. et al. Highly Enantioselective Copper-Phosphoramidite-Catalyzed Conjugate Addition of Dialkylzinc Reagents to Acyclic α,β-Unsaturated Imides. Adv. Synth. Catal. 2006, vol. 348, p. 302.*

Fujii, T. et al. Lactams. XVII. Synthesis and Stereochemical Characterization of Diethyl cis- and trans-5-Ethyl-2-oxo-4-pipendinemalonate. Chem. Pharm. Bull. 1979, vol. 27, p. 2842.*

Dodson, CD. et al. Cenocladamide, a dihydropyridone alkaloid from Piper cenocladum. Phytochemistry. 2000, vol. 53, p. 53.*

Kong, Eh. et al. Piplartine induces caspase-mediated apoptosis in PC-3 human prostate cancer cells. Oncology Reports. 2008, vol. 20, p. 786.*

Chakravarthi et al., "The Role of Glutathione in Disulphide Bond Formation and Endoplasmic-Reticulum-Generated Oxidative Stress", EMBO Reports, 2006, pp. 271-275, vol. 7 No. 3.

Cooper et al., "Reversible and Irreversible Protein Glutathionylation: Biological and Clinical Aspects", Expert Opinion on Drug Metabolism & Toxicology, 2011, pp. 891-910, vol. 7 No. 7.

Corson et al, "Design and Applications of Bifunctional Small Molecules: Why Two Heads Are Better Than One", ACS Chemical Biology, 2008, pp. 677-692, vol. 3 No. 11.

(Continued)

*Primary Examiner* — Rita Desai
*Assistant Examiner* — Ben S Michelson
(74) *Attorney, Agent, or Firm* — Thompson Coburn LLP; Charles P. Romano

(57) ABSTRACT

Compounds including various oligomers of piperlongumine and/or piperlongumine analogues as well as certain piperlongumine analogues that exhibit improved toxicity to cancer cells are disclosed. Also provided are compositions that comprise the compounds, methods of making compositions comprising the compounds, methods of making the compounds, and the use of compounds in methods for treating cancer.

13 Claims, 28 Drawing Sheets

(56) References Cited

OTHER PUBLICATIONS

Dalle-Donne et al., "Molecular Mechanisms and Potential Clinical Significance of S-Glutathionylation", Antioxidants & Redox Signaling, 2008, pp. 445-473, vol. 10 No. 3.

Dinkova-Kostova et al., "Extremely Potent Triterpenoid Inducers of the Phase 2 Response: Correlations of Protection Against Oxidant and Inflammatory Stress", Proceedings of the National Academy of Sciences of the United States of America, 2005, pp. 4584-4589, vol. 102 No. 12.

Dolma et al., "Identification of Genotype-selective Antitumor Agents Using Synthetic Lethal Chemical Screening in Engineered Human Tumor Cells", Cancer Cell, 2003, pp. 285-296, vol. 3 No. 3.

Duh et al., "Cytotoxic Pyridone Alkaloids from Piper Aborescens", Phytochemistry, 1990, pp. 2689-2691, vol. 29.

Duh et al., "Cytotoxic Pyridone Alkaloids from the Leaves of Piper Arborescens", Journal of Natural Products, Nov.-Dec. 1990, pp. 1575-1577, vol. 53 No. 6.

Fruehauf et al., "Reactive Oxygen Species: A Breath of Life or Death?", Clinical Cancer Research, 2007, pp. 789-794, vol. 13 No. 3.

Goto et al., "Lack of Mitochondrial Depolarization by Oxidative Stress is Associated with Resistance to Buthionine Sulfozimine in Acute Lymphoblastic Leukemia Cells", Leukemia Research, 2007, pp. 1293-1301, Vo. 31 No. 9.

Green et al., "Subcellular Compartmentalization of Glutathione: Correlations with Parameters of Oxidative Stress Related to Genotoxicity", Mutagenesis, 2006, pp. 383-390, vol. 21 No. 6.

Guzman et al., "An Orally Bioavailable Parthenolide Analog Selectively Eradicates Acute Myelogenous Leukemia Stem and Progenitor Cells", Blood, 2007, pp. 4427-4435, vol. 110 No. 13.

Hahn et al., "Creation of Human Tumour Cells with Defined Genetic Elements", Nature, 1999, pp. 464-468, vol. 400 No. 6743.

Huang et al., "S-Nitrosoproteome in Endothelial Cells Revealed by a Modified Biotin Switch Approach Coupled with Western Blot-Based Two-Dimensional Gel Electrophoresis", Journal of Proteome Research, 2009, pp. 4835-4843, vol. 8 No. 10.

Huang et al., "Superoxide Dismutase as a Target for the Selective Killing of Cancer Cells", Nature, 2000, pp. 390-395, vol. 407 No. 6802.

Klatt et al., "Regulation of Protein Function by S-Glutathiolation in Response to Oxidative and Nitrosative Stress", European Journal of Biochemistry, 2000, pp. 4928-4944, vol. 267 No. 16.

Koshiyama et al., "Synthesis and Evaluation of a Fluorogenic Reagent for Proteomic Studies: 7-Fluoro-N-[2-(Dimethylamino)ethyl]-2, 1, 3-Benzooxadiazole-4-Sulfonamide (DAABD-F)", Analyst, 2010, pp. 2119-2124, vol. 135 No. 8.

Lee et al., "Ras Proteins Induce Senescence by Altering the Intracellular Levels of Reactive Oxygen Species", The Journal of Biological Chemistry, 1999, pp. 7936-7940, vol. 274 No. 12.

Liebler, "Protein Damage by Reactive Electrophiles: Targets and Consequences", Chemical Research in Toxicology, 2008, pp. 117-128, vol. 21 No. 1.

Luo et al., "Principles of Cancer Therapy: Oncogene and Non-Oncogene Addiction", Cell, Mar. 6, 2009, pp. 823-837, vol. 136 Issue 5.

Marengo et al., "GSH Loss Per Se Does not Affect Neuroblastoma Survival and is Not Genotoxic", International Journal of Oncology, 2008, pp. 121-127, vol. 32 No. 1.

Rabilloud et al., "Proteomics Analysis of Cellular Response to Oxidative Stress. Evidence for in Vivo Overoxidation and Peroxiredoxins at their Active Site", Journal of Biological Chemistry, 2002, pp. 19396-19401, vol. 277 No. 22.

Raj et al., "Selective Killing of Cancer Cells by a Small Molecule Targeting the Stress Response to ROS", Nature, 2011, pp. 231-234, vol. 475 No. 7355.

Rao et al., "Synthesis and Biological Evaluation of New Piplartine Analogues as Potent Aldose Reductase Inhibitors (ARIs)", European Journal of Medicine, 2012, pp. 344-361, vol. 57.

Shaw et al., "Selective Killing of K-Ras Mutant Cancer Cells by Small Molecule Inducers of Oxidative Stress", Proceedings of the National Academy of Sciences of the United States of America, pp. 8773-8778, vol. 108 No. 21, (2011).

Shenton et al., "Protein S-Thiolation Targets Glycolysis and Protein Synthesis in Response to Oxidative Stress in the Yeast Saccharomyces Cerevisiae", Biochemical Journal, 2003, pp. 513-519, vol. 374 Pt. 2.

Szatrowski et al., "Production of Large Amounts of Hydrogen Peroxide by Human Tumor Cells", Cancer Research, Feb. 1, 1999, pp. 794-798, vol. 51 No. 3.

Trachootham et al., "Selective Killing of Oncogenically Transformed Cells Through a ROS-Mediated Mechanism by Beta-Phenylethyl Isothiocyanate", Cancer Cell, 2006, pp. 241-252, vol. 10 No. 3.

Trachootham et al., "Targeting Cancer Cells by ROSmediated Mechanisms: A Radical Therapeutic Approach?", Nature Reviews Drug Discovery, 2009, pp. 579-591, vol. 8 No. 7.

West et al., "Enhanced Toxicity of the Protein Cross-Linkers Divinyl Sulfone and Diethyl Acetylenedicarboxylate in Comparison to Related Monofunctional Electrophiles", Chemical Research in Toxicology, 2011, pp. 1457-1459, vol. 24 No. 9.

Wissner et al., "Synthesis and Structure-Activity Relationships of 6, 7-Disubstituted 4-Anilinoquinoline-3-Carbonitriles. The Design of an Orally Active, Irreversible Inhibitor of the Tyrosine Kinase Activity of the Epidermal Growth Factor Receptor (EGFR) and the Human Epidermal Growth Factor Receptor-2 (HER-2)", Journal of Medicinal Chemistry, 2003, pp. 49-63, vol. 46 No. 1.

Wondrak, "Redox-Directed Cancer Therapeutics: Molecular Mechanisms and Opportunities", Antioxidants & Redox Signaling, 2009, pp. 3013-3069, vol. 11 No. 12.

Zhao et al., "Intracellular Water-Specific MR of Microbead-Adherent Cells: The HeLa Cell Intracellular Water Exchange Lifetime", NMR in Biomedicine, 2008, pp. 159-164, vol. 21 No. 2.

Zhu et al., "Covalent Crosslinking of Glutathione and Carnosine to Proteins by 4-Oxo-2-Nonenal", Chemical Research in Toxicology, 2009, pp. 1050-1059, vol. 22 No. 6.

\* cited by examiner

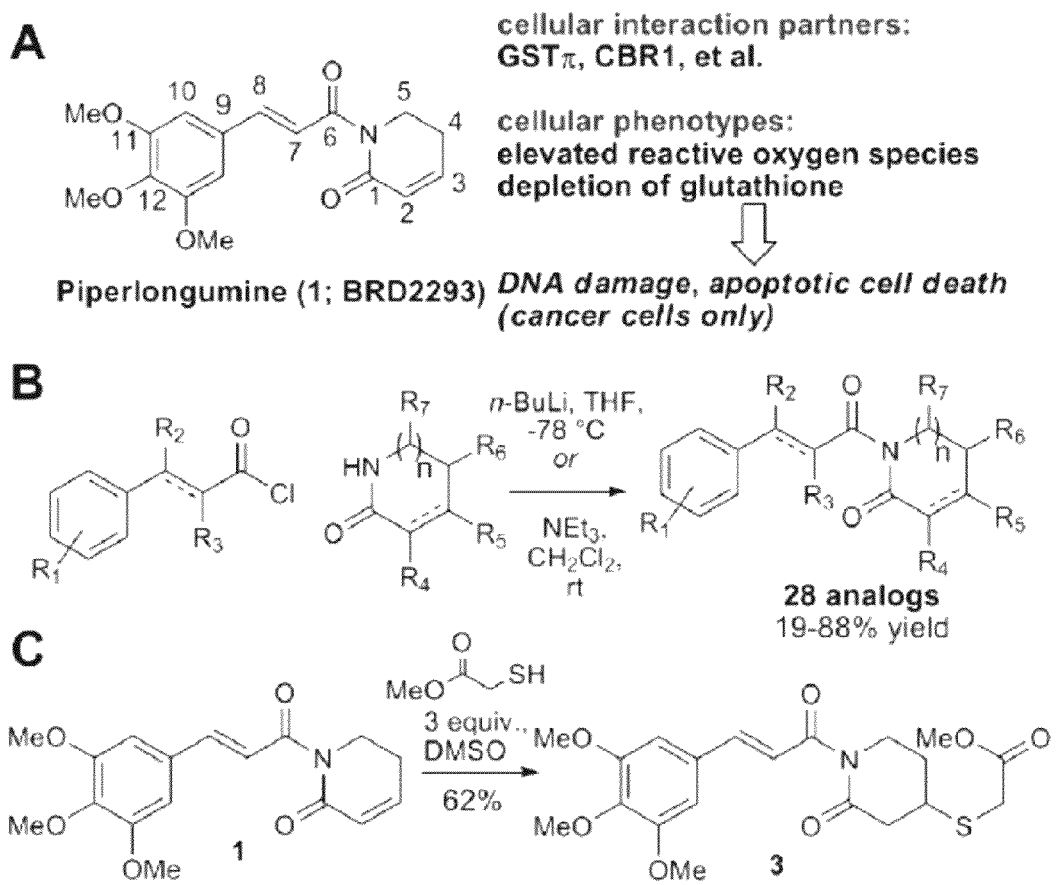
Figure 1A,B,C

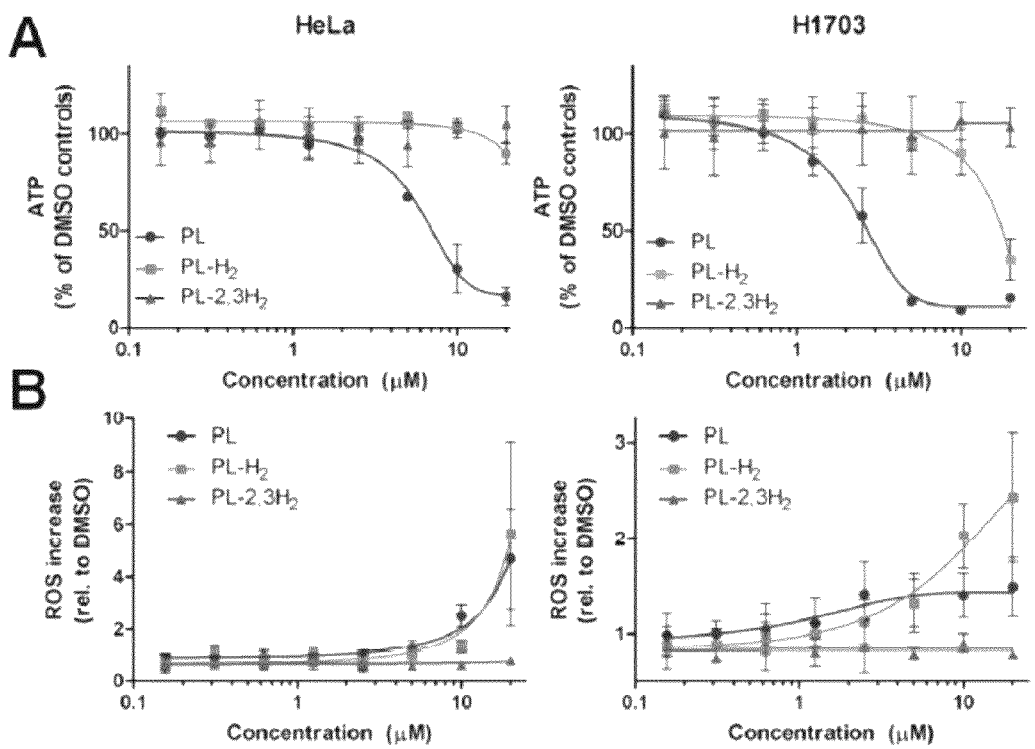
Figure 2A,B

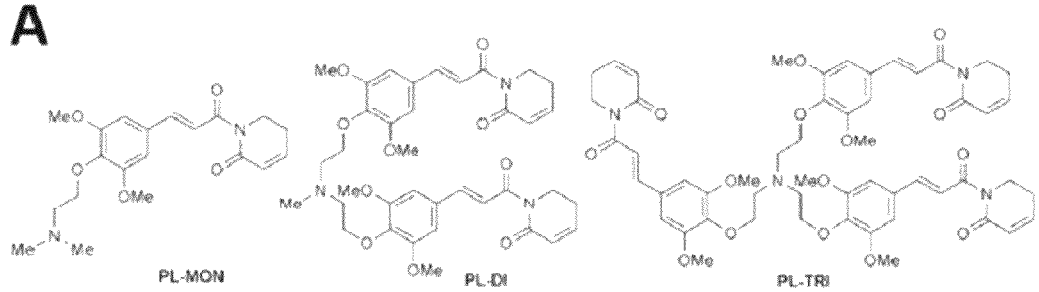
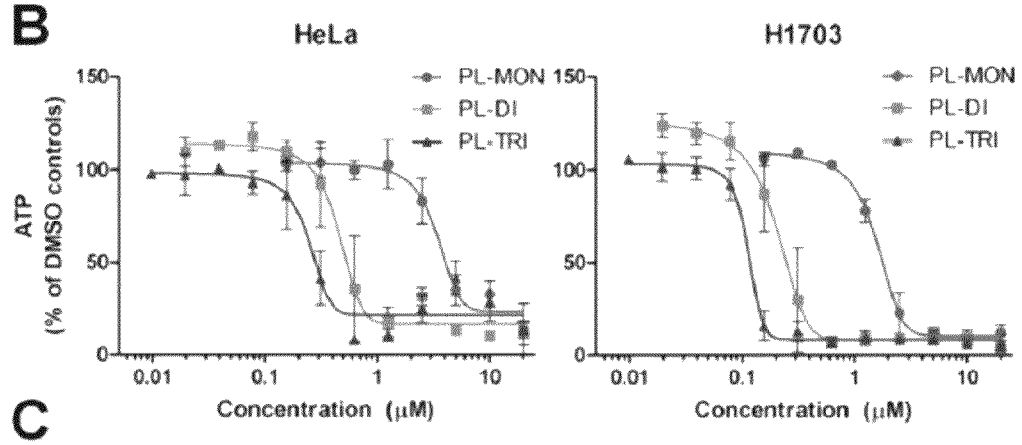
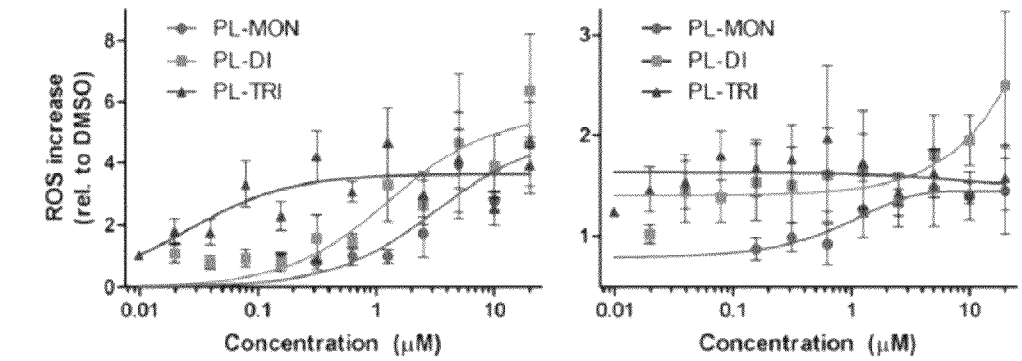
Figure 3A,B,C

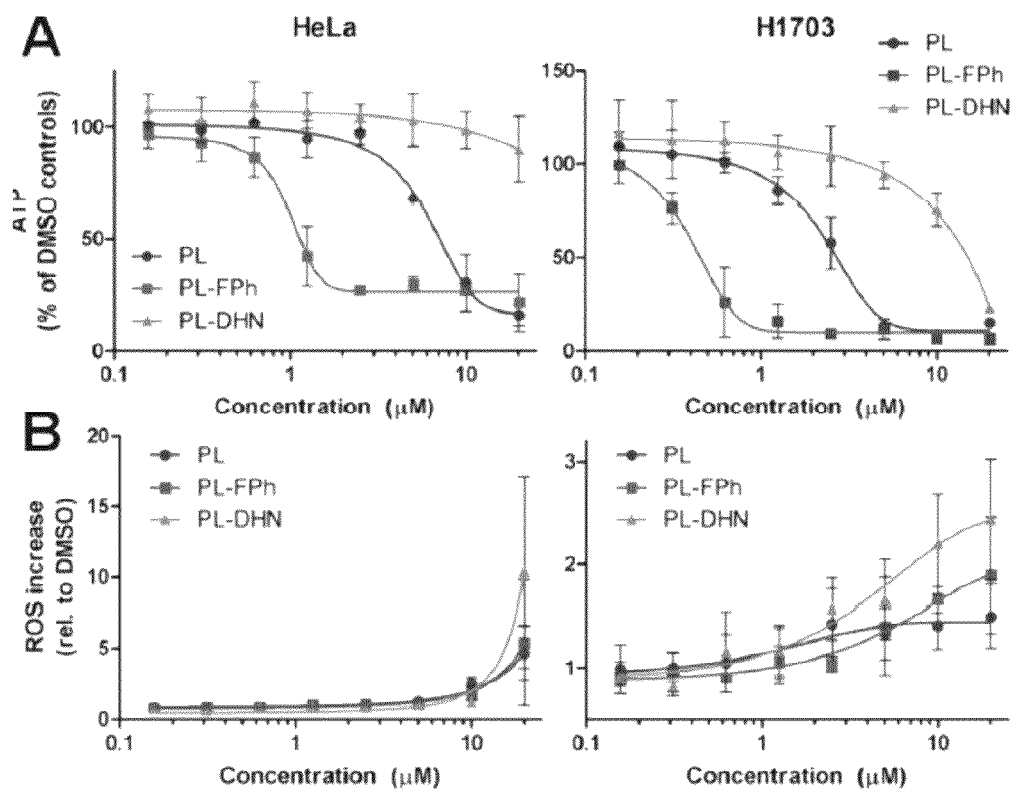
Figure 4A,B

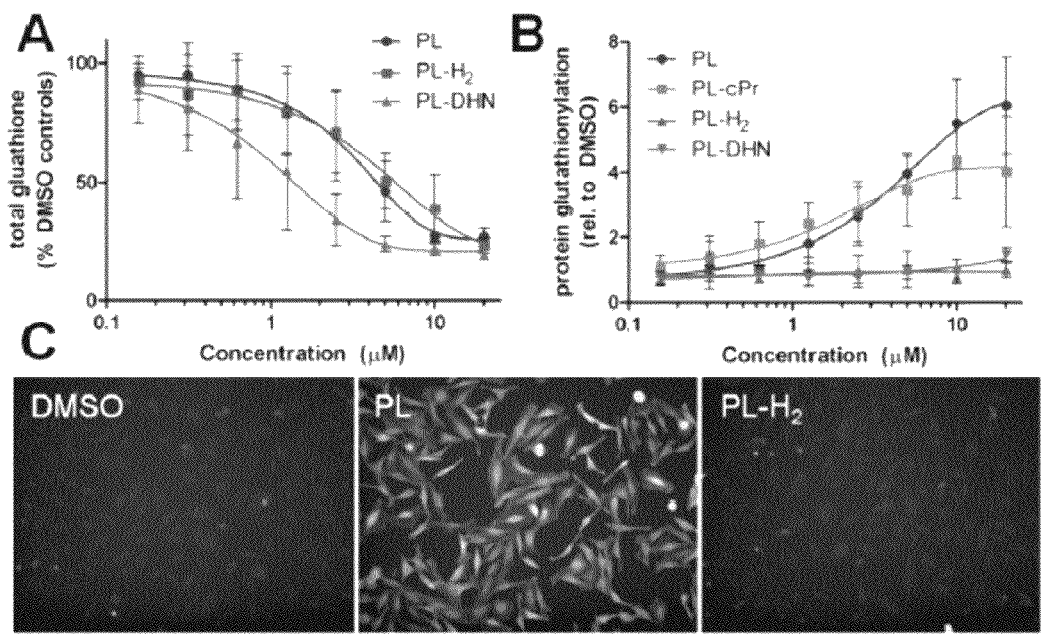
Figure 5A,B,C

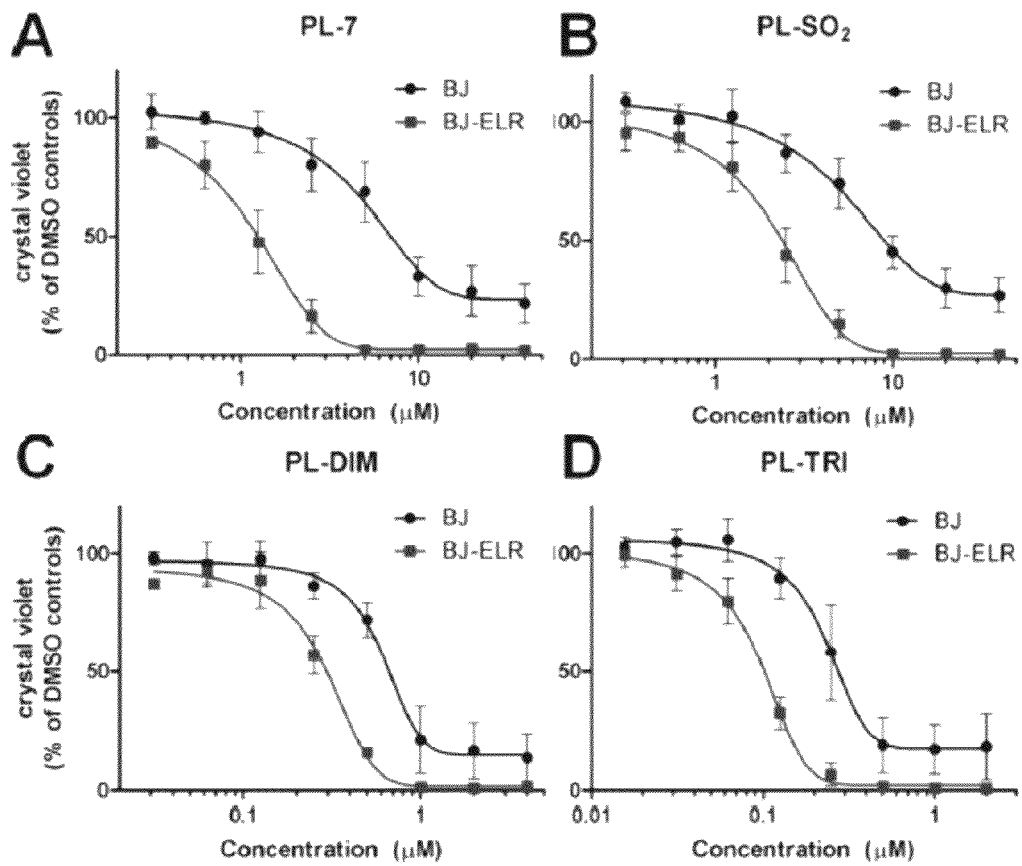
Figure 6A,B,C,D

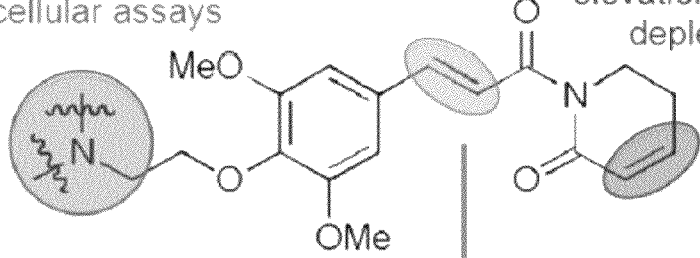
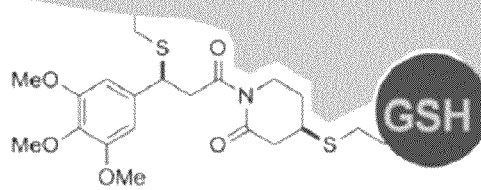
Figure 7A,B

A) Synthesis of C4- and C5-substituted analogs[a]

[a]Conditions: (a) aq. NH$_3$, dodecylbenzenesulfonic acid; (b) H$_3$CC(OMe)$_3$, Δ; (c) LiOH, THF/H$_2$O; (d) diphenylphosphoryl azide, NEt$_3$, PhH, reflux; *t*-BuOH, reflux; (e) TFA, CH$_2$Cl$_2$; (f) acryloyl chloride, NEt$_3$, CH$_2$Cl$_2$, 0 °C; (c) Grubbs' 2nd generation catalyst, CH$_2$Cl$_2$, reflux.

Conditions: (a) methyl thioglycolate (3 equiv.), DMSO, 3d.

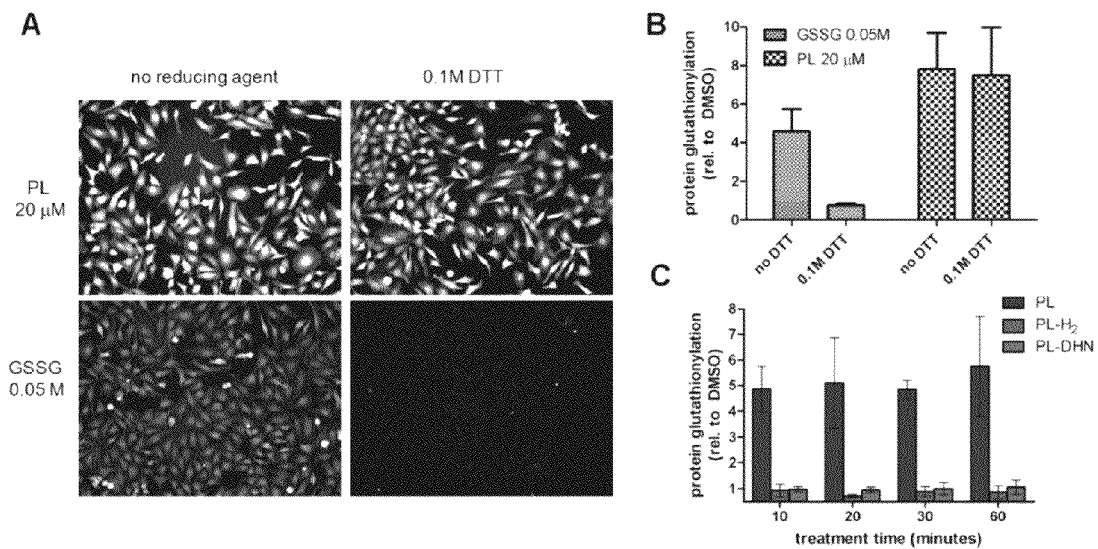
Figure 12,A,B,C

A

D

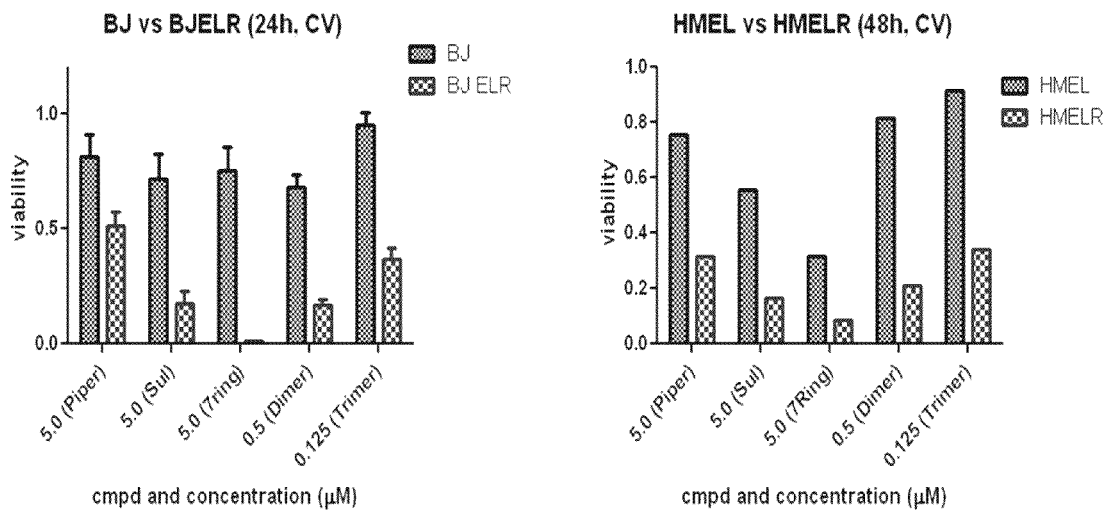
LEGEND:
Piper= Piperlongumine
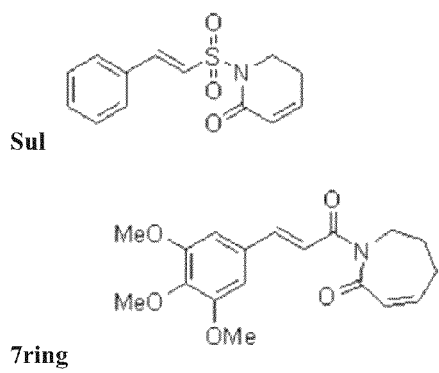
Sul
7ring
Figure 19

COMPOUNDS, COMPOSITIONS, AND METHODS FOR CANCER THERAPY

CROSS-REFERENCE TO RELATED APPLICATIONS

This U.S. Non-Provisional patent application claims the benefit of U.S. Provisional Patent Application No. 61/779,434, filed Mar. 13, 2013, which is incorporated herein by reference in its entirety, and the benefit of U.S. Provisional Patent Application No. 61/674,100, filed Jul. 20, 2012, which is incorporated herein by reference in its entirety.

STATEMENT REGARDING FEDERALLY SPONSORED RESEARCH OR DEVELOPMENT

This invention was made with government support under R01GM038627, awarded by the National Institutes of Health. The government has certain rights to this invention.

BACKGROUND

Reactive oxygen species (ROS) are natural byproducts of oxidative respiration and can function in signal transduction and clearance of pathogens during innate immune responses. Cancer cells have been reported to harbor higher levels of ROS than non-transformed cells, and in some cases activation of a specific oncogene (for example, HRAS) is sufficient to elevate levels of ROS (1, 2). Since ROS are capable of damaging crucial cellular macromolecules, including DNA, some cancer cells may be faced with chronic 'oxidative stress' that requires active enzymatic ROS detoxification to prevent induction of cell death. As such, one consequence of some of the genomic alterations leading to tumorigenesis may be a dependency on pathways facilitating the detoxification of ROS for survival, a form of 'nononcogene addiction' or 'non-oncogene co-dependency' (3-5). Importantly, this dependency might not be shared by many non-transformed cells, whose lower basal ROS levels and/or elevated antioxidant capacity could provide resistance to treatments that impair ROS metabolism. Various small molecules, including many with disulfide, -unsaturated carbonyl, sulfonate, or other electrophilic functional groups, have previously been shown to elevate ROS levels and induce cancer cell death (6). A subset of such compounds has also demonstrated a degree of selective toxicity toward cancer cells in in vitro and in vivo models (7-12).

A cell-based, high-throughput screening approach was used to identify piperlongumine (PL), a naturally occurring, electrophilic small molecule capable of selectively killing a variety of transformed cell types while sparing primary normal cells (5). Piperlongumine's in vivo antitumor efficacy was illustrated in mouse models of cancer, including xenograft and spontaneous mammary tumor formation models. Mechanistic investigations correlated the observed selective toxicity with a cancer-selective increase in ROS and other markers of oxidative stress following treatment with PL, as well as increases in DNA damage and apoptotic cell death (FIG. 1A). The small-molecule nucleophile and antioxidant N-acetyl-L-cysteine prevents PL-mediated cell death, and several proteins known to bind glutathione and detoxify ROS were identified as potential cellular interaction partners of PL through affinity purification and quantitative proteomics.

Piperlongumine analogs where methoxy groups of piperlongumine are substituted with hydrogen, hydroxy, methyl, or other groups have been described (UA 2009/0312373; UA 2011/0053938; UA 2012/0059004, UA 2012/0157455; Duh et al. J. Nat. Prod. 1990 November-December, 53(6) 1575-1577; Duh et al., Phytochemistry 1990, 29: 2689-2691; Raj et al. Nature 475, 231-234 (2011)).

SUMMARY

Compounds comprising oligomers of piperlongumine (PL) and/or piperlongumine analogues (PLA) as well as certain PLA compounds that exhibit improved toxicity to cancer cells are provided herein. The compounds provided herein are collectively referred to herein as "iPLA" compounds (for "improved piperlongumine analogues"). In certain embodiments, such improvements exhibited by iPLA compounds can comprise about a 10- to 2-fold decrease in $EC_{50}$ values for cancer cell toxicity relative to the corresponding $EC_{50}$ values for PL. In certain embodiments, such improvements in $EC_{50}$ values for cancer cell toxicity exhibited by iPLA compounds are accompanied by selective toxicity towards cancer cells that is comparable to that exhibited by PL. In certain embodiments, iPLA compounds are accompanied by selective toxicity towards cancer cells that is improved relative to that exhibited by PLA are provided. Also provided herein are compositions comprising iPLA compounds, methods of making compositions comprising the iPLA compounds, methods of making iPLA compounds, and the use of iPLA compounds in methods for treating cancer.

Oligomers comprising monomers independently selected from the group consisting of a piperlongumine (PL) monomer, a piperlongumine analog (PLA) monomer, and pharmaceutically acceptable salts thereof, wherein said monomers are covalently linked at a position in their respective carbon chains that is independently selected from the group consisting of the C11 position, the C12 position, and the C13 position are provided. In certain embodiments, the monomers are linked via a chain selected from the group consisting of alkyl, alkenyl, alkoxy, aminoalkyl, aminoalkenyl, and an aminoalkoxy group. In certain embodiments, the monomers are linked via one or more chain(s) independently selected from the group consisting of alkyl, alkenyl, alkoxy, aminoalkyl, aminoalkenyl, and an aminoalkoxy group, wherein at least one of said groups are joined in said chain via an ether, ester, thioester, thioether, amide, or keto group. In certain embodiments, the C11, C12, or C13 positions are linked by a 3 to 15 atom chain. In certain embodiments, the chain is a branched chain. In certain embodiments, the aminoalkoxy group is of the formula —O—$(CH_2)_{n1}$—N($R_7$)—$(CH_2)_{n2}$—O—, wherein $n_1$=1-6, $n_2$=1-6, and $R_7$ is selected from the group consisting of hydrogen, alkyl, alkenyl, alkoxy, aminoalkyl, aminoalkenyl, aminoalkoxy, and an aminoalkoxy group. In certain embodiments, a first and a second PL or PLA monomer are linked by an aminoalkoxy group is of the formula —O—$(CH_2)_{n1}$—N($R_7$)—$(CH_2)_{n2}$—O—, wherein $n_1$=1-6, $n_2$=1-6, and $R_7$ is selected from the group consisting of alkyl, alkenyl, alkoxy, aminoalkyl, aminoalkenyl, aminoalkoxy, wherein said $R_7$ group is linked to a third PL monomer or to a third PLA monomer. In certain embodiments, the, oligomer is a dimer or a trimer. In certain embodiments, the PLA monomer is a compound having the formula:

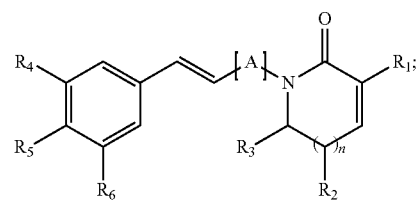

wherein A is C(O) or S(O)$_2$; wherein n=0, 1, 2, or 3; wherein the ortho-carbon of the phenyl ring is unsubstituted or substituted with a halogen; wherein R$_1$ is selected from the group consisting of hydrogen, halogen, C≡C-alkyl, C≡C-cycloalkyl, C≡C-cycloakyl halide, C≡C-aryl, C≡C-aryl halide, and an aryl group; wherein R$_2$ is selected from the group consisting of hydrogen, alkyl, alkenyl, and an aryl group; wherein R$_3$ is selected from the group consisting of hydrogen, alkyl, alkenyl, and an aryl group; and, wherein each of R$_4$, R$_5$, and R$_6$ is independently selected from the group consisting of hydrogen, bromine, chlorine, fluorine, keto, hydroxyl, alkyl, alkenyl, alkoxy, aminoalkyl, aminoalkenyl, and an aminoalkoxy group, with the proviso that said compound is not a PL monomer. In certain embodiments, R$_1$ is a C≡C-cycloalkyl group, wherein said cycloalkyl is a C3 to C6 ring. In certain embodiments, R$_1$ is a C≡C-cycloalkyl, wherein said cycloakyl is substituted at the ring carbon that is bound to the alkynyl carbon with a hydroxyl group. In certain embodiments, R$_1$ is a C≡C-phenyl or a C≡C-phenyl halide wherein a halide is substituted ortho or para to the phenyl ring carbon that is bound to the alkynyl carbon. In certain embodiments, the oligomer is a compound of a formula selected from the group consisting of:

wherein R is selected from the group consisting of C1-C4 alkyl, —C(O)—(CH2)n-COOH where n=1-4, and salts thereof.

Also provided are compositions comprising any of the aforementioned oligomers and a pharmaceutically acceptable excipient. In certain embodiments, the compositions can further comprise an additional chemotherapeutic agent.

Also provided are methods of treating cancer comprising administration of a therapeutically effective amount of any of the aforementioned oligomers to a subject in need thereof. In certain embodiments, the methods can further comprise administration of an additional chemotherapeutic agent.

Also provided are methods of making an oligomer of a piperlongumine (PL) monomer and/or a piperlongumine analog (PLA) monomer, comprising the steps of reacting an alkyl diol, an aminoalkyl diol, an alkyl triol, or an aminoalkyl triol with piperlongumine or piperlongumine analogue under conditions that provide for ether bond formation between said hydroxyl group and said diols or triols, wherein at least one of the C11, C12, or C13 positions of said piperlongumine (PL) monomer and/or a piperlongumine analog (PLA) monomer is substituted with a hydroxyl group.

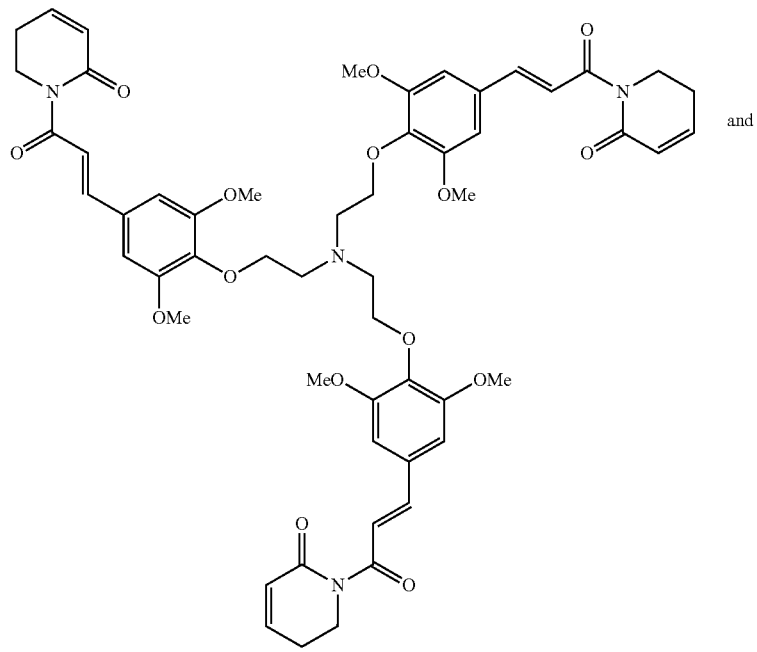

and

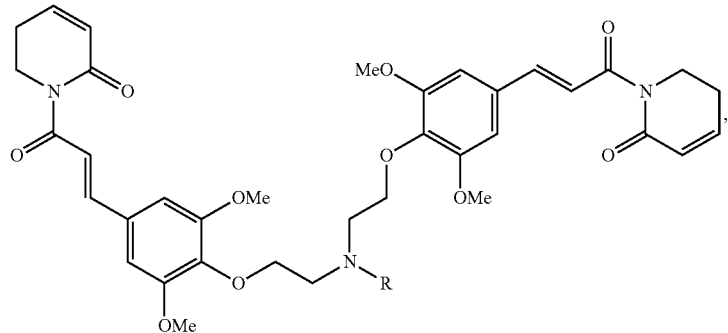

,

Also provided are compounds having the formula:

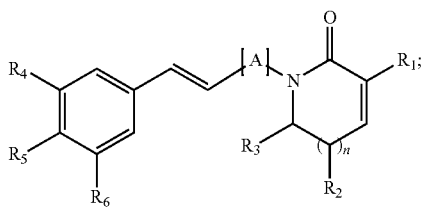

wherein A is C(O) or S(O)₂; wherein n=0, 1, 2, or 3; wherein the ortho-carbon of the phenyl ring is unsubstituted or substituted with a halogen; wherein R₁ is selected from the group consisting of a halogen, C≡C-alkyl, C≡C-cycloalkyl, C≡C-cycloakyl halide, C≡C-aryl, a C≡C-aryl halide, and an aryl group; wherein R₂ is selected from the group consisting of hydrogen, alkyl, alkenyl, and an aryl group; wherein R₃ is selected from the group consisting of hydrogen, alkyl, alkenyl, and an aryl group; and, wherein each of R₄, R₅, and R₆ is independently selected from the group consisting of hydrogen, bromine, chlorine, fluorine, keto, hydroxyl, alkyl, alkenyl, alkoxy, aminoalkyl, aminoalkenyl, and an aminoalkoxy group. In certain embodiments, R₁ is a C≡C-cycloalkyl group wherein said cycloalkyl is a C3 to C6 ring. In certain embodiments, R₁ is a C≡C-cycloalkyl, wherein said cycloakyl is substituted at the ring carbon that is bound to the alkynyl carbon with a hydroxyl group. In certain embodiments, R₁ is a C≡C-phenyl or a C≡C-phenyl halide wherein a halide is substituted ortho or para to the phenyl ring carbon that is bound to the alkynyl carbon. In certain embodiments, the compound has a formula selected from the group consisting of:

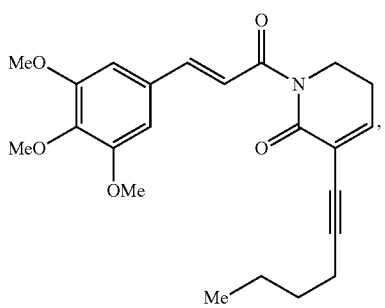

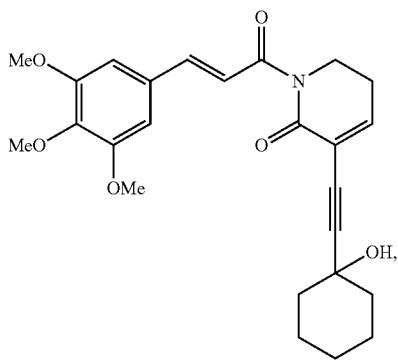

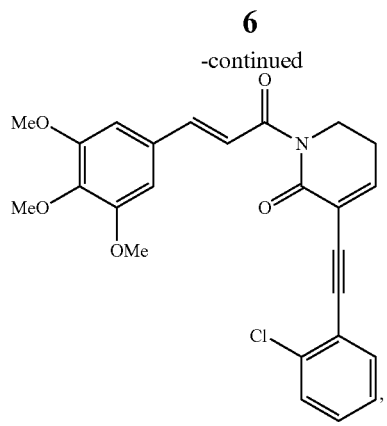

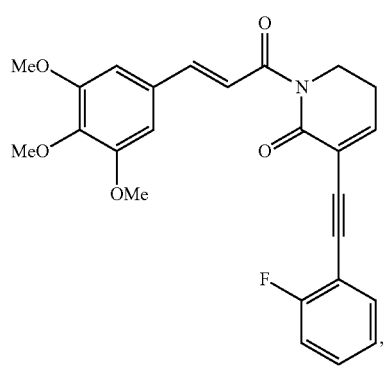

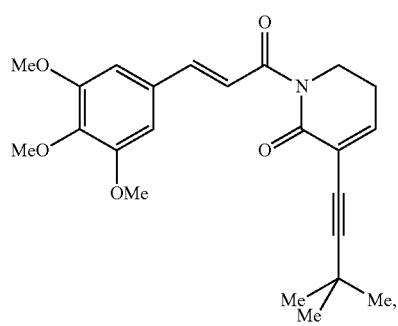

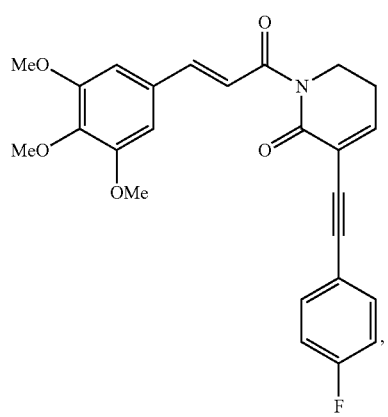

-continued

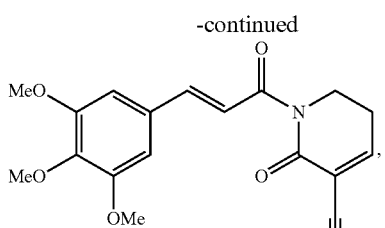

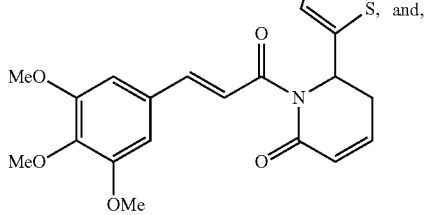

Also provided are compositions comprising any of the aforementioned compounds having the formula:

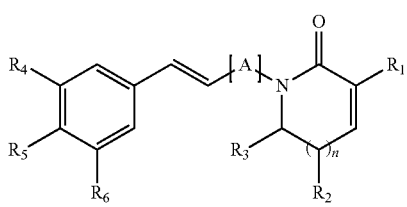

and a pharmaceutically acceptable excipient. In certain embodiments, the composition can further comprise an additional chemotherapeutic agent.

Also provided are methods of treating cancer comprising administration of a therapeutically effective amount of any of the aforementioned compounds having the formula:

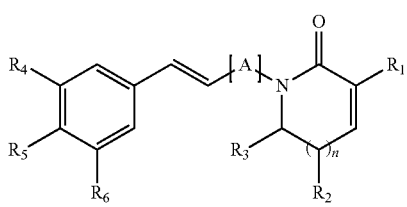

to a subject in need thereof. In certain embodiments, the methods can further comprise administration of an additional chemotherapeutic agent.

Also provided is a compound with the formula:

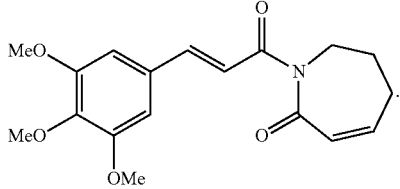

Also provided are compositions comprising the compound with the formula:

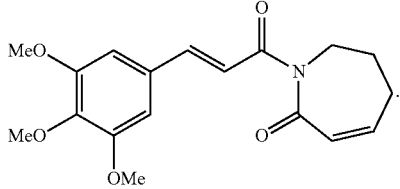

and a pharmaceutically acceptable excipient. In certain embodiments, the compositions can further comprise an additional chemotherapeutic agent.

Also provided are methods of treating cancer comprising administration of a therapeutically effective amount of the compound with the formula:

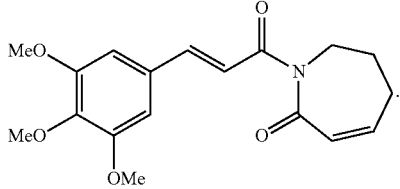

to a subject in need thereof. In certain embodiments, the methods can further comprise administration of an additional chemotherapeutic agent.

Also provide herein are compounds having the formula:

(II)

wherein A is C(O) or S(O)$_2$; wherein B is an alkyl, alkenyl, or alkynyl; wherein n=0, 1, 2, or 3; wherein R$_1$ is selected from the group consisting of a halogen, hydrogen, C≡C-alkyl, C≡C-cycloalkyl, C≡C-cycloakyl halide, C≡C-aryl, a C≡C-aryl halide, and an aryl group; wherein R₂ is selected from the group consisting of hydrogen, alkyl, alkenyl, and an aryl group; wherein R₃ is selected from the group consisting of hydrogen, alkyl, alkenyl, and an aryl group; and, wherein R₄ is selected from the group consisting of hydrogen, alkyl, a compound of the formula:

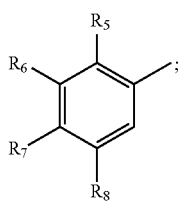

(III)

wherein B is alkenyl or alkynyl, R₅ is selected from the group consisting of hydrogen, halogen, and methoxy, and wherein each of R₆, R₇, and R₈ are independently selected from the group consisting of hydrogen, bromine, chlorine, fluorine, keto, hydroxyl, alkyl, alkenyl, alkoxy, an aminoalkenyl, and an aminoalkoxy group with the proviso that at least one of R₅, R₆, and R₇ is not a methoxy group when A is C(O), n=0, and R₁, R₂, and R₃ are hydrogen, and with the proviso that at least one of R₆, R₇, and R₈ is not a hydrogen, methoxy group, alkoxy, or aminoalkoxy group when R₁, R₂, and R₃ are hydrogen,
and a compound of the formula:

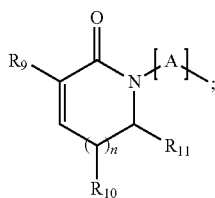

(IV)

wherein A is C(O) or S(O)₂, and is optionally joined to B by X; wherein X, when present, is an alkyl, alkenyl, alkynyl, aryl, or combination thereof; wherein n=0, 1, 2, or 3; wherein R₉ is selected from the group consisting of a halogen, hydrogen, C≡C-alkyl, C≡C-cycloalkyl, C≡C-cycloakyl halide, C≡C-aryl, a C≡C-aryl halide, and an aryl group; wherein R₁₀ is selected from the group consisting of hydrogen, alkyl, alkenyl, and an aryl group; and, wherein R₁₁ is selected from the group consisting of hydrogen, alkyl, alkenyl, and an aryl group. In certain embodiments, compounds of the formula II wherein R4 is independently selected from the group consisting of hydrogen, alkyl, phenyl, and a compound of the formula:

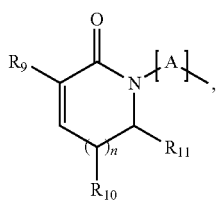

(IV)

wherein A is C(O) or S(O)₂, and is optionally joined to B by X, wherein X, when present, is an alkyl, alkenyl, alkynyl, aryl, or combination thereof; wherein n=0, 1, 2, or 3; wherein R₉ is selected from the group consisting of a halogen, hydrogen, C≡C-alkyl, C≡C-cycloalkyl, C≡C-cycloakyl halide, C≡C-aryl, a C≡C-aryl halide, and an aryl group; wherein R₁₀ is selected from the group consisting of hydrogen, alkyl, alkenyl, and an aryl group; and, wherein R₁₁ is selected from the group consisting of hydrogen, alkyl, alkenyl, and an aryl group are provided. In certain embodiments, R₁ is a C≡C-cycloalkyl group wherein said cycloalkyl is a C3 to C6 ring and/or wherein R₃ is hydrogen or a thienyl group. In certain embodiments, R₁ is a C≡C-cycloalkyl, wherein said cycloakyl is substituted at the ring carbon that is bound to the alkynyl carbon with a hydroxyl group and/or wherein R₃ is hydrogen or a thienyl group. In certain embodiments, R₁ is a C≡C-phenyl or a C≡C-phenyl halide wherein the halide is substituted ortho or para to the phenyl ring carbon that is bound to the alkynyl carbon and/or wherein R₃ is hydrogen or a thienyl group. In certain embodiments where R₄ is a compound of formula IV, R₁ and R₉ are independently selected from a group consisting of hydrogen, a halogen, and a C≡C-cycloalkyl group wherein said cycloalkyl is a C3 to C6 ring and/or wherein R₃ and R₁₁ are independently selected from a group consisting of hydrogen and a thienyl group or, alternatively, R₁ and R₉ are independently selected from the group consisting of hydrogen, a halogen, and a C≡C-cycloalkyl group, wherein said cycloakyl is substituted at the ring carbon that is bound to the alkynyl carbon with a hydroxyl group and/or wherein R₃ is hydrogen or a thienyl group. In certain embodiments where R₄ is a compound of formula IV, R₁ and R₉ are independently selected from the group consisting of hydrogen, a halogen, and is a C≡C-phenyl or a C≡C-phenyl halide wherein the halide is substituted ortho or para to the phenyl ring carbon that is bound to the alkynyl carbon and/or wherein R₃ is hydrogen or a thienyl group. Also provided are compounds having a formula selected from the group consisting of:

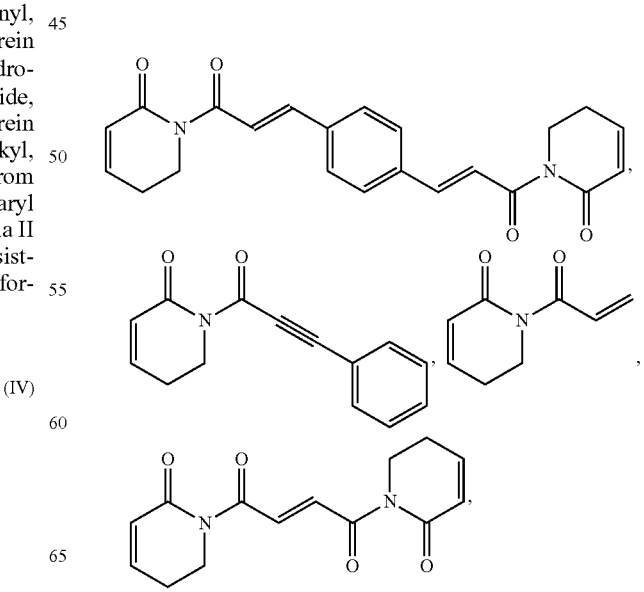

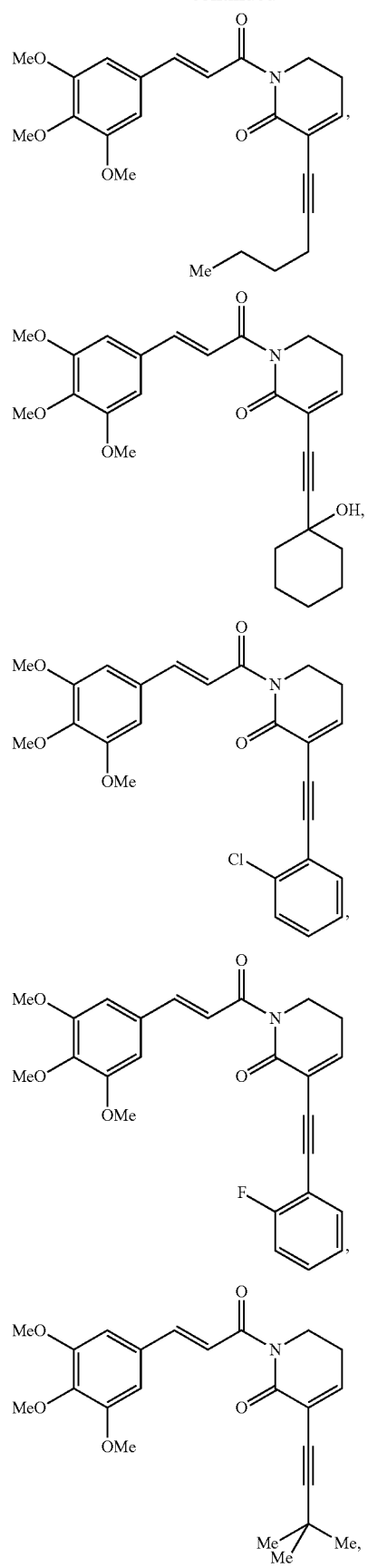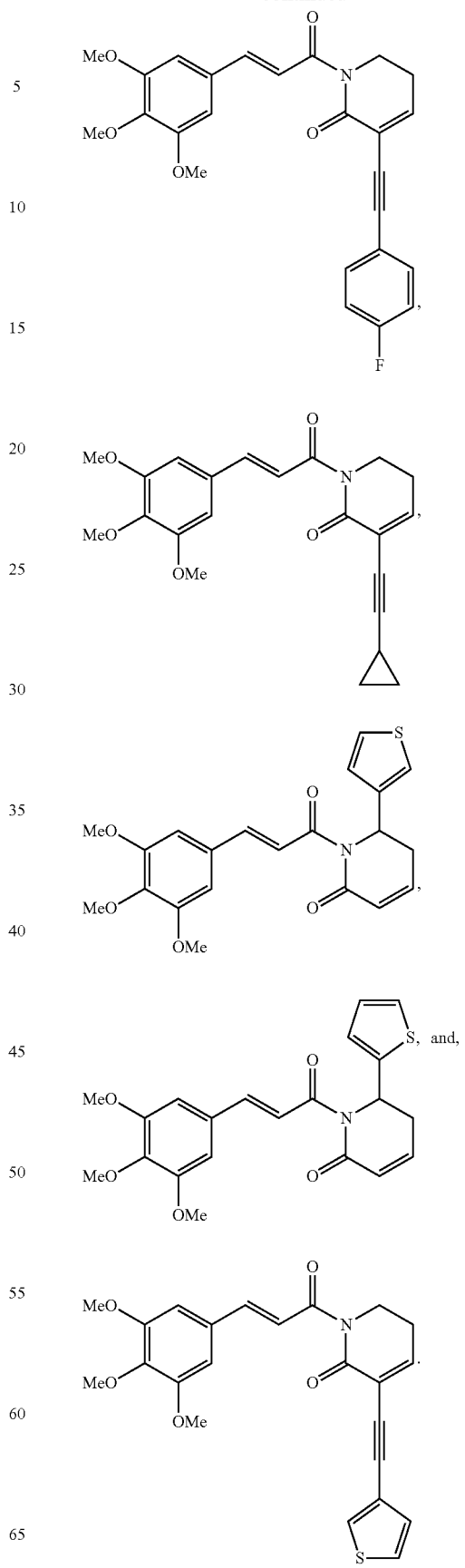

Also provided are compounds of the formula:

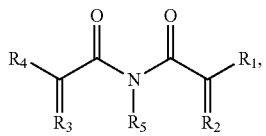

wherein $R_1$ is either: (i) halogen, C≡C-alkyl, C≡C-cycloakyl, C≡C-cycloakyl halide, C≡C-aryl, a C≡C-aryl halide, or an aryl group; or, (ii) an alkyl, thioalkyl, aminoalkyl, or alkenyl group that is optionally fused to $R_2$ when $R_2$ is alkyl and wherein the ring formed by the fusion consists of 5, 6, 7, or 8 members; wherein $R_2$ is alkyl; wherein $R_3$ is alkyl; wherein $R_4$ is selected from the group consisting of hydrogen, halogen, C≡C-alkyl, C≡C-cycloalkyl, C≡C-cycloakyl halide, C≡C-aryl, a C≡C-aryl halide, and an aryl group; and, wherein $R_5$ is selected from the group consisting of hydrogen, alkyl, $S(O)_2$—$R_6$, and C(O)—$R_6$, wherein $R_6$ is alkyl, alkenyl, or alkynyl. In certain embodiments, the compound has the structure:

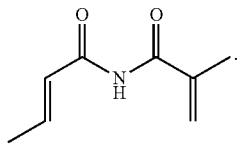

Also provided herewith are compositions comprising any of the aforementioned compounds and a pharmaceutically acceptable excipient. In certain embodiments, the composition can further comprise an additional chemotherapeutic agent Also provided herewith are methods of treating cancer that comprise administration of a therapeutically effective amount of any of the aforementioned compounds to a subject in need thereof. In certain embodiments, the methods can further comprise administration of an additional chemotherapeutic agent. Also provided herein is the use of any of the aforementioned compounds for treating cancer in a subject in need thereof. Also provided herein is the use of any of the aforementioned compounds in the manufacture of a medicament for treatment of cancer.

BRIEF DESCRIPTION OF THE DRAWINGS

The accompanying drawings, which are incorporated in and form a part of the specification, illustrate certain embodiments of the present invention. In the drawings:

FIGS. 1 A, B, and C illustrate A) Piperlongumine and its cellular phenotypes (5); B) Convergent strategy for the synthesis of PL analogs; and C) PL reacts with small-molecule thiols at C3 under neutral conditions, reaction time, 72 h.

FIG. 3 illustrates that oligomerization of PL leads to greatly elevated potency for elevation of ROS and cell death in two cell lines. A) aminoalkoxy C12 substituted monomer of PL (PL-MON), dimer (PL-DI), and trimer (PLTRI). B) ATP levels and C) ROS levels in HeLa and H1703 cells after 48 h (ATP) or 1.5 h (ROS) treatment with the indicated concentrations of oligomer. Data are expressed as mean±SD for four (CTG) or three (ROS) independent experiments.

FIG. 4 illustrates that certain piperlongumine analogs decouple ROS elevation and cellular viability. A) ATP levels and B) ROS levels in HeLa and H1703 cells after 48 h (ATP) or 1.5 h (ROS) treatment with the indicated concentrations of analog. Data are expressed as mean±SD for four (CTG) or three (ROS) independent experiments.

FIG. 5 illustrates that Piperlongumine's C7-C8 olefin is unnecessary for depletion of cellular glutathione but essential for protein glutathionylation. A) Levels of total cellular glutathione were measured after 3-hour treatment of EJ cells with the indicated concentrations of each analog. B) Quantification of protein gluathionylation in HeLa cells after 6 h treatment, as detected by immunofluorescence using a monoclonal antibody against glutathione. Data are expressed as mean±SD for three (A) or four (B) independent experiments. C) Representative fluorescence microscopy images showing protein glutathionylation following 6 h treatment with either DMSO, PL, or PL-H2.

FIG. 6 illustrates that certain piperlongumine analogs show selective toxicity toward transformed human fibroblasts (BJ-ELR). Viability was measured by Crystal Violet staining after 48 h treatment with A) PL-7, B) PL-SO2, C) PL-DIM, or D) PL-TRI. Data are expressed as mean±SD for three independent experiments.

FIG. 7 illustrates: A) Proposed non-limiting model for PL-mediated protein glutathionylation of glutathione-binding proteins (5). Note that the proposed protein glutathionylation does not involve a direct reaction between the protein and glutathione. Rather, the non-limiting model predicts that the glutathionylation involves a linking PL molecule between the protein and glutathione. B) Summary of the role of electrophilic functionalities of PL analogs on cellular assay performance.

FIG. 12 illustrates A) increased protein glutathionylation is observed for both PL and glutathione disulfide (GSSG) by immunofluorescence. Although treatment with the dithiol reducing agent DTT is able to reverse the signal increase observed for GSSG, no change in signal is observed for PL-treated wells following DTT treatment. B) Quantitation of IF images. Data are expressed as mean±SD for three independent experiments. C) Protein glutathionylation occurs within minutes of PL treatment. Data are expressed as mean±SD for three independent experiments.

FIG. 19 illustrates selective cell death induced by improved piperlongumine analogs in cancer cells. Piperlongumine analogs selectively induced cell death in oncogenically transformed human BJ skin fibroblasts (BJ vs BJELR) and human mammary epithelial cells (HMEL vs HMELR). Isogenic non-transformed and transformed cell line pairs: BJ vs BJEL-Ras HMEL vs HMELRas. Assays performed in a 12-well plate with crystal violet. "Dimer" and "Trimer" compounds are as shown in FIG. 18.

DESCRIPTION

Definitions

Figure 2C:
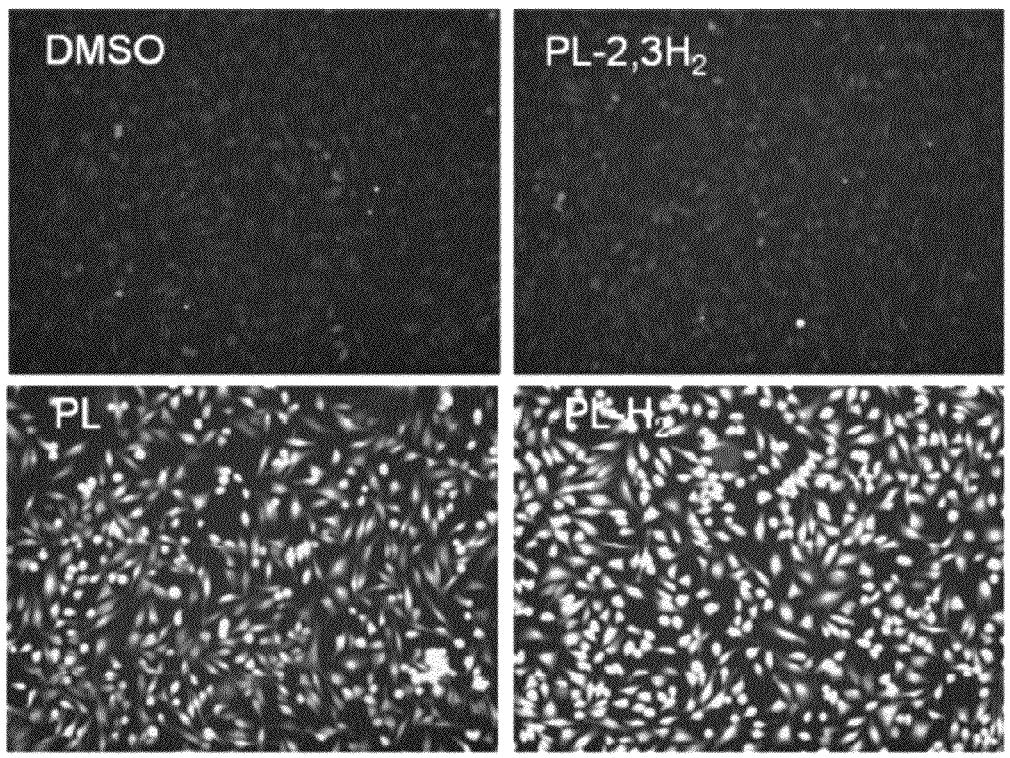
FIGS. 2 A, B, and C illustrate the contribution of PL's electrophilic functionalities to cellular phenotypes. A) Measurement of cellular ATP as a surrogate of viability (CellTiter-Glo) and B) cellular reactive oxygen species levels (CM-H2DCF-DA) in two cell lines. Data are expressed as mean±SD for four (CTG) or three (ROS) independent experiments. C) Representative fluorescence microscopy images of HeLa cells treated for 1 h with 20·M PL, PL-H2, or PL-2,3H2.
Figure 8A:
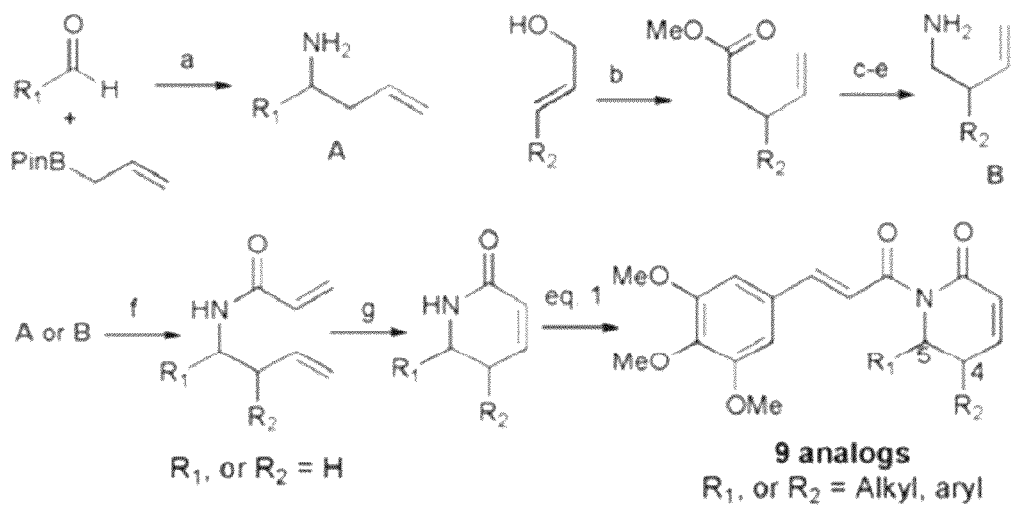
FIG. 8 A, B, C illustrates approaches to the synthesis of diverse piperlongumine analogs. A) Synthesis of C4- and C5-substituted analogs; B) Synthesis of C2-substituted analogs; C) Synthesis of oligomeric piperlongumine analogs.
Figure 8B:
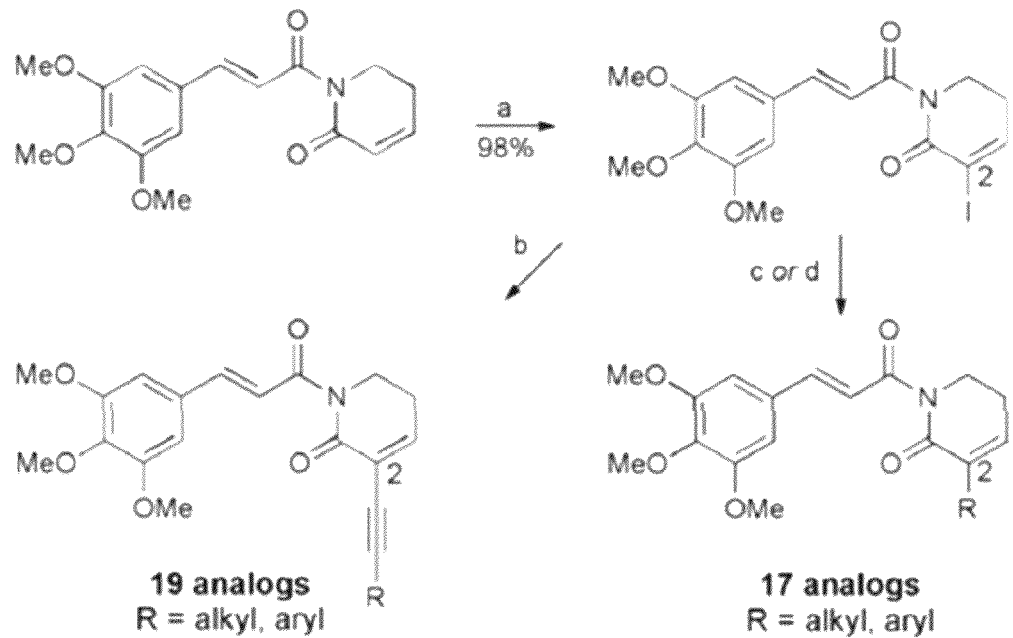
Figure 8C:
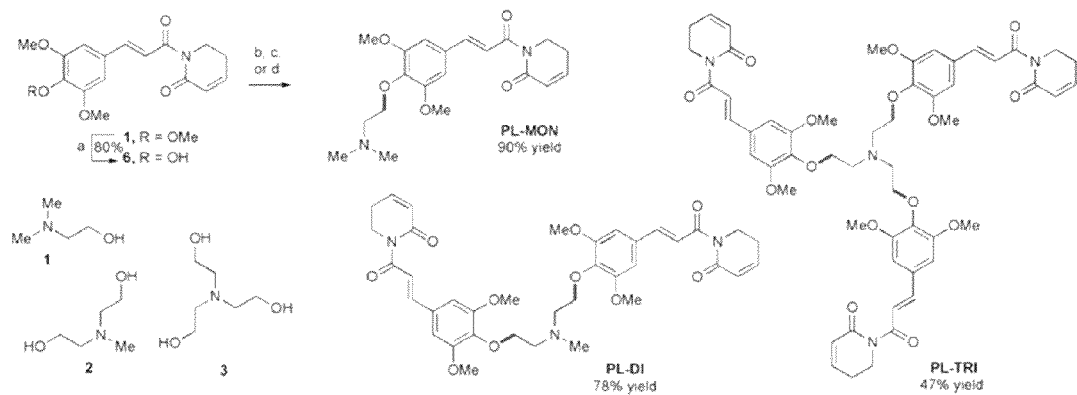

Unless otherwise defined, all technical and scientific terms used herein have the same meaning as commonly understood by one of ordinary skill in the art to which this invention pertains. In the case of inconsistencies between the present disclosure and the issued patents, applications, and references that are cited herein, the present disclosure will prevail. The nomenclature used to describe organic radicals, e.g., hydrocarbons and substituted hydrocarbons, generally follows standard nomenclature known in the art, unless otherwise specifically defined.

As used herein, the term "salt(s)", refer to acidic salts formed with inorganic and/or organic acids, as well as basic salts formed with inorganic and/or organic bases. In addition, when a compound contains both a basic moiety, such as, but not limited to, a pyridine or imidazole, and an acidic moiety, such as, but not limited to, a carboxylic acid, zwitterions ("inner salts") may be formed and are included within the term "salt(s)" as used herein.

As used herein the term "pharmaceutically acceptable salt", is intended to include nontoxic, physiologically acceptable salts synthesized from a compound which contains a basic or acidic moiety.

As used herein the term "prodrug", refers to a compound that is a drug precursor which, upon administration to a subject, undergoes chemical conversion by metabolic and/or chemical processes to yield an active compound or a salt and/or solvate thereof. Prodrugs include acid derivatives well known to practitioners of the art, such as, for example, esters prepared by reaction of the parent acidic compound with a suitable alcohol, or amides prepared by reaction of the parent acid compound with a suitable amine.

As used herein, the term "solvate", means a physical association of a compound with one or more solvent molecules, whether organic or inorganic. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolated solvates. Non-limiting examples of suitable solvates include hydrates, ethanolates, methanolates, isopropanolates and the like. "Hydrate" is a solvate wherein the solvent molecule is water (H2O).

As used herein, the term "subject", refers to both human and non-human mammals.

As used herein, the phrase "therapeutically effective amount", refers to an amount of a compound which, when administered to a subject in need thereof, is sufficient to cause any beneficial change in any symptom or marker associated with cancer.

As used herein, the terms "alkyl", "alkenyl", "alkoxy", "aminoalkyl", "aminoalkenyl", "aminoalkoxy", "cycloalkyl", "aryl", and "phenyl" refer to both substituted and unsubstituted alkyl, alkenyl, alkoxy, aminoalkyl, aminoalkenyl, aminoalkoxy, cycloalkyl, aryl, and phenyl groups. The terms "alkyl", "alkenyl", "alkoxy", "aminoalkyl", "aminoalkenyl", "aminoalkoxy", "cycloalkyl", "aryl", and "phenyl" as used herein also refer to both branched and unbranched alkyl, alkenyl, alkoxy, aminoalkyl, aminoalkenyl, aminoalkoxy, cycloalkyl, aryl, and phenyl groups.

As used herein, the term "alkoxy" refers to C1-C6 alkoxys.

As used herein in the context of a chain, the term "alkoxy" refers to both C1-C6 alkoxys and chains comprising repeating C1-C6 alkoxy subunits. In certain embodiments, an alkoxy chain can thus be a polymethoxy, polyethoxy, polypropoxy, or polybutoxy chain.

As used herein, the term "aryl" refers to both homocyclic and heterocyclic aryls.

As used herein, the term "halogen" refers to chlorine, bromine, fluorine, or iodide.

As used herein, the term "substituted" refers to replacement of one or more hydrogen atoms on a given group with one or more of a cyano, hydroxyl, hydroxyalkyl, nitro, halogen, amino, carboxyl, or —CO—NH2 group.

As used herein, the phrase "pharmaceutically acceptable" refers to those compounds, materials, compositions, and/or dosage forms which are suitable for use in contact with the tissues of subjects without excessive toxicity, irritation, allergic response, or other problem or complication commensurate with a reasonable risk/benefit ratio.

iPLA Compounds

In certain embodiments, iPLA compounds provided herein that comprise oligomers containing PL monomers, iPLA monomers, and/or PLA monomers are referred to herein as "iPLA oligomers". Such iPLA oligomers can exhibit marked increases in cancer cell toxicity relative to their constituent monomers. Also provided herein are iPLA compounds that comprise iPLA monomers of the instant invention. In general, such iPLA oligomers can comprise any combination of PL, PLA, and/or iPLA monomers. In certain embodiments, iPLA oligomers can contain 2-3, 2-4, 2-5, or 2-6 PL, iPLA, and/or PLA monomers. However, preferred embodiments contain 2-3 PL and/or PLA monomers and more preferred embodiments contain 2 PL, iPLA, and/or PLA monomers. Also provided herein are pharmaceutically acceptable salts, solvates, and prodrugs of iPLA compounds and thus iPLA oligomers.

Multimerization of PL and/or PLA monomers can be accomplished by a covalent linkage between any one of carbons 11, 12, or 13 (C11, C12, or C13) in the carbon chain of a PL and/or PLA monomer. Numbering of the carbons of the PL and PLA carbon chain is shown in FIG. 1A, where carbons 11, 12, and 13 correspond to carbons of the phenyl ring of PL that are substituted with methoxyl groups in PL. Without seeking to be limited by theory, it is believed that any of C11, C12, or C13 carbons of the PL or PLA monomer can serve as a linkage site as it is shown herein that the methoxy groups that are linked to C11, C12, or C13 can be replaced by other substituents without substantially altering biological activity of the monomer (i.e. elevation of ROS or cellular toxicity). In certain embodiments, monomers can be joined at either the same carbon or at distinct carbons in the backbone of the PL or PLA carbon chain. Thus, iPLA oligomers can, in certain embodiments, comprise monomers that are both linked at C11, C12, or C13 (i.e. a C11 to C11, a C12 to C12, or a C13 to C13 linkage). Oligomers where the monomers are both linked at C12 of their respective carbon chains are also provided. In other embodiments, PL and/or PLA monomers are linked via distinct carbons in their backbones (i.e. C11 to C12, C11 to C13, or C12 to C13) in an iPLA oligomer.

Covalent linkage of PL and/or PLA monomers in an iPLA oligomer can be effected by a variety of molecules referred to herein as "chains". Such chains can be either branched or unbranched. Chain lengths include, but are not limited to chains of any one of 2, 3, 4, 5, 6, 7, or 8 atoms to any one of 9, 10, 12, 13, 14, 15, 16, 17, 18, 19, 20, 21, 22, 23, 24, 25, or 26 atoms in length. Such chains can also be substituted or unsubstituted. In certain embodiments, the chain can comprise a branched or unbranched alkyl, alkenyl, alkoxy, aminoalkyl, aminoalkenyl, and/or an aminoalkoxy group that can be substituted or unsubstituted. In certain embodiments, the chain can be joined to the C11, C12, or C13 carbons of the PL or PLA monomer by groups comprising a part of the chain that include, but are not limited to, an ether, ester, a thioester, a thioether, an amide, or a keto group. In still other embodiments, the chain can comprise a branched or unbranched alkyl, alkenyl, alkoxy, aminoalkyl, aminoalkenyl, and/or aminoalkoxy group that can be substituted or unsubstituted, where at least one of said groups are joined in said chain via an ether, ester, thioester, thioether, amide, —$CH_2$—, or a keto group. Also provided are embodiments where the chain comprises a branched or unbranched alkyl, alkenyl, alkoxy, aminoalkyl, aminoalkenyl, or an aminoalkoxy group that can be substituted or unsubstituted is joined by an ether, ester, a thioester, a thioether, an amide, —$CH_2$—, or a keto group to one or more of a branched or unbranched alkyl, alkenyl, alkoxy, aminoalkyl, aminoalkenyl, or an aminoalkoxy group that can be substituted or unsubstituted. In certain embodiments, chains that can be used to link PL or PLA monomers include, but are not limited to, any of the following compounds that can be branched and/or substituted, where X and Y are independently selected from a group consisting of an ether, ester, thioester, thioether, amide, —$CH_2$—, and a keto group:

a) —X—$(CH_2)_{n1}$—N($R_7$)—$(CH_2)_{n2}$—Y—, where $n_1$=1-8, $n_2$=1-8, and $R_7$ is selected from the group consisting of hydrogen, alkyl, alkenyl, alkoxy, aminoalkyl, aminoalkenyl, aminoalkoxy, and an aminoalkoxy group;

b) —X—$(CH_2)_{n1}$—N($R_7$)—$(CH_2)_{n2}$—Y—, where $n_1$=1-8, $n_2$=1-8, and $R_7$ is selected from the group consisting of alkyl, alkenyl, alkoxy, aminoalkyl, aminoalkenyl, aminoalkoxy, and the $R_7$ group is linked to a third PL monomer or to a third PLA monomer;

c) —X—$(CH_2)_{n1}$—O—$(CH_2)_{n2}$—Y—, wherein $n_1$=1-8, $n_2$=1-8;

d) —X—$(CH_2)_{n1}$—C(O)—O—$(CH_2)_{n2}$—Y—, wherein $n_1$=1-8, $n_2$=1-8;

e) —X—$(CH_2)_{n1}$—S(O)—$(CH_2)_{n2}$—Y—, wherein $n_1$=1-8, $n_2$=1-8;

f) —X—$(CH_2)_{n1}$—S—$(CH_2)_{n2}$—Y—, wherein $n_1$=1-8, $n_2$=1-8;

g) —X—$(CH_2)_{n1}$—C(O)—N($R_8$)—$(CH_2)_{n2}$—Y—, wherein $n_1$=1-8, $n_2$=1-8, and $R_8$ is selected from the group consisting of hydrogen, alkyl, alkenyl, alkoxy, aminoalkyl, aminoalkenyl, aminoalkoxy, and an aminoalkoxy group;

h) X—$(CH_2)_{n1}$—C(O)—N($R_8$)—$(CH_2)_{n2}$—Y—, wherein $n_1$=1-8, $n_2$=1-8, and $R_8$ is selected from the group consisting of alkyl, alkenyl, alkoxy, aminoalkyl, aminoalkenyl, aminoalkoxy, and the aminoalkoxy group said $R_7$ group is linked to a third PL monomer or to a third PLA monomer;

i) X—$(CH_2O)_{n3}$—Y—, wherein $n_3$=1-8, and, j) —X—$(CH_2)$n1-C(O)—$(CH_2)$n2-Y—, wherein n1=1-8, n2=1-8.

Oligomers comprising PLA monomers are also provided herein. In the broadest sense, any PLA monomer disclosed herein may be multimerized or combined with PL to yield an iPLA oligomer.

In certain embodiments, the PLA monomer will be of the Formula I:

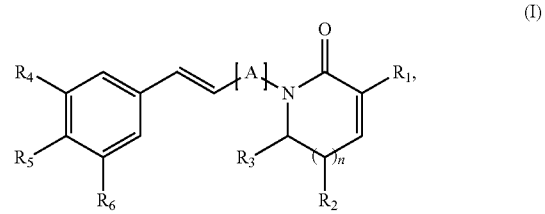

where A is C(O) or S(O)$_2$; where n=0, 1, 2, or 3; where the ortho-carbon of the phenyl ring is unsubstituted or substituted with a halogen; where $R_1$ is selected from the group consisting of hydrogen, halogen, C≡C-alkyl, C≡C-cycloalkyl, C≡C-cycloakyl halide, C≡C-aryl, C≡C-aryl halide, and an aryl group; where $R_2$ is selected from the group consisting of hydrogen, alkyl, alkenyl, and an aryl group; where $R_3$ is selected from the group consisting of hydrogen, alkyl, alkenyl, and an aryl group; and, where each of $R_4$, $R_5$, and $R_6$ is independently selected from the group consisting of hydrogen, bromine, chlorine, fluorine, keto, hydroxyl, alkyl, alkenyl, alkoxy, aminoalkyl, aminoalkenyl, and an aminoalkoxy group, with the proviso that said compound is not a PL monomer. Such PLA monomers can be linked to one another or to a PL monomer via a covalent chain between any one of the C11, C12, or C13 groups. In certain embodiments, any one of the $R_4$, $R_5$, and $R_6$ groups of one PLA monomer can be linked to any one of the $R_4$, $R_5$, and $R_6$ groups of another PLA monomer, where the PLA monomers are either identical or distinct. In certain embodiments, any one of the $R_4$, $R_5$, and $R_6$ groups of one PLA monomer can be linked to any one of the C11, C12, or C13 groups of a PLA monomer. In certain embodiments, $R_1$ is a halogen in the PLA monomer. In certain embodiments, $R_1$ is a sulfur containing heteroaryl group in in the PLA monomer. In certain embodiments, $R_1$ is a thiophene group in the in the PLA monomer.

In certain embodiments, the PLA monomer used in the iPLA oligomer can comprise or consist of the compound of Formula I where n=1, 2, 3. Such iPLA oligomers containing "ring expanded" PLA monomers are anticipated to provide for improved selective toxicity towards cancer cells relative to toxicity observed in non-cancer cells. Ring expanded analogs comprising or consisting of the compound of Formula I where n=1, 2, 3 and where any of the corresponding $R_1$-$R_6$ positions shown in Formula I are substituted with the corresponding Formula I R$_1$-R$_6$ groups can be used as PLA monomers in iPLA oligomers. In certain embodiments, such ring expanded analogs can consist of a substituted derivative of the compound of Formula II, where the ortho-carbon of the phenyl ring is substituted with a halogen. In certain embodiments, such ring expanded analogs can consist of a substituted derivative of the compound of Formula II, where the ortho-carbon of the phenyl ring is substituted with a fluorine. In certain embodiments, such ring expanded analogs can consist of a substituted derivative of the compound of Formula II, where the saturated carbon immediately adjacent to the nitrogen of the cycloheptenimide ring (i.e the R$_1$ group in the compound of Formula I) is substituted with a heteroaryl group containing a sulfur heteroatom. In certain embodiments, the saturated carbon immediately adjacent to the nitrogen of the cycloheptenimide ring (i.e the R$_1$ group in the compound of Formula I) is substituted with a 5 membered heteroaryl group having a sulfur heteroatom. In certain embodiments, A is a S(O)$_2$ in the ring expanded analog. In certain embodiments, R$_1$ is a halogen in the ring expanded analog. In certain embodiments, R$_1$ is a sulfur containing heteroaryl group in the ring expanded analog. In certain embodiments, R$_1$ is a sulfur containing pentacyclic heteroaryl group in the ring expanded analog. In certain embodiments, n is 1 in the ring expanded analog.

In certain embodiments, the PLA monomer used in the iPLA oligomer can comprise ring expanded cycloheptenimide analogs. An exemplary ring expanded cycloheptenimide analog can comprise an unsubstituted or substituted derivative of the compound with the formula:

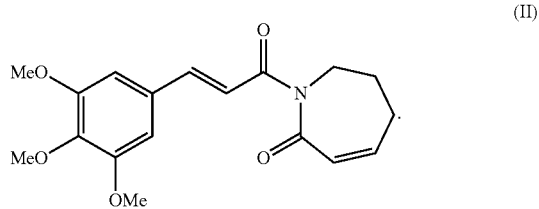 [SMILES: COc1cc(/C=C/C(=O)N2CCCC=CC2=O)cc(OC)c1OC]

(II)

Certain iPLA compounds provided herein comprise unmultimerized PLA monomers. Such iPLA compounds are referred to herein as "iPLA monomers" and can exhibit improved cancer cell toxicity in their monomeric form relative to PL. The iPLA monomers can thus be used in either their monomeric or multimeric forms in methods and compositions provided herein. Also provided herein are pharmaceutically acceptable salts, solvates, and prodrugs of iPLA monomers.

In general, iPLA monomers can in certain embodiments be compounds where an alkynyl, halogen, or aryl group is substituted at the R$_1$ position of compounds of Formula I. Such alkynl groups at the R$_1$ position can also be linked to a variety of substituted or unsubstituted alkyl, cycloakyl, or aryl groups. Suitable substitutions for such alkyl, cycloakyl, or aryl groups include, but are not limited to, hydroxyls and halogens. In certain embodiments, the iPLA monomers can thus comprise compounds of formula I, where A is C(O) or S(O)$_2$, where n=0, 1, 2, or 3; where the ortho-carbon of the phenyl ring is unsubstituted or substituted with a halogen, where R$_1$ is selected from the group consisting of a halogen, C≡C-alkyl, C≡C-cycloalkyl, C≡C-cycloakyl halide, C≡C-aryl, C≡C-aryl halide, and an aryl group, where R$_2$ is selected from the group consisting of hydrogen, alkyl, alkenyl, and an aryl group, where R$_3$ is selected from the group consisting of hydrogen, alkyl, alkenyl, and an aryl group, and where each of R$_4$, R$_5$, and R$_6$ is independently selected from the group consisting of hydrogen, bromine, chlorine, fluorine, keto, hydroxyl, alkyl, alkenyl, alkoxy, aminoalkyl, aminoalkenyl, and an aminoalkoxy group. In certain embodiments, n is 1 in iPLA monomers where an alkynyl group is substituted at the R$_1$ position of compounds of Formula I. In certain embodiments, A is S(O)$_2$ in iPLA monomers where an alkynyl group is substituted at the R$_1$ position of compounds of Formula I. In certain embodiments, n is 1 and A is S(O)$_2$ in iPLA monomers where an alkynyl group is substituted at the R$_1$ position of compounds of Formula I. In certain embodiments, R$_1$ is a halogen in the iPLA monomer. In certain embodiments, R$_1$ is a sulfur containing heteroaryl group in in the iPLA monomer. In certain embodiments, R$_1$ is a thiophene group in the in the iPLA monomer.

In certain embodiments, iPLA monomers can comprise or consist of the compound of Formula I where n=1, 2, 3. Such "ring expanded" iPLA monomers can provide for improved selective toxicity towards cancer cells relative to toxicity observed in non-cancer cells. Improved selectivity (i.e. "therapeutic index") associated with such ring-expanded iPLA monomers can provide for methods of treatment where increased dosages of the iPLA monomer can be provided while minimizing undesirable side effects.

Ring expanded analogs comprising or consisting of the compound of Formula I where n=1, 2, 3 and where any of the corresponding R$_1$-R$_6$ positions shown in Formula I are substituted with the corresponding Formula I R$_1$-R$_6$ groups provided herein can also be used as iPLA monomers. In certain embodiments, such ring expanded analogs can consist of a substituted derivative of the compound of Formula I, where the ortho-carbon of the phenyl ring is substituted with a halogen. In certain embodiments, such ring expanded analogs can consist of a substituted derivative of the compound of Formula I, where the ortho-carbon of the phenyl ring is substituted with a fluorine. In certain embodiments, such ring expanded analogs can consist of a substituted derivative of the compound of Formula I, where the R$_1$ group in the compound of Formula I is substituted with a heteroaryl group containing a sulfur heteroatom. In certain embodiments, the saturated carbon immediately adjacent to the nitrogen of the cycloheptenimide ring (i.e the R$_1$ group in the compound of Formula I) is substituted with a 5 membered heteroaryl group having a sulfur heteroatom. In certain embodiments, A is a S(O)$_2$ in the ring expanded analog of Formula I. In certain embodiments, n is 1 in the ring expanded analog of Formula I. In certain embodiments, R$_1$ is a halogen in the ring expanded analog. In certain embodiments, R$_1$ is a sulfur containing heteroaryl group in the ring expanded analog. In certain embodiments, R$_1$ is a thiophene group in the ring expanded analog.

In certain embodiments, iPLA monomers can comprise or consist of the compound of Formula III where n=1, 2, 3.

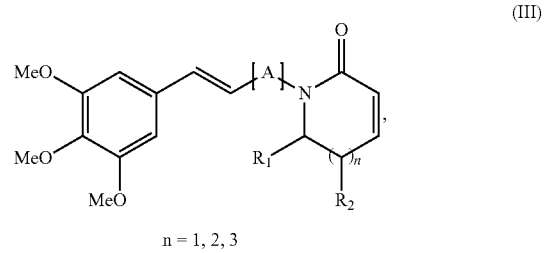

(III)

n = 1, 2, 3 where A is C(O) or S(O)$_2$, R$_1$ is selected from the group consisting of hydrogen, alkyl, alkenyl, and an aryl group, and R$_2$ is selected from the group consisting of hydrogen, alkyl, alkenyl, and an aryl group. In certain embodiments, such ring expanded analog can consist of a substituted derivative of the compound of Formula III, where the ortho-carbon of the phenyl ring is substituted with a halogen. In certain embodiments, such ring expanded analogs can consist of a substituted derivative of the compound of Formula III, where the ortho-carbon of the phenyl ring is substituted with a fluorine. In certain embodiments, such ring expanded analogs can consist of a substituted derivative of the compound of Formula III, where the saturated carbon immediately adjacent to the nitrogen of the cycloheptenimide ring (i.e the R$_1$ group in the compound of Formula I) is substituted with a heteroaryl group containing a sulfur heteroatom. In certain embodiments, the saturated carbon immediately adjacent to the nitrogen of the cycloheptenimide ring (i.e the R$_1$ group in the compound of Formula I) is substituted with a 5 membered heteroaryl group having a sulfur heteroatom. In certain embodiments, A is a S(O)$_2$ in the ring expanded analog of Formula III. In certain embodiments, n is 1 in the ring expanded analog of Formula III. A compound of Formula III where n=1, A is a S(O)$_2$, and R$_1$ is selected from the group consisting of hydrogen, alkyl, alkenyl, and an aryl group, and R$_2$ is selected from the group consisting of hydrogen, alkyl, alkenyl, and an aryl group.

In certain embodiments, the iPLA monomer can comprise ring expanded cycloheptenimide analogs. An exemplary ring expanded cycloheptenimide analog can comprise an unsubstituted or substituted derivative of the compound with the formula:

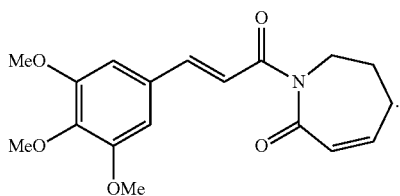

II

In certain embodiments, such ring expanded cycloheptenimide analogs can consist of a substituted derivative of the compound of Formula II, where the ortho-carbon of the phenyl ring is substituted with a halogen. In certain embodiments, such cycloheptenimide analogs can consist of a substituted derivative of the compound of Formula II, where the ortho-carbon of the phenyl ring is substituted with a fluorine.

Methods for Making iPLA Compounds

Methods for synthesizing both iPLA oligomers and iPLA monomers of the invention are also provided herein.

In certain embodiments, iPLA monomers can be obtained by a convergent synthetic scheme as follows:

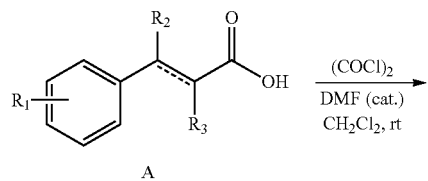

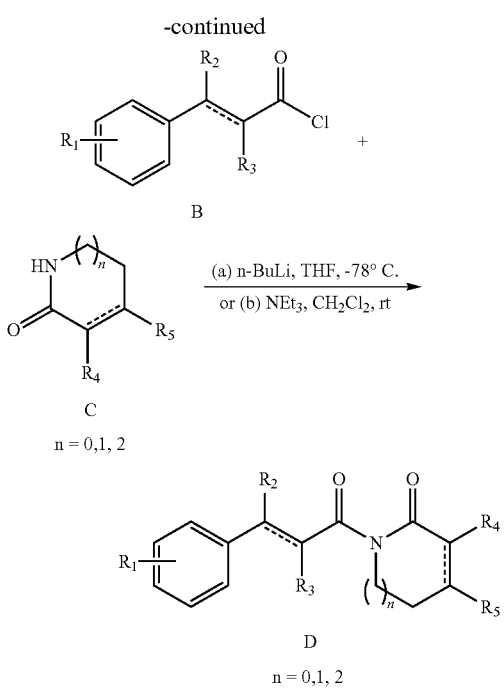

where constituent rings of the iPLA monomer comprising desired R groups or comprising desired R group precursors are conjoined. One skilled in the art will also recognize that this scheme could also be used for "C" compounds where n=3 to obtain compounds of Formula (I) where n=3.

A two-step procedure for obtaining iPLA monomers where an R$_1$ of a compound of Formula I comprising an alkynyl group is illustrated by the following exemplary reactions:

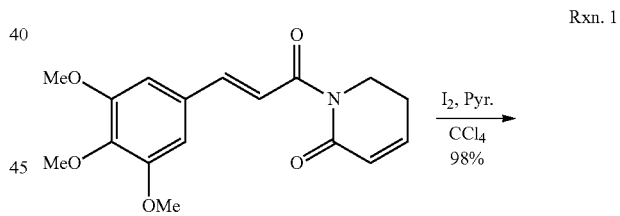

Rxn. 1

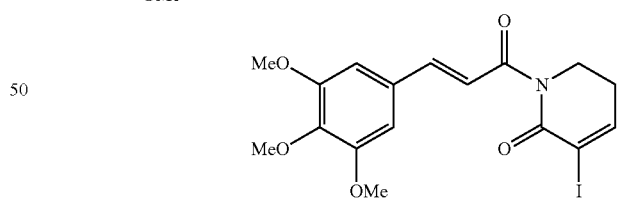

Rxn. 2

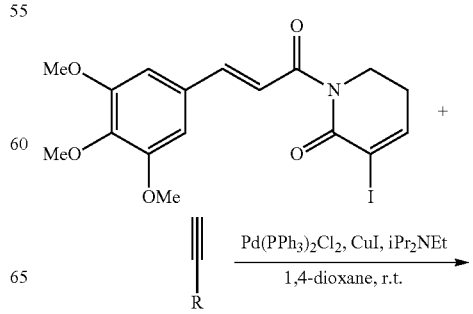

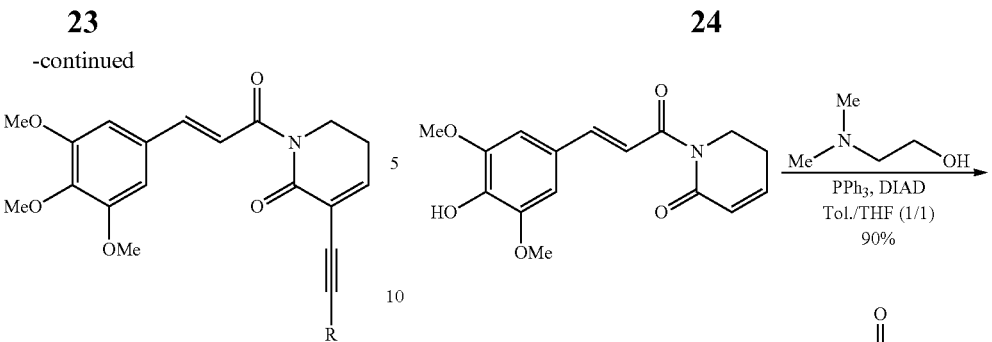

Although the precursor compound of Formula I used in these reactions contains an unsubstituted ortho carbon on the phenyl ring and a methoxy group at $R_4$, $R_5$, and $R_6$, other precursor compounds containing any of an unsubstituted or substituted ortho carbon on the phenyl ring and/or a group other than hydrogen at any one of $R_2$ or $R_3$ and/or a group other than methoxy group at any one or more of $R_4$, $R_5$, and/or $R_6$ can be used to obtain a desired iPLA monomer with an alkynyl group at $R_1$.

To synthesize iPLA oligomers, it is typically useful to first synthesize a PLA or iPLA precursor monomer containing a desired group at any one of $R_4$, $R_5$, and/or $R_6$. A procedure for obtaining a useful iPLA precursor is illustrated by the following exemplary reaction:

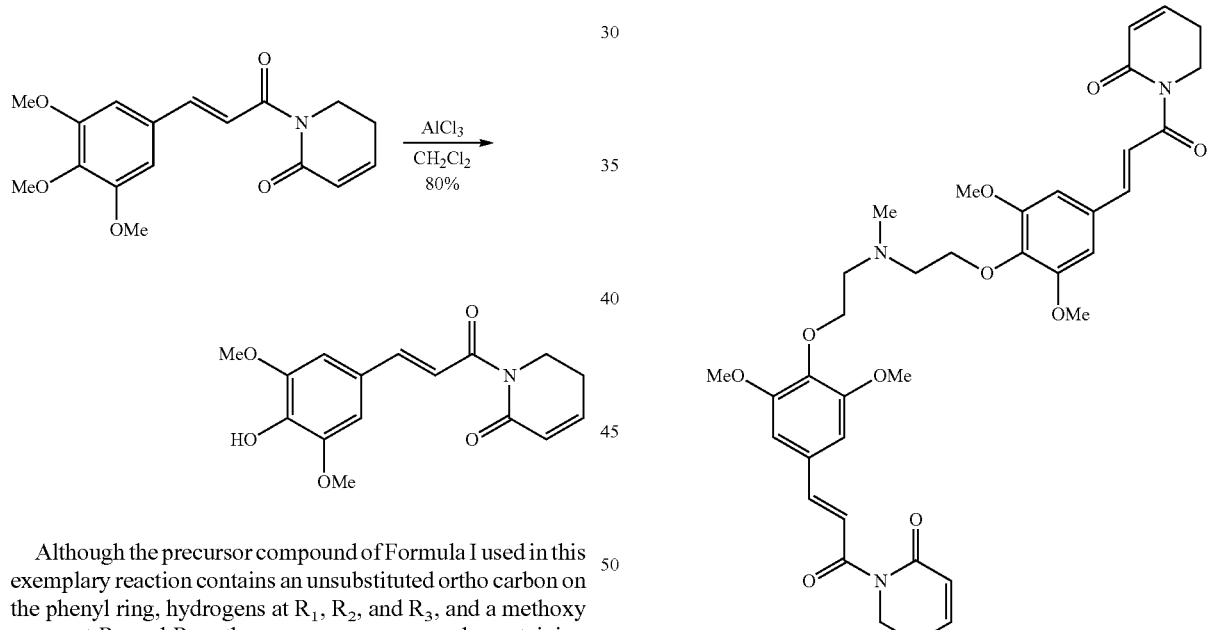

Although the precursor compound of Formula I used in this exemplary reaction contains an unsubstituted ortho carbon on the phenyl ring, hydrogens at $R_1$, $R_2$, and $R_3$, and a methoxy group at $R_4$ and $R_6$, other precursor compounds containing any of an unsubstituted or substituted ortho carbon on the phenyl ring and/or groups other than hydrogen at any one or more of $R_1$, $R_2$, and $R_3$, and/or a group other than methoxy group at any one or more of $R_4$ and/or $R_6$, can be used to obtain a desired iPLA monomer with a hydroxy group at $R_5$.

An iPLA monomer precursor where a hydroxyl precursor group is of $R_4$, $R_5$, and/or $R_6$ can also be obtained by the convergent synthetic techniques described herein. Such iPLA monomer precursors can be used to obtain iPLA oligomers where PL, PLA and/or iPLA monomers are joined at any one of C11, C12, or C13.

Synthesis of useful iPLA oligomers with a PLA or iPLA precursor is illustrated by the following exemplary reactions:

-continued

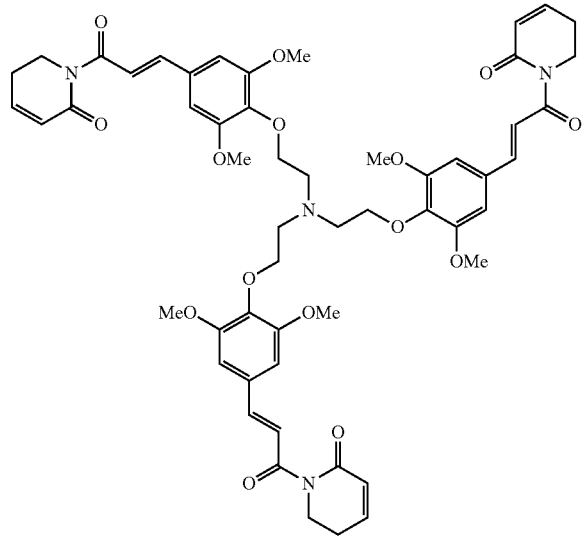

Again, such reactions can be performed with other precursor compounds containing any of an unsubstituted or substituted ortho carbon on the phenyl ring and/or groups other than hydrogen at any one or more of $R_1$, $R_2$, and $R_3$, and/or a group other than methoxy group at any one or more of $R_4$ and/or $R_6$, to obtain a desired iPLA oligomer.

The synthesis of additional PLA and iPLA monomer precursors useful for synthesis of iPLA oligomers is also shown in the following exemplary reactions It is anticipated that PLA and iPLA monomeric precursors comprising ethoxy chains with terminal carboxyl groups can be multimerized with other PLA and iPLA monomeric precursors containing suitable reactive groups. Again, such reactions can be performed with other precursor compounds containing any of an unsubstituted or substituted ortho carbon on the phenyl ring and/or groups other than hydrogen at any one or more of $R_1$, $R_2$, and $R_3$, and/or a group other than methoxy group at any one or more of $R_4$ and/or $R_6$, to obtain a desired iPLA monomer precursor for synthesis of a desired iPLA oligomer.

It is further contemplated that other synthetic methods for obtaining certain iPLA oligomers and iPLA monomers described in the Examples provided herein can be adapted by those skilled in the art to provide for the synthesis of other iPLA oligomers and iPLA monomers disclosed herein.

Other Compounds of the Invention and Methods of Making the Same

Also provided herein are various compounds of the formula:

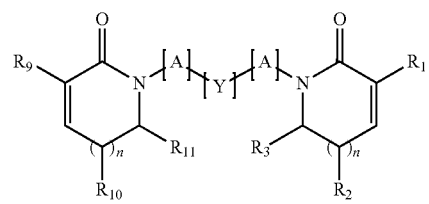

wherein A is C(O) or S(O)$_2$;
wherein B is an alkenyl or alkynyl;
wherein Y is alkyl, alkenyl, alkynyl, aryl, or a combination thereof,

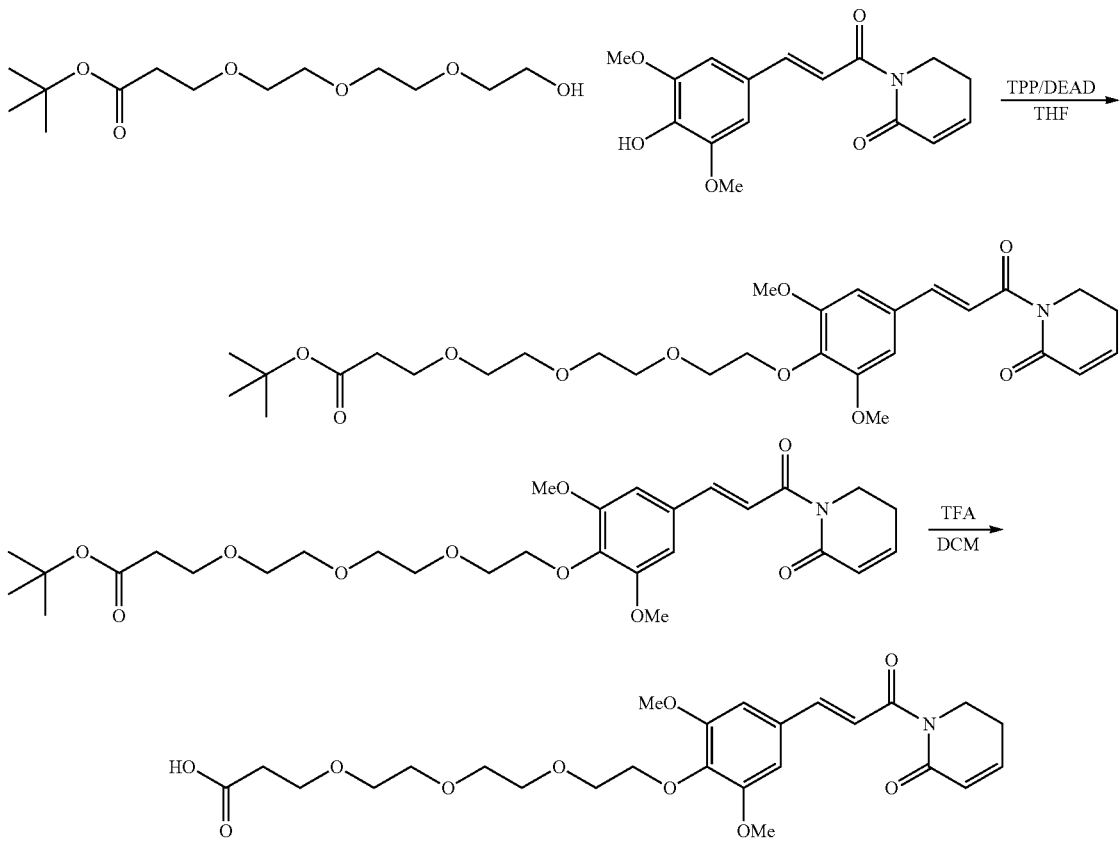

wherein n=0, 1, 2, or 3;

wherein $R_1$ is selected from the group consisting of a halogen, hydrogen, C≡C-alkyl, C≡C-cycloalkyl, C≡C-cycloakyl halide, C≡C-aryl, a C≡C-aryl halide, and an aryl group;

wherein $R_2$ is selected from the group consisting of hydrogen, alkyl, alkenyl, and an aryl group;

wherein $R_3$ is selected from the group consisting of hydrogen, alkyl, alkenyl, and an aryl group;

wherein $R_9$ is selected from the group consisting of a halogen, hydrogen, C≡C-alkyl, C≡C-cycloalkyl, C≡C-cycloakyl halide, C≡C-aryl, a C≡C-aryl halide, and an aryl group;

wherein $R_{10}$ is selected from the group consisting of hydrogen, alkyl, alkenyl, and an aryl group; and, wherein $R_{11}$ is selected from the group consisting of hydrogen, alkyl, alkenyl, and an aryl group.

An exemplary reaction that can provide for such compounds is shown below:

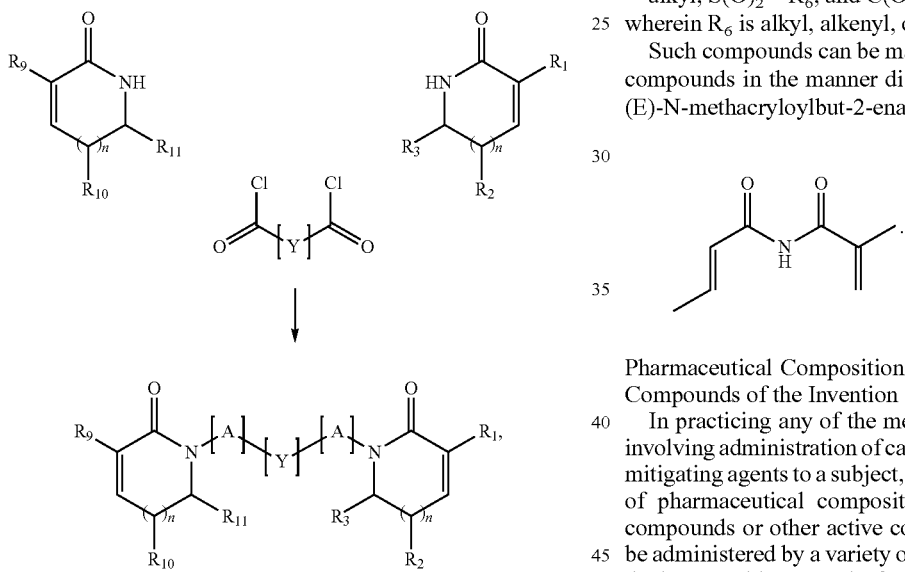

where A is C(O) and Y is alkyl, alkenyl, alkynyl, aryl, or a combination thereof.

To accomplish such reactions, to the solution of the heterocyclic reactants in THF at about −78° C. is added solution of n-BuLi in hexanes and stirred for about 15 minutes. To this solution is added the compound

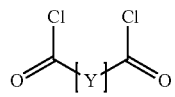

and the reaction is stirred at about −78° C. for about 3 hours. The reaction mixture is diluted with ethyl acetate, quenched with aqueous ammonium chloride, extracted with EtOAc, washed with brine, dried with anhydrous sodium sulfate and purified by column chromatography using hexanes-ethyl acetate gradient (0 to 80% EtOAc), to yield the product.

Also provided herein are compounds of the structure:

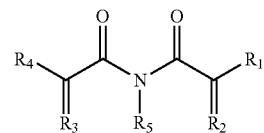

wherein $R_1$ is either: (i) halogen, C≡C-alkyl, C≡C-cycloalkyl, C≡C-cycloakyl halide, C≡C-aryl, a C≡C-aryl halide, or an aryl group; or, (ii) an alkyl, thioalkyl, aminoalkyl, or alkenyl group that is optionally fused to $R_2$ when $R_2$ is alkyl and wherein the ring formed by the fusion consists of 5, 6, 7, or 8 members;

wherein $R_2$ is alkyl;

wherein $R_3$ is alkyl;

wherein $R_4$ is selected from the group consisting of hydrogen, halogen, C≡C-alkyl, C≡C-cycloalkyl, C≡C-cycloakyl halide, C≡C-aryl, a C≡C-aryl halide, and an aryl group; and, wherein $R_5$ is selected from the group consisting of hydrogen, alkyl, $S(O)_2$—$R_6$, and $C(O)$—$R_6$, wherein $R_6$ is alkyl, alkenyl, or alkynyl.

Such compounds can be made by using suitable precursor compounds in the manner disclosed herein for synthesis of (E)-N-methacryloylbut-2-enamide:

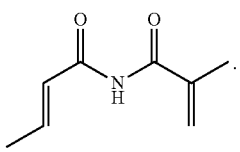

Pharmaceutical Compositions Comprising iPLA and Other Compounds of the Invention In practicing any of the methods of the present invention involving administration of cancer inhibitory, preventative, or mitigating agents to a subject, it is contemplated that a variety of pharmaceutical compositions comprising active iPLA compounds or other active compounds provided herein can be administered by a variety of techniques. Such pharmaceutical compositions may be formulated in various ways known in the art for administration purposes. To prepare pharmaceutical compositions, a therapeutically effective amount of an active iPLA compound, or a salt, solvate, or prodrug thereof, is combined with one or more pharmaceutically acceptable carriers and/or delivery vehicles. The active ingredient, i.e., iPLA compound, in such compositions typically comprises from about 0.1 percent by weight to about 99.9 percent by weight of the composition, and often comprises from about 5 percent by weight to about 95 percent by weight. Numerous pharmaceutically acceptable carriers and delivery vehicles exist that are readily accessible and well known in the art. Non-limiting illustrative examples of pharmaceutically acceptable carriers and delivery vehicles include aluminum stearate, lecithin, serum proteins such as human serum albumin, buffer substances such as the various phosphates, glycine, sorbic acid, potassium sorbate, partial glyceride mixtures of saturated vegetable fatty acids, water, salts or electrolytes such as protamine sulfate, disodium hydrogen phosphate, potassium hydrogen phosphate, sodium chloride, and zinc salts, colloidal silica, magnesium trisilicate, polyvinyl pyrrolidone, cellulose-based substances, polyethylene glycol, sodium carboxymethylcellulose, polyacrylates, waxes, polyethylene, polyoxypropylene-block polymers, polyethylene glycol and wool fat, and the like.

The pharmaceutical compositions described herein may further be prepared in a form suitable for administration orally, percutaneously, by parenteral injection (including subcutaneous, intramuscular, intravenous and intradermal), topically, intranasally, by inhalation, or for application to a medical device, such as an implant, catheter, or other device. Oral administration or administration by injection are generally preferred. In preparing compositions that permit oral delivery of liquid preparations such as suspensions, syrups, elixirs and solutions, any of the pharmaceutically acceptable carriers known in the art may be used such as but not limited to, water, glycols, oils, alcohols and the like. When solid pharmaceutically acceptable carriers are desired, such as those that permit oral or rectal administration; starches, sugars, kaolin, lubricants, binders, cellulose and its derivatives, and disintegrating agents and any other pharmaceutically acceptable carriers known in the art may be used to prepare, for example, powders, pills, capsules and tablets. For pharmaceutically acceptable compositions and preparations that permit parenteral administration, the pharmaceutically acceptable carriers often comprise sterile water, which may be supplemented with various solutes to, for example, increase solubility. Injectable solutions may be prepared in which the pharmaceutically acceptable carrier comprises saline solution, glucose solution, or a mixture thereof, which may include certain well-known anti-oxidants, buffers, bacteriostats, and other solutes that render the formulation isotonic with the blood of the intended patient. The preparation of pharmaceutically acceptable formulations is described in. e.g., *Remington: The Science and Practice of Pharmacy*, 20$^{th}$ Ed., ed. A. Gennaro, Lippincott Williams & Wilkins, 2000.

Active iPLA compounds provided herein in the compositions may be used to treat cancer in combination with one another, or with at least one additional biologically active agent. Non-limiting illustrative examples of biologically active compounds or agents that can be combined with iPLA compounds in compositions provided herein include, but are not limited to, additional chemotherapeutic agents. Such additional chemotherapeutic agents include, but are not limited to, alkylating agents (including but not limited to cyclophosphamide, mechlorethamine, chlorambucil, melphalan), anthracyclines (including, but are not limited, to daunorubicin, doxorubicin, epirubicin, idarubicin mitoxantrone, valrubicin), cytoskeletal disruptors (including but are not limited to taxanes such as paclitaxel and docetaxel), epothilones, histone deacetylase inhibitors (including but not limited to vorinostat, romidepsin), topoisomerase ii inhibitors (including but not limited to etoposide, teniposide, tafluposide), kinase inhibitors (including but are not limited to bortezomib, erlotinib, gefitinib, imatinib, vismodegib), monoclonal antibodies (including but not limited to bevacizumab, cetuximab, ipilimumab, ofatumumab, ocrelizumab, panitumab, rituximab), nucleotide analogs and precursor analogs (including but are not limited to azacytidine, azathioprine, capecitabine, cytarabine, doxifluridine, fluorouracil, gemcitabine, hydroxyurea, mercaptopurine, methotrexate, and thioguanine), peptide antibiotics (including but not limited to bleomycin, actinomycin), platinum-based agents (including but not limited to carboplatin, cisplatin, oxaliplatin), retinoids (tretinoin, alitretinoin, bexarotene) and vinca alkaloids and derivatives (including but not limited to vinblastine, vincristine, vindesine, and vinorelbine). In certain embodiments, the additional chemotherapeutic agent can comprise another compound, antibody, or protein that potentiates and/or relieves the side effects of anti-cancer drugs. In certain embodiments, such additional chemotherapeutic agent thus include, but are not limited to, anti-angiogenesis, anti-nausea agents, and the like. In certain embodiments, such additional chemotherapeutic agent thus include, but are not limited to agents such as erythropoietin and the like.

It is further contemplated that the pharmaceutical compositions provided herein can include agents that promote uptake of iPLA compounds by target cells or regions of interest in a subject or a patient. Such target cells and regions of interest include, but are not limited to, cancer cells, tumors, and their metastases. Agents that promote uptake of iPLA compounds, include but are not limited to, a variety of organic and/or amphiphilic compounds. In certain embodiments, the agent can comprise DMSO, PEG, phospholipids, fatty acids, and combinations thereof. In certain embodiments, the composition can comprise liposomes or micelles that contain the iPLA compound and facilitate uptake by target cells or regions of interest in a subject or a patient. In certain embodiments, the composition can comprise nanoparticles that facilitate uptake of the iPLA compound by target cells or regions of interest in a subject or a patient. Conjugates of iPLA compounds to any of the aforementioned agents are also provided herein.

Methods of Treating Cancer

Certain aspects of the current disclosure provide methods for treating cancer. As used herein, treatment of cancer is understood to embrace methods whereby establishment, progression, recurrence, or spread of at least one of a malignant growth, tumor, solid tumor, or its metastases are inhibited, delayed, arrested, or otherwise controlled in a subject. Such subjects can be mammals susceptible to cancer that include, but are not limited to, humans, companion animals (dogs, cats, and the like), and livestock (horses, cows, sheep, pigs, and the like).

Cancers that can be treated by the iPLA compounds, compositions, and methods provided herein include, but are not limited to, cancers of major organ systems and their metastases. Treatment of cancers including, but not limited to, cancers of the brain, breast, thyroid, blood, skin, lung, liver, pancreas, colon, prostate, endometrium, cervix, ovaries, larynx, oropharynx, esophagus, bladder, and their metastases are thus provided herein.

Administration of a combination of one or more of the iPLA compounds provided herein and one or more additional chemotherapeutic agents is also contemplated. Administration of a combination can be sequential, wherein treatment with one agent is done before treatment with a second agent. Alternatively, administration can be concurrent where treatment with two or more agents occurs at the same time. Sequential administration can be done within a reasonable time after the completion of a first therapy before beginning a second therapy. Administration of multiple agents concurrently can be in the same daily dose or in separate doses.

In certain embodiments, the additional chemotherapeutic agent can comprise another compound, antibody, or protein that is an anti-cancer agent. Such anti-cancer agents include, but are not limited to, alkylating agents (including, but not limited to, cyclophosphamide, mechlorethamine, chlorambucil, melphalan), anthracyclines (including, but are not limited to, daunorubicin, doxorubicin, epirubicin, idarubicin, mitoxantrone, valrubicin), cytoskeletal disruptors (including, but are not limited to, taxanes such as paclitaxel and docetaxel), epothilones, histone deacetylase inhibitors (including, but not limited to, vorinostat, romidepsin), topoisomerase II inhibitors (including, but not limited to, etoposide, teniposide, tafluposide), kinase Inhibitors (including, but are not limited to, bortezomib, erlotinib, gefitinib, imatinib, vismodegib), monoclonal antibodies (including but not limited to bevacizumab, cetuximab, ipilimumab, ofatumumab, ocrelizumab, panitumab, rituximab), nucleotide analogs and precursor analogs (including, but are not limited to, azacytidine, azathioprine, capecitabine, cytarabine, doxifluridine, fluorouracil, gemcitabine, hydroxyurea, mercaptopurine, methotrexate, and thioguanine), peptide antibiotics (including, but not limited to, bleomycin, actinomycin), platinum-based agents (including, but not limited to, carboplatin, cisplatin, oxaliplatin), retinoids (tretinoin, alitretinoin, bexarotene) and vinca alkaloids and derivatives (including, but not limited to, vinblastine, vincristine, vindesine, and vinorelbine).

In certain embodiments, the additional chemotherapeutic agent can comprise another compound, antibody, or protein that potentiates and/or relieves the side effects of anti-cancer drugs. In certain embodiments, such additional chemotherapeutic agent thus includes, but are not limited to, anti-angiogenesis, anti-nausea agents, and the like. In certain embodiments, such additional chemotherapeutic agents include, but are not limited to, agents such as erythropoietin and the like.

The pharmaceutical compositions of the present invention may be formulated into a variety of dosage forms depending upon the particular composition contemplated. Likewise, a variety of modes of administration are possible depending upon the particular composition and dosage form. In certain embodiments, administration is by intravenous injection. In certain embodiments, administration is by delivery to a location of interest. Locations of interest include, but are not limited to, tumors and their metastases or locations of one or more cancer cells. Delivery to a location of interest can be effected by any method that provides for directed introduction of the iPLA compound or a composition comprising the same to a site in a subject or patient and include, but are not limited to, direct injection, delivery by a cathether, delivery by a stereotactically guided instrument, implantation of a drug delivery device, implantation of a device or substance that provides for release of the iPLA compound, and the like. Impregnation of devices and or substances with iPLA compounds or compositions to provide for release at a location of interest is thus provided herein. In certain embodiments, a location of interest can be a site from which a tumor, cancer cells, or other cancerous growth have been resected or otherwise ablated or removed. In such cases, any of the aforementioned delivery methods, devices, or substances can be used to provide the iPLA compound or composition at the location of interest to prevent or delay recurrence. Exemplary substances that are useful for localized delivery of anti-cancer agents include, but are not limited to, various poly(ester-carbonate)-collagen and/or poly(carbonate ester)s comprising 6-hydroxyhexanoic acid monomers that are disclosed by Wolinsky et al. J Control Release. 2010 Jun. 15; 144(3):280-7; Liu et al. Ann Surg Oncol. 2010 April; 17(4):1203-13; and Wolinsky et al., *Macromolecules,* 2007, 40, 7065-7068. Therapeutically effective amounts of an active compound, its salts, prodrugs, solvates, a pharmaceutical composition thereof, or a combination therapy will depend on absorption, distribution, metabolism, and excretion rates of the components of the therapy. Dosage values will also vary with the severity of the condition to be alleviated. It is further understood that for any particular subject, specific dosage regimens and schedules may be adjusted over time according to the individual's need and the professional judgment of the person administering or supervising the administration. The therapeutically effective amount of the inhibitory compound administered will be determined empirically, and will also be based on considerations such as the particular inhibitor or combination used, the age, sex, diet, body weight, and general health status of the individual, the treatment effect desired, administration route, the severity and course of the disease, and the like. It is expected that in certain embodiments, the typical therapeutically effective dose range will be from about 0.1 mg/kg to about 50 mg/kg per dose, which can be given one to several times per day, or alternatively as a continuous infusion. Such administration can be used as a chronic or acute therapy. In still other embodiments, a therapeutically effective dose can range from about 0.1, 0.2, 0.3, 0.4, or 0.5 mg/kg to any one of about 1.0, 2.0, 2.3, 2, 4, 2.5, 3.0, 5.0, 10, 15, 20, 25, 30, 40, 50 or 100 mg/kg. In still other embodiments, a therapeutically effective dose can range from about 0.1, 0.2, 0.3, 0.4, 0.5, 2.0, 2.3, 2, 4, or 2.5 mg/kg to any one of about 3.0, 5.0, 10, 15, 20, 25, 30, 40, 50 or 100 mg/kg. In still other embodiments, a therapeutically effective dose can range from about 0.2 mg/kg to about 2.4 mg/kg or about 0.2 mg/kg to about 5 mg/kg. In still other embodiments, a therapeutically effective dose can range from about 2.5 mg/kg to about 50 mg/kg or about 100 mg/kg. When the compositions comprise a combination of an iPLA compound and one or more additional biologically active agent(s), both the compound and the additional agent(s) are usually present at dosage levels of between about 10 to 100%, and more preferably between about 10 and 80% of the dosage normally administered in a monotherapy regimen.

In certain embodiments, therapeutically effective amounts of compounds and/or compositions provided herein can be determined and/or adjusted by any of a variety of biological markers of cancer. In certain embodiments, the therapeutically effective amounts can be determined and/or adjusted by monitoring the levels of certain metabolites, proteins and/or nucleic acids in a subject. In certain embodiments, the DNA methylation status of the subject or patient can serve as a useful cancer biomarker to determine and/or adjust therapeutically effective amounts of compounds and/or compositions provided herein.

Kit for Treating Cancer

In certain embodiments contemplated herein, kits comprising at least one pharmaceutical composition of an iPLA compound or combination of iPLA compounds and one or more pharmaceutically acceptable carriers, as well as one or more containers are provided.

The composition(s) of the kit that comprise an iPLA compound may be provided in any form. Composition forms provided in the kit can include, but are not limited to, tablets, capsules, pills, liquid solutions or dried powders. In certain embodiments where the composition(s) are provided in a liquid solution, such liquid solution can be for example an aqueous solution. When the composition(s) provided are a dry powder, the powder can be reconstituted by the addition of a suitable solvent, which can also be provided.

The container will generally include a vial into which the pharmaceutical composition may be placed, and preferably suitably aliquotted. The kits of the present invention will also typically include a means for containing the composition(s) in a container in close confinement for commercial sale. Such containers may include injection or blow-molded plastic containers into which the desired vials are retained.

The kit can also comprise a device or a component of a device for performing the methods provided herein. Devices, or components of devices, include, but are not limited to, syringes and other implements useful for delivery of the composition to the blood stream or a specific organ, e.g. the liver. In certain embodiments, compositions comprising an iPLA compound can be provided in unit dose form. In addition or in the alternative, the kits can provide an instructional material which describes performance of one or more methods for treatment of cancer that are provided herein, or a notice in the form prescribed by a governmental agency regulating the manufacture, use or sale of pharmaceuticals or biological products, which notice reflects approval by the agency of manufacture, use or sale for human administration. Instructions can also be provided as a fixed, fully detachable, or partially detachable label that is associated with one or more containers in the kit. The instructions associated with the kit can provide directions for preparing the pharmaceutical composition for administration and/or instructions for administration of the iPLA compound containing pharmaceutical composition to a subject in need thereof.

EXAMPLES

The following disclosed embodiments are merely representative of the invention, which may be embodied in various forms. It is anticipated that methods disclosed herein for the synthesis of certain compounds can be adapted to provide for the synthesis of other compounds disclosed or claimed herein. Thus, specific structural and functional details disclosed herein are not to be interpreted as limiting.

Example 1

Synthesis of Exemplary iPLA Compounds

Synthesis of piperlongumine analogs. Piperlongumine analogs were in general synthesized by a convergent strategy that entailed coupling commercially available or synthetically accessible lactams and carboxylic acid chlorides (FIG. 1B). Additional analogs bearing substituents at C2 were generated by selective iodination of PL at C2 and palladium catalyzed cross-coupling (for complete synthesis details, see FIG. S1).

General Methods:

Dry solvents (anhydrous THF, $CH_2C_{12}$ and toluene etc.) were purchased from Sigma-Aldrich. Unless otherwise stated, all reagents were obtained from commercial sources and used without further purification. Infrared spectra were recorded on a Nicolet Avatar 370 DTGS FTIR. 1H NMR spectra were recorded on Varian Unity/Inova 500 (500 MHz), or Bruker Ultrashield 300 (300 MHz) spectrometers. 1H NMR data are reported as follows: chemical shift in parts per million relative to $CHCl_3$ (7.26 ppm), multiplicity (s, singlet; d, doublet; t, triplet; q, quartet; m, multiplet; br, broadened), coupling constant (Hz), and integration. 13C NMR spectra were recorded on Varian Unity/Inova 500 (125 MHz) or Bruker Ultrashield 300 (75 MHz) spectrometers. $^{13}C$ NMR chemical shifts are reported in parts per million relative to solvent. All $^{13}C$ NMR spectra were determined with broadband decoupling. High-resolution mass spectra (HRMS) were obtained through the Broad Institute Chemical Biology Analytical Chemistry facility. All reactions were magnetically stirred and monitored by thin-layer chromatography (TLC) using E. Merck silica gel 60 F254 precoated plates (0.25 mm) Flash chromatography was performed either on EM Science silica gel 60 (230-400 mesh) or using a Combi-Flash companion system (Teledyne ISCO, Inc.) with pre-packed FLASH silica gel columns (Biotage, Inc.).

Experimental Procedures and Spectra Data

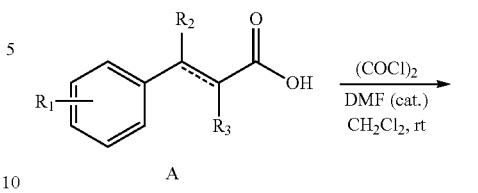

A

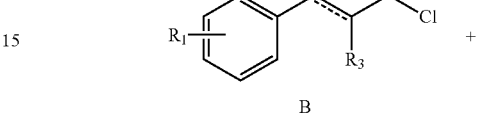

B

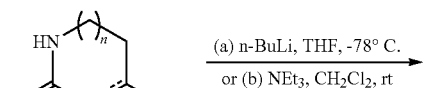

C n = 0, 1, 2

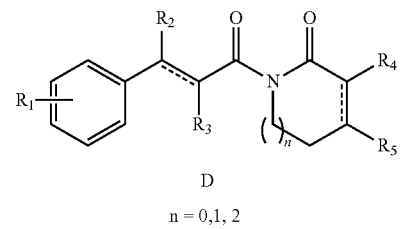

D n = 0, 1, 2

Synthesis of non-commercially available acid chloride: To a solution of acids (A, 0.1-0.2 M) in dry $CH_2C_{12}$ was added oxalyl chloride (5.0 equiv., 2.0 M in $CH_2Cl_2$) and catalytic amount of DMF (0.01 equiv.). The reaction mixture was stirred at room temperature for 2-5 hours before the solvent was removed. The residue was dried under high vacuum, then used to the next step without any further purification.

Amide Formation:

Method a: To a solution of compound C (0.1 M, 1.2 equiv.) in dry THF in a flame-dried Schlenk flask was added 1.6 M solution of n-BuLi (1.3 equiv.) dropwise at −78° C. under nitrogen atmosphere. After 15 min, a solution of the corresponding acid chloride B (1.0 equiv.) in dry THF was added dropwise. After 10 min, the reaction was gradually warmed up to room temperature and the solvent was evaporated under vacuum. The residue was purified by flash chromatography to provide the desired amide D.

Method b: To a solution of acid chloride B (1.0 equiv., 0.1 M) in $CH_2Cl_2$ was added triethylamine (TEA, 3.0 equiv.) and compound C (1.2 equiv.). The reaction mixture was stirred at room temperature for overnight before it was quenched with saturated aqueous NH4Cl, and extracted with $CH_2Cl_2$ (3 times). The combined organic phases were washed with brine and dried over $MgSO_4$. After filtration and concentration, the residue was purified by flash chromatography provide the desired amide D.

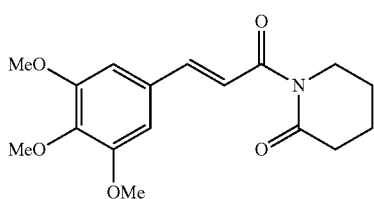 [SMILES: COc1cc(/C=C/C(=O)N2CCCCC2=O)cc(OC)c1OC]

1-[(2E)-3-(3,4,5-trimethoxyphenyl)prop-2-enoyl]piperidin-2-one

Method a; Yield: 95%; $^1$H NMR (300 MHz, CDCl$_3$) δ 7.64 (d, J=15.6 Hz, 1H), 7.36 (d, J=15.5 Hz, 1H), 6.78 (s, 2H), 3.88 (s, 6H), 3.87 (s, 3H), 3.80 (m, 2H), 2.60 (m, 2H), 1.88 (m, 4H); $^{13}$C NMR (75 MHz, CDCl$_3$) δ 173.9, 169.5, 153.4, 143.5, 140.2, 130.7, 121.3, 105.5, 60.9, 56.2, 44.6, 34.9, 22.6, 20.6; IR (thin film, cm$^{-1}$) 2941, 2839, 1671, 1614, 1579, 1503, 1454, 1416, 1348, 1386, 1315, 1267, 1242, 1196, 1152, 1121, 1174, 1002, 969, 915, 888, 825, 730, 775, 700, 675, 595, 527; m/z found: 320.56 [M+H$^+$]; HRMS (FAB) calcd for C$_{17}$H$_{21}$NO$_5$: 319.1420; found 319.1419.

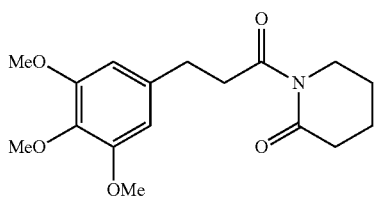 [SMILES: COc1cc(CCC(=O)N2CCCCC2=O)cc(OC)c1OC]

1-(3-(3,4,5-trimethoxyphenyl)propanoyl)piperidin-2-one

Method a; Yield: 64%; $^1$H NMR (300 MHz, CDCl$_3$) δ 6.44 (s, 2H), 3.83 (s, 6H), 3.80 (s, 3H), 3.70 (m, 2H), 3.21 (t, J=6.0 Hz, 2H), 2.89 (t, J=6.0 Hz, 2H), 2.51 (m, 2H), 1.80 (m, 4H); $^{13}$C NMR (75 MHz, CDCl$_3$) δ 176.4, 173.7, 153.3, 137.3, 136.4, 105.6, 61.1, 56.3, 44.3, 41.6, 35.2, 31.8, 22.7, 20.5; IR (thin film, cm$^{-1}$) 2939, 1688, 1588, 1508, 1457, 1421, 1365, 1343, 1291, 1238, 1194, 1153, 1125, 1005, 827, 581; m/z found: 323.31 [M+H$^+$]; HRMS (FAB) calcd For C$_{17}$H$_{23}$NO$_5$: 321.1576; found 321.1568.

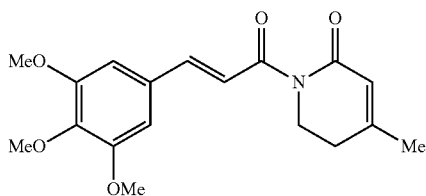 [SMILES: COc1cc(/C=C/C(=O)N2CCC(C)=CC2=O)cc(OC)c1OC]

4-methyl-1-[(2E)-3-(3,4,5-trimethoxyphenyl)prop-2-enoyl]-5,6-dihydropyridin-2(1H)-one Method a; Yield: 52%; $^1$H NMR (300 MHz, CDCl$_3$) δ 7.66 (d, J=15.6 Hz, 1H), 7.44 (d, J=15.6 Hz, 1H), 6.80 (s, 2H), 5.84 (s, 1H), 4.02 (t, J=6.3 Hz, 2H), 3.89 (s, 6H), 3.87 (s, 3H), 2.40 (t, J=6.3 Hz, 2H), 2.03 (s, 3H); $^{13}$C NMR (75 MHz, CDCl$_3$) δ 168.7, 166.0, 157.7, 153.3, 143.4, 139.9, 130.7, 121.3, 121.2, 105.5, 60.9, 56.1, 41.5, 29.9, 22.9; IR (thin film, cm$^{-1}$) 2939, 1679, 1644, 1580, 1613, 1504, 1464, 1386, 1417, 1352, 1277, 1241, 1318, 1214, 1123, 1182, 1153, 1068, 1105, 1002, 1049, 1019, 971, 913, 862, 778, 824, 791, 643; m/z found: 332.07 [M+H$^+$]; HRMS (FAB) calcd for C$_{18}$H$_{21}$NO$_5$: 331.1420; found 331.1420.

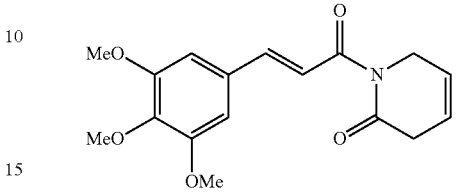

1-[(2E)-3-(3,4,5-trimethoxyphenyl)prop-2-enoyl]-3,6-dihydropyridin-2(1H)-one Method b; Yield: 42%; $^1$H NMR (300 MHz, CDCl$_3$) δ 7.60 (d, J=15.6 Hz, 1H), 7.42 (d, J=15.3 Hz, 1H), 6.79 (s, 2H), 5.88 (m, 1H), 5.83 (m, 1H), 4.36 (m, 2H), 3.89 (s, 6H), 3.87 (s, 3H), 3.19 (m, 2H); 13C NMR (75 MHz, CDCl$_3$) δ 171.0, 169.1, 153.4, 144.0, 136.5, 130.6, 122.1, 121.4, 121.0, 105.6, 61.0, 56.2, 45.8, 35.1; IR (thin film, cm$^{-1}$) 2939, 2839, 1687, 1580, 1613, 1504, 1418, 1383, 1462, 1397, 1349, 1316, 1272, 1244, 1154, 1183, 1124, 1003, 944, 825, 676, 589; m/z found: 317.64 [M+H$^+$]; HRMS (FAB) calcd for C$_{17}$H$_{19}$NO$_5$: 317.1263; found 317.1261.

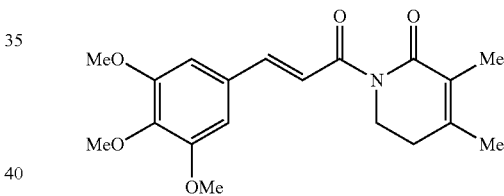

3,4-dimethyl-1-[(2E)-3-(3,4,5-trimethoxyphenyl)prop-2-enoyl]-5,6-dihydropyridin-2(1H)-one Method a; Yield: 46%; $^1$H NMR (300 MHz, CDCl$_3$) δ 7.65 (d, J=15.6 Hz, 1H), 7.42 (d, J=15.6 Hz, 1H), 6.80 (s, 2H), 3.95 (t, J=6.3 Hz, 2H), 3.89 (s, 6H), 3.87 (s, 3H), 2.41 (t, J=6.3 Hz, 2H), 1.99 (s, 3H), 1.91 (s, 3H); $^{13}$C NMR (75 MHz, CDCl$_3$) δ 169.1, 167.0, 153.3, 150.0, 143.0, 139.9, 130.8, 125.8, 121.4, 105.5, 60.8, 56.1, 41.0, 31.1, 20.6, 12.2; IR (thin film, cm$^{-1}$) 2936, 2838, 1666, 1615, 1579, 1503, 1453, 1417, 1390, 1353, 1316, 1279, 1208, 1256, 1175, 1153, 1067, 1122, 1096, 1002, 981, 895, 824, 730, 782, 758, 701, 671, 619, 593; m/z found: 345.92 [M$^+$]; HRMS (FAB) calcd for C$_{19}$H$_{23}$NO$_5$: 345.1576; found 345.1574.

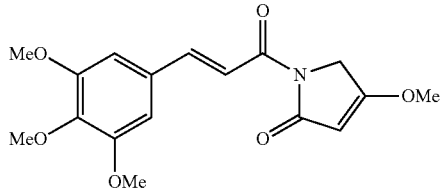 [SMILES: COC1=CC(=O)N(C(=O)/C=C/c2cc(OC)c(OC)c(OC)c2)C1]

4-methoxy-1-[(2E)-3-(3,4,5-trimethoxyphenyl)prop-2-enoyl]-1,5-dihydro-2H-pyrrol-2-one Method a; Yield: 32%; $^1$H NMR (300 MHz, CDCl$_3$) δ 7.94 (d, J=15.9 Hz, 1H), 7.77 (d, J=15.9 Hz, 1H), 6.85 (s, 2H), 5.15 (s, 1H), 4.38 (s, 2H), 3.90 (s, 9H), 3.88 (s, 3H); $^{13}$C NMR (75 MHz, CDCl$_3$) δ 176.2, 170.2, 164.8, 153.4, 145.2, 140.3, 130.5, 118.7, 105.7, 94.8, 60.9, 58.7, 56.2, 48.7; IR (thin film, cm$^{-1}$) 3099, 2947, 1720, 1665, 1622, 1581, 1506, 1470, 1449, 1420, 1435, 1327, 1368, 1311, 1279, 1181, 1252, 1192, 1125, 1155, 1046, 971, 992, 913, 842, 819, 666; m/z found: 334.37 [M+H$^+$]; HRMS (FAB) calcd for C$_{17}$H$_{19}$NO$_6$: 333.1212; found 333.1211.

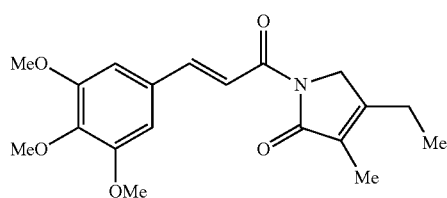 [SMILES: CCC1=C(C)C(=O)N(C(=O)/C=C/c2cc(OC)c(OC)c(OC)c2)C1]

3-ethyl-4-methyl-1-[(2E)-3-(3,4,5-trimethoxyphenyl)prop-2-enoyl]-1,5-dihydro-2H-pyrrol-2-one Method a; Yield: 30%; $^1$H NMR (300 MHz, CDCl$_3$) δ 8.01 (d, J=15.9 Hz, 1H), 7.81 (d, J=15.9 Hz, 1H), 6.86 (s, 2H), 4.29 (s, 2H), 3.91 (s, 6H), 3.88 (s, 3H), 2.32 (q, J=7.5 Hz, 2H), 2.08 (s, 3H), 1.10 (t, J=7.5 Hz, 3H); $^{13}$C NMR (75 MHz, CDCl$_3$) δ 171.0, 165.0, 153.4, 150.9, 145.5, 140.1, 134.4, 130.5, 118.3, 105.7, 60.9, 56.2, 52.2, 16.8, 13.4, 12.8; IR (thin film, cm$^{-1}$) 2966, 2936, 1710, 1665, 1580, 1616, 1504, 1453, 1418, 1365, 1391, 1320, 1281, 1226, 1245, 1155, 1124, 1174, 1081, 1013, 934, 826, 801, 777, 729, 604; m/z found: 346.51 [M+H$^+$]; HRMS (FAB) calcd for C$_{19}$H$_{23}$NO$_5$: 345.1576; found 345.1577.

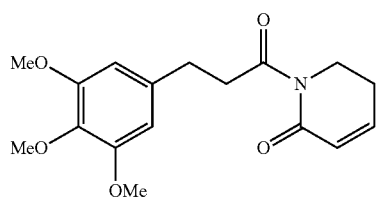 [SMILES: COc1cc(CCC(=O)N2CCC=CC2=O)cc(OC)c1OC]

1-(3-(3,4,5-trimethoxyphenyl)propanoyl)-5,6-dihydropyridin-2(1H)-one

Method a; 86%; $^1$H NMR (300 MHz, CDCl$_3$) δ 6.89 (m, 1H), 6.47 (s, 2H), 6.00 (m, 1H), 3.97 (t, J=6.3 Hz, 2H), 3.84 (s, 6H), 3.81 (s, 3H), 3.25 (t, J=7.5 Hz, 2H), 2.93 (t, J=7.5 Hz, 2H), 2.40 (m, 2H); $^{13}$C NMR (75 MHz, CDCl$_3$) δ 175.4, 165.3, 153.0, 145.2, 136.8, 136.2, 125.8, 105.5, 60.7, 56.0, 40.9, 40.8, 31.5, 24.5; IR (cm$^{-1}$) 2930, 1686, 1627, 1588, 1508, 1457, 1421, 1385, 1303, 1237, 1216, 1179, 1124, 1027, 1007, 818, 731, 587; m/z found: 320.26 [M+H$^+$]; HRMS (FAB) calcd for C$_{17}$H$_{21}$NO$_5$: 319.1420; found 319.1421.

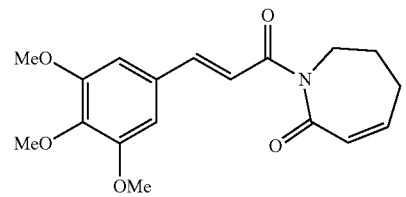 [SMILES: COc1cc(/C=C/C(=O)N2CCCC=CC2=O)cc(OC)c1OC]

1-[(2E)-3-(3,4,5-trimethoxyphenyl)prop-2-enoyl]-1,5,6,7-tetrahydro-2H-azepin-2-one Method a; Yield: 75%; $^1$H NMR (300 MHz, CDCl$_3$) δ 7.67 (d, J=15.6 Hz, 1H), 7.35 (d, J=15.6 Hz, 1H), 6.76 (s, 2H), 6.51 (m, 1H), 6.08 (d, J=11.7 Hz, 1H), 3.97 (t, J=6.0 Hz, 2H), 3.86 (s, 6H), 3.85 (s, 3H), 2.38 (q, J=6.3 Hz, 2H), 1.97 (m, 2H); $^{13}$C NMR (75 MHz, CDCl$_3$) δ 171.3, 167.7, 153.4, 144.2, 142.0, 140.1, 130.5, 128.0, 120.2, 105.6, 60.9, 56.2, 41.2, 26.1, 25.5; IR (thin film, cm$^{-1}$) 2937, 1669, 1615, 1580, 1504, 1453, 1417, 1390, 1318, 1358, 1274, 1200, 1152, 1077, 1124, 1003, 926, 812, 730, 588; m/z found: 332.00 [M+H$^+$]; HRMS (FAB) calcd for C$_{18}$H$_{21}$NO$_5$: 331.1420; found 331.1423.

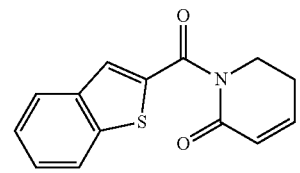

1-(1-benzothien-2-ylcarbonyl)-5,6-dihydropyridin-2(1H)-one

Method a; Yield: 60%; $^1$H NMR (300 MHz, CDCl$_3$) δ 7.82 (m, 3H), 7.39 (m, 2H), 6.96 (m, 1H), 6.04 (d, J=9.6 Hz, 1H), 3.96 (t, J=6.6 Hz, 2H), 2.58 (m, 2H); $^{13}$C NMR (125 MHz, CDCl$_3$) δ 167.8, 165.5, 145.6, 141.7, 138.4, 138.0, 129.7, 126.7, 125.6, 125.0, 124.7, 122.5, 44.1, 24.8; IR (thin film, cm$^{-1}$) 3057, 2889, 1659, 1593, 1559, 1516, 1423, 1458, 1469, 1383, 1334, 1227, 1184, 1159, 1128, 1086, 1011, 972, 904, 866, 819, 845, 801, 722, 636, 678; m/z found: 258.32 [M+H$^+$]; HRMS (FAB) calcd for C$_{14}$H$_{11}$NO$_2$S: 257.0510; found 257.0511.

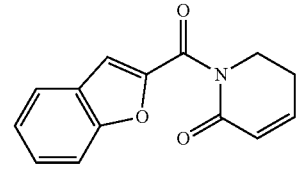

1-(1-benzofuran-2-ylcarbonyl)-5,6-dihydropyridin-2(1H)-one

Method a; Yield, 80%; $^1$H NMR (300 MHz, CDCl$_3$) δ 7.68 (d, J=7.8 Hz, 1H), 7.52 (d, J=8.4 Hz, 1H), 7.42 (m, 2H), 7.28 (m, 1H), 7.00 (m, 1H), 6.07 (d, J=9.6 Hz, 1H), 4.00 (t, J=6.6 Hz, 2H), 2.61 (m, 2H); $^{13}$C NMR (75 MHz, CDCl$_3$) δ 164.9, 163.8, 155.0, 149.3, 145.6, 127.3, 127.1, 125.0, 123.5, 122.7, 113.0, 112.1, 43.4, 24.8; IR (cm$^{-1}$) 3059, 2889, 2359, 1666, 1590, 1561, 1471, 1382, 1447, 1422, 1350, 1291, 1245, 1220, 1178, 1128, 1111, 1048, 1019, 968, 939, 908, 885, 846, 814, 747, 702, 612; m/z found: 241.97 [M+H$^+$]; HRMS (FAB) calcd for $C_{14}H_{11}NO_3$: 241.0739; found 241.0744.

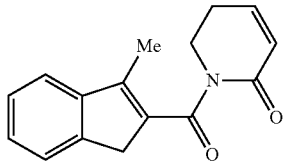 [SMILES: CC1=C(C(=O)N2CCC=CC2=O)Cc2ccccc21]

1-(3-methyl-1H-indene-2-carbonyl)-5,6-dihydropyridin-2(1H)-one

Method a; Yield, 13%; $^1$H NMR (300 MHz, CDCl$_3$) δ 7.43 (m, 2H), 7.33 (m, 21-1), 6.95 (dt, J=9.9, 3.9 Hz, 1H), 6.00 (d, J=9.9 Hz, 1H), 3.96 (t, J=6.6 Hz, 2H), 3.67 (q, J=2.1 Hz, 2H), 2.55 (m, 2H), 2.32 (q, J=2.1 Hz, 3H); HRMS (FAB) calcd for $C_{16}H_{15}NO_2$: 253.1103; found 253.1106.

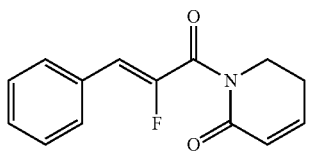 [SMILES: O=C1C=CCCN1C(=O)/C(F)=C/c1ccccc1]

1-[(2Z)-2-fluoro-3-phenylprop-2-enoyl]-5,6-dihydropyridin-2(1H)-one

Method a; 38%; $^1$H NMR (300 MHz, CDCl$_3$) δ 7.63 (dd, J=8.1, 1.2 Hz, 2H), 7.36 (m, 3H), 6.94 (dt, J=9.9, 4.2 Hz, 1H), 6.69 (d, J=35.7 Hz, 1H), 6.02 (dt, J=9.9, 1.8 Hz, 1H), 3.88 (t, J=6.6 Hz, 2H), 2.55 (m, 2H); $^{13}$C NMR (75 MHz, CDCl$_3$) δ 166.1 (d, J=33.5 Hz, 1C), 164.5, 151.2 (d, J=273.4 Hz, 1C), 145.9, 131.7 (d, J=4.0 Hz, 1C), 130.3 (d, J=7.8 Hz, 1C), 129.3 (d, J=2.6 Hz, 1C), 128.6, 124.6, 116.1 (d, J=5.3 Hz, 1C), 43.2, 24.6; IR (thin film, cm$^{-1}$) 3057, 2892, 1698, 1678, 1650, 1493, 1470, 1449, 1422, 1383, 1344, 1306, 1231, 1212, 1197, 1108, 1049, 1019, 1001, 973, 954, 923, 910, 873, 835, 817, 773, 760, 692, 645; m/z found: 246.25 [M+H$^+$]; HRMS (FAB) calcd for $C_{14}H_{12}FNO_2$: 245.0852; found 245.0853.

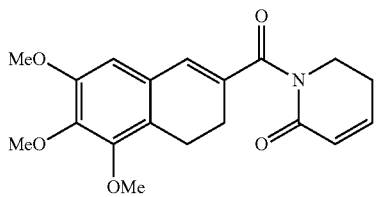 [SMILES: COc1cc2c(c(OC)c1OC)CCC(C(=O)N1CCC=CC1=O)=C2]

1-(5,6,7-trimethoxy-3,4-dihydronaphthalene-2-carbonyl)-5,6-dihydropyridin-2(1H)-one Method b; Yield, 66%; $^1$H NMR (300 MHz, CDCl$_3$) δ 6.91-6.95 (m, 2H), 6.55 (s, 1H), 5.99 (dt, J=9.6, 1.8 Hz, 1H), 3.89 (t, J=6.6 Hz, 2H), 3.89 (s, 3H), 3.84 (s, 3H), 3.82 (s, 3H), 2.85 (t, J=8.1 Hz, 2H), 2.50 (m, 4H); $^{13}$C NMR (75 MHz, CDCl$_3$) δ 174.0, 165.2, 151.5, 150.4, 145.2, 143.0, 134.8, 132.9, 128.4, 125.0, 122.6, 107.9, 60.8, 60.6, 55.9, 43.0, 24.6, 23.5, 20.5; HRMS (FAB) calcd for $C_{19}H_{21}NO_5$: 343.1420; found 343.1415.

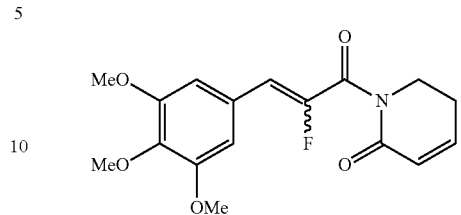

1-(2-fluoro-3-(3,4,5-trimethoxyphenyl)prop-2-enoyl)-5,6-dihydropyridin-2(1H)-one Method a; Yield, 43%; Characterized as a 2/1 mixture with trans as major; $^1$H NMR (300 MHz, CDCl$_3$) δ 6.93-6.99 (m, 1H, major), 6.87 (s, 2H, major), 6.84-6.88 (m, 0.5H, minor), 6.64 (d, J=35.4 Hz, 1H, major), 6.57 (s, 1H, minor), 6.51 (d, J=20.4 Hz, 0.5H, minor), 6.04 (dt, J=9.9, 1.8 Hz, 1H, major), 5.93 (dt, J=9.9, 1.8 Hz, 0.5H, minor), 3.80-3.90 (m, 2H (major), 1H (minor)), 3.86 (s, 3H, major), 3.85 (s, 6H, major), 3.81 (s, 1.5H, minor), 3.80 (s, 3H, minor), 2.50-2.68 (m, 2H, major), 2.33-2.40 (m, 1H, minor); $^{13}$C NMR (75 MHz, CDCl$_3$) δ 166.1 (d, J=33.3 Hz, 1C, major), 164.5 (major), 163.9 (d, J=36.2 Hz, 1C, minor), 163.8 (minor), 153.2 (??), 152.7 (??), 152.5 (??), 149.6 (d, J=512.8 Hz, 1C, minor), 149.5 (d, J=536.3 Hz, 1C, major), 149.2 (minor), 148.9, (major), 139.3 (d, J=3.3 Hz, 1C), 138.2 (??), 127.0 (d, J=4.0 Hz, 1C), 126.8 (d, J=10.4 Hz, 1C), 124.6 (major), 124.4 (minor), 118.9 (d, J=3.9 Hz, 1C), 116.4 (d, J=5.0 Hz, 1C), 114.0 (d, J=23.55 Hz, 1C), 107.8, 107.7, 106.2 (d, J=2.7 Hz, 1C), 60.9, 56.1, 43.3, 41.8, 24.6, 24.2; HRMS (FAB) calcd for $C_{17}H_{18}FNO_5$: 335.1169; found 335.1171.

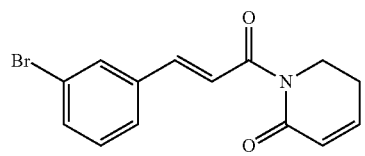 [SMILES: O=C1C=CCCN1C(=O)/C=C/c1cccc(Br)c1]

(E)-1-(3-(3-bromophenyl)prop-2-enoyl)-5,6-dihydropyridin-2(1H)-one

Method a; Yield, 71%; $^1$H NMR (300 MHz, CDCl$_3$) δ 7.54 (s, 1H), 7.46 (d, J=15.6 Hz, 1H), 7.26-7.31 (m, 3H), 7.04-7.09 (m, 1H), 6.75-6.81 (m, 1H), 5.87 (dt, J=9.6, 1.8 Hz, 1H), 3.86 (t, J=6.6 Hz, 2H), 2.28-2.33 (m, 2H); $^{13}$C NMR (75 MHz, CDCl$_3$) δ 168.5, 165.8, 145.6, 141.6, 137.2, 132.8, 130.8, 130.2, 127.0, 125.7, 123.3, 122.9, 41.6, 24.8; HRMS (FAB) calcd for $C_{14}H_{12}BrNO_2$: 305.0051; found 305.0050.

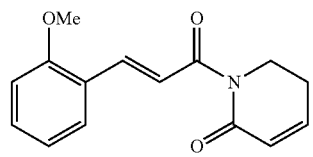 [SMILES: COc1ccccc1/C=C/C(=O)N1CCC=CC1=O]

(E)-1-(3-(2-methoxyphenyl)prop-2-enoyl)-5,6-dihydropyridin-2(1H)-one

Method a; Yield, 35%; $^1$H NMR (300 MHz, CDCl$_3$) δ 8.09 (d, J=15.9 Hz, 1H), 7.58 (m, 2H), 7.32 (td, J=8.1, 1.5 Hz, 1H), 6.91 (m, 3H), 6.03 (dt, J=9.6, 1.8 Hz, 1H), 4.03 (t, J=6.3 Hz, 2H), 3.88 (s, 3H), 2.46 (m, 2H); $^{13}$C NMR (75 MHz, CDCl$_3$) δ 169.3, 165.7, 158.4, 145.2, 138.9, 131.2, 128.8, 125.9, 124.2, 122.1, 120.6, 111.1, 55.5, 41.6, 24.8; HRMS (FAB) calcd for C$_{15}$H$_{15}$NO$_3$: 257.1052; found 257.1053.

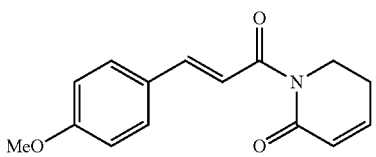 [SMILES: COc1ccc(/C=C/C(=O)N2CCC=CC2=O)cc1]

(E)-1-(3-(4-methoxyphenyl)prop-2-enoyl)-5,6-dihydropyridin-2(1H)-one

Method a; Yield, 15%; $^1$H NMR (300 MHz, CDCl$_3$) δ 7.73 (d, J=15.6 Hz, 1H), 7.54 (d, J=8.7 Hz, 2H), 7.41 (d, J=15.3 Hz, 1H), 6.94 (m, 1H), 6.89 (d, J=8.7 Hz, 2H), 6.04 (dt, J=9.9, 1.8 Hz 1H), 4.03 (t, J=6.6 Hz, 2H), 3.83 (s, 3H), 2.46 (m, 2H); $^{13}$C NMR (75 MHz, CDCl$_3$) δ 169.1, 165.8, 161.3, 145.2, 143.6, 130.0, 127.9, 126.0, 119.5, 114.5, 55.4, 41.6, 24.8; IR (thin film, cm$^{-1}$) 2932, 1683, 1600, 1573, 1512, 1466, 1387, 1422, 1333, 1304, 1289, 1255, 1216, 1173, 1136, 1114, 1051, 1032, 980, 913, 822, 610. m/z found: 258.11 [M+H$^+$]; HRMS (FAB) calcd for C$_{15}$H$_{15}$NO$_3$: 257.1052; found 257.1053.

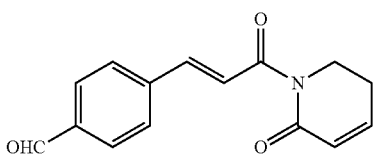

(E)-4-(3-oxo-3-(2-oxo-5,6-dihydropyridin-1(2H)-yl)prop-1-enyl)benzaldehyde

Method a; Yield, 15%; $^1$H NMR (300 MHz, CDCl$_3$) δ 10.02 (s, 1H), 7.88 (d, J=8.7 Hz, 2H), 7.70 (m, 3H), 7.58 (d, J=15.6 Hz, 1H), 6.97 (m, 1H), 6.05 (dt, J=9.6 Hz, 1.8 Hz, 1H), 4.05 (t, J=6.6 Hz, 2H), 2.50 (m, 2H); IR (thin film, cm$^{-1}$) 2940, 2839, 1698, 1681, 1579, 1505, 1453, 1418, 1385, 1343, 1313, 1278, 1225, 1158, 1121, 1049, 1020, 1000, 938, 910, 870, 818, 778, 762, 731, 703, 644, 615, 560; m/z found: 256.27 [M+H$^+$]; HRMS (FAB) calcd for C$_{15}$H$_{13}$NO$_3$: 255.0895; found 255.0901.

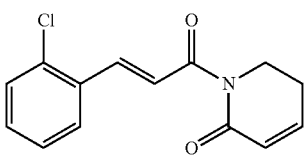 [SMILES: O=C1C=CCCN1C(=O)/C=C/c1ccccc1]

1-[(2E)-3-(2-chlorophenyl)prop-2-enoyl]-5,6-dihydropyridin-2(1H)-one

Method a; Yield: 53%; $^1$H NMR (300 MHz, CDCl$_3$) δ 8.15 (d, J=15.6 Hz, 1H), 7.73 (m, 1H), 7.50 (d, J=15.6 Hz, 1H), 7.42 (m, 1H), 7.29 (m, 3H), 6.98 (m, 1H), 6.07 (dt, J=9.6, 1.8 Hz, 1H), 4.08 (t, J=6.6 Hz, 2H), 2.51 (m, 2H); $^{13}$C NMR (75 MHz, CDCl$_3$) δ 168.5, 165.8, 145.6, 139.1, 135.0, 133.4, 130.7, 130.0, 128.0, 127.0, 125.8, 124.4, 41.6, 24.8; IR (thin film, cm$^{-1}$) 2934, 1677, 1616, 1470, 1385, 1330, 1298, 1216, 1185, 1135, 1054, 1038, 972, 818, 758; m/z found: 262.09 [M+H$^+$]; HRMS (FAB) calcd for C$_{14}$H$_{12}$C$_1$NO$_2$: 261.0557; found 261.0560.

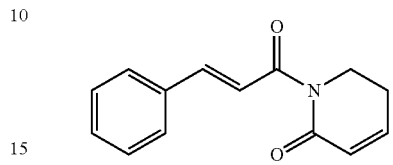

1-[(2E)-3-phenylprop-2-enoyl]-5,6-dihydropyridin-2(1H)-one

Method b; Yield 40%; $^1$H NMR (300 MHz, CDCl$_3$) δ 7.75 (d, J=15.6 Hz, 1H), 7.56-7.58 (m, 2H), 7.50 (d, J=15.6 Hz, 1H), 7.34-7.37 (m, 3H), 6.90-6.96 (m, 1H), 6.03 (dt, J=9.9, 1.5 Hz, 1H), 4.03 (t, J=6.6 Hz, 2H), 2.43-2.49 (m, 2H); $^{13}$C NMR (75 MHz, CDCl$_3$) δ 168.9, 165.7, 145.4, 143.5, 135.1, 130.0, 128.7, 128.3, 125.8, 121.9, 41.4, 24.7; HRMS (FAB) calcd for C$_{14}$H$_{13}$NO$_2$: 227.0946; found 227.0946.

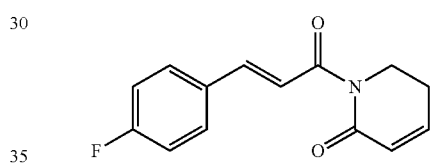

(E)-1-(3-(4-fluorophenyl)prop-2-enoyl)-5,6-dihydropyridin-2(1H)-one

Method a; Yield 74%; $^1$H NMR (300 MHz, CDCl$_3$) δ 7.71 (d, J=15.6 Hz, 1H), 7.56 (m, 2H), 7.44 (d, J=15.6 Hz, 1H), 7.06 (m, 2H), 6.94 (m, 1H), 6.05 (dt, J=9.9, 1.8 Hz, 1H), 4.04 (t, J=6.6 Hz, 2H), 2.48 (m, 2H); 13C NMR (75 MHz, CDCl3) δ 168.8, 165.8, 160.4 (d, J=259.0 Hz, 1C), 145.5, 142.3, 131.4 (d, J=3.5 Hz, 1C), 130.2 (d, J=8.2 Hz, 1C), 125.8, 121.7 (d, J=2.3 Hz, 1C), 115.9 (d, J=21.5 Hz, 1C), 41.6, 24.8; IR (thin film, cm$^{-1}$) 2932, 1674, 1620, 1598, 1507, 1470, 1414, 1386, 1330, 1298, 1215, 1159, 1136, 1183, 1096, 1119, 1051, 977, 864, 820, 738, 648, 610, 570; m/z found: 246.24 [M+H$^+$]; HRMS (FAB) calcd for C14H12FNO2: 245.0852; found 254.0858.

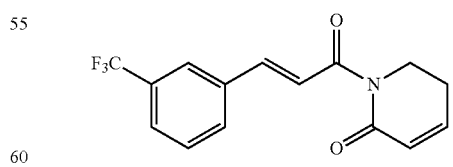

1-{(2E)-3-[3-(trifluoromethyl)phenyl]prop-2-enoyl}-5,6-dihydro pyridin-2(1H)-one Method a; Yield: 88%; $^1$H NMR (300 MHz, CDCl$_3$) δ 7.69-7.78 (m, 3H), 7.46-7.61 (m, 3H), 6.93-6:99 (m, 1H), 6.05 (dt, J=9.6, 1.8 Hz, 1H), 4.04 (t, J=6.6 Hz, 2H), 2.50 (m, 2H); $^{13}$C NMR (75 MHz, CDCl$_3$) δ 168.5, 165.8, 145.7, 141.3, 135.9, 131.3 (q, 2J=32.3 Hz, 1C), 131.2, 129.3, 126.3 (q, 3J=3.7 Hz, 1C), 125.6, 124.8 (q, 3'J=3.75 Hz, 1C), 123.8 (q, 1J=269.0 Hz, 1C), 123.7, 41.6, 24.7; IR (thin film, cm$^{-1}$) 2917, 1683, 1623, 1471, 1438, 1387, 1335, 1299, 1270, 1249, 1217, 1185, 1165, 1121, 1096, 1076, 1051, 974, 911, 857, 822, 802, 693, 660, 578, 560; m/z found: 296.27 [M+H$^+$]; HRMS (FAB) calcd for C$_{15}$H$_{12}$F$_3$NO$_2$: 295.0820; found 295.0823.

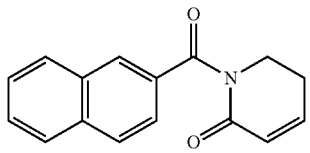 [SMILES: O=C1C=CCCN1C(=O)c1ccc2ccccc2c1]

1-(2-naphthoyl)-5,6-dihydropyridin-2(1H)-one

Method a; Yield 87%; $^1$H NMR (300 MHz, CDCl$_3$) δ 8.16 (s, 1H), 7.91 (d, J=8.4 Hz, 1H), 7.83 (m, 2H), 7.53 (m, 3H), 6.98 (m, 1H), 5.99 (dt, J=9.6, 1.8 Hz, 1H), 4.04 (t, J=6.3 Hz, 2H), 2.61 (m, 2H); $^{13}$C NMR (75 MHz, CDCl$_3$) δ 173.9, 165.4, 145.5, 134.8, 133.4, 132.5, 129.1, 127.7, 127.6, 127.5, 126.4, 125.3, 124.8, 43.4, 24.9; IR (thin film, cm$^{-1}$) 3055, 2889, 1626, 1670, 1599, 1506, 1467, 1422, 1381, 1354, 1289, 1244, 1222, 1192, 1151, 1102, 1048, 1019, 968, 929, 911, 864, 815, 801, 775, 759, 731, 701, 665, 646, 621; m/z found: 252.20 [M+H$^+$]; HRMS (FAB) calcd for C$_{16}$H$_{13}$NO$_2$: 251.0946; found 251.0954.

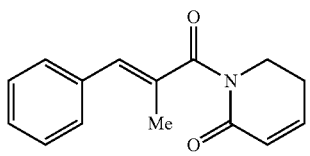 [SMILES: C/C(=C\c1ccccc1)C(=O)N1CCC=CC1=O]

(E)-1-(2-methyl-3-phenylprop-2-enoyl)-5,6-dihydro-pyridin-2(1H)-one

Method b; Yield 57%; $^1$H NMR (300 MHz, CDCl$_3$) δ 7.26-7.42 (m, 5H), 6.90-6.96 (m, 2H), 5.99 (dt, J=9.9, 1.8 Hz, 1H), 3.92 (t, J=6.3 Hz, 2H), 2.49-2.55 (m, 2H), 2.14 (d, J=1.5 Hz, 3H); $^{13}$C NMR (75 MHz, CDCl$_3$) δ 176.1, 165.0, 145.3, 136.0, 134.9, 132.8, 129.3, 128.1, 127.6, 125.1, 42.7, 24.6, 15.5; HRMS (FAB) calcd for C$_{15}$H$_{15}$NO$_2$: 241.1103; found 241.1107.

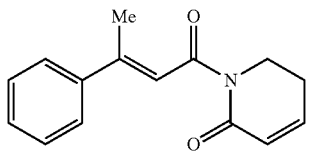 [SMILES: C/C(=C\C(=O)N1CCC=CC1=O)c1ccccc1]

(E)-1-(3-phenylbut-2-enoyl)-5,6-dihydropyridin-2(1H)-one

Method a; 10%; $^1$H NMR (300 MHz, CDCl$_3$) δ 7.56 (m, 2H), 7.37 (m, 3H), 6.92 (m, 2H), 6.02 (dt, J=9.9, 1.8 Hz, 1H), 4.00 (t, J=6.6 Hz, 2H), 2.51 (d, J=1.2 Hz, 3H), 2.46 (m, 2H); $^{13}$C NMR (75 MHz, CDCl$_3$) δ 170.0, 165.6, 151.6, 145.0, 142.7, 128.7, 128.4, 126.6, 125.9, 121.8, 41.1, 24.8, 18.6; HRMS (FAB) calcd for C$_{15}$H$_{15}$NO$_2$: 241.1103; found 241.1110.

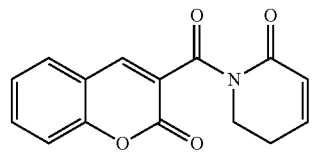 [SMILES: O=C1C=CCCN1C(=O)c1cc2ccccc2oc1=O]

1-[(2-oxo-2H-chromen-3-yl)carbonyl]-5,6-dihydro-pyridin-2(1H)-one

Method a; Yield 86%; $^1$H NMR (300 MHz, CDCl$_3$) δ 7.91 (s, 1H), 7.55 (m, 2H), 7.26 (m, 2H), 6.98 (m, 1H), 5.96 (dt, J=9.6, 1.8 Hz, 1H), 4.06 (t, J=6.3 Hz, 2H), 2.57 (m, 2H); $^{13}$C NMR (75 MHz, CDCl$_3$) δ 169.3, 165.7, 158.4, 145.2, 138.9, 131.2, 128.9, 125.9, 124.2, 122.2, 120.6, 111.1, 55.5, 41.6, 24.8; IR (thin film, cm$^{-1}$) 1726, 1691, 1671, 1609, 1570, 1457, 1386, 1318, 1265, 1229, 1130, 1011, 820, 730. m/z found: 270.25 [M+H$^+$]; HRMS (FAB) calcd For C$_{15}$H$_{11}$N$_4$: 269.0688; found 269.0687.

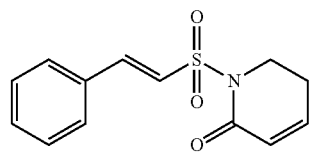 [SMILES: O=C1C=CCCN1S(=O)(=O)/C=C/c1ccccc1]

1-{[(E)-2-phenylvinyl]sulfonyl}-5,6-dihydropyridin-2(1H)-one

Method a; Yield 57%; $^1$H NMR (300 MHz, CDCl$_3$) δ 7.59 (d, J=15.6 Hz, 1H), 7.43 (m, 2H), 7.33-7.35 (m, 3H), 7.17 (d, J=15.3 Hz, 1H), 6.75-6.82 (m, 1H), 5.90 (dt, J=9.6, 1.8 Hz, 1H), 3.90 (t, J=6.6 Hz, 2H), 2.44-2.50 (m, 2H); $^{13}$C NMR (75 MHz, CDCl$_3$) δ 163.8, 144.9, 144.1, 132.1, 131.3, 129.0, 128.6, 124.8, 124.3, 43.3, 25.1; IR (thin film, cm$^{-1}$) 3061, 2923, 1682, 1612, 1576, 1470, 1449, 1381, 1350, 1287, 1239, 1155, 1132, 996, 863, 848, 817, 746, 672; HRMS (FAB) calcd for C$_{13}$H$_{13}$NO$_3$S: 263.0616; found 263.0623.

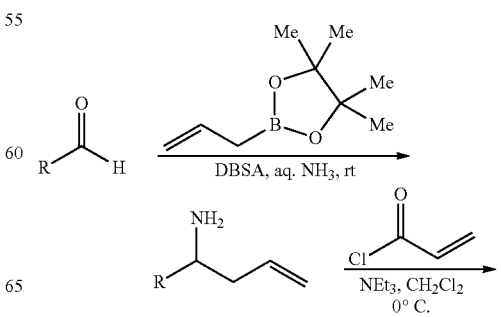

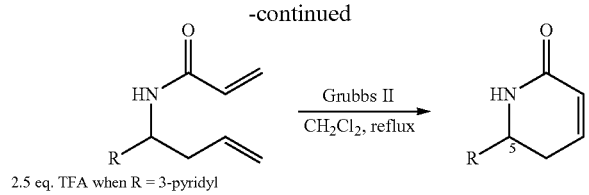

2.5 eq. TFA when R = 3-pyridyl

General Procedure for the Synthesis of 5-substituted dihydropyridone:

An oven-dried, two-necked, round-bottomed flask is charged with dodecylbenzenesulfonic acid (216 mg, 0.66 mmol) flushed with nitrogen, and equipped with a rubber septum, and an argon inlet. The flask is charged with 28% aqueous ammonia (13.2 mL) by syringe. After the gas evolution ceases, the mixture is stirred at room temperature to give a clear solution, then cooled to 0° C. in an ice-water bath. 2-Allyl-4,4,5,5-tetramethyl-1,3,2-dioxaborolane (1.33 g, 7.93 mmol) is added dropwise over 5 min via a syringe and the mixture is stirred at room temperature for 30 min. One of the aldehydes (6.61 mmol) is added drop-wise via a syringe over 5 min at room temperature. The slurry mixture is vigorously stirred at room temperature for 6 h and transferred to a separatory funnel with water (15 mL) and saturated aqueous NaCl solution (30 mL). The aqueous layer is extracted three times with diethyl ether (30 mL), and the combined organic layers were washed with saturated aqueous NaCl solution (15 mL), dried over anhydrous MgSO$_4$, filtered, and concentrated under reduced pressure to afford crude amine, which was purified by flash chromatography (isopropylamine 4.8% in hexane/ethyl acetate from 100:0 to 90:10) to afford pure amine.

One of the amine products (11.3 mmol) was dissolved in dry THF (55 mL); triethylamine (NEt$_3$, 1.50 g, 16.93 mmol) and N,N-dimethylpyridin-4-amine (DMAP, 140 mg, 1.13 mmol) were added. The mixture was then cooled at 0° C. and acryloyl chloride (1.50 g, 16.9 mmol) dissolved in dry THF (55 mL) was added drop-wise; a yellow/white precipitate formed immediately. The reaction was stirred at 0° C. for 30 min and then warmed up to room temperature and stirred for another 2 hours. At the end, the solvent was removed under reduced pressure; crude product was subject to flash chromatography (hexane/ethyl acetate 100:0 to 70:30):

One of the intermediates (500 mg, 2.16 mmol) was dissolved in dry CH$_2$Cl$_2$ (22 mL); Grubbs catalyst 2$^{nd}$ generation (184 mg, 0.22 mmol) was added and the mixture was heated at reflux. For the case where R=3-pyridyl, TFA (0.41 mL, 5.40 mmol) was added. After 1 h the mixture was cooled to room temperature and concentrate to dryness to give a brown oil. Purification by flash chromatography (hexane/ethyl acetate=30/70 to 0/100 except for R=3-pyridyl: only ethyl acetate) provides the desired lactam, which was used in the amide formation step under either condition a or b.

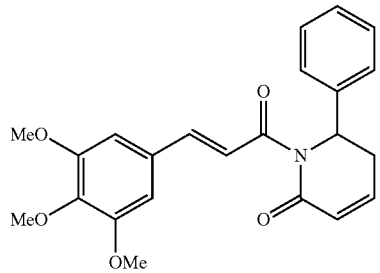

(E)-6-phenyl-1-(3-(3,4,5-trimethoxyphenyl)prop-2-enoyl)-5,6-dihydropyridin-2(1H)-one Method a; Yield 88%; $^1$H NMR (300 MHz, CDCl$_3$) δ 7.61 (d, J=15.6 Hz, 1H), 7.44 (d, J=15.6 Hz, 1H), 7.13-7.26 (m, 5H), 6.80 (s, 2H), 6.63 (m, 1H), 6.01 (dd, J=9.9, 2.7 Hz, 1H), 5.94 (d, J=6.6 Hz, 1H), 3.82 (s, 6H), 3.81 (s, 3H), 2.97-3.06 (m, 1H), 2.76 (dd, J=18.6, 5.7 Hz, 1H); $^{13}$C NMR (75 MHz, CDCl$_3$) δ 168.5, 165.8, 153.2, 144.0, 142.4, 140.2, 140.0, 130.5, 128.4, 127.2, 125.9, 125.8, 120.8, 105.4, 60.8, 56.0, 54.2, 31.3; IR (thin film, cm$^{-1}$) 1683, 1580, 1504, 1315, 1275, 1242, 1185, 1124, 908; 818, 749, 729, 697; m/z found: 394.45 [M+H$^+$]; HRMS (FAB) calcd for C$_{23}$H$_{23}$NO$_5$: 393.1576; found 393.1583.

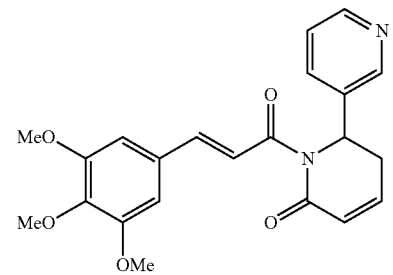 [SMILES: COc1cc(/C=C/C(=O)N2C(=O)C=CCC2c2cccnc2)cc(OC)c1OC]

(E)-6-(pyridin-3-yl)-1-(3-(3,4,5-trimethoxyphenyl)prop-2-enoyl)-5,6-dihydropyridin-2(1H)-one Method a; Yield 54%; $^1$H NMR (300 MHz, CDCl$_3$) δ 8.58 (d, J=1.5 Hz, 1H), 8.52 (d, J=4.8 Hz, 1H), 7.69 (d, J=15.6 Hz, 1H), 7.55 (d, J=8.1 Hz, 1H), 7.49 (d, J=15.5 Hz, 1H), 7.23-7.28 (m, 1H), 6.81 (s, 2H), 6.75 (d, J=7.8 Hz, 1H), 6.13 (dd, J=9.6, 2.7 Hz, 1H), 6.05 (d, J=6.6 Hz, 1H), 3.90 (s, 6H), 3.89 (s, 3H), 3.12-3.18 (m, 1H), 2.82 (dd, J=18.6, 6.3 Hz, 1H); $^{13}$C NMR (75 MHz, CDCl$_3$) δ 168.5, 165.2, 153.4, 148.7, 147.7, 144.7, 142.1, 140.2, 135.9, 133.8, 130.4, 126.3, 123.3, 120.5, 105.6, 60.9, 56.2, 52.6, 30.9; IR (thin film, cm$^{-1}$) 2938, 2839, 1683, 1614, 1579, 1503, 1454, 1418, 1388, 1349, 1314, 1275, 1243, 1188, 1154, 1123, 1039, 1004, 820, 733, 712; m/z found: 395.53 [M+H$^+$]; HRMS (FAB) calcd for C$_{22}$H$_{22}$N$_2$O$_5$: 394.1529; Found 394.1533.

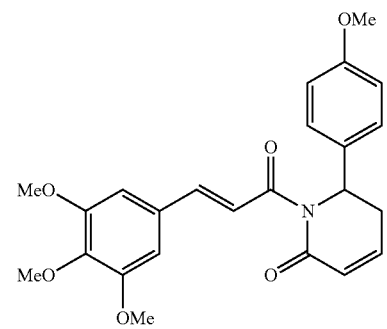 [SMILES: COc1ccc(C2CC=CC(=O)N2C(=O)/C=C/c2cc(OC)c(OC)c(OC)c2)cc1]

(E)-6-(4-methoxyphenyl)-1-(3-(3,4,5-trimethoxyphenyl)prop-2-enoyl)-5,6-dihydropyridin-2(1H)-one Method a; Yield 35%; $^1$H NMR (300 MHz, CDCl$_3$) δ 7.67 (d, J=15.6 Hz, 1H), 7.48 (d, J=15.5 Hz, 1H), 7.14 (d, J=8.7 Hz, 2H), 6.83 (d, J=8.7 Hz, 2H), 6.80 (s, 2H), 6.70-6.75 (m, 1H), 6.08 (dd, J=9.6, 3.0 Hz, 1H), 5.97 (d, J=6.6 Hz, 1H), 3.89 (s, 6H), 3.88 (s, 3H), 3.76 (s, 3H), 3.01-3.08 (m, 1H), 2.79 (dd, J=18.6, 6.6 Hz, 1H); $^{13}$C NMR (75 MHz, CDCl$_3$) δ 168.5, 165.8, 158.8, 153.3, 144.0, 142.6, 140.0, 132.3, 130.6, 127.1, 126.0, 121.0, 113.8, 105.5, 60.8, 56.1, 55.2, 53.8, 31.4; IR (thin film, cm$^{-1}$) 2936, 1683, 1613, 1581, 1505, 1455, 1418, 1389, 1350, 1277, 1248, 1221, 1154, 1125, 1034, 824, 731; m/z found: 424.36 [M+H$^+$]; HRMS (FAB) calcd for C$_{24}$H$_{25}$NO$_6$: 423.1682; found 423.1689.

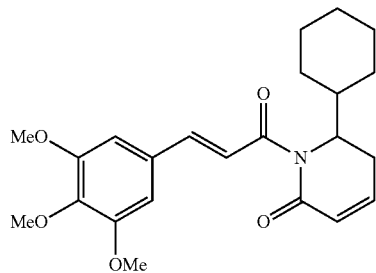 [SMILES: COc1cc(/C=C/C(=O)N2C(=O)C=CCC2C2CCCCC2)cc(OC)c1OC]

(E)-6-cyclohexyl-1-(3-(3,4,5-trimethoxyphenyl) prop-2-enoyl)-5,6-dihydropyridin-2(1H)-one Method a; Yield 78%; $^1$H NMR (300 MHz, CDCl$_3$) δ 7.66 (d, J=15.6 Hz, 1H), 7.39 (d, J=15.3 Hz, 1H), 6.78 (s, 2H), 6.01-6.04 (m, 1H), 4.73 (m, 1H), 3.88 (s, 6H), 3.87 (s, 3H), 2.58 (m, 2H), 1.62-1.71 (m, 6H), 1.01-1.10 (m, 5H); $^{13}$C NMR (75 MHz, CDCl$_3$) δ 168.2, 166.0, 153.2, 143.7, 143.5, 139.8, 130.7, 125.6, 120.7, 105.4, 60.8, 56.0, 55.9, 40.0, 30.8, 29.4, 26.5, 26.00, 25.98, 25.95; IR (thin film, cm$^{-1}$) 2927, 2850, 1681, 1614, 1580, 1504, 1417, 1449, 1389, 1347, 1316, 1241, 1274, 1183, 1124, 1153, 1033, 1004, 976, 912, 818, 778, 728, 647; m/z found: 400.39 [M+H$^+$]; HRMS (FAB) calcd for C$_{23}$H$_{29}$NO$_5$: 399.2046; found 399.2054.

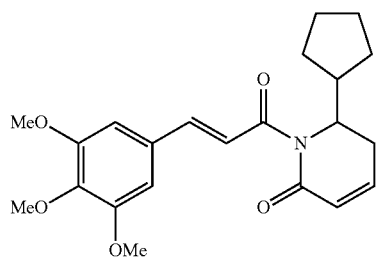 [SMILES: COc1cc(/C=C/C(=O)N2C(=O)C=CCC2C2CCCC2)cc(OC)c1OC]

(E)-6-cyclopentyl-1-(3-(3,4,5-trimethoxyphenyl) prop-2-enoyl)-5,6-dihydropyridin-2(1H)-one Method a; Yield 72%; $^1$H NMR (300 MHz, CDCl$_3$) δ 7.66 (d, J=15.6 Hz, 1H), 7.39 (d, J=15.5 Hz, 1H), 6.81 (m, 1H), 6.78 (s, 2H), 6.05 (dd, J=9.9, 3.0 Hz, 1H), 4.85 (dd, J=10.2, 6.0 Hz, 1H), 3.88 (s, 6H), 3.86 (s, 3H), 2.63-2.73 (m, 1H), 2.45 (dd, J=18.6, 6.3 Hz, 1H), 2.18-2.30 (m, 1H), 1.15-1.70 (m, 8H); $^{13}$C NMR (75 MHz, CDCl$_3$) δ 168.1, 165.8, 153.3, 143.7, 143.4, 139.9, 130.7, 125.7, 120.7, 105.4, 60.8, 56.1, 55.3, 42.7, 30.7, 29.7, 28.5, 25.0, 24.9; IR (thin film, cm$^{-1}$) 2944, 2870, 1684, 1615, 1581, 1505, 1454, 1418, 1389, 1366, 1351, 1318, 1276, 1244, 1195, 1154, 1127, 1006, 823; m/z found: 386.60 [M+H$_+$]; HRMS (FAB) calcd for C$_{22}$H$_{27}$NO$_5$: 385.1899; found 385.1894.

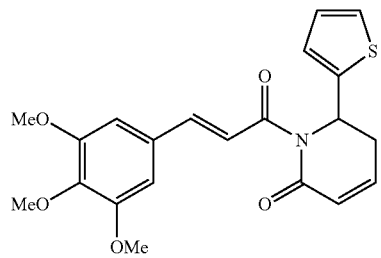 [SMILES: COc1cc(/C=C/C(=O)N2C(=O)C=CCC2c2cccs2)cc(OC)c1OC]

(E)-6-(thiophen-2-yl)-1-(3-(3,4,5-trimethoxyphenyl) prop-2-enoyl)-5,6-dihydropyridin-2(1H)-one Method a; Yield 19%; $^1$H NMR (300 MHz, CDCl3) δ 7.71 (d, J=15.6 Hz, 1H), 7.43 (d, J=15.6 Hz, 1H), 7.13 (d, J=5.1 Hz, 1H), 6.84-6.95 (m, 3H), 6.79 (s, 2H), 6.26 (d, J=6.0 Hz, 1H), 6.08 (dd, J=9.9, 3.0 Hz, 1H), 3.87 (s, 6H), 3.86 (s, 3H), 2.98-3.07 (m, 1H), 2.86 (dd, J=18.6, 6.0 Hz, 1H); $^{13}$C NMR (75 MHz, CDCl$_3$) δ 168.2, 165.0, 153.4, 144.5, 143.4, 142.7, 140.2, 130.6, 126.5, 126.2, 125.8, 124.5, 120.7, 105.6, 60.9, 56.2, 50.9, 31.5; IR (cm$^{-1}$) 2938, 2838, 1683, 1612, 1579, 1503, 1453, 1417, 1389, 1350, 1315, 1274, 1242, 1184, 1154, 1123, 1040, 1003, 913, 818, 778, 732, 703, 591; m/z found: 400.06 [M+H$^+$]; HRMS (FAB) calcd for C$_{21}$H$_{21}$NO$_5$S: 399.1140; found 399.1140.

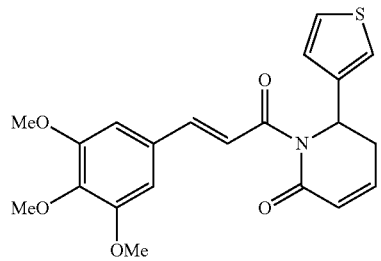 [SMILES: COc1cc(/C=C/C(=O)N2C(=O)C=CCC2c2ccsc2)cc(OC)c1OC]

(E)-6-(thiophen-3-yl)-1-(3-(3,4,5-trimethoxyphenyl) prop-2-enoyl)-5,6-dihydropyridin-2(1H)-one Method a; Yield 53%; $^1$H NMR (300 MHz, CDCl$_3$) δ 7.63 (d, J=15.6 Hz, 1H), 7.38 (d, J=15.6 Hz, 1H), 7.17-7.19 (m, 1H), 6.98 (s, 1H), 6.92 (d, J=4.8 Hz, 1H), 6.73 (s, 2H), 6.68-6.73 (m, 1H), 5.96-6.03 (m, 2H), 3.81 (s, 6H), 3.80 (s, 3H), 2.85-2.98 (m, 1H), 2.75 (dd, J=18.6, 6.0 Hz, 1H); $^{13}$C NMR (75 MHz, CDCl$_3$) δ 168.3, 165.5, 153.3, 144.2, 142.8, 141.3, 140.1, 130.5, 126.3, 126.1, 126.0, 121.7, 120.8, 105.5, 60.9, 56.1, 51.2, 30.7; IR (thin film, cm$^{-1}$) 3102, 2937, 2838, 1732, 1682, 1613, 1579, 1503, 1453, 1417, 1384, 1354, 1314, 1274, 1242, 1183, 1152, 1122, 1042, 1002, 974, 923, 864, 816, 772, 732, 684, 638, 593; m/z found: 400.46 [M+H$^+$]; HRMS (FAB) calcd for C$_{21}$H$_{21}$NO$_5$S: 399.1140; found 399.1152.

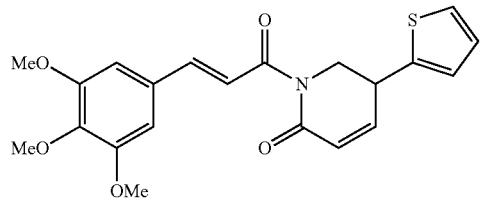 [SMILES: COc1cc(/C=C/C(=O)N2CC(c3cccs3)C=CC2=O)cc(OC)c1OC]

(E)-5-(thiophen-2-yl)-1-(3-(3,4,5-trimethoxyphenyl)prop-2-enoyl)-5,6-dihydropyridin-2(1H)-one Method a; Yield 64%; $^1$H NMR (300 MHz, CDCl$_3$) δ 7.67 (d, J=15.6 Hz, 1H), 7.43 (d, J=15.6 Hz, 1H), 7.23-7.27 (m, 1H), 6.93-7.03 (m, 3H), 6.81 (s, 2H), 6.15 (dd, J=9.6, 1.5 Hz, 1H), 4.34 (dd, J=18.6, 7.8 Hz, 1H), 4.11-4.18 (m, 2H), 3.90 (s, 6H), 3.88 (s, 3H); $^{13}$C NMR (75 MHz, CDCl$_3$) δ 168.6, 165.2, 153.3, 147.1, 144.3, 140.8, 140.2, 130.5, 127.1, 125.5, 125.4, 125.0, 120.6, 105.6, 60.9, 56.2, 48.4, 36.4; m/z found: 400.03 [M+H$^+$]; HRMS (FAB) calcd For C$_{21}$H$_{21}$NO$_5$S: 399.1140; found 399.1144.

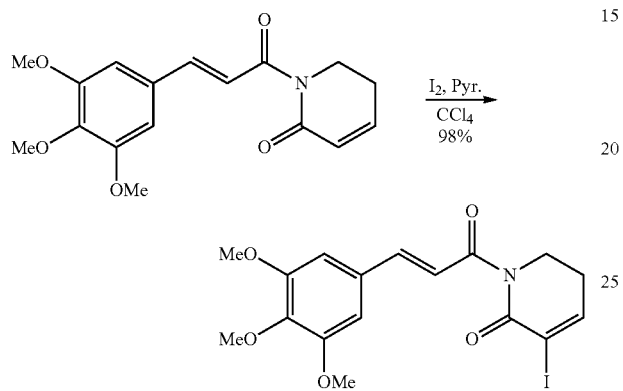

Experiment Procedure: Iodine (2.00 g, 7.89 mmol) was added to a solution of piperlongumine (1.00 g, 3.15 mmol) in a 1:1 mixture of CCl$_4$ and pyridine (32 mL) at room temperature. The mixture was stirred overnight, wrapped, in an aluminium foil before saturated aqueous NH$_4$Cl (160 mL) was added. The mixture was extracted with ethyl acetate (3×65 mL). The organic extract was dried over MgSO$_4$, filtered, and concentrated under vacuum. The crude product was purified by flash chromatography (hexane/ethyl acetate=80/20 to 50/50) to give the desired iodide in 98% yield. $^1$H NMR (300 MHz, CDCl$_3$) δ 7.69 (d, J=15.0 Hz, 1H), 7.67 (m, 1H), 7.39 (d, J=15.6 Hz, 1H), 6.80 (s, 2H), 4.09 (t, J=6.6 Hz, 2H), 3.90 (s, 6H), 3.88 (s, 3H), 2.50 (m, 2H); $^{13}$C NMR (125 MHz, CDCl$_3$) δ 168.7, 161.3, 154.5, 153.3, 144.8, 140.1, 130.3, 120.3, 105.6, 96.6, 60.9, 56.2, 42.1, 28.5; IR (thin film, cm$^{-1}$) 2938, 1672, 1612, 1579, 1503, 1453, 1417, 1318, 1271, 1151, 1121, 1051, 1000, 824, 730; m/z found: 444.12 [M+H$^+$]; HRMS (FAB) calcd for C$_{17}$H$_{18}$INO$_5$: 443.0230; found 443.0217.

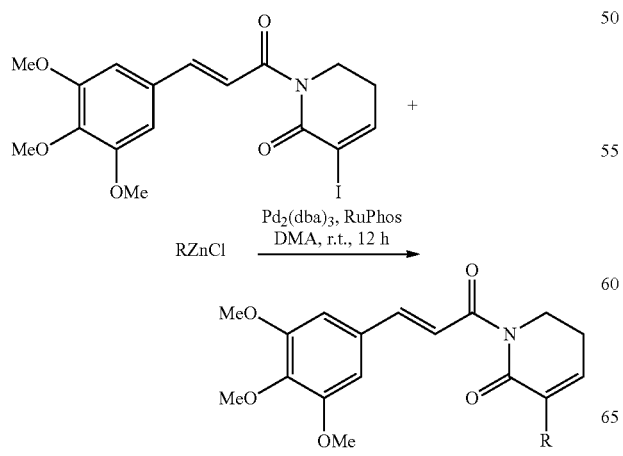

General procedure for Negishi Coupling: Iodopiperlongumine (50.0 mg, 0.11 mmol) was added to a solution of tris(dibenzylideneacetone)dipalladium(0) (Pd$_2$(dba)$_3$, 5.16 mg, 5.64 µmol) and 2-dicyclohexylphosphino-2',6'-diisopropoxybiphenyl (RuPhos, 10.5 mg, 0.02 mmol) in dry dimethylacetamide (1.10 mL) at room temperature. After the mixture had been stirred for 10 min, alkylzinc bromide (0.23 mmol) was added immediately. After the reaction mixture had been stirred at room temperature for 14 h, the solvent was removed under reduced pressure. The residue was purified by flash chromatography (hexane/ethyl acetate=100/0 to 60/40).

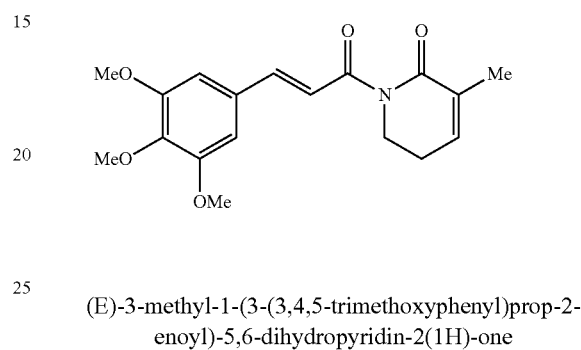

(E)-3-methyl-1-(3-(3,4,5-trimethoxyphenyl)prop-2-enoyl)-5,6-dihydropyridin-2(1H)-one Yield: 99%; $^1$H NMR (300 MHz, CDCl$_3$) δ 7.65 (d, J=15.6 Hz, 1H), 7.39 (d, J=15.6 Hz, 1H), 6.79 (s, 2H), 6.69 (m, 1H), 4.00 (t, J=6.6 Hz, 2H), 3.89 (s, 6H), 3.86 (s, 3H), 2.41 (m, 2H), 1.94 (s, 3H) $^{13}$C NMR (75 MHz, CDCl$_3$) δ 169.1, 167.1, 153.3, 143.4, 140.1, 140.0, 131.9, 130.7, 121.3, 105.6, 60.9, 56.2, 42.3, 24.6, 16.9; IR (thin film, cm$^{-1}$) 2938, 2839, 1677, 1652, 1615, 1580, 1504, 1453, 1418, 1388, 1352, 1318, 1293, 1276, 1242, 1204, 1154, 1125, 1092, 1050, 1004, 895, 853. m/z found: 332.44 [M+H$^+$]; HRMS (FAB) calcd for C$_{18}$H$_{21}$NO$_5$: 331.1420; found 331.1407.

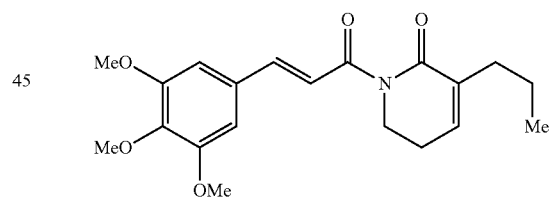

(E)-3-propyl-1-(3-(3,4,5-trimethoxyphenyl)prop-2-enoyl)-5,6-dihydropyridin-2(1H)-one Yield: 42%; $^1$H NMR (300 MHz, CDCl$_3$) δ 7.66 (d, J=15.6 Hz, 1H), 7.39 (d, J=15.3 Hz, 1H), 6.80 (s, 2H), 6.67 (t, J=4.2 Hz, 1H), 3.99 (t, J=6.6 Hz, 2H), 3.89 (s, 6H), 3.88 (s, 3H), 2.43 (m, 2H), 2.31 (t, J=7.5 Hz, 2H), 1.47-1.54 (m, 2H), 0.95 (t, J=7.5 Hz, 3H); $^{13}$C NMR (126 MHz, CDCl$_3$) δ 169.3, 166.7, 153.4, 143.4, 140.0, 139.5, 136.2, 130.8, 121.4, 105.6, 60.9, 56.2, 42.2, 32.5, 24.7, 21.8, 13.8; IR (thin film, cm$^{-1}$) 2931, 2838, 1673, 1614, 1579, 1504, 1454, 1417, 1386, 1352, 1316, 1295, 1274, 1240, 1152, 1121, 1051, 1004, 975, 906, 844, 826; m/z found: 360.60 [M+H$^+$]; HRMS (FAB) calcd for C$_{20}$H$_{25}$NO$_5$: 359.1733; found 359.1733.

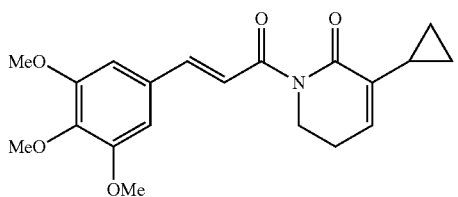 [SMILES: COc1cc(/C=C/C(=O)N2CCC=C(C3CC3)C2=O)cc(OC)c1OC]

(E)-3-cyclopropyl-1-(3-(3,4,5-trimethoxyphenyl)prop-2-enoyl)-5,6-dihydropyridin-2(1H)-one Yield: 70%; $^1$H NMR (500 MHz, CDCl$_3$) δ 7.66 (d, J=15.5 Hz, 1H), 7.46 (d, J=15.5 Hz, 1H), 6.78 (s, 2H), 6.43 (t, J=4.5 Hz, 1H), 3.95 (t, J=6.5 Hz, 2H), 3.89 (s, 6H), 3.87 (s, 3H), 2.37-2.41 (m, 2H), 1.85 (m, 1H), 0.82 (dd, J=13.0, 5.0, 2H), 0.46 (dd, J=10.5, 5.0, 2H); $^{13}$C NMR (125 MHz, CDCl$_3$) δ 169.2, 167.0, 153.3, 143.5, 139.8, 137.5, 136.0, 130.7, 121.3, 105.5, 60.9, 56.2, 41.9, 24.3, 10.5, 6.6; IR (cm$^{-1}$) 2937, 1672, 1613, 1579, 1503, 1464, 1417, 1383, 1348, 1316, 1275, 1243, 1152, 1123, 1052, 1003, 974, 879, 853, 827, 792, 750, 734, 700, 618.68; m/z found: 358.25 [M+H$^+$].

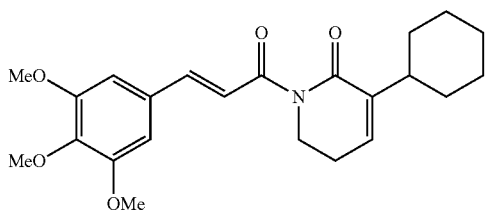 [SMILES: COc1cc(/C=C/C(=O)N2CCC=C(C3CCCCC3)C2=O)cc(OC)c1OC]

(E)-3-cyclohexyl-1-(3-(3,4,5-trimethoxyphenyl)prop-2-enoyl)-5,6-dihydropyridin-2(1H)-one Yield: 30%; $^1$H NMR (300 MHz, CDCl$_3$) δ 7.65 (d, J=15.6 Hz, 1H), 7.39 (d, J=15.6 Hz, 1H), 6.80 (s, 2H), 6.60 (t, J=4.3 Hz, 1H), 3.95 (t, J=6.6 Hz, 2H), 3.89 (s, 6H), 3.87 (s, 3H), 2.63 (t, J=11.7 Hz, 1H), 2.42 (dd, J=11.1, 6.0, 2H), 1.61-1.81 (m, 5H), 1.04-1.45 (m, 6H); $^{13}$C NMR (125 MHz, CDCl$_3$) δ 169.7, 166.7, 153.5, 143.5, 141.7, 137.6, 133.6, 131.0, 121.8, 105.7, 61.2, 56.5, 42.2, 37.3, 33.1, 26.9, 26.5, 24.9; IR (cm$^{-1}$) 2925, 2850, 1673, 1613, 1580, 1504, 1450, 1417, 1388, 1351, 1316, 1295, 1240, 1274, 1179, 1124, 1151, 1096, 1052, 1003, 974, 952, 927, 905, 888, 854, 825, 780, 731, 701; m/z found: 400.34 [M+H$^+$]; HRMS (FAB) calcd For C$_{23}$H$_{29}$NO$_5$: 399.2046; found 399.2042.

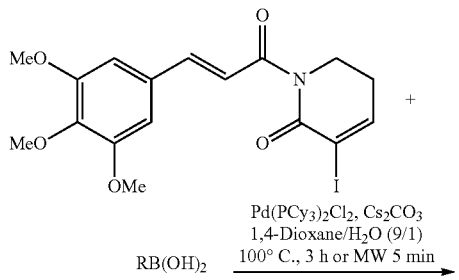

General procedure for Negishi Coupling: A mixture of Cs$_2$CO$_3$ (74.0 mg, 0.23 mmol), dichlorobis(tricyclohexylphosphine) palladium(II) (4.16 mg, 5.64 mmol), arylboronic acid (0.23 mmol) and compound iodopiperlongumine (50.0 mg, 0.11 mmol) were stirred at reflux for 3 h or microwave at 100° C. for 5 min in a 9:1 mixture of 1,4-dioxane and water (1.20 ml). At the end, the solvent was evaporated under reduced pressure and the residue was purified by flash column chromatography (hexane/ethyl acetate=100/0 to 60/40) to give the coupling products.

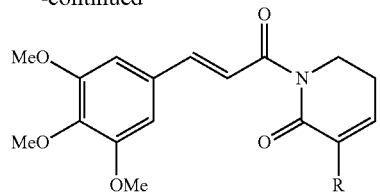

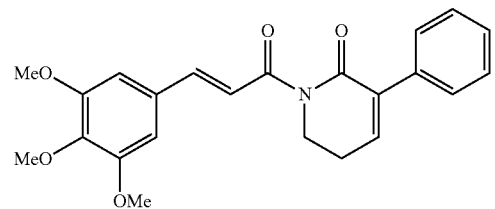 [SMILES: COc1cc(/C=C/C(=O)N2CCC=C(c3ccccc3)C2=O)cc(OC)c1OC]

(E)-3-phenyl-1-(3-(3,4,5-trimethoxyphenyl)prop-2-enoyl)-5,6-dihydropyridin-2(1H)-one Yield: 90%; $^1$H NMR (300 MHz, CDCl$_3$) δ 7.69 (d, J=15.3 Hz, 1H), 7.43 (d, J=15.3 Hz, 1H), 7.35-7.43 (m, 5H), 7.03 (t, J=4.2 Hz, 1H), 6.78 (s, 2H), 4.13 (t, J=6.3 Hz, 2H), 3.86 (s, 9H), 2.59-2.65 (m, 2H); $^{13}$C NMR (75 MHz, CDCl$_3$) δ 169.3, 165.8, 153.4, 143.9, 142.4, 140.1, 137.1, 136.0, 130.6, 128.7, 128.2, 128.1, 121.2, 105.7, 60.9, 56.3, 42.1, 25.1; IR (thin film, cm$^{-1}$) 2937, 2840, 1676, 1614, 1580, 1504, 1463, 1418, 1349, 1317, 1276, 1154, 1125, 1053, 1004, 826, 700; m/z found: 394.18 [M+H$^+$]; HRMS (FAB) calcd for C$_{23}$H$_{23}$NO$_5$: 393.1576; found 393.1568.

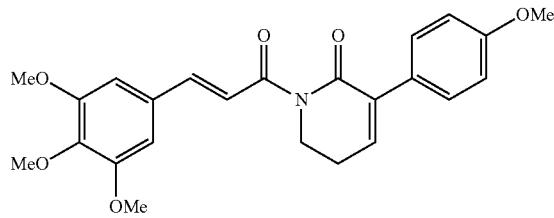 [SMILES: COc1ccc(C2=CCCN(C(=O)/C=C/c3cc(OC)c(OC)c(OC)c3)C2=O)cc1]

(E)-3-(4-methoxyphenyl)-1-(3-(3,4,5-trimethoxyphenyl)prop-2-enoyl)-5,6-dihydropyridin-2(1H)-one Yield: 86%; $^1$H NMR (300 MHz, CDCl$_3$) δ 7.69 (d, J=15.6, 1H), 7.43 (d, J=15.3 Hz, 1H), 7.34 (d, J=8.7 Hz, 2H), 6.97 (t, J=4.5 Hz, 1H), 6.92 (d, J=8.7 Hz, 2H), 6.78 (s, 2H), 4.12 (t, J=6.3 Hz, 2H), 3.86 (s, 9H), 3.82 (s, 3H), 2.57-2.63 (m, 2H); $^{13}$C NMR (75 MHz, CDCl$_3$) δ 169.3, 166.0, 159.6, 153.3, 143.8, 141.2, 137.5, 136.5, 130.7, 129.9, 128.4, 121.2, 113.7, 105.7, 60.9, 56.2, 55.32, 42.1, 25.0; IR (cm–1) 2937, 2837, 1679, 1606, 1580, 1504, 1464, 1416, 1343, 1317, 1278, 1246, 1154, 1126, 1044, 1027, 1004, 879, 830, 802, 781, 734, 693, 598; m/z found: 424.52 [M+H⁺]; HRMS (FAB) calcd for $C_{24}H_{25}NO_6$: 423.1682; found 423.1677.

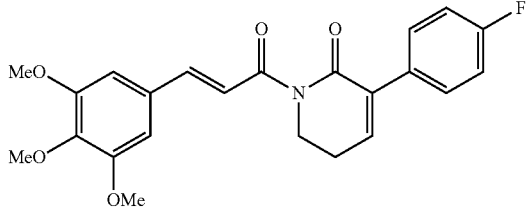 [SMILES: COc1cc(/C=C/C(=O)N2CCC=C(c3ccc(F)cc3)C2=O)cc(OC)c1OC]

(E)-3-(4-fluorophenyl)-1-(3-(3,4,5-trimethoxyphenyl)prop-2-enoyl)-5,6-dihydropyridin-2(1H)-one Yield: 85%; ¹H NMR (300 MHz, CDCl₃) δ 7.70 (d, J=15.6 Hz, 1H), 7.36-7.44 (m, 3H), 7.02-7.10 (m, 2H), 7.01 (d, J=4.5 Hz, 1H), 6.78 (s, 2H), 4.12 (t, J=6.3 Hz, 2H), 3.86 (s, 9H), 2.59-2.65 (m, 2H); ¹³C NMR (75 MHz, CDCl₃) δ 169.3, 165.7, 162.2 (d, J=247.6 Hz, 1C), 153.3, 144.0, 142.4, 138.0 (d, J=8.65 Hz, 1C), 136.1, 131.9 (d, J=3.38 Hz, 1C), 130.6, 130.4, 121.1, 115.1 (d, J=21.4 Hz, 1C), 105.7, 60.9, 56.2, 42.1, 25.0; IR (thin film, cm⁻¹) 2939, 2839, 1678, 1613, 1580, 1504, 1464, 1417, 1385, 1349, 1316, 1266, 1224, 1152, 1124, 1052, 1001, 930, 860, 880, 833, 812, 781, 730, 701; m/z found: 412.16 [M+H⁺]; HRMS (FAB) calcd for $C_{23}H_{22}FNO_5$: 411.1482; found 411.1478.

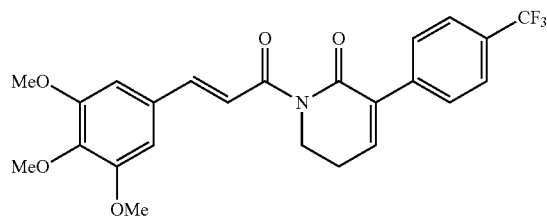 [SMILES: COc1cc(/C=C/C(=O)N2CCC=C(c3ccc(C(F)(F)F)cc3)C2=O)cc(OC)c1OC]

(E)-3-(4-(trifluoromethyl)phenyl)-1-(3-(3,4,5-trimethoxyphenyl)prop-2-enoyl)-5,6-dihydropyridin-2(1H)-one Yield: 99%; ¹H NMR (300 MHz, CDCl₃) δ 7.71 (d, J=15.3 Hz, 1H), 7.65 (d, J=8.4 Hz, 1H), 7.53 (d, J=8.4 Hz, 1H), 7.41 (d, J=15.3 Hz, 1H), 7.09 (t, J=4.5 Hz, 1H), 6.78 (s, 2H), 4.15 (t, J=6. Hz, 2H), 3.86 (s, 9H), 2.63-2.69 (m, 2H); ¹³C NMR (75 MHz, CDCl₃) δ 169.2, 165.3, 153.4, 144.3, 143.6, 140.2, 139.5, 136.1, 130.5, 130.4, 127.9 (q, J=302.0 Hz, 1C), 129.2, 125.1 (q, J=3.6 Hz, 1C), 120.9, 105.7, 60.9, 56.2, 42.0, 25.1; IR (thin film, cm⁻¹) 2941, 1677, 1615, 1580, 1504, 1465, 1417, 1386, 1347, 1321, 1298, 1275, 1243, 1162, 1121, 1068, 1053, 1037, 1016, 1002, 934, 907, 882, 863, 837, 782; m/z found: 462.41 [M+H⁺]; HRMS (FAB) calcd for $C_{24}H_{22}F_3NO_5$: 461.1450; found 461.1446.

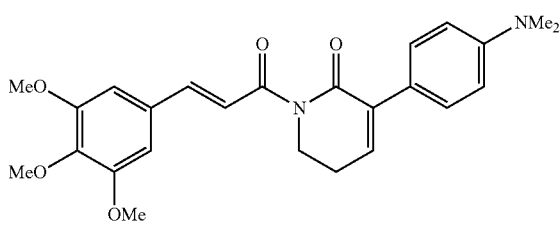 [SMILES: COc1cc(/C=C/C(=O)N2CCC=C(c3ccc(N(C)C)cc3)C2=O)cc(OC)c1OC]

(E)-3-(4-(dimethylamino)phenyl)-1-(3-(3,4,5-trimethoxyphenyl)prop-2-enoyl)-5,6-dihydropyridin-2(1H)-one Yield: 50%; ¹H NMR (300 MHz, CDCl₃) δ 7.68 (d, J=15.6 Hz, 1H), 7.44 (d, J=15.3 Hz, 1H), 7.30 (d, J=8.7 Hz, 2H), 6.94 (t, J=4.5 Hz, 1H), 6.78 (s, 2H), 6.73 (d, J=8.7 Hz, 2H), 4.11 (t, J=6.6 Hz, 2H), 3.87 (s, 9H), 2.97 (s, 6H), 2.55-2.61 (m, 2H); ¹³C NMR (75 MHz, CDCl₃) δ 169.4, 166.2, 153.3, 150.4, 143.6, 140.0, 139.8, 136.7, 130.7, 129.4, 123.8, 121.4, 112.0, 105.6, 60.9, 56.2, 42.2, 40.4, 25.0; IR (thin film, cm⁻¹) 2937, 2838, 1672, 1609, 1579, 1521, 1503, 1452, 1417, 1383, 1347, 1316, 1266, 1226, 1199, 1150, 1122, 1051, 1002, 973, 946, 876, 853, 818, 781, 730, 700; m/z found: 437.50 [M+H⁺]; HRMS (FAB) calcd for $C_{25}H_{28}N_2O_5$: 436.1998; found 436.2000.

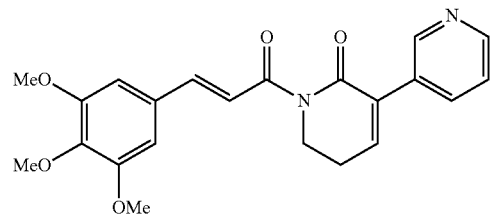 [SMILES: COc1cc(/C=C/C(=O)N2CCC=C(c3cccnc3)C2=O)cc(OC)c1OC]

(E)-3-(pyridin-3-yl)-1-(3-(3,4,5-trimethoxyphenyl)prop-2-enoyl)-5,6-dihydropyridin-2(1H)-one Yield: 45%; ¹H NMR (300 MHz, CDCl₃) δ 8.63 (d, J=1.5 Hz, 1H), 8.59 (dd, J=4.8, 1.5 Hz, 1H), 7.77-7.80 (m, 1H), 7.70 (d, J=15.6 Hz, 1H), 7.39 (d, J=15.6 Hz, 1H), 7.29-7.34 (m, 1H), 7.10 (t, J=4.5 Hz, 1H), 6.78 (s, 2H), 4.15 (t, J=6.3 Hz, 2H), 3.87 (s, 6H), 3.86 (s, 3H), 2.64-2.70 (m, 2H); ¹³C NMR (75 MHz, CDCl₃) δ 169.1, 165.3, 153.4, 149.3, 144.2, 143.6, 140.2, 136.4, 134.1, 131.8, 130.5, 122.8, 120.9, 105.7, 60.9, 56.2, 42.0, 25.1; IR (thin film, cm⁻¹) 2940, 2839, 1674, 1614, 1580, 1504, 1464, 1417, 1386, 1350, 1317, 1266, 1242, 1154, 1123, 1055, 1001, 933, 881, 856, 826, 812, 789, 774, 729, 712, 700; m/z found: 395.14 [M+H⁺]; HRMS (FAB) calcd for $C_{22}H_{22}N_2O_5$: 394.1529; found 394.1536.

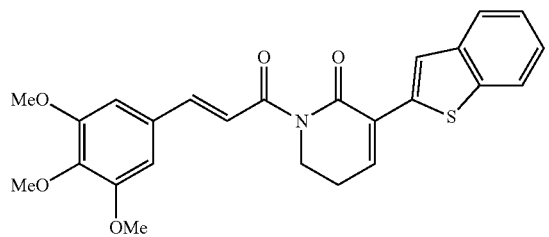 [SMILES: COc1cc(/C=C/C(=O)N2CCC=C(c3cc4ccccc4s3)C2=O)cc(OC)c1OC]

(E)-3-(benzo[b]thiophen-2-yl)-1-(3-(3,4,5-trimethoxyphenyl)prop-2-enoyl)-5,6-dihydropyridin-2(1H)-one Yield: 53%; ¹H NMR (300 MHz, CDCl₃) δ 7.62-7.75 (m, 4H), 7.38 (d, J=15.3 Hz, 1H), 7.25-7.28 (m, 3H), 6.76 (s, 2H), 4.04 (t, J=6.3 Hz, 2H), 3.83 (s, 6H), 3.81 (s, 3H), 2.57-2.62 (m, 2H); ¹³C NMR (75 MHz, CDCl₃) δ 169.2, 164.6, 153.4, 144.1, 141.9, 140.2, 139.8, 139.6, 137.1, 130.6, 130.2, 124.8, 124.4, 123.9, 123.8, 121.9, 121.1, 105.8, 60.9, 56.3, 41.7, 25.3; IR (thin film, cm⁻¹) 2935, 1674, 1612, 1579, 1503, 1456, 1433, 1417, 1350, 1315, 1271, 1242, 1150, 1123, 1000, 904, 859, 825, 728, 700; m/z found: 450.34 [M+H⁺]; HRMS (FAB) calcd for $C_{25}H_{23}NO_5S$: 449.1297; found 449.1296.

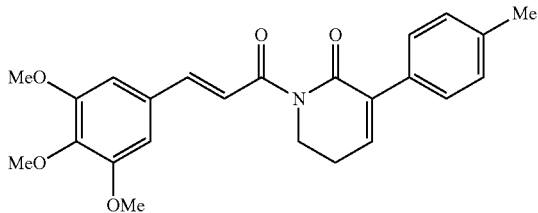 [SMILES: COc1cc(/C=C/C(=O)N2CCC=C(c3ccc(C)cc3)C2=O)cc(OC)c1OC]

(E)-3-p-tolyl-1-(3-(3,4,5-trimethoxyphenyl)prop-2-enoyl)-5,6-dihydropyridin-2(1H)-one Yield: 98%; ¹H NMR (300 MHz, CDCl₃) δ 7.69 (d, J=15.6 Hz, 1H), 7.43 (d, J=15.6 Hz, 1H), 7.29 (d, J=8.4 Hz, 2H), 7.20 (d, J=8.4 Hz, 2H), 7.00 (t, J=4.5 Hz, 1H), 6.78 (s, 2H), 4.13 (t, J=6.6 Hz, 2H), 3.87 (s, 9H), 2.58-2.63 (m, 2H), 2.37 (s, 3H); ¹³C NMR (75 MHz, CDCl₃) δ 169.3, 165.9, 153.3, 143.8, 141.7, 137.9, 137.0, 135.7, 133.1, 130.6, 128.9, 128.6, 121.2, 105.7, 60.9, 56.2, 42.1, 25.0, 21.2; IR (thin film, cm⁻¹) 2938, 2838, 1675, 1611, 1579, 1503, 1453, 1417, 1382, 1343, 1315, 1295, 1266, 1241, 1151, 1122, 1052, 1002, 973, 932, 906, 878, 857, 819, 776, 756, 731, 669; m/z found: 408.49 [M+H⁺]; HRMS (FAB) calcd for $C_{24}H_{25}NO_5$: 407.1733; found 407.1731.

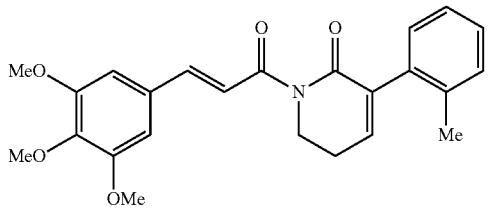

(E)-3-o-tolyl-1-(3-(3,4,5-trimethoxyphenyl)prop-2-enoyl)-5,6-dihydropyridin-2(1H)-one Yield: 98%; ¹H NMR (300 MHz, CDCl₃) δ 7.72 (d, J=15.6 Hz, 1H), 7.48 (d, J=15.5 Hz, 1H), 7.16-7.31 (m, 4H), 6.91 (t, J=4.2 Hz, 1H), 6.79 (s, 2H), 4.20 (t, J=6.3 Hz, 2H), 3.86 (s, 9H), 2.62-2.66 (m, 2H), 2.25 (s, 3H); ¹³C NMR (75 MHz, CDCl₃) δ 169.1, 165.4, 153.3, 144.2, 143.2, 140.1, 137.9, 136.4, 136.07, 130.6, 130.0, 129.6, 128.4, 125.8, 121.0, 105.7, 60.9, 56.2, 42.1, 25.0, 20.0; IR (thin film, cm⁻¹) 2939, 1677, 1613, 1580, 1504, 1384, 1454, 1417, 1341, 1316, 1274, 1242, 1152, 1124, 1101, 1053, 1002, 975, 930, 908, 881, 857, 826, 804, 788, 728, 701, 620; m/z found: 408.53 [M⁺]; HRMS (FAB) calcd for $C_{24}H_{25}NO_5$: 407.1733; found 407.1735

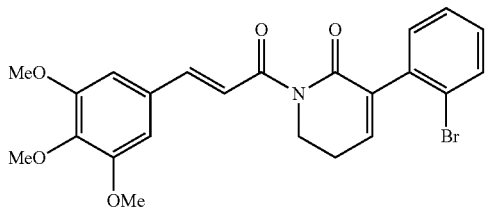 [SMILES: COc1cc(/C=C/C(=O)N2CCC=C(c3ccccc3Br)C2=O)cc(OC)c1OC]

(E)-3-(2-bromophenyl)-1-(3-(3,4,5-trimethoxyphenyl)prop-2-enoyl)-5,6-dihydropyridin-2(1H)-one Yield: 61%; ¹H NMR (300 MHz, CDCl₃) δ 7.63 (d, J=15.6 Hz, 1H), 7.55 (d, J=8.1 Hz, 1H), 7.41 (d, J=15.6 Hz, 1H), 7.28 (d, J=7.5 Hz, 1H), 7.14-7.22 (m, 2H), 6.84 (t, J=4.5 Hz, 1H), 6.70 (s, 2H), 4.13 (m, 2H), 3.79 (s, 9H), 2.53-2.59 (m, 2H); ¹³C NMR (75 MHz, CDCl₃) δ 168.9, 164.7, 153.3, 144.3, 143.6, 140.1, 138.0, 137.4, 132.6, 131.0, 130.6, 129.7, 127.5, 123.8, 121.0, 105.7, 60.9, 56.2, 41.9, 25.0; IR (thin film, cm⁻¹) 3055, 2938, 2838, 1675, 1613, 1580, 1503, 1464, 1417, 1384, 1346, 1316, 1272, 1242, 1153, 1124, 1052, 1021, 1002, 930, 880, 853, 826, 783, 755, 729, 700, 662, 634, 619, 606; m/z found: 472.41 [M+H⁺ (⁷⁹Br)]; HRMS (FAB) calcd for $C_{23}H_{22}^{79}BrNO_5$: 471.0681; found 471.0680.

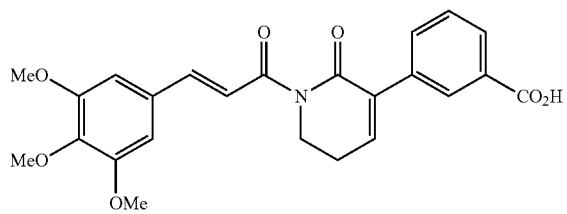 [SMILES: COc1cc(/C=C/C(=O)N2CCC=C(c3cccc(C(=O)O)c3)C2=O)cc(OC)c1OC]

(E)-3-(2-oxo-1-(3-(3,4,5-trimethoxyphenyl)prop-2-enoyl)-1,2,5,6-tetrahydropyridin-3-yl)benzoic acid Yield: 30%; ¹H NMR (300 MHz, CDCl₃) δ 8.02-8.07 (m, 2H), 7.60-7.66 (m, 2H), 7.43 (t, J=7.8 Hz, 1H), 7.34 (d, J=15.3 Hz, 1H), 7.04 (t, J=3.9 Hz, 1H), 6.72 (s, 2H), 4.09 (t, J=6.6 Hz, 2H), 3.79 (s, 9H), 2.56-2.62 (m, 2H); m/z found: 437.91 [M+H⁺]; HRMS (FAB) calcd For $C_{24}H_{23}NO_7$: 437.1475; found 437.1473.

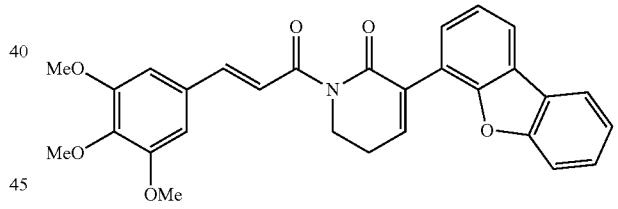

Yield: 77%; ¹H NMR (300 MHz, CDCl₃) δ 7.94-7.97 (m, 2H), 7.72 (d, J=15.6 Hz, 1H), 7.56 (d, J=8.1 Hz, 1H), 7.32-7.49 (m, 6H), 6.76 (s, 2H), 4.26 (t, J=6.3 Hz, 2H), 3.85 (s, 3H), 3.83 (s, 6H), 2.72-2.78 (m, 2H); ¹³C NMR (75 MHz, CDCl₃) δ 169.2, 165.0, 156.0, 153.7, 153.3, 144.8, 144.0, 140.0, 132.4, 130.6, 128.1, 127.2, 124.5, 124.1, 122.8, 122.6, 121.1, 120.7, 120.5, 111.7, 105.6, 60.9, 56.2, 42.0, 25.2; IR (thin film, cm⁻¹) 3055, 2939, 1681, 1613, 1581, 1504, 1464, 1451, 1416, 1385, 1349, 1317, 1265, 1242, 1190, 1153, 1125, 1086, 1053, 1002, 936, 902, 867, 838, 827, 802, 776, 755, 729, 701, 624; m/z found: 484.45 [M+H⁺]; HRMS (FAB) calcd For $C_{29}H_{25}NO_6$: 483.1682; found 483.1682.

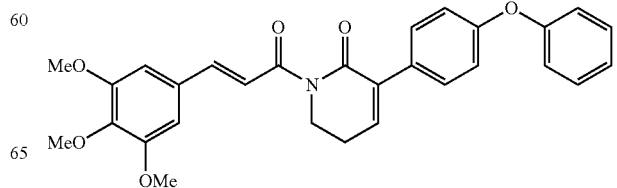

(E)-3-(4-phenoxyphenyl)-1-(3-(3,4,5-trimethoxyphenyl)prop-2-enoyl)-5,6-dihydropyridin-2(1H)-one Yield: 99%; $^1$H NMR (300 MHz, CDCl$_3$) δ 7.68 (d, J=15.3 Hz, 1H), 7.46 (d, J=15.6 Hz, 1H), 7.16-7.37 (m, 5H), 7.06 (t, J=7.5 Hz, 1H), 6.95-6.99 (m, 4H), 6.78 (s, 2H), 3.97 (t, J=6.3 Hz, 2H), 3.89 (s, 3H), 3.88 (s, 6H), 2.49-2.55 (m, 2H); $^{13}$C NMR (75 MHz, CDCl$_3$) δ 169.0, 165.0, 157.4, 154.5, 153.3, 143.8, 143.3, 140.0, 134.5, 131.1, 130.7, 129.7, 129.6, 128.3, 123.6, 123.0, 121.2, 119.3, 118.4, 105.7, 60.9, 56.2, 41.8, 25.0; IR (thin film, cm$^{-1}$) 2938, 1678, 1613, 1579, 1504, 1484, 1465, 1449, 1417, 1384, 1348, 1316, 1272, 1224, 1152, 1124, 1099, 1052, 1001, 930, 908, 886, 864, 847, 826, 801, 784, 753, 730, 693; m/z found: 486.54 [M+H$^+$]; HRMS (FAB) calcd for C$_{29}$H$_{27}$NO$_6$: 485.1838; found 485.1838.

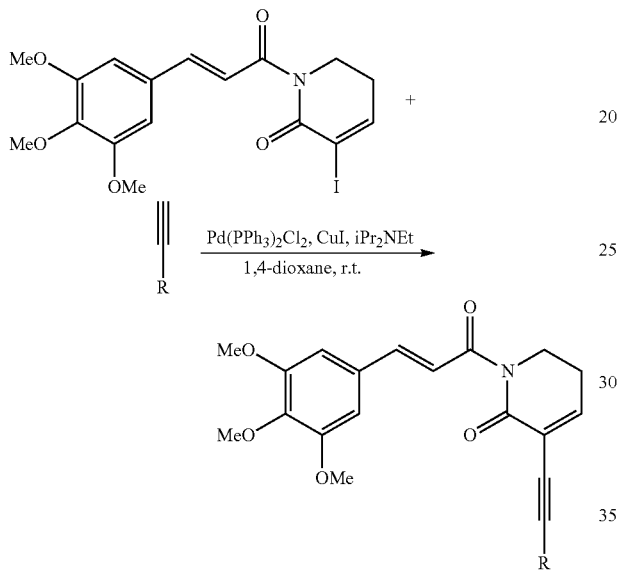

General Procedure for Sonogashira Coupling: A flame dried flask was charged with bis-(triphenylphosphine)palladium (II) dichloride (15.8 mg, 23.0 mop, iodopiperlongumine (100 mg, 0.23 mmol), 1,4-dioxane (2.20 mL) and DIPEA (0.11 mL, 0.68 mmol) via syringe. After the resulting solution was carefully degassed with nitrogen for 10 min, copper iodide (6.45 mg, 34.0 μmol) and one of the selected alkynes (0.68 mmol) were added. The resulting solution was stirred for 2-12 h (using TLC and LC-MS to monitor the reaction process). Upon completion, the reaction was diluted with saturated aqueous NH$_4$Cl, extracted with CH$_2$Cl$_2$ (3×5 mL) and dried over MgSO$_4$. The solution was filtered, concentrated and then purified by flash chromatography (hexane/ethyl acetate=60/40 to 40/60) to afford the desired compound.

(E)-3-(phenylethynyl)-1-(3-(3,4,5-trimethoxyphenyl)prop-2-enoyl)-5,6-dihydropyridin-2(1H)-one Yield: 84%; $^1$H NMR (300 MHz, CDCl$_3$) δ 7.72 (d, J=15.6 Hz, 1H), 7.51-7.55 (m, 2H), 7.48 (d, J=15.6 Hz, 1H); 7.28-7.35 (m, 4H), 6.83 (s, 2H), 4.08 (t, J=6.3 Hz, 2H), 3.90 (s, 6H), 3.89 (s, 3H), 2.57-2.63 (m, 2H); $_{13}$C NMR (75 MHz, CDCl$_3$) δ 168.7, 163.6, 153.3, 148.7, 144.4, 140.1, 131.8, 130.5, 128.7, 128.3, 122.3, 121.4, 120.7, 105.7, 92.2, 83.4, 60.9, 56.2, 41.5, 25.2; IR (thin film, cm$^{-1}$) 2937, 2839, 1678, 1614, 1580, 1503, 1464, 1418, 1388, 1350, 1318, 1274, 1243, 1168, 1125, 1085, 1050, 1003, 919, 903, 861, 826, 758, 734, 692, 670; m/z found: 418.54 [M+H$^+$]; HRMS (FAB) calcd for C$_{25}$H$_{23}$NO$_5$: 417.1576; found 417.1572.

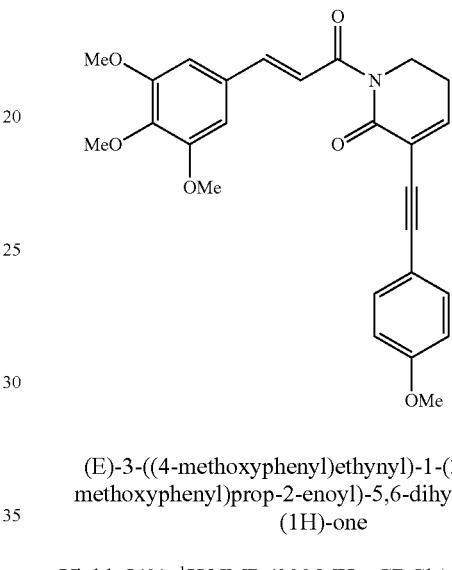

(E)-3-((4-methoxyphenyl)ethynyl)-1-(3-(3,4,5-trimethoxyphenyl)prop-2-enoyl)-5,6-dihydropyridin-2(1H)-one Yield: 54%; $^1$H NMR (300 MHz, CDCl$_3$) δ 7.62 (d, J=15.6 Hz, 1H), 7.40 (d, J=15.6 Hz, 1H), 7.39 (d, J=8.4 Hz, 2H), 7.18 (t, J=4.5 Hz, 1H), 6.78 (d, J=8.7 Hz, 2H), 6.74 (s, 2H), 3.99 (t, J=6.3 Hz, 2H), 3.82 (s, 6H), 3.80 (s, 3H), 3.73 (s, 3H), 2.48-2.54 (m, 2H); $^{13}$C NMR (75 MHz, CDCl$_3$) δ 168.8, 163.7, 159.9, 153.3, 147.9, 144.3, 140.1, 133.3, 130.5, 121.6, 120.8, 114.4, 113.9, 105.7, 92.3, 82.2, 60.9, 56.2, 55.2, 41.5, 25.2; IR (thin film, cm$^{-1}$) 2935, 2838, 1675, 1601, 1580, 1504, 1463, 1417, 1388, 1349, 1317, 1273, 1246, 1166, 1123, 1083, 1049, 1028, 1001, 925, 902, 859, 828, 791, 773, 731, 700, 667; m/z found: 448.14 [M+H$^+$]; HRMS (FAB) calcd for C$_{26}$H$_{25}$NO$_6$: 447.1682; found 447.1681.

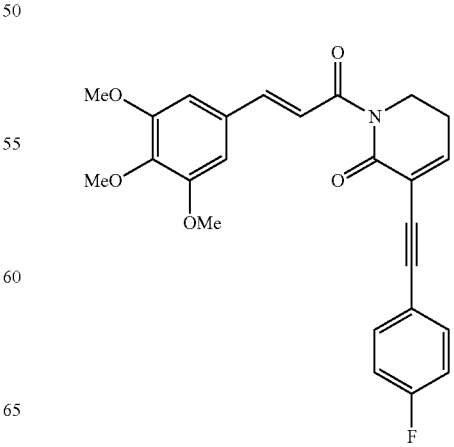

(E)-3-((4-fluorophenyl)ethynyl)-1-(3-(3,4,5-trimethoxyphenyl)prop-2-enoyl)-5,6-dihydropyridin-2(1H)-one Yield: 82%; $^1$H NMR (300 MHz, CDCl$_3$) δ 7.70 (d, J=15.5 Hz, 1H), 7.44-7.51 (m, 3H), 7.29 (t, J=4.8 Hz, 1H), 7.03 (t, J=8.7 Hz, 2H), 6.82 (s, 2H), 4.07 (t, J=6.3 Hz, 2H), 3.90 (s, 6H), 3.88 (s, 3H), 2.57-2.63 (m, 2H); $^{13}$C NMR (75 MHz, CDCl$_3$) δ 168.7, 163.5, 162.7 (d, J=248.9 Hz, 1C), 153.3, 148.8, 144.4, 140.1, 133.7 (d, J=8.4 Hz, 1C), 130.4, 121.3, 120.7, 118.4 (d, J=3.53 Hz, 1C), 115.6 (d, J=22.05 Hz, 1C), 105.7, 91.1, 83.1, 60.8, 56.2, 41.5, 25.2; IR (thin film, cm$^{-1}$) 2925, 1677, 1614, 1597, 1580, 1504, 1464, 1417, 1389, 1349, 1317, 1272, 1227, 1155, 1167, 1124, 1050, 1001, 902, 861, 835, 797, 773, 731, 701, 667, 620; m/z found: 436.15 [M+H$^+$]; HRMS (FAB) calcd for C$_{25}$H$_{22}$FNO$_5$: 435.1482; found 435.1477.

(E)-3-(cyclohexenylethynyl)-1-(3-(3,4,5-trimethoxyphenyl)prop-2-enoyl)-5,6-dihydropyridin-2(1H)-one Yield: 76%; $^1$H NMR (300 MHz, CDCl$_3$) δ 7.65 (d, J=15.6 Hz, 1H), 7.43 (d, J=15.6 Hz, 1H), 7.13 (t, J=4.5 Hz, 1H), 6.78 (s, 2H), 6.21 (s, 1H), 4.01 (t, J=6.6 Hz, 2H), 3.87 (s, 6H), 3.85 (s, 3H), 2.49-2.55 (m, 2H), 2.08-2.16 (m, 4H), 1.50-1.66 (m, 4H); $^{13}$C NMR (75 MHz, CDCl$_3$) δ 168.8, 163.7, 153.3, 147.6, 144.2, 140.0, 136.5, 130.5, 121.6, 120.8, 120.0, 105.6, 94.2, 80.8, 60.9, 56.2, 41.5, 28.9, 25.7, 25.1, 22.1, 21.3; IR (thin film, cm$^{-1}$) 2923, 2853, 1674, 1613, 1580, 1504, 1454, 1417, 1388, 1348, 1317, 1273, 1242, 1153, 1123, 1080, 1050, 1002, 974, 917, 901, 860, 825, 799, 774, 731, 701, 670; m/z found: 422.19 [M+H$^+$]; HRMS (FAB) calcd for C$_{25}$H$_{27}$NO$_5$: 421.1889; found 421.1890.

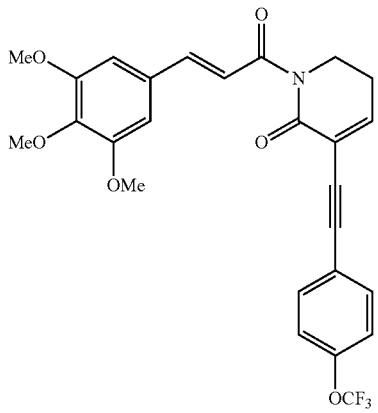 [SMILES: COc1cc(/C=C/C(=O)N2CCC=C(C#Cc3ccc(OC(F)(F)F)cc3)C2=O)cc(OC)c1OC]

(E)-3((4-(trifluoromethoxy)phenyl)ethynyl)-1-(3-(3,4,5-trimethoxyphenyl)prop-2-enoyl)-5,6-dihydropyridin-2(1H)-one Yield: 63%; $^1$H NMR (300 MHz, CDCl$_3$) δ 7.70 (d, J=15.6 Hz, 1H), 7.54 (d, J=8.7 Hz, 2H), 7.45 (d, J=15.6 Hz, 1H), 7.30 (t, J=4.5 Hz, 1H), 7.17 (d, J=8.4 Hz, 2H), 6.81 (s, 2H), 4.07 (t, J=6.3 Hz, 2H), 3.88 (s, 6H), 3.87 (s, 3H), 2.57-2.63 (m, 2H); $^{13}$C NMR (75 MHz, CDCl$_3$) δ 168.7, 163.5, 153.3, 149.2, 144.6, 140.2, 133.3, 130.4, 121.3, 121.2, 120.7, 120.6, 120.3 (q, J=256.4 Hz, 1C), 114.6, 105.7, 90.7, 84.2, 60.9, 56.2, 41.5, 25.3; IR (cm$^{-1}$) 2924, 2852, 1678, 1614, 1580, 1504, 1464, 1418, 1389, 1350, 1318, 1250, 1204, 1157, 1122, 1083, 1050, 1002, 920, 902, 854, 825, 799, 774, 734, 703, 669; m/z found: 502.14 [M+H$^+$]; HRMS (FAB) calcd For C$_{26}$H$_{22}$F$_3$NO$_6$: 501.1399; found 501.1398.

(E)-3-((2-chlorophenyl)ethynyl)-1-(3-(3,4,5-trimethoxyphenyl)prop-2-enoyl)-5,6-dihydropyridin-2(1H)-one Yield: 68%; $^1$H NMR (300 MHz, CDCl$_3$) δ 7.63 (d, J=15.3 Hz, 1H), 7.49 (dd, J=7.2, 2.1, 1H), 7.39 (d, J=15.6 Hz, 1H), 7.28-7.37 (m, 2H), 7.13-7.22 (m, 2H), 6.74 (s, 2H), 4.01 (t, J=6.3 Hz, 2H), 3.82 (s, 6H), 3.80 (s, 3H), 2.51-2.57 (m, 2H); $^{13}$C NMR (75 MHz, CDCl$_3$) δ 168.7, 163.4, 153.3, 149.6, 144.5, 140.1, 136.0, 133.5, 130.5, 129.7, 129.2, 126.4, 122.4, 121.3, 120.7, 105.7, 88.9, 88.4, 60.9, 56.2, 41.5, 25.3; IR (thin film, cm$^{-1}$) 2924, 2852, 1674, 1613, 1579, 1503, 1464, 1417, 1388, 1349, 1316, 1291, 1272, 1242, 1167, 1146, 1122, 1086, 1053, 1001, 974, 955, 925, 902, 861, 825, 755, 732, 701, 680; m/z found: 452.13 [M+H$^+$]; HRMS (FAB) calcd for C$_{25}$H$_{22}$ClNO$_5$: 451.1187; found 451.1187.

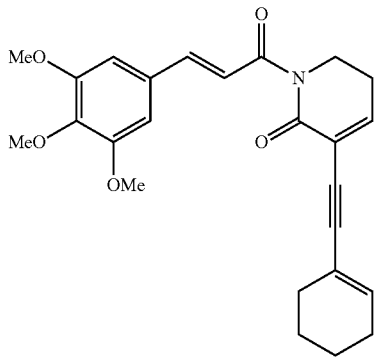 [SMILES: COc1cc(/C=C/C(=O)N2CCC=C(C#CC3=CCCCC3)C2=O)cc(OC)c1OC]

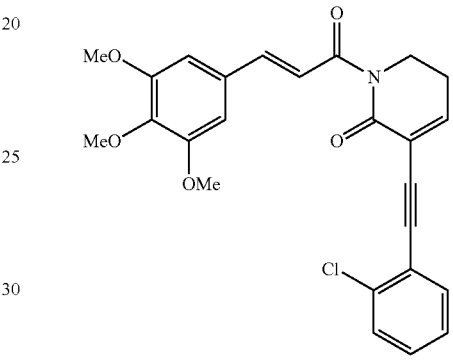

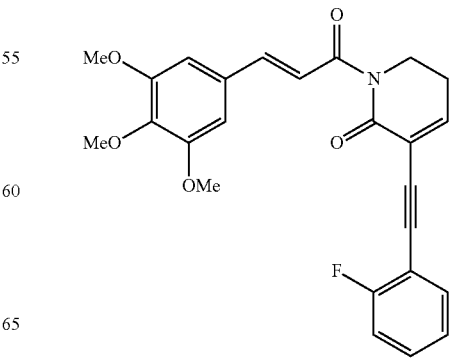

(E)-3-((2-fluorophenyl)ethynyl)-1-(3-(3,4,5-trimethoxyphenyl)prop-2-enoyl)-5,6-dihydropyridin-2(1H)-one Yield: 87%; $^1$H NMR (300 MHz, CDCl$_3$) δ 7.69 (d, J=15.6, 1H), 7.48-7.53 (m, 1H), 7.46 (d, J=15.3, 1H), 7.26-7.34 (m, 2H), 7.05-7.12 (m, 2H), 6.80 (s, 2H), 4.07 (t, J=6.6 Hz, 2H), 3.88 (s, 6H), 3.86 (s, 3H), 2.57-2.63 (m, 2H); $^{13}$C NMR (75 MHz, CDCl$_3$) δ 168.7, 163.4, 162.7 (d, J=250.65 Hz, 1C), 153.3, 149.5, 144.5, 140.2, 133.6, 130.6, 130.5, 123.9 (d, J=3.68 Hz, 1C), 121.3, 120.7, 115.5 (d, J=20.70 Hz, 1C), 111.1 (d, J=15.6 Hz, 1C), 105.7, 88.3 (d, J=3.23 Hz, 1C), 85.5, 60.9, 56.2, 41.5, 25.3; IR (thin film, cm$^{-1}$) 2924, 2852, 1679, 1614, 1580, 1504, 1491, 1451, 1417, 1387, 1349, 1317, 1273, 1242, 1168, 1154, 1124, 1103, 1081, 1050, 1001, 974, 925, 902, 862, 828, 797, 758, 731, 701; m/z found: 435.15 [M$^+$]; HRMS (FAB) calcd for C$_{25}$H$_{22}$FNO$_5$: 435.1482; found 435.1483.

(E)-3-(cyclopentylethynyl)-1-(3-(3,4,5-trimethoxyphenyl)prop-2-enoyl)-5,6-dihydropyridin-2(1H)-one Yield: 76%; $^1$H NMR (300 MHz, CDCl$_3$) δ 7.65 (d, J=15.6 Hz, 1H), 7.43 (d, J=15.3 Hz, 1H), 7.10 (t, J=4.5 Hz, 1H), 6.78 (s, 2H), 3.99 (t, J=6.3 Hz, 2H), 3.87 (s, 6H), 3.85 (s, 3H), 2.80 (p, J=7.5 Hz, 1H), 2.46-2.53 (m, 2H), 1.95-2.02 (m, 2H), 1.54-1.70 (m, 6H); $^{13}$C NMR (75 MHz, CDCl$_3$) δ 168.8, 164.0, 153.2, 147.4, 144.2, 140.0, 130.5, 121.6, 120.9, 105.6, 97.9, 74.2, 60.9, 56.2, 41.6, 33.7, 30.6, 25.0; IR (thin film, cm$^{-1}$) 2923, 2869, 1674, 1614, 1579, 1504, 1453, 1417, 1386, 1316, 1273, 1244, 1152, 1122, 1051, 1002, 973, 932, 897, 857, 824, 775, 732, 701, 669; m/z found: 410.45 [M+H$^+$]; HRMS (FAB) calcd for C$_{24}$H$_{27}$NO$_5$: 409.1899; found 409.1883.

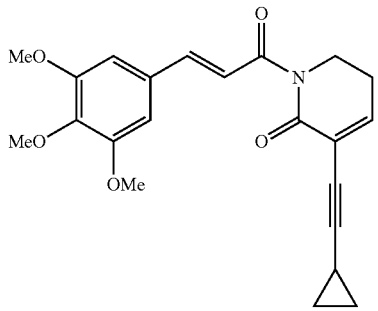 [SMILES: COc1cc(/C=C/C(=O)N2CCC=C(C#CC3CC3)C2=O)cc(OC)c1OC]

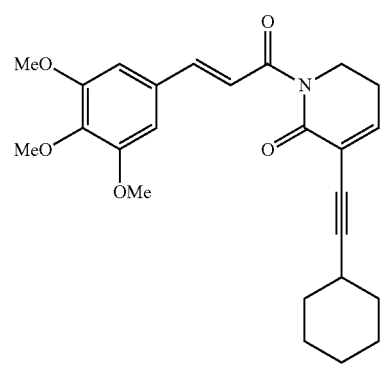

(E)-3-(cyclopropylethynyl)-1-(3-(3,4,5-trimethoxyphenyl)prop-2-enoyl)-5,6-dihydropyridin-2(1H)-one Yield: 68%; $^1$H NMR (300 MHz, CDCl$_3$) δ 7.65 (d, J=15.6 Hz, 1H), 7.42 (d, J=15.6 Hz, 1H), 7.09 (t, J=4.5 Hz, 1H), 6.78 (s, 2H), 3.99 (d, J=6.3 Hz, 2H), 3.87 (s, 6H), 3.85 (s, 3H), 2.46-2.52 (m, 2H), 1.36-1.47 (m, 1H), 0.75-0.88 (m, 4H); $^{13}$C NMR (75 MHz, CDCl$_3$) δ 168.8, 164.0, 153.3, 147.6, 144.2, 140.1, 130.5, 121.5, 120.8, 105.6, 96.7, 69.9, 60.9, 56.2, 41.5, 25.0, 8.7, 0.1; IR (thin film, cm$^{-1}$) 2939, 1684, 1615, 1581, 1504, 1464, 1418, 1389, 1319, 1276, 1246, 1166, 1155, 1125, 1083, 1051, 1003, 931, 892, 858, 826, 775, 734, 621; m/z found: 382.42 [M+H$^+$]; HRMS (FAB) calcd for C$_{22}$H$_{23}$NO$_5$: 381.1576; found 381.1570.

(E)-3-(cyclohexylethynyl)-1-(3-(3,4,5-trimethoxyphenyl)prop-2-enoyl)-5,6-dihydropyridin-2(1H)-one Yield: 70%; $^1$H NMR (300 MHz, CDCl$_3$) δ 7.65 (d, J=15.6 Hz, 1H), 7.42 (d, J=15.6 Hz, 1H), 7.11 (t, J=4.5 Hz, 1H), 6.78 (s, 2H), 4.00 (t, J=6.3 Hz, 2H), 3.87 (s, 6H), 3.85 (s, 3H), 2.46-2.57 (m, 3H), 1.28-1.90 (m, 10H); $^{13}$C NMR (75 MHz, CDCl$_3$) δ 168.8, 164.0, 153.3, 147.5, 144.1, 140.0, 130.5, 121.6, 120.9, 105.6, 97.6, 74.7, 60.8, 56.2, 41.6, 32.4, 29.6, 25.7, 25.0, 24.8; IR (thin film, cm$^{-1}$) 2928, 2852, 1677, 1614, 1580, 1504, 1450, 1417, 1386, 1348, 1317, 1274, 1153, 1124, 1052, 1003, 976, 931, 889, 857, 825, 776, 733, 700; m/z found: 424.51 [M+H$^+$]; HRMS (FAB) calcd for C$_{25}$H$_{29}$NO$_5$: 423.2046; found 423.2049.

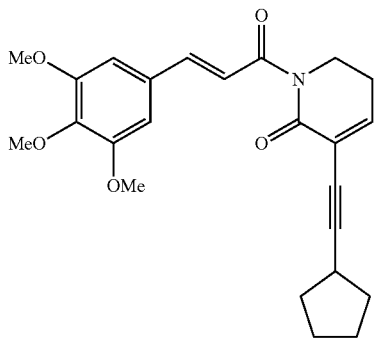 [SMILES: COc1cc(/C=C/C(=O)N2CCC=C(C#CC3CCCC3)C2=O)cc(OC)c1OC]

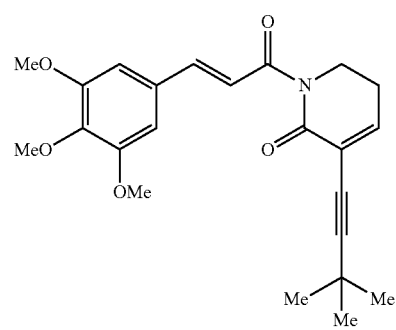 [SMILES: COc1cc(/C=C/C(=O)N2CCC=C(C#CC(C)(C)C)C2=O)cc(OC)c1OC]

(E)-3-(3,3-dimethylbut-1-ynyl)-1-(3-(3,4,5-trimethoxyphenyl)prop-2-enoyl)-5,6-dihydropyridin-2(1H)-one Yield: 88%; $^1$H NMR (300 MHz, CDCl$_3$) δ 7.63 (d, J=15.6 Hz, 1H), 7.40 (d, J=15.6 Hz, 1H), 7.09 (t, J=4.5 Hz, 1H), 6.77 (s, 2H), 3.97 (t, J=6.3 Hz, 2H), 3.86 (s, 6H), 3.83 (s, 3H), 2.44-2.50 (m, 2H), 1.26 (s, 9H); $^{13}$C NMR (75 MHz, CDCl$_3$) δ 168.8, 163.8, 153.2, 147.5, 144.0, 140.0, 130.5, 121.4, 120.9, 105.6, 101.5, 73.2, 60.8, 56.1, 41.6, 30.7, 27.9, 25.0; IR (thin film, cm$^{-1}$) 2968, 1673, 1614, 1580, 1504, 1454, 1417, 1386, 1345, 1317, 1273, 1241, 1152, 1123, 1092, 1051, 1002, 976, 928, 904, 868, 849, 825, 795, 774, 732, 701, 666; m/z found: 398.46 [M+H$^+$]; HRMS (FAB) calcd for C$_{23}$H$_{27}$NO$_5$: 397.1889; found 397.1882.

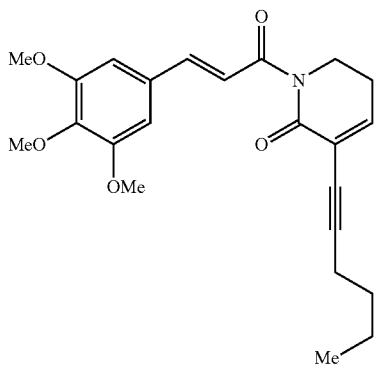 [SMILES: CCCCC#CC1=CCCN(C(=O)/C=C/c2cc(OC)c(OC)c(OC)c2)C1=O]

(E)-3-(hex-1-ynyl)-1-(3-(3,4,5-trimethoxyphenyl)prop-2-enoyl)-5,6-dihydropyridin-2(1H)-one Yield: 59%; $^1$H NMR (300 MHz, CDCl$_3$) δ 7.66 (d, J=15.6 Hz, 1H), 7.43 (d, J=15.6 Hz, 1H), 7.11 (t, J=4.5 Hz, 1H), 6.78 (s, 2H), 4.00 (t, J=6.3 Hz, 2H), 3.87 (s, 6H), 3.86 (s, 3H), 2.47-2.53 (m, 2H), 2.39 (t, J=6.9 Hz, 2H), 1.38-1.60 (m, 4H), 0.90 (t, J=7.2 Hz, 3H); $^{13}$C NMR (75 MHz, CDCl$_3$) δ 168.8, 164.1, 153.3, 147.6, 144.2, 140.1, 130.5, 121.6, 120.8, 105.6, 93.8, 74.7, 60.9, 56.2, 41.5, 30.5, 25.0, 22.0, 19.1, 13.5; IR (cm$^{-1}$) 2939, 2843, 1668, 1592, 1511, 1452, 1423, 1383, 1341, 1318, 1297, 1244, 1211, 1157, 1182, 1140, 1109, 1053, 1038, 989, 913, 862, 820, 801, 734, 700, 673, 636, 594; m/z found: 398.47 [M+H$^+$]; HRMS (FAB) calcd for C$_{23}$H$_{27}$NO$_5$: 397.1889; found 397.1882.

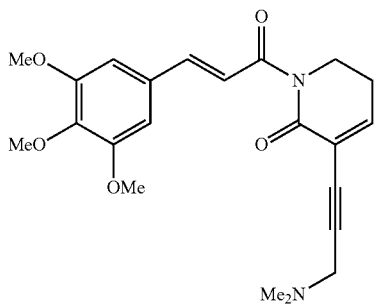 [SMILES: COc1cc(/C=C/C(=O)N2CCC=C(C#CCN(C)C)C2=O)cc(OC)c1OC]

(E)-3-(3-(dimethylamino)prop-1-ynyl)-1-(3-(3,4,5-trimethoxyphenyl)prop-2-enoyl)-5,6-dihydropyridin-2(1H)-one Yield: 42%; $^1$H NMR (300 MHz, CDCl$_3$) δ 7.67 (d, J=15.6 Hz, 1H), 7.41 (d, J=15.3 Hz, 1H), 7.20 (t, J=4.5 Hz, 1H), 6.79 (s, 2H), 4.03 (t, J=6.6 Hz, 2H), 3.88 (s, 6H), 3.86 (s, 3H), 3.45 (s, 2H), 2.51-2.56 (m, 2H), 2.33 (s, 6H); $^{13}$C NMR (75 MHz, CDCl$_3$) δ 168.7, 163.8, 153.3, 148.6, 144.4, 140.1, 130.5, 121.2, 120.7, 105.7, 88.1, 79.4, 60.9, 56.2, 48.5, 44.2, 41.5, 25.1; IR (thin film, cm$^{-1}$) 2940, 1675, 1614, 1580, 1504, 1454, 1417, 1387, 1350, 1316, 1272, 1243, 1152, 1124, 1050, 1001, 929, 826, 775, 729, 700; m/z found: 399.16 [M+H$^+$]; Compound decomposes slowly at room temperature.

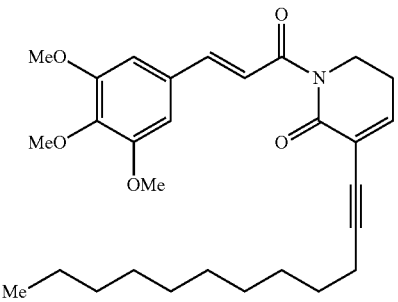 [SMILES: CCCCCCCCCCC#CC1=CCCN(C(=O)/C=C/c2cc(OC)c(OC)c(OC)c2)C1=O]

(E)-3-(dodec-1-ynyl)-1-(3-(3,4,5-trimethoxyphenyl)prop-2-enoyl)-5,6-dihydropyridin-2(1H)-one Yield: 58%; $^1$H NMR (300 MHz, CDCl$_3$) δ 7.65 (d, J=15.3 Hz, 1H), 7.43 (d, J=15.6 Hz, 1H), 7.11 (t, J=4.5 Hz, 1H), 6.78 (s, 2H), 4.00 (t, J=6.3 Hz, 2H), 3.87 (s, 6H), 3.85 (s, 3H), 2.47-2.53 (m, 2H), 2.37 (t, J=7.2 Hz, 2H), 1.51-1.60 (m, 2H), 1.23-1.38 (s, 14H), 0.84 (t, J=6.9 Hz, 3H); $^{13}$C NMR (75 MHz, CDCl$_3$) δ 168.7, 164.0, 153.3, 147.6, 144.2, 140.0, 130.5, 121.6, 120.8, 105.6, 93.8, 74.6, 60.8, 56.2, 41.5, 31.8, 29.5, 29.4, 29.2, 29.0, 28.9, 28.5, 25.0, 22.6, 19.4, 14.0; IR (thin film, cm$^{-1}$) 2924, 2853, 1675, 1615, 1580, 1504, 1464, 1417, 1386, 1350, 1317, 1274, 1243, 1225, 1153, 1124, 1100, 1050, 1004, 977, 825, 775, 733, 702, 620, 608; m/z found: 482.62 [M$^+$]; HRMS (FAB) calcd for C$_{29}$H$_{39}$NO$_5$: 481.2828; found 481.2827.

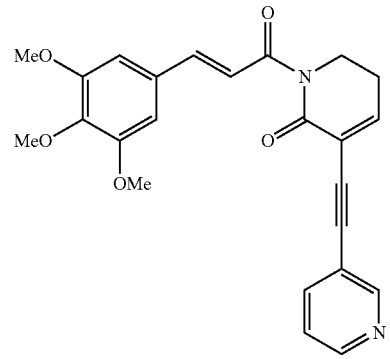 [SMILES: COc1cc(/C=C/C(=O)N2CCC=C(C#Cc3cccnc3)C2=O)cc(OC)c1OC]

(E)-3-(pyridin-3-ylethynyl)-1-(3-(3,4,5-trimethoxyphenyl)prop-2-enoyl)-5,6-dihydropyridin-2(1H)-one Yield: 82%; $^1$H NMR (300 MHz, CDCl$_3$) δ 8.76 (s, 1H), 8.56 (d, J=4.5 Hz, 1H), 7.82 (d, J=7.8 Hz, 1H), 7.72 (d, J=15.6 Hz, 1H), 7.47 (d, J=15.3 Hz, 1H), 7.36 (t, J=4.5 Hz, 1H), 7.29 (t, J=4.8 Hz, 1H), 6.82 (s, 2H), 4.09 (t, J=6.3 Hz, 2H), 3.90 (s, 6H), 3.88 (s, 3H), 2.61-2.66 (m, 2H); $^{13}$C NMR (75 MHz, CDCl$_3$) δ 168.7, 163.3, 153.3, 152.3, 149.7, 149.0, 144.6, 140.2, 138.6, 130.4, 122.9, 121.1, 120.6, 119.6, 105.7, 88.7, 86.6, 60.9, 56.2, 41.4, 25.3; IR (thin film, cm$^{-1}$) 2939, 2839, 1681, 1615, 1581, 1504, 1465, 1418, 1351, 1319, 1275, 1170, 1125, 1022, 1003, 826, 774, 705; HRMS (FAB) calcd for C$_{24}$H$_{22}$N$_2$O$_5$: 418.1529; found 418.1533.

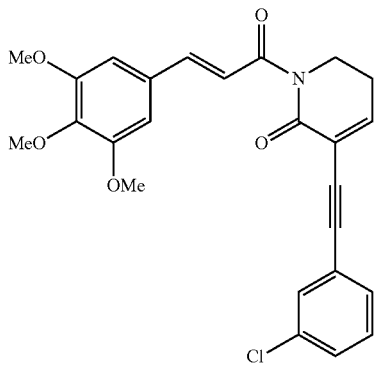 [SMILES: COc1cc(/C=C/C(=O)N2CCC=C(C#Cc3cccc(Cl)c3)C2=O)cc(OC)c1OC]

(E)-3-((3-chlorophenyl)ethynyl)-1-(3-(3,4,5-tri-methoxyphenyl)prop-2-enoyl)-5,6-dihydropyridin-2(1H)-one Yield: 81%; $^1$H NMR (300 MHz, CDCl$_3$) δ 7.71 (d, J=15.3 Hz, 1H), 7.39-7.52 (m, 3H), 7.24-7.33 (m, 3H), 6.82 (s, 2H), 4.08 (t, J=6.6 Hz, 2H), 3.90 (s, 6H), 3.88 (s, 3H), 2.59-2.64 (m, 2H); $^{13}$C NMR (75 MHz, CDCl$_3$) δ 168.7, 163.4, 153.3, 149.3, 144.6, 140.2, 134.2, 131.6, 130.4, 129.9, 129.5, 129.0, 124.1, 121.2, 120.6, 105.7, 90.7, 84.6 60.9, 56.2, 41.5, 25.3; IR (thin film, cm$^{-1}$) 2936, 1679, 1615, 1581, 1504, 1465, 1418, 1388, 1350, 1319, 1275, 1243, 1170, 1147, 1126, 1003, 826, 787; m/z found: 452.13 [M+H$^+$]; HRMS (FAB) calcd for C$_{25}$H$_{22}$ClNO$_5$: 451.1187; found 451.1182.

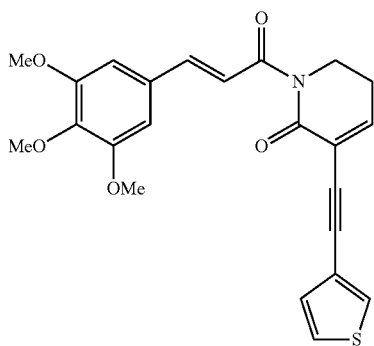 [SMILES: COc1cc(/C=C/C(=O)N2CCC=C(C#Cc3ccsc3)C2=O)cc(OC)c1OC]

(E)-3-(thiophen-3-ylethynyl)-1-(3-(3,4,5-trimethoxyphenyl)prop-2-enoyl)-5,6-dihydropyridin-2(1H)-one Yield: 70%; $^1$H NMR (300 MHz, CDCl$_3$) δ 7.71 (d, J=15.3 Hz, 1H), 7.56 (d, J=2.1 Hz, 1H), 7.48 (d, J=15.6 Hz, 1H), 7.28-7.30 (m, 2H), 7.19 (d, J=5.1 Hz, 1H), 6.82 (s, 2H), 4.08 (t, J=6.3 Hz, 2H), 3.90 (s, 6H), 3.88 (s, 3H), 2.57-2.62 (m, 2H); $^{13}$C NMR (75 MHz, CDCl$_3$) δ 168.6, 163.6, 153.3, 148.5, 144.5, 140.2, 130.5, 129.8, 129.6, 125.4, 121.5, 121.4, 120.7, 105.7, 87.4, 83.0, 60.9, 56.2, 41.5, 25.3; IR (thin film, cm$^{-1}$) 3104, 2935, 2829, 1673, 1613, 1579, 1503, 1463, 1417, 1385, 1350, 1316, 1274, 1242, 1153, 1121, 1049, 1000, 971, 857, 824, 785; HRMS (FAB) calcd for C$_{23}$H$_{21}$NO$_5$S: 423.1140; found 423.1137.

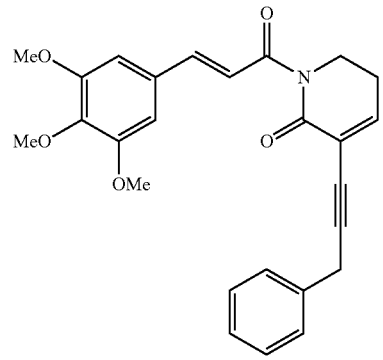 [SMILES: COc1cc(/C=C/C(=O)N2CCC=C(C#CCc3ccccc3)C2=O)cc(OC)c1OC]

(E)-3-(3-phenylprop-1-ynyl)-1-(3-(3,4,5-trimethoxyphenyl)prop-2-enoyl)-5,6-dihydropyridin-2(1H)-one Yield: 43%; $^1$H NMR (300 MHz, CDCl$_3$) δ 7.70 (d, J=15.6 Hz, 1H), 7.46 (d, J=15.6 Hz, 1H), 7.24-7.40 (m, 5H), 7.20 (d, J=4.8 Hz, 1H), 6.81 (s, 2H), 4.04 (t, J=6.3 Hz, 2H), 3.89 (s, 6H), 3.88 (s, 3H), 3.83 (s, 2H), 2.51-2.56 (m, 2H); $^{13}$C NMR (75 MHz, CDCl$_3$) δ 168.8, 164.0, 153.3, 148.3, 144.4, 140.1, 136.1, 130.5, 128.5, 127.9, 126.7, 121.4, 120.8, 105.7, 90.9, 76.8, 60.9, 56.2, 41.5, 25.7, 25.1; HRMS (FAB) calcd for C$_{26}$H$_{25}$NO$_5$: 431.1733; found 431.1733.

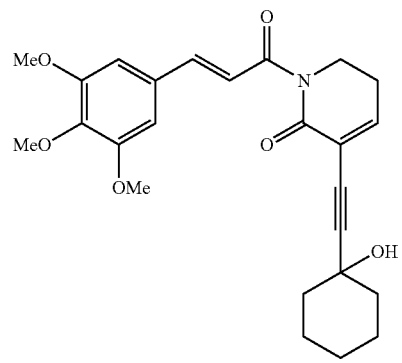 [SMILES: COc1cc(/C=C/C(=O)N2CCC=C(C#CC3(O)CCCCC3)C2=O)cc(OC)c1OC]

(E)-3-((1-hydroxycyclohexyl)ethynyl)-1-(3-(3,4,5-trimethoxyphenyl)prop-2-enoyl)-5,6-dihydropyridin-2(1H)-one Yield: 95%; $^1$H NMR (300 MHz, CDCl$_3$) δ 7.64 (d, J=15.6 Hz, 1H), 7.36 (d, J=15.3 Hz, 1H), 7.15 (d, J=4.5 Hz, 1H), 6.78 (s, 2H), 3.98 (t, J=6.3 Hz, 2H), 3.87 (s, 6H), 3.85 (s, 3H), 3.04 (br, 1H), 2.47-2.53 (m, 2H), 1.86-1.97 (m, 2H), 1.50-1.69 (m, 8H); $^{13}$C NMR (75 MHz, CDCl$_3$) δ 168.8, 163.6, 153.3, 148.6, 144.2, 140.1, 130.4, 120.9, 120.8, 105.7, 96.2, 78.2, 68.7, 56.2, 41.5, 39.7, 25.1, 25.06, 23.1; HRMS (FAB) calcd for C$_{25}$H$_{29}$NO$_6$: 439.1995; found 439.1994.

1-Methacryloyl-5,6-dihydropyridin-2(1H)-one $^1$H NMR (300 MHz, CHLOROFORM-d) δ 2.01 (t, J=1.2 Hz, 3H), 2.50 (tdd, J=6.4, 6.4, 4.3, 1.9 Hz, 2H), 3.89 (t, J=6.5

Hz, 2H), 5.24 (quin, J=1.4 Hz, 1H), 5.29 (t, J=0.9 Hz, 1H), 5.98 (dt, J=9.7, 1.9 Hz, 1H), 6.93 (dt, J=9.7, 4.1 Hz, 1H); $^{13}$C NMR (75 MHz, CHLOROFORM-d) δ 18.9, 24.7, 42.3, 117.6, 125.2, 142.6, 145.3, 165.1, 175.0. Exact mass (M+H)$^+$ calc'd: 166.0868; found: 166.0862.

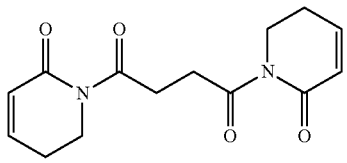 [SMILES: O=C1C=CCCN1C(=O)CCC(=O)N1CCC=CC1=O]

1,4-bis(2-Oxo-5,6-dihydropyridin-1(2H)-yl)butane-1,4-dione $^1$H NMR (500 MHz, CHLOROFORM-d) δ ppm 2.41 (dtd, J=8.5, 4.3, 4.3, 2.0 Hz, 4H), 3.26 (s, 4H), 3.95 (t, J=6.6 Hz, 4H), 5.98 (dt, J=9.8, 2.0 Hz, 2H), 6.76-6.95 (m, 2H); $^{13}$C NMR (126 MHz, CHLOROFORM-d) δ 24.5, 34.3, 40.9, 125.8, 145.1, 165.2, 175.3. Exact mass (M+Na)$^+$ calc'd: 299.1008; found 299.1013.

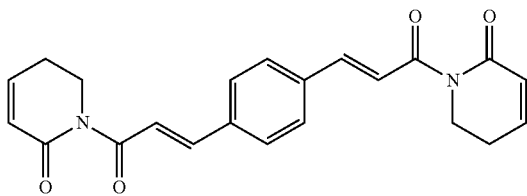 [SMILES: O=C1C=CCCN1C(=O)/C=C/c1ccc(/C=C/C(=O)N2CCC=CC2=O)cc1]

1,1'-((2E,2'E)-3,3'-(1,4-phenylene)bis(acryloyl)bis(5,6-dihydropyridin-2(1H)-one)

$^1$H NMR (500 MHz, CHLOROFORM-d) δ 2.49 (tdd, J=6.5, 6.5, 4.4, 1.7 Hz, 4H), 4.05 (t, J=6.3 Hz, 4H), 6.06 (dt, J=9.6, 1.8 Hz, 2H), 6.95 (dt, J=9.3, 4.4 Hz, 2H), 7.54 (d, J=15.6 Hz, 1H), 7.59 (s, 3H), 7.73 (d, J=15.6 Hz, 2H); $^{13}$C NMR (126 MHz, CHLOROFORM-d) δ 24.8, 41.6, 122.7, 125.8, 128.7, 136.6, 142.5, 145.5, 165.7, 168.8. Exact mass (M+Na)$^+$ calc'd: 399.1321; found 399.1319.

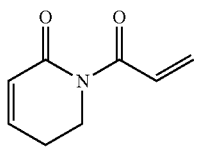

1-Acryloyl-5,6-dihydropyridin-2(1H)-one $^1$H NMR (500 MHz, CHLOROFORM-d) δ 2.47 (tdd, J=6.3, 6.3, 4.4, 2.0 Hz, 2H), 4.00 (t, J=6.6 Hz, 2H), 5.76 (dd, J=10.3, 1.5 Hz, 1H), 6.02 (dt, J=9.8, 1.7 Hz, 1H), 6.40 (dd, J=17.1, 2.0 Hz, 1H), 6.87-6.98 (m, 1H), 7.06 (dd, J=16.8, 10.5 Hz, 1H); $^{13}$C NMR (126 MHz, CHLOROFORM-d) δ 24.7, 41.4, 125.6, 128.5, 131.6, 145.7, 165.5, 168.8. Exact mass (M+H)$^+$ calc'd: 152.0712: found: 152.0699

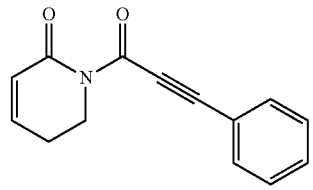 [SMILES: O=C(C#Cc1ccccc1)N1CCC=CC1=O]

1-(3-Phenylpropioloyl)-5,6-dihydropyridin-2(1H)-one $^1$H NMR (500 MHz, CHLOROFORM-d) δ 2.43-2.53 (m, 2H), 4.06 (t, J=6.3 Hz, 2H), 6.07 (dt, J=9.8, 1.5 Hz, 1H), 6.93-6.99 (m, 1H), 7.33-7.40 (m, 2H), 7.41-7.46 (m, 2H), 7.65 (d, J=7.8 Hz, 1H); $^{13}$C NMR (126 MHz, CHLOROFORM-d) δ 24.4, 40.8, 83.7, 93.3, 120.5, 125.1, 128.4, 130.4, 133.0, 145.6, 153.0, 163.7. Exact mass (M+Na)$^+$ calc'd: 248.0687; found 248.0685.

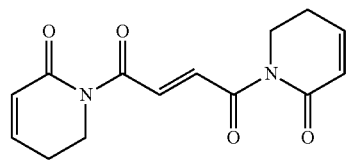 [SMILES: O=C1C=CCCN1C(=O)/C=C/C(=O)N1CCC=CC1=O]

(E)-1,4-bis(2-oxo-5,6-dihydropyridin-1(2H)-yl)but-2-ene-1,4-dione $^1$H NMR (500 MHz, CHLOROFORM-d+few drops of METHANOL-d4) δ 7.56 (s, 2H), 6.97-6.87 (m, 2H), 5.96 (d, J=9.8 Hz, 2H), 3.94 (t, J=6.5 Hz, 4H), 2.48-2.38 (m, 4H); $^{13}$C NMR (126 MHz, CHLOROFORM-d) δ 168.1, 165.6, 146.6, 134.1, 125.1, 41.6, 24.7. Exact mass (M+H)$^+$ calc'd: 275.1032, found 275.1039

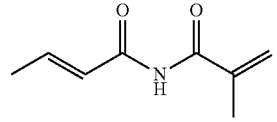

(E)-N-methacryloylbut-2-enamide $^1$H NMR (300 MHz, CHLOROFORM-d) δ 8.35 (s, 1H), 7.25-6.90 (m, 2H), 5.79 (d, J=0.6 Hz, 1H), 5.56 (dd, J=3.0, 1.4 Hz, 1H), 1.94 (s, 3H), 1.89 (dd, J=6.5, 1.2 Hz, 3H); $^{13}$C NMR (75 MHz, CHLOROFORM-d) δ 167.4, 166.8, 147.1, 140.1, 124.3, 122.7, 18.7, 18.6. Exact mass (M+Na)$^+$ calc'd: 176.0687, found 176.0690

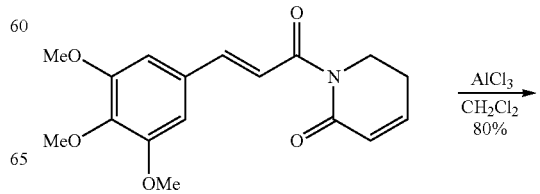

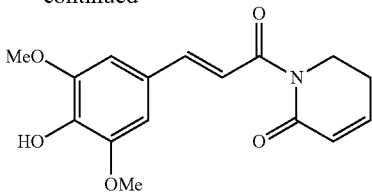

Experimental Procedure: Piperlongumine (300 mg, 0.94 mmol) was dissolved in CH$_2$Cl$_2$ (6 mL). Aluminum trichloride (874 mg, 6.55 mmol) was added portion-wise at 0° C. The reaction was then warmed to room temperature and stirred for 1 h. At the end, the reaction was quenched with saturated aqueous NH$_4$Cl solution (1 mL): the aqueous layer was extracted twice with CH$_2$Cl$_2$ (3 mL) and the organic layers were collected, washed with saturated aqueous NaCl solution (3 mL) and dried over MgSO$_4$. The solution was filtered and the solvent was evaporated under vacuum. The crude was subjected to flash chromatography (hexane/ethyl acetate=100/0 to 60/40) to afford the monodemethylated product in 80% yield. Note: It's very difficult to separate the desired product from the bis-demethylated byproduct. But the quality of the desired product is very important for the next Mitsunobu reaction.

Yield: 80%; $^1$H NMR (300 MHz, CDCl$_3$) δ 7.63 (d, J=15.3 Hz, 1H), 7.33 (d, J=15.6 Hz, 1H), 6.85-6.91 (m, 1H), 6.76 (s, 2H), 6.06 (s, 1H), 5.99 (d, J=9.6 Hz, 1H), 3.97 (t, J=6.6 Hz, 2H), 3.84 (s, 6H), 2.38-2.43 (m, 2H); $^{13}$C NMR (75 MHz, CDCl$_3$) δ 168.8, 165.7, 147.0, 145.4, 144.1, 137.0, 126.3, 125.6, 119.4, 105.2, 56.1, 41.5, 24.6; IR (thin film, cm$^{-1}$) 3368, 2939, 1676, 1593, 1511, 1455, 1424, 1384, 1344, 1316, 1286, 1243, 1212, 1181, 1157, 1136, 1110, 1053, 975, 912, 819, 798, 734, 701, 674; m/z found: 304.15 [M+H$^+$]; HRMS (FAB) calcd for C$_{16}$H$_{17}$NO$_5$: 303.1107; found 303.1111.

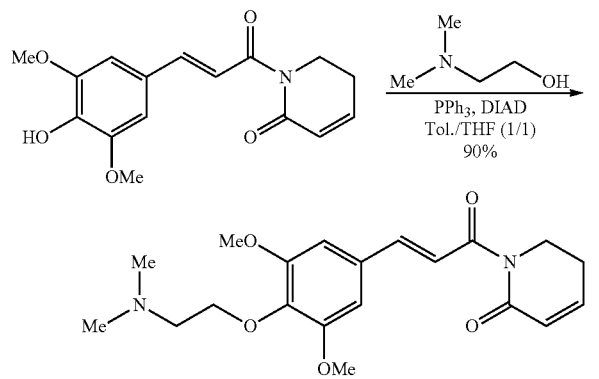

Experimental Procedure: Triphenylphosphine (92.0 mg, 0.35 mmol) and (E)-diisopropyl diazene-1,2-dicarboxylate (DIAD, 71.0 mg, 0.35 mmol) were dissolved to a 1:1 mixture of THF and toluene (4 mL); then mono-demethylated piperlongumine (50.0 mg, 0.18 mmol) was added. After 10 min, 2-(dimethylamino) ethanol (31.0 mg, 0.35 mmol) was added to the mixture. The reaction was stirred at room temperature for 3 h. At the end, the solvent was evaporated under vacuum, and the crude product was subjected to flash chromatography (hexane/ethyl acetate=100/0 to 50:50), to afford the desired product in 90% yield.

Yield: 90%; $^1$H NMR (300 MHz, CDCl$_3$) δ 7.67 (d, J=15.6 Hz, 1H), 7.41 (d, J=15.6 Hz, 1H), 6.91-6.97 (m, 1H), 6.78 (s, 2H), 6.04 (d, J=9.9 Hz, 1H), 4.10 (t, J=5.7 Hz, 2H), 4.03 (t, J=6.3 Hz, 2H), 3.86 (s, 6H), 2.76 (t, J=6.0 Hz, 2H), 2.44-2.50 (m, 2H), 2.39 (s, 6H); $^{13}$C NMR (75 MHz, CDCl$_3$) δ 168.8, 165.8, 153.5, 145.4, 143.8, 139.0, 130.7, 125.9, 121.1, 105.5, 70.7, 58.7, 56.1, 45.5, 41.6, 24.8; IR (thin film, cm$^{-1}$) 2935, 1683, 1614, 1580, 1502, 1463, 1418, 1386, 1352, 1317, 1276, 1243, 1215, 1182, 1125, 1156, 1052, 1033, 999, 974, 912, 825, 731, 700, 634, 593; m/z found: 374.98 [M+H$^+$]; HRMS (FAB) calcd for C$_{20}$H$_{26}$N$_2$O$_5$: 374.1842; found 374.1845.

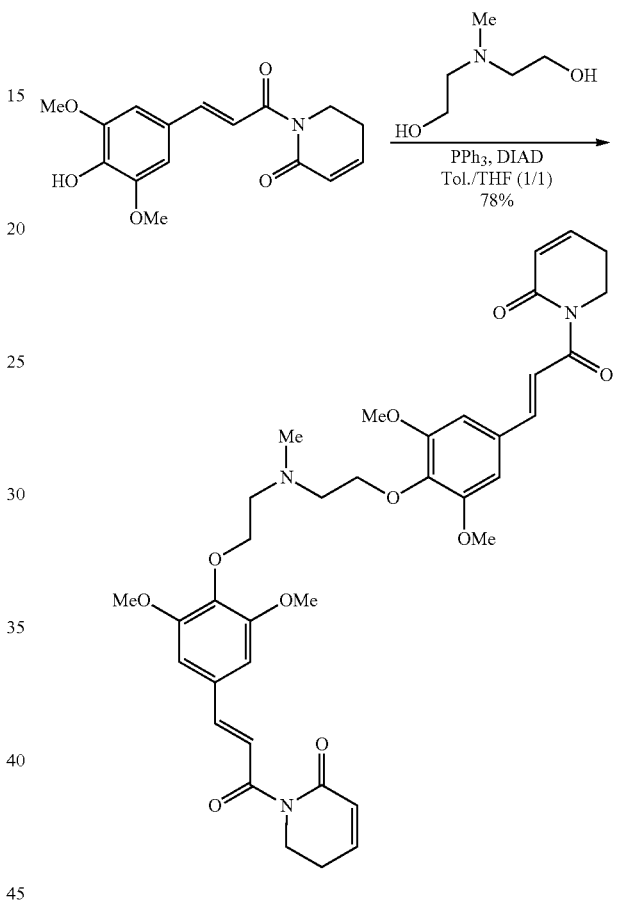

Experimental Procedure: Triphenylphosphine (77.0 mg, 0.29 mmol) and DIAD (60.0 mg, 0.29 mmol) were dissolved to a 1:1 mixture of THF and toluene (2 mL); then mono-demethylated piperlongumine (40.0 mg, 0.13 mmol) was added. After 10 min, N-methyldiethanolamine (120 mg, 0.06 mmol) was added to the mixture; the reaction was stirred at room temperature for 3 h. At the end, the solvent was evaporated under vacuum. The crude product was purified by preparative TLC (CH$_2$Cl$_2$/MeOH=9/1) to afford the desired product in 78% yield.

Yield: 78%; $^1$H NMR (300 MHz, CDCl$_3$) δ 7:66 (d, J=15.6 Hz, 2H), 7.40 (d, J=15.3 Hz, 2H), 6.91-6.96 (m, 2H), 6.77 (s, 4H), 6.03 (d, J=9.9 Hz, 2H), 4.14 (t, J=6.0 Hz, 4H), 4.03 (t, J=6.3 Hz, 4H), 3.84 (s, 12H), 2.98 (m, 4H), 2.52 (s, 3H), 2.44-2.48 (m, 4H); $^{13}$C NMR (75 MHz, CDCl$_3$) δ 168.8, 165.8, 153.5, 145.4, 143.8, 139.1, 130.6, 125.8, 121.0, 105.5, 70.7, 57.0, 56.1, 42.8, 41.6, 24.8; IR (thin film, cm$^{-1}$) 2936, 1684, 1614, 1581, 1502, 1464, 1418, 1386, 1352, 1317, 1265, 1243, 1215, 1183, 1156, 1127, 1053, 1038, 998, 912, 826, 730, 701, 594; m/z found: 690.29 [M+H$^+$]; HRMS (FAB) calcd for C$_{37}$H$_{43}$N$_3$O$_{10}$: 689.2948; found 689.2949.

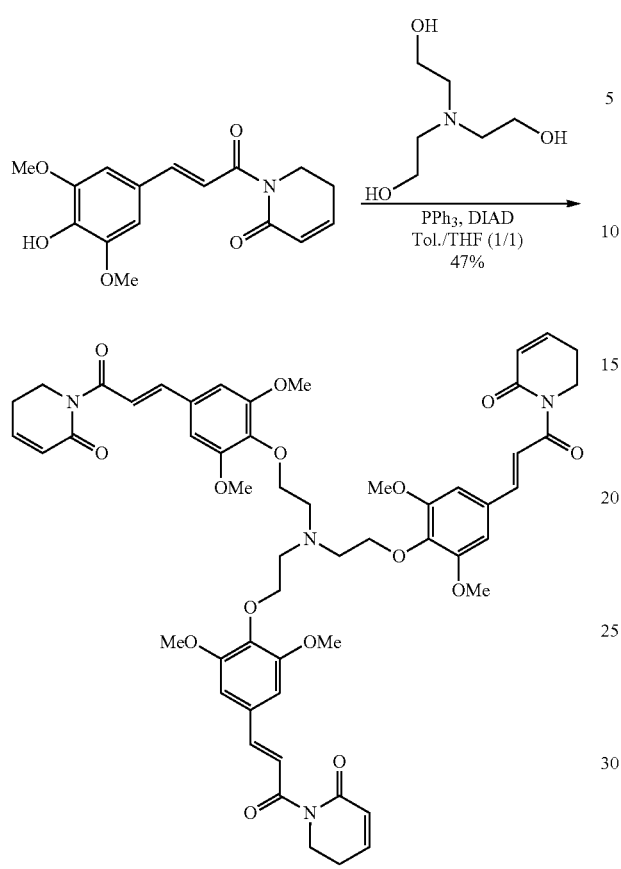

Experimental Procedure: Triphenylphosphine (79.0 mg, 0.30 mmol) and DIAD (61.0 mg, 0.30 mmol) were dissolved to a 1:1 mixture of THF and toluene (2 mL); then mono-demethylated piperlongumine (46.0 mg, 0.15 mmol) was added. After 10 min, triethanolamine (6.80 mg, 0.05 mmol) was added to the mixture. The reaction was stirred at room temperature for 3 h. At the end, the solvent was evaporated under vacuum. The crude product was purified by preparative TLC(CH$_2$Cl$_2$/MeOH=9/1) to afford the desired product in 47% yield.

Yield: 47%; $^1$H NMR (300 MHz, CDCl$_3$) δ 7.66 (d, J=15.6 Hz, 3H), 7.40 (d, J=15.3 Hz, 3H), 6.91-6.97 (m, 3H), 6.76 (s, 6H), 6.04 (d, J=9.6 Hz, 3H), 4.10 (m, 6H), 4.03 (t, J=6.3 Hz, 6H), 3.81 (s, 18H), 3.10 (m, 6H), 2.45-2.49 (m, 6H); $^{13}$C NMR (75 MHz, CDCl$_3$) δ 168.9, 165.8, 153.5, 145.3, 143.9, 139.4, 130.4, 125.9, 120.9, 105.6, 71.5, 56.1, 54.6, 41.6, 24.8; IR (cm$^{-1}$) 2925, 2853, 1684, 1614, 1580, 1502, 1464, 1418, 1386, 1352, 1317, 1243, 1275, 1215, 1156, 1182, 1127, 1053, 1038, 997, 912, 826, 731; m/z found: 1005.41 [M+H$^+$]; HRMS (FAB) calcd for C$_{54}$H$_{60}$N$_4$O$_{15}$: 1004.4055; found 1004.4050.

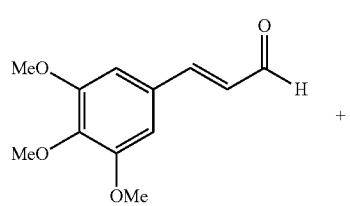

3-methylene-5-[(E)-2-(3,4,5-trimethoxyphenyl)vinyl]dihydrofuran-2(3H)-one

Experimental Procedure: To a mixture of (2E)-3-(3,4,5-trimethoxyphenyl)acrylaldehyde (50 mg, 0.22 mmol) in THF (2 mL), methyl 2-(bromomethyl)acrylate (43 mg, 0.24 mmol) and Zn—Cu couple powder (60 mesh, 25 mg) were added. The reaction was stirred overnight at room temperature. At the end, the mixture was filtrated in order to get rid of Zn—Cu powder and the solvent was evaporated under vacuum. The crude product was subjected to flash chromatography (Hex/EtOAc=50/50) to give the desired compound in 94% yield.

Yield: 94%; $^1$H NMR (300 MHz, CDCl$_3$) δ 6.60 (m, 3H), 6.26 (t, J=2.7 Hz, 1H), 6.09 (dd, J=15.6, 6.9 Hz, 1H), 5.67 (t, J=2.4 Hz, 1H), 5.11 (q, J=6.9, 1H), 3.86 (s, 6H), 3.83 (s, 3H), 3.24 (ddt, J=17.1, 8.1, 2.4 Hz, 1H), 2.81 (m, 1H); $^{13}$C NMR (75 MHz, CDCl$_3$) δ 170.0, 153.3, 138.4, 134.0, 133.1, 131.2, 126.1, 122.4, 103.8, 77.3, 60.8, 56.0, 34.2; IR (thin film, cm$^{-1}$) 2939, 1762, 1583, 1507, 1464, 1421, 1329, 1265, 1242, 1184, 1126, 1002, 964, 816, 730, 701, 624, 528, 423; m/z found: 291.31 [M+H$^+$]; HRMS (FAB) calcd for C$_{16}$H$_{18}$O$_5$: 290.1154; found 290.1154.

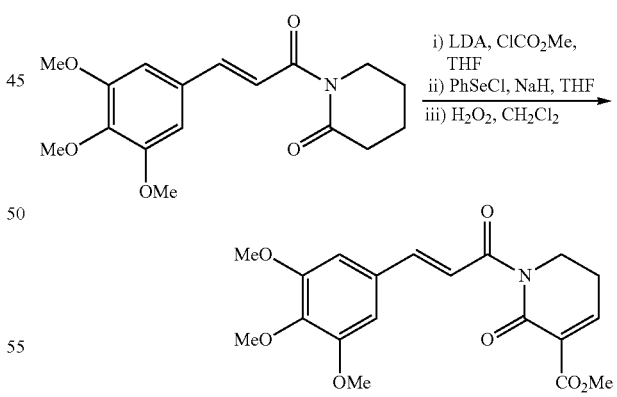

Experimental Procedure: To a solution of dihydropiperlongumine (346 mg, 1.08 mmol) in THF (8 mL) was added LDA (1.5 equiv., 1.625 mmol, prepared freshly from n-BuLi and i-Pr$_2$NH) at −78° C. After 30 min, methyl carbonochloride (113 mg, 1.19 mmol) was added dropwise. The reaction mixture was slowly warmed up to room temperature and stirred for overnight. The reaction was then quenched with saturated aqueous NH$_4$Cl solution (10 mL): the aqueous layer was extracted with CH$_2$Cl$_2$ (3×10 mL) and the organic layers were collected, washed with saturated aqueous NaCl solution (30 mL) and dried over MgSO$_4$. The solution was filtrated and the solvent was evaporated under vacuum. The crude was subjected to flash chromatography (hexane/ethyl acetate=3/1) to afford the desired product in 49% yield.

Yield: 49%; $^1$H NMR (300 MHz, CDCl$_3$) δ 7.66 (d, J=15.6 Hz, 1H), 7.32 (d, J=15.3 Hz, 1H), 6.78 (s, 2H), 3.88 (s, 6H), 3.87 (s, 3H), 3.81 (s, 3H), 3.83 (m, 2H), 3.63 (t, J=6.9 Hz, 1H), 1.80-2.30 (m, 4H); $^{13}$C NMR (75 MHz, CDCl$_3$) δ 170.2, 170.0, 169.3, 153.4, 144.3, 130.5, 120.7, 105.7, 60.9, 56.2, 52.7, 51.4, 44.2, 24.4, 20.8; HRMS (FAB) calcd for C$_{19}$H$_{23}$NO$_7$: 377.1475; found 377.1475.

Experimental Procedure: To a solution of the above carboxylate (76 mg, 0.20 mmol) in THF (2 mL) was added NaH (6.1 mg, 0.24 mmol, 95%) at 0° C. After 30 min, PhSeCl (46.3 mg, 0.24 mmol) was added in one portion. The reaction mixture was slowly warmed up to room temperature and stirred for overnight. The reaction was then quenched with saturated aqueous NH$_4$Cl solution (5 mL): the aqueous layer was extracted with CH$_2$Cl$_2$ (3×5 mL) and the organic layers were collected, washed with saturated aqueous NaCl solution (15 mL) and dried over MgSO$_4$. The solution was filtrated and the solvent was evaporated under vacuum. The crude was subjected to flash chromatography (hexane/ethyl acetate=100/0 to 85/15) to afford the desired product in 61% yield.

Yield: 61%; $^1$H NMR (300 MHz, CDCl$_3$) δ 7.66-7.70 (m, 3H), 7.42-7.46 (m, 1H), 7.32-7.37 (m, 2H), 7.25 (d, J=15.6 Hz, 1H), 3.91 (s, 6H), 3.89 (s, 3H), 3.81 (s, 3H), 3.64-3.70 (m, 2H), 3.31-3.37 (m, 1H), 1.97-2.08 (m, 1H), 1.91-1.96 (m, 1H), 1.66-1.80 (m, 1H); $^{13}$C NMR (75 MHz, CDCl$_3$) δ 170.3, 170.1, 169.1, 153.3, 144.4, 140.2, 138.4, 130.4, 129.9, 128.9, 126.2, 120.2, 105.7, 60.9, 56.9, 56.2, 53.4, 43.9, 32.0, 20.8; m/z found: 533.97 [M+H$^+$].

Experimental Procedure: To a solution of the above senelide (60 mg, 0.11 mmol) in CH$_2$Cl$_2$ (2 mL) was added H$_2$O$_2$ (0.029 mL, 0.28 mmol, 30%) at 0° C. After 40 min, the reaction mixture was slowly warmed up to room temperature and stirred for another 30 min. The reaction was then quenched with saturated aqueous NH$_4$Cl solution (5 mL): the aqueous layer was extracted with CH$_2$Cl$_2$ (3×5 mL) and the organic layers were collected, washed with saturated aqueous NaCl solution (15 mL) and dried over MgSO$_4$. The solution was filtrated and the solvent was evaporated under vacuum. The crude was subjected to flash chromatography (hexane/ethyl acetate=100/0 to 60/40) to afford the desired product in 57% yield.

Yield: 57%; $^1$H NMR (300 MHz, CDCl$_3$) δ 7.66-7.71 (m, 2H), 7.50 (d, J=15.3 Hz, 1H), 6.79 (s, 2H), 4.05 (d, J=6.3 Hz, 2H), 3.88 (s, 6H), 3.87 (s, 3H), 3.85 (s, 3H), 2.57-2.63 (m, 2H); $^{13}$C NMR (75 MHz, CDCl$_3$) δ 168.7, 164.1, 162.2, 153.3, 151.2, 144.8, 140.2, 130.5, 130.1, 120.7, 105.7, 60.9, 56.2, 52.5, 41.2, 24.9; HRMS (FAB) calcd for C$_{19}$H$_{21}$NO$_7$: 375.1318; found 375.1319.

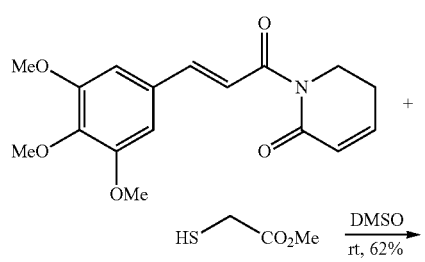

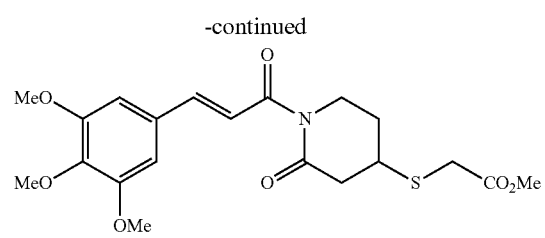

Experimental Procedure: A mixture of piperlongumine (89 mg, 0.28 mmol) and methyl 2-mercaptoacetate (89 mg, 0.84 mmol) in DMSO (1 mL) was stirred at room temperature for overnight. The reaction was then quenched with saturated aqueous NH$_4$Cl solution (5 mL): the aqueous layer was extracted with CH$_2$Cl$_2$ (3×5 mL) and the organic layers were collected, washed with saturated aqueous NaCl solution (15 mL) and dried over MgSO$_4$. The solution was filtrated and the solvent was evaporated under vacuum. The crude was subjected to flash chromatography (hexane/ethyl acetate=100/0 to 75/25) to afford the desired product in 62% yield.

Yield: 62%; $^1$H NMR (300 MHz, CDCl$_3$) δ 7.62 (d, J=15.6 Hz, 1H), 7.32 (d, J=15.6 Hz, 1H), 6.76 (s, 2H), 3.99-4.10 (m, 1H), 3.86 (s, 6H), 3.85 (s, 3H), 3.73 (s, 3H), 3.62-3.68 (m, 1H), 3.33-3.39 (m, 1H), 3.29 (s, 2H), 3.00 (dd, J=17.1, 5.4 Hz, 1H), 2.61 (dd, J=17.1, 9.0 Hz, 1H), 2.57-2.32 (m, 1H), 1.79-1.92 (m, 1H); $^{13}$C NMR (75 MHz, CDCl$_3$) δ 171.0, 170.3, 169.0, 153.3, 144.0, 140.0, 130.4, 120.7, 105.5, 60.9, 56.1, 52.5, 42.4, 40.9, 37.4, 32.0, 28.8; HRMS (FAB) calcd for C$_{20}$H$_{25}$NO$_7$S: 423.1352; found 423.1351.

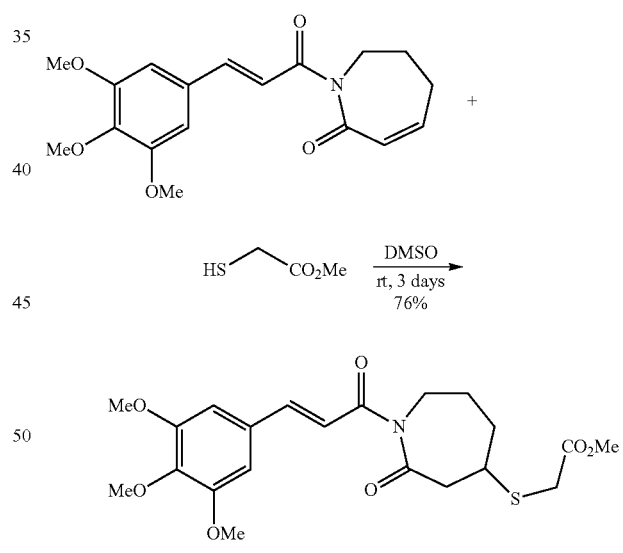

Experimental Procedure: A mixture of homo-piperlongumine (36 mg, 0.11 mmol) and methyl 2-mercaptoacetate (35 mg, 0.22 mmol) in DMSO (2.5 mL) was stirred at room temperature for 3 days. The reaction was then quenched with saturated aqueous NH$_4$Cl solution (5 mL): the aqueous layer was extracted with CH$_2$Cl$_2$ (3×5 mL) and the organic layers were collected, washed with saturated aqueous NaCl solution (15 mL) and dried over MgSO$_4$. The solution was filtrated and the solvent was evaporated under vacuum. The crude was subjected to flash chromatography (hexane/ethyl acetate=80/20) to afford the desired product in 76% yield.

Yield: 76%; $^1$H NMR (300 MHz, CDCl$_3$) δ 7.62 (d, J=15.6 Hz, 1H), 7.29 (d, J=15.3 Hz, 1H), 6.78 (s, 2H), 3.94-4.01 (m, 2H), 3.88 (s, 6H), 3.86 (s, 3H), 3.74 (s, 3H), 3.25-3.42 (m, 3H), 3.07-3.09 (m, 2H), 2.08-2.19 (m, 1H), 1.86-2.01 (m, 2H), 1.69-1.80 (m, 1H); $^{13}$C NMR (75 MHz, CDCl$_3$) δ 174.3, 170.5, 168.6, 153.3, 143.8, 140.0, 130.6, 121.0, 105.5, 60.9, 56.1, 52.5, 44.6, 43.3, 40.0, 34.9, 32.3, 26.2; m/z found: 438.48; [M+H$^+$]; HRMS (FAB) calcd for C$_{21}$H$_{27}$NO$_7$S: 437.1508; found 437.1507.

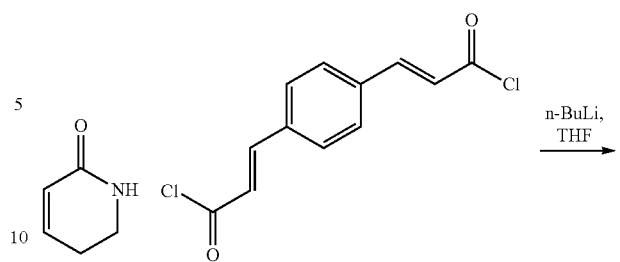

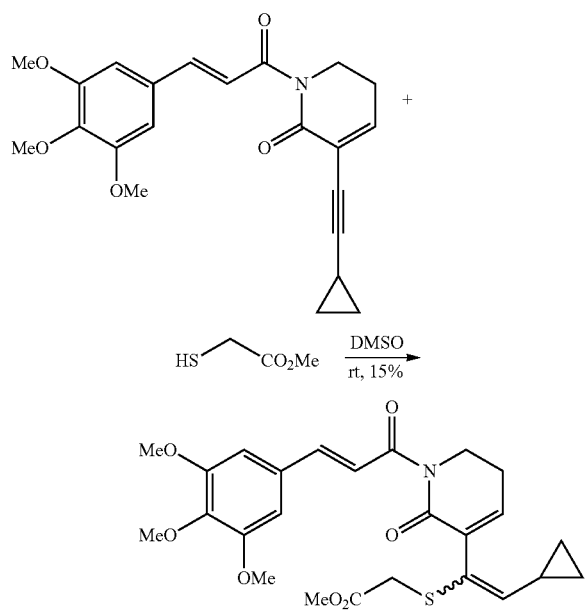

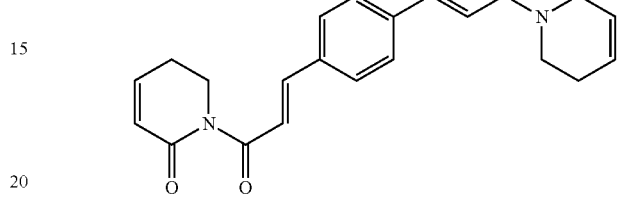

Experimental Procedure: To the solution of 5,6-dihydropyridine-2(1H)one (64.1 mg, 0.66 mmol, 2.2 equiv) in THF (3.0 mL, 0.1 M) at −78° C. was added solution of n-BuLi in hexanes (413 µL, 1.6 M, 0.66 mmol, 2.2 equiv) and stirred for 15 minutes. To this solution was added 1,4-phenylenediacryloyl chloride (77 mg, 0.30 mmol) and the reaction was stirred at −78° C. for 3 hours. Reaction mixture was diluted with ethyl acetate, quenched with aqueous ammonium chloride, extracted with EtOAc, washed with brine, dried with anhydrous sodium sulfate and purified by column chromatography using hexanes-ethyl acetate gradient (0 to 80% EtOAc), yielding 81.3 mg of the product (72%).

For (E)-N-methacryloylbut-2-enamide (BRD7991; Cpd. 76).

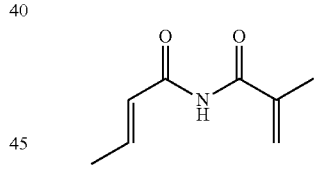

Experimental Procedure: A mixture of cyclopropylalkyne piperlongumine (93 mg, 0.244 mmol) and methyl 2-mercaptoacetate (155 mg, 1.46 mmol) in DMSO (3 mL) was stirred at room temperature for 3 days. The reaction was then quenched with saturated aqueous NH$_4$Cl solution (5 mL): the aqueous layer was extracted with CH$_2$Cl$_2$ (3×5 mL) and the organic layers were collected, washed with saturated aqueous NaCl solution (15 mL) and dried over MgSO$_4$. The solution was filtrated and the solvent was evaporated under vacuum. The crude was subjected to flash chromatography (hexane/ethyl acetate=80/20) to afford the desired product as an inseparable 2/1 mixture in 20% yield.

Yield: 15%; $^1$H NMR (300 MHz, CDCl$_3$) δ 7.71 (d, J=15.6 Hz, 1H, major), 7.67 (d, J=15.6 Hz, 1H, minor), 7.53 (d, J=15.6 Hz, 1H, major), 7.47 (d, J=15.6 Hz, 1H, minor), 6.97 (t, J=4.2 Hz, 1H, major), 6.93 (t, J=4.5 Hz, 1H, minor), 6.81 (s, 2H, major), 6.80 (s, 2H, minor), 5.56 (d, J=10.2 Hz, 1H, major), 5.48 (d, J=9.9 Hz, 1H, minor), 4.10 (t, J=6.6 Hz, 2H, major), 4.04 (t, J=6.6 Hz, 2H, minor), 3.90 (s, 6H, minor), 3.89 (s, 6H, major), 3.87 (s, 3H, major and minor), 3.70 (s, 3H, major), 3.69 (s, 3H, minor), 3.33 (s, 2H, minor), 3.31 (s, 2H, major), 2.56-2.62 (m, 2H, major), 2.48-2.54 (m, 2H, minor), 1.34-1.45 (m, 1H, major and minor), 0.87-0.93 (m, 2H, minor), 0.76-0.81 (m, 2H, major), 0.49-0.54 (m, 2H, major and minor); $^{13}$C NMR (75 MHz, CDCl$_3$) δ major 170.3, 169.1, 164.5, 153.3, 145.4, 144.9, 144.3, 140.1, 133.5, 130.6, 124.5, 121.1, 105.7, 60.9, 56.3, 52.3, 41.9, 35.6, 24.9, 12.9, 7.8; HRMS (FAB) calcd For C$_{25}$H$_{29}$NO$_7$S: 487.1665; found 487.1669.

$^1$H NMR (300 MHz, CHLOROFORM-d) δ 8.35 (s, 1H), 7.25-6.90 (m, 2H), 5.79 (d, J=0.6 Hz, 1H), 5.56 (dd, J=3.0, 1.4 Hz, 1H), 1.94 (s, 3H), 1.89 (dd, J=6.5, 1.2 Hz, 3H); $^{13}$C NMR (75 MHz, CHLOROFORM-d) δ 167.4, 166.8, 147.1, 140.1, 124.3, 122.7, 18.7, 18.6. Exact mass (M+Na)$^+$ calc'd: 176.0687, found 176.0690.

Experimental Procedure: To a suspension of (E)-but-2-enamide (1.0 equiv) in 3.5 mL THF was added n-BuLi in hexanes (2.5 M, 1.2 equiv) slowly at −78° C. The reaction mixture was warmed up to room temperature and stirred for 8 h before a solution of methacryloyl chloride (2.0 equiv) in 2 mL of THF was added drop wise at −78° C. The reaction mixture was allowed to warm up to rt overnight. The crude reaction mixture was diluted with ethyl acetate, and quenched with cold NH$_4$Cl$_{(aq, sat)}$, and the organic layer separated. The aqueous layer was extracted twice with ethyl acetate. The combined organic layers were washed with brine and dried over MgSO$_4$. After filtration and evaporation under reduced pressure, the residue was purified by column chromatography to yield the pure compound.

Example 2

Methods

Cell culture. HeLa, U2OS, EJ, and H1703 were obtained from ATCC. HeLa and U2OS were cultured in DMEM+10% FBS in a 37° C. incubator (5% $CO_2$); H1703 was cultured in RPMI+10% FBS, and EJ in McCoy's 5A+10% FBS. HEC108 were obtained from the Broad Institute/Novartis Cancer Cell Line Encyclopedia and cultured in EMEM+15% FBS. BJ (human fibroblasts) were obtained from ATCC, while BJ-ELR (a fully transformed derivative containing hTERT, large-T antigen, and activated H-RAS) were a gift of Prof. Brent Stockwell, Columbia University, New York, N.Y. Both lines were maintained in 4:1 DMEM:M1999 supplemented with 15% FBS. BJ were maintained below 70% confluency and used below passage 8.

ROS Assay. Cells were plated at 5,000 cells/well in black 384-well plates (Corning) and allowed to attach overnight. The next day (ca. 90% confluency), dilutions of compounds in DMSO were added by pin transfer (CyBio Vario, 100 mL per well), and incubated for 90 minutes. Media was changed using a Thermo Multidrop Combi liquid handler to phenol red-free DMEM containing 10 µM $CM-H_2DCF-DA$ and 10 µg/mL Hoechst 33342. Following incubation for 15-30 minutes, cells were washed twice with PBS. Images were obtained using an IX_Micro automated fluorescence microscope (Molecular Devices). Quantitation of pixel intensity was performed using MetaXpress software and signal intensity was calculated relative to wells in the same plate treated with DMSO.

ATP Assay. Cells were plated at 1,000 per well in white 384-well plates and allowed to attach overnight. After addition of compounds by pin transfer, plates were incubated 48 h. At that time, media was removed and replaced with a solution of CellTiter-Glo reagent (Promega) in PBS. After ten minutes, luminescence was read using an EnVision multilabel plate reader (Perkin-Elmer) and signal intensity was calculated relative to in-plate DMSO control wells.

Glutathione Assay. Cells were plated at 1,000 per well in white 384-well plates and allowed to attach overnight. After addition of compounds by pin transfer, plates were incubated for 3 h (EJ) or 6 h (HeLa). Cells were washed with PBS, and total glutathione was measured using GSH/GSSG-Glo, according to manufacturer's instructions (Promega). Luminescence was measured with an EnVision multilabel plate reader.

Immunofluorescence Detection of Glutathionylated Proteins. Cells were plated at 3,000 (HeLa) or 5,000 (EJ) per well and allowed to attach overnight. After addition of compounds by pin transfer, plates were incubated for between 10 minutes and 6 h. At the appropriate time, cells were fixed with 1% paraformaldehyde in PBS (20 minutes), permeabilized 30 minutes with PBS+0.1% TritonX-100 ("PBST"), and blocked 30 minutes with PBST+2% BSA. Primary antibody (Ms anti-glutathione, Abcam Ab19534) was added (1:1250 in PBST+2% BSA) and incubated at 4° C. overnight. Following two washes with PBST, cells were incubated at RT 1 h in the dark with secondary antibody solution (Cy-2 or Cy-3-conjugated goat anti-mouse, Jackson Immuno chemicals, 1:500, plus Hoechst 33342, 10 µg/ml in PBST+2% BSA). Following two washes with PBST, images were collected using an IX_Micro automated fluorescence microscope (Molecular Devices). Quantitation of pixel intensity was performed as above.

Assessment of Cancer/Normal Selective Toxicity. BJ vs. BJ-ELR: In 12-well dishes, BJ (33,000 cells/well) or BJ-ELR (25,000 cells/well) were seeded and allowed to grow to 40-50% confluency (24-36 h). Compound solutions in DMSO were added (0.2% DMSO final) and incubated 48 h. Cells were fixed with 2% paraformaldehyde (15 minutes), followed by staining with 0.01% aqueous crystal violet (30 minutes). Cells were washed twice with water and allowed to dry overnight. Once dry, the stain was resolubilized using ethylene glycol (2 mL per well, 2-16 hr with shaking). When cells retained no stain, duplicate samples of 50 µL were then transferred to wells of a 384-well plate. Absorbance at 540 nm was measured with an EnVision plate reader, and relative viability was calculated relative to DMSO-treated control wells.

Example 3

Chemical Reactivity of Piperlongumine and its Analogs

Figure 9:
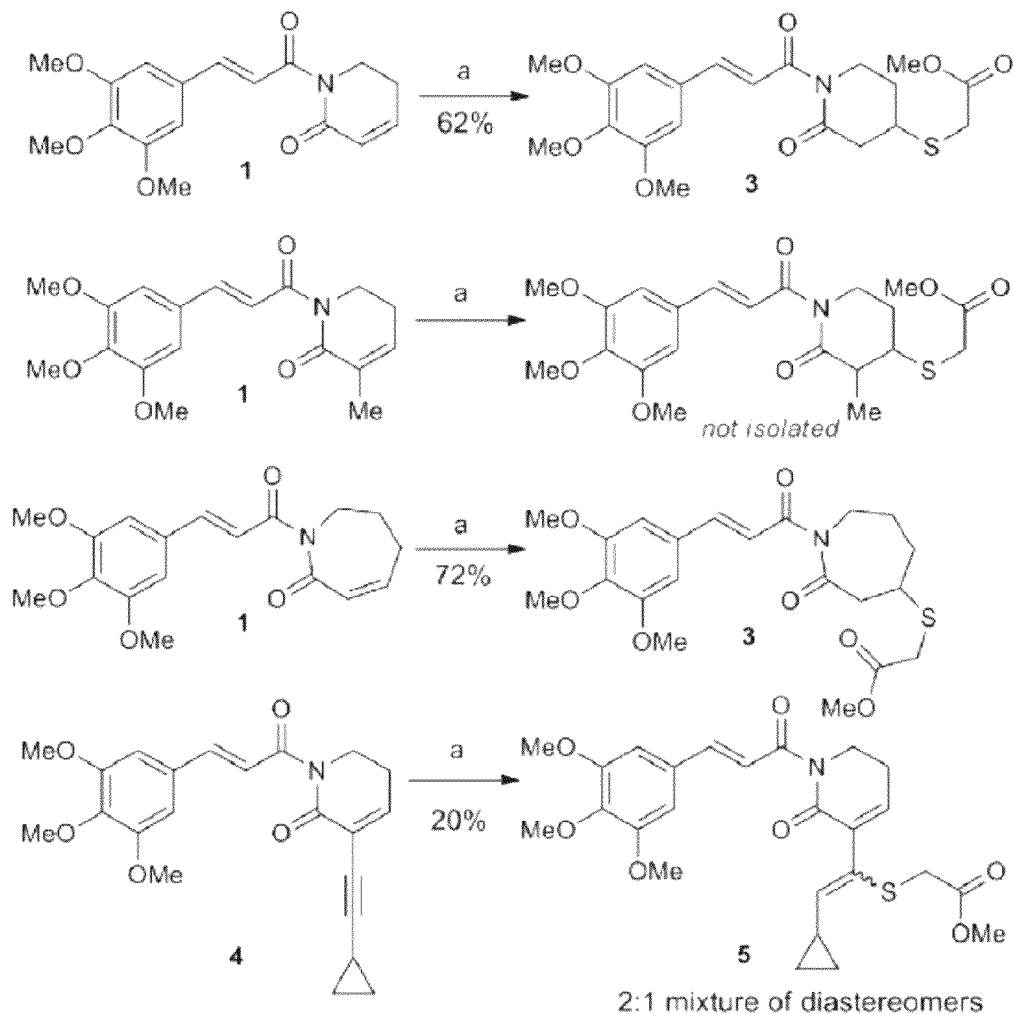
FIG. 9 illustrates reactivity of piperlongumine with methyl thioglycolate, a thiol nucleophile.
Figure 10:
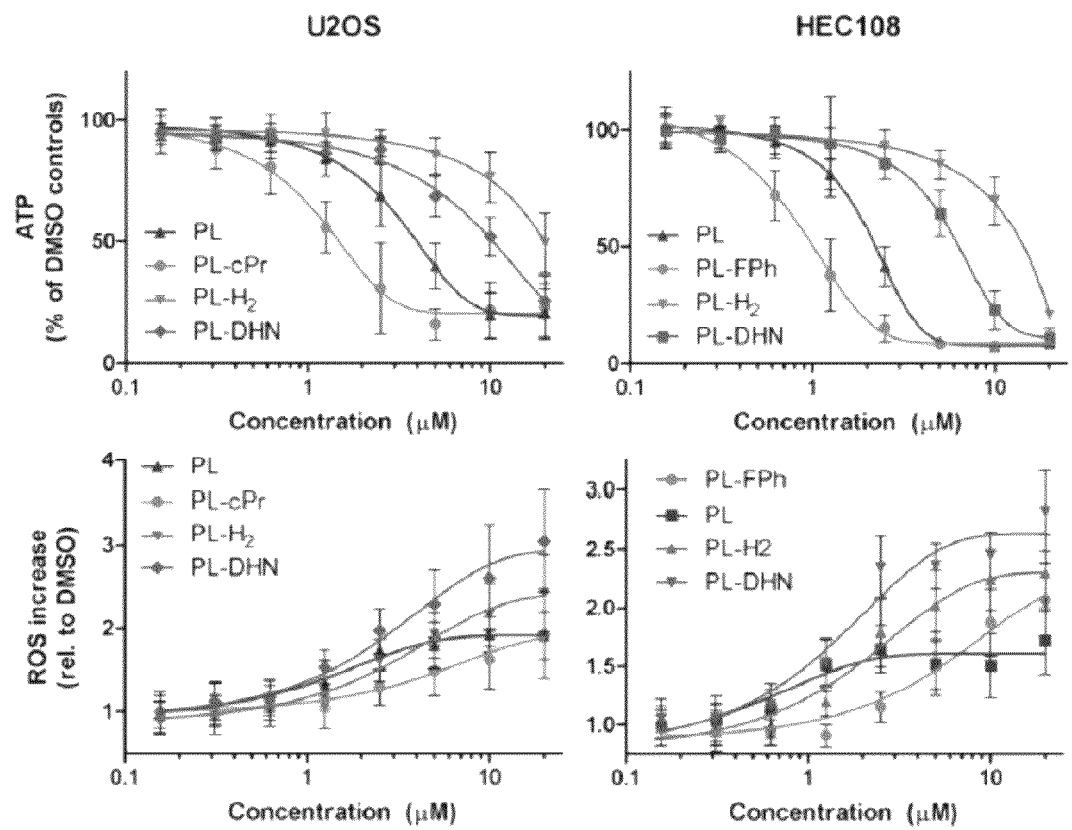
FIG. 10 illustrates piperlongumine analogs elevate ROS comparably with PL but show divergent outcomes in cell viability in two additional cell lines (see also FIG. 4). Data are expressed as mean±SD for three independent experiments.
Figure 11:
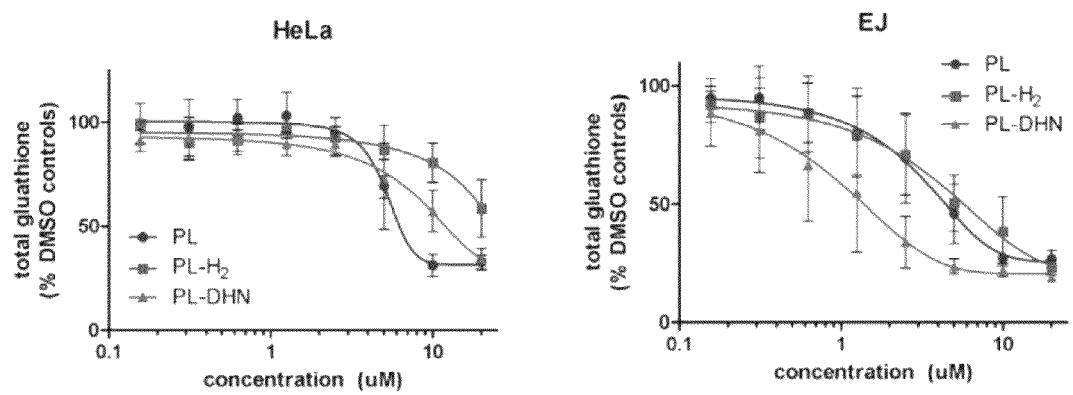
FIG. 11 illustrates comparable depletion of total cellular glutathione by PL and two less toxic analogs in HeLa cells after 6 h compound treatment. Data are expressed as mean±SD for three independent experiments. Comparable data for the EJ cell line (FIG. 5) is shown for comparison.

As PL contains multiple potentially electrophilic sites that may influence its actions on cells, we assessed the chemical reactivity of PL and several of our analogs using methyl thioglycolate as a representative achiral thiol nucleophile. Treatment of PL with 3 equivalents of methyl thioglycolate in DMSO provided the product of conjugate addition at C3 in 62% yield (FIG. 1C). No addition was observed at C8 by LC-MS or 1H NMR, and 2,3-dihydropiperlongumine (Table 1, entry 2) was unreactive under these conditions. We next assessed whether PL analogs with modifications proximal to the highly reactive C2-C3 olefin yield similar patterns of reactivity. Substitution of methyl at C2 (Table 1, entry 3) ablated hetero-conjugate addition, indicating that C2 alkyl substituents can impede reaction at C3. A ring-expanded cycloheptenimide analog (PL-7; Table 1, entry 4) also provided the expected hetero-conjugate addition product at C3 (74% yield), while C2 alkyne 4 (PL-cPr; Table 1, entry 5) underwent further reaction to provide a rearranged thiol enol ether product (FIG. 9).

TABLE 1

Effects on cellular ATP levels for PL and selected PL analogs in two cell lines.

| | | $EC^{50}$ H1703 (µM) | $EC^{50}$ HeLa (µM) |
|---|---|---|---|
| 1 | PL | 2.8 | 7.1 |
| 2 | PL-2,3$H_2$ | n.t. | n.t. |

TABLE 1-continued

Effects on cellular ATP levels for PL and selected PL analogs in two cell lines.

| # | Structure | EC$_{50}$ H1703 (μM) | EC$_{50}$ HeLa (μM) |
|---|---|---|---|
| 3 | 3,4,5-trimethoxycinnamoyl-3-methyl-dihydropyridinone | n.t. | n.t. |
| 4 (PL-7) | 3,4,5-trimethoxycinnamoyl-azepinone | 1.9 | 5.1 |
| 5 (PL-cPr) | 3,4,5-trimethoxycinnamoyl-3-(cyclopropylethynyl)-dihydropyridinone | 0.7 | 1.3 |
| 6 (PL-H$_2$) | 3-(3,4,5-trimethoxyphenyl)propanoyl-dihydropyridinone | 17.5 | n.t. |
| 7 (PL-MTG) | 3,4,5-trimethoxycinnamoyl-4-(methoxycarbonylmethylthio)-piperidinone | 7.9 | >20 |
| 8 | 3,4,5-trimethoxycinnamoyl-4-methyl-dihydropyridinone | n.t. | n.t. |
| 9 | β-methylcinnamoyl-dihydropyridinone | 14 | >20 |
| 10 | benzothiophene-2-carbonyl-dihydropyridinone | 18 | >20 |
| 11 (PL-DHN) | 5,6,7-trimethoxy-dihydronaphthalene-carbonyl-dihydropyridinone | 14 | n.t. |
| 12 | cinnamoyl-dihydropyridinone | 3.5 | 7.1 |
| 13 | 2-chlorocinnamoyl-dihydropyridinone | 4.0 | 7.5 |
| 14 | 3,4,5-trimethoxycinnamoyl-6-phenyl-dihydropyridinone | 3.6 | 6.8 |
| 15 | 3,4,5-trimethoxycinnamoyl-5-(2-thienyl)-dihydropyridinone | 6.5 | 15 |
| 16 (PL-SO$_2$) | styrylsulfonyl-dihydropyridinone | 2.7 | 4.1 |

TABLE 1-continued

Effects on cellular ATP levels for PL and selected PL analogs in two cell lines.

| | | $EC^{50}$ H1703 (µM) | $EC^{50}$ HeLa (µM) |
|---|---|---|---|
| 17 | PL-FPh | 0.4 | 1.0 |
| 18 | (structure with Ph) | n.t. | n.t. |

Effects on cellular ATP levels for selected PL analogs in two cell lines (H1073 and HeLa). n.t. indicates no loss of viability at 20 µM; >20 µM indicates less than 50% decrease in viability observed at 20 µM. Column 1: Entry number; Column 3: $EC_{50}$ H1703 (µM); Column 4: $EC_{50}$ HeLa (µM).

Example 4

Cellular Actions

We next sought to determine the performance of the synthetic analogs relative to PL in cells. Changes in ROS levels were assessed 90 minutes after compound treatment by automated microscopy using the redox-sensitive dye CM-H$_2$DCF-DA, which shows greatest sensitivity to hydroxyl radical and other highly reactive species. As a second assay, effects of compound treatments on ATP levels, a surrogate for cell viability, were measured after 48 hours. (A second assay monitoring cellular reducing equivalents as a surrogate for viability gave closely correlated results. See Example 9.) Both assays were performed in 384-well plates on two human cancer cell lines, H1703 (lung) and HeLa (cervix).

As PL contains multiple electrophilic sites and can undergo hetero-conjugate addition with small-molecule thiols, we hypothesized that the electrophilicity of PL might be central to its bioactivity. Our first analogs sequentially eliminated the two reactive α,β-unsaturated olefins (Table 1, entries 1-2, 6. Table 1 includes viability data for representative analogs in two cell lines). For viability and ROS dose-response data for all 80 analogs, see Example 9. 2,3-dihydro-piperlongumine (PL-2,3H2, Table 1, entry 2), lacking the C2-C3 olefin, neither elevated ROS levels nor decreased viability of the two cell lines tested, demonstrating that this functionality is essential for PL's biological activity (FIG. 2). By contrast, removal of the C7-C8 olefin (PL-H2) led to substantial reductions in toxicity (FIG. 2A), but did not diminish ROS elevation (Table 1, entry 6; FIG. 2B, C). These results indicate that while the presence of the C2-C3 olefin is sufficient to elevate ROS, both olefins are necessary to recapitulate the level of cellular toxicity observed for PL.

The study of additional analogs confirmed that modifications diminishing the reactivity of the C2-C3 olefin yielded compounds with minimal activity in these assays (Table 1, entries 7, 8). Piperlongumine-thiol adduct PL-MTG, a potential PL pro-drug, was found to be substantially less potent than PL at inducing cancer cell death and elevating ROS (Table 1, entry 7).

Additional analogs disrupting the electrophilicity of the C7-C8 olefin by steric blockade or cyclization to an aromatic heterocycle showed substantially diminished toxicity in cells (Table 1, entries 9-11). Together with 7,8-dihydropiperlongumine PL-H2 discussed above, these analogs highlight the need for both Michael acceptors to observe potent cell death.

Although the C2-C3 and C7-C8 olefins appear critical for PL's actions on cells, many modifications can be made at positions distal from these olefins without greatly affecting performance in our ROS and ATP assays. Modification of the aromatic substituents of PL was largely without effect: all three aryl methoxyl groups could be removed and replaced with a variety of substituents at the ortho, meta, or para positions without substantially altering elevation of ROS or cellular toxicity (Table 1, entries 12, 13). Likewise, substitution at C5 or C4 with aromatic, heteroaromatic, and some alkyl substituents provided analogs of comparable potency to PL (Table 1, entries 14, 15). Ring expansion of the dihydropyridone, replacement of the C6 carbonyl with a sulfonyl moiety, and several other modifications also were largely neutral (Table 1, entry 4, 16).

Analogs with substituents at C2 provided a wide range of activities. A variety of alkynyl substituents at C2 induced cell death more potently than PL, with EC50 values as low as 0.4·µM (Table 1, entries 5, 17). However, other substituents at C2 were uniformly less potent than PL, with C2 alkyl or aryl groups lacking activity in both assays (Table 1, entries 3, 18). The diminished chemical reactivity of analogs with C2 alkyl substituents may be one factor contributing to the observed lack of cellular activity (FIG. 9).

Since both the C2-C3 and C7-C8 olefins are necessary to observe the levels of toxicity seen for PL, we speculated that multivalency—the ability to interact with multiple cellular targets or a single cellular target at more than one location—might alter toxicity in this system (13-16). Thus, we synthesized a structurally analogous PL 'monomer', 'dimer', and 'trimer' using a Mitsunobu inversion approach (FIG. 3A, S1). Remarkably, the PL dimer (PL-DI) showed roughly 10-fold greater potency in the ATP and ROS assays relative to a closely related monomeric analog (PL-MON) (FIG. 3B, C). Moreover, a PL trimer (PL-TRI) was found to be two-fold more potent than the dimeric analog.

Example 5

Separation of ROS Elevation from Cellular Toxicity

For PL and many analogs, doses at which ROS and cellular toxicity are elevated are closely correlated. However, two series of analogs appear to decouple the elevation of ROS and cell death. In both cell lines tested, 7,8-dihydropiperlongumine (PL-H2) and a dihydronaphthalene analog (PL-DHN) led to robust enhancement of ROS levels but to diminished cell death relative to PL (FIGS. 2, 4). Conversely, various analogs bearing alkynes at C2 showed greatly enhanced toxicity (FIG. 4A) without altering potency for the elevation of ROS (FIG. 4B). Although this enhanced cell death could be explained by C2-alkynyl analogs having additional toxic mechanisms of action, we were surprised to find analogs like PL-H2 and PL-DHN that showed elevation of ROS comparable to PL but greatly diminished cellular toxicity. A similar pattern was observed in two additional cancer cell lines (U2OS, osteosarcoma; HEC108, endometrial), indicating that the observed decoupling of ROS and cell death may be general (FIG. S2). Although elevation of cellular ROS likely places cancer cell lines under enhanced oxidative stress, this stress appears insufficient in some cases to induce cell death.

Example 6

Additional Cellular Actions

Beyond elevation of ROS, PL affects other cellular markers of oxidative stress, including depletion of glutathione (5). We next characterized a subset of analogs in additional oxidative stress assays to identify phenotypes that might correlate with cellular toxicity more closely than ROS elevation. Using a luminescence-based assay for cellular glutathione (GSH/GSSG-Glo) in the EJ bladder carcinoma line (5), a similar decrease in total cellular glutathione (ca. 60%) was observed for PL and two analogs with diminished toxicity (PLH2, PL-DHN; FIG. 5A). Decreases in total glutathione were also observed for all three compounds in HeLa cells, with PL most effective (FIG. S4). We also examined an additional oxidative stress phenotype, protein glutathionylation, using an immunofluorescence approach that relies on a monoclonal antibody recognizing glutathione. In HeLa cells, we observed large and rapid elevations in protein glutathionylation for PL and its potently toxic cyclopropyl alkynyl analog PL-cPr (FIG. 5B, C, FIG. 12). However, no elevation in protein glutathionylation was observed for PL-H2, and minimal elevation was observed for PL-DHN. Examination of our 80-analog set in both HeLa and EJ cells suggests that an unhindered, chemically reactive C7-C8 olefin is necessary for elevation of protein glutathionylation. Analogs with an unreactive or absent C7-C8 olefin, modifications that also diminish toxicity, show minimal elevation of protein glutathionylation (see Example 9). Similarly, several small molecules unrelated to piperlongumine bearing two Michael acceptor functionalities elevated glutathionylation, while nine other small molecules with a single electrophilic site did not (FIG. S6). Elevation of protein glutathionylation also correlated with toxicity, as toxic PL analogs bearing multiple Michael acceptor functionalities showed robust protein glutathionylation.

Additionally, although proteins are commonly glutathionylated during periods of oxidative stress via readily reversible disulfide bond linkages (17, 18), the protein gluathionylation observed following PL treatment could not be reversed by treatment with 0.1 M dithiothreitol, indicating a role or roles for non-disulfide covalent attachments. By contrast, the elevation of protein glutathionylation observed following treatment with glutathione disulfide (GSSG) was strikingly reversed by treatment with 0.1 M dithiothreitol (Supporting FIG. 5).

Example 7

Selectivity for Cancer Cells Over Nontransformed Cells

Figure 13A:
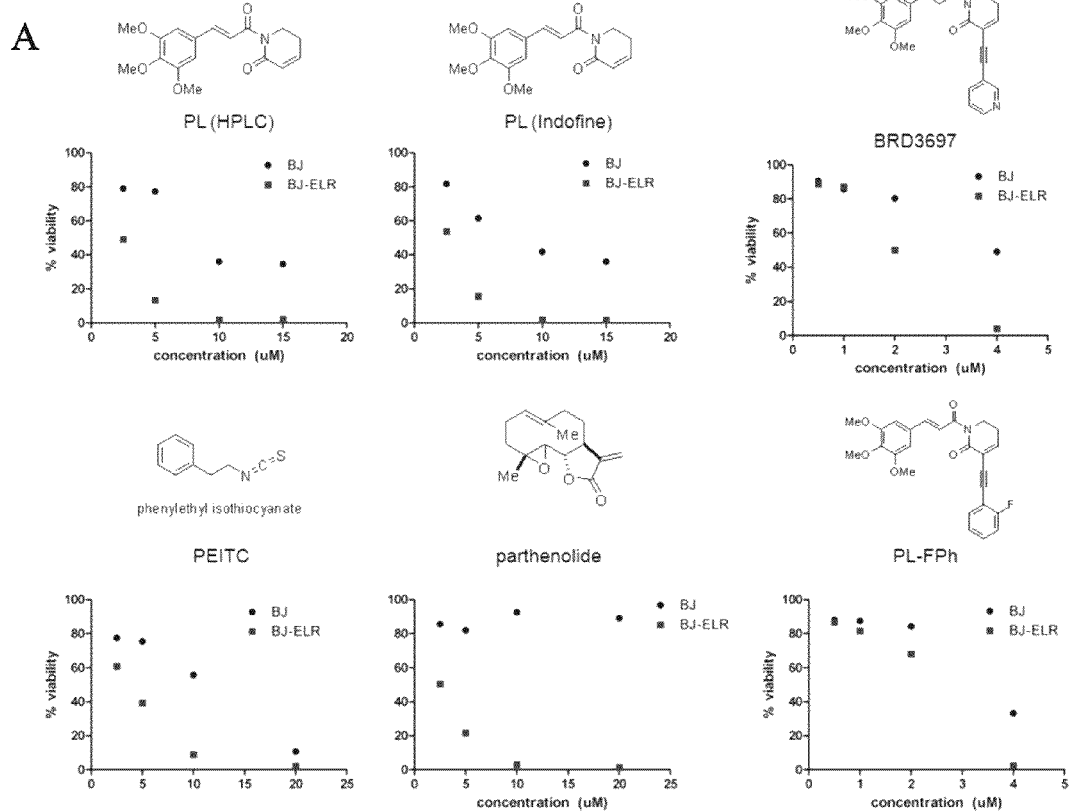
FIG. 13 A, B illustrate results of an initial screen for selective toxicity with PL and 8 analogs in the BJ/BJ-ELR model of tumorigenesis. Viability was measured using crystal violet.
Figure 13B:
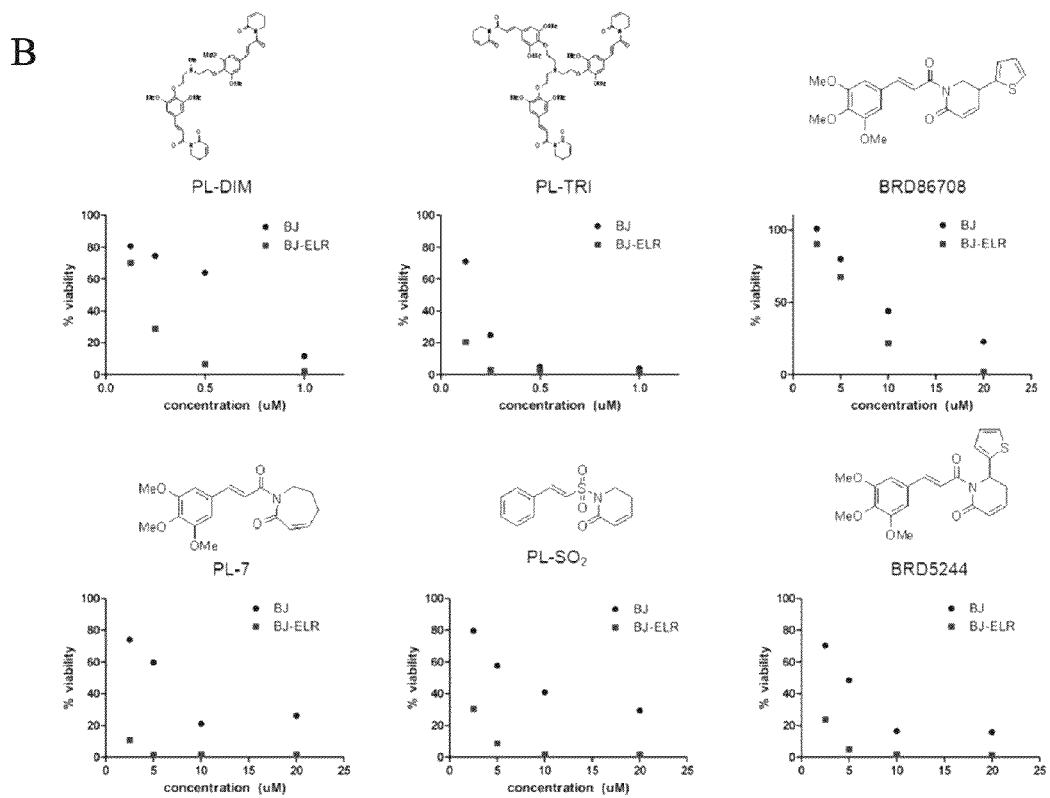
Figure 14A:
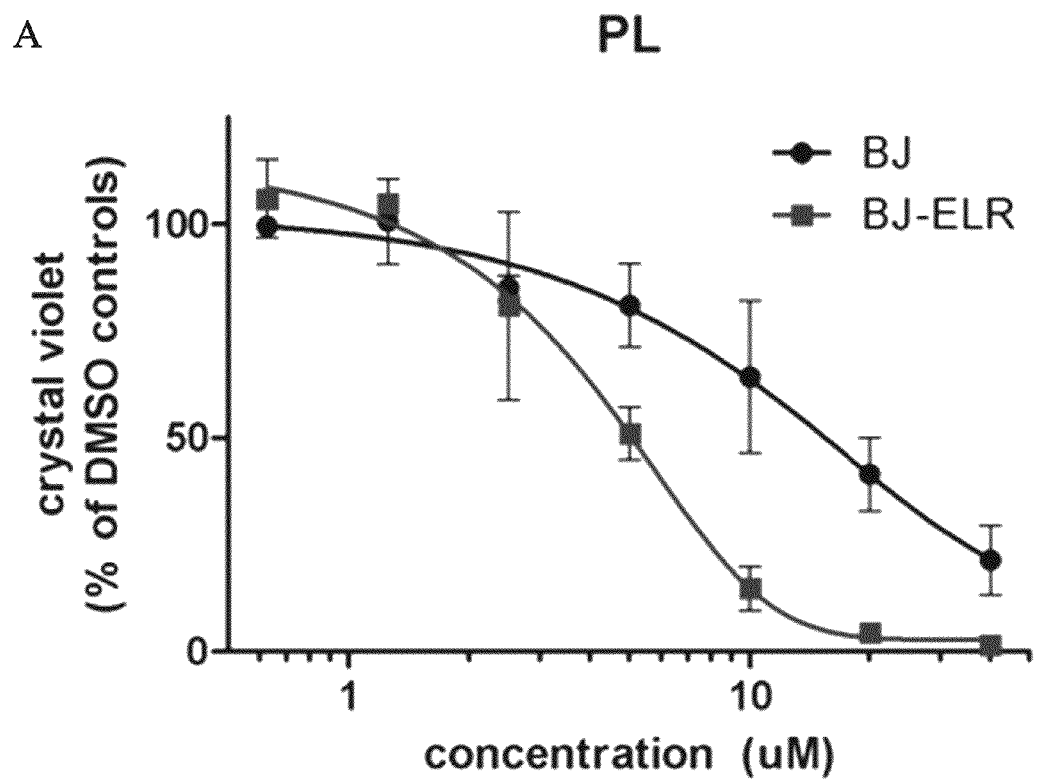
FIG. 14A, B, C illustrate the performance of PL and analogs in the BJ/BJ-ELR model tumorigenesis. A) PL performance. B) Bright-field images confirming selective loss of viability at stated doses. C) Performance of analogs as shown in FIG. 6. Data are expressed as mean±SD for three independent experiments.
Figure 14B:
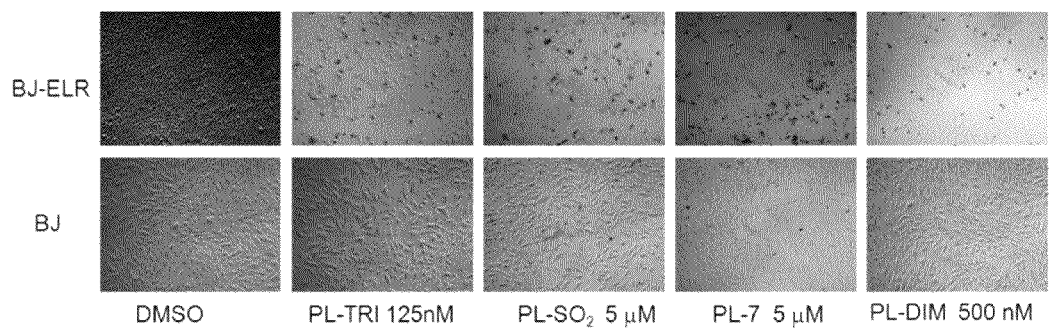
Figure 14C:
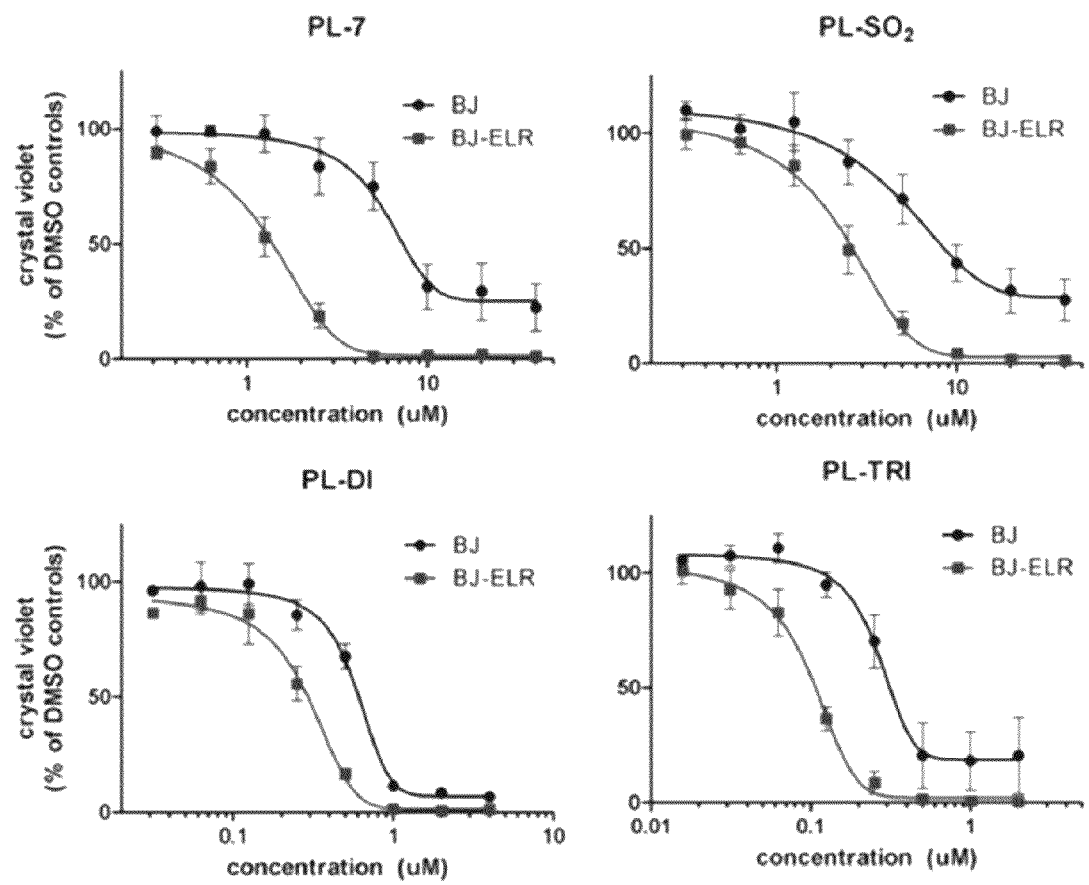
Figure 15:
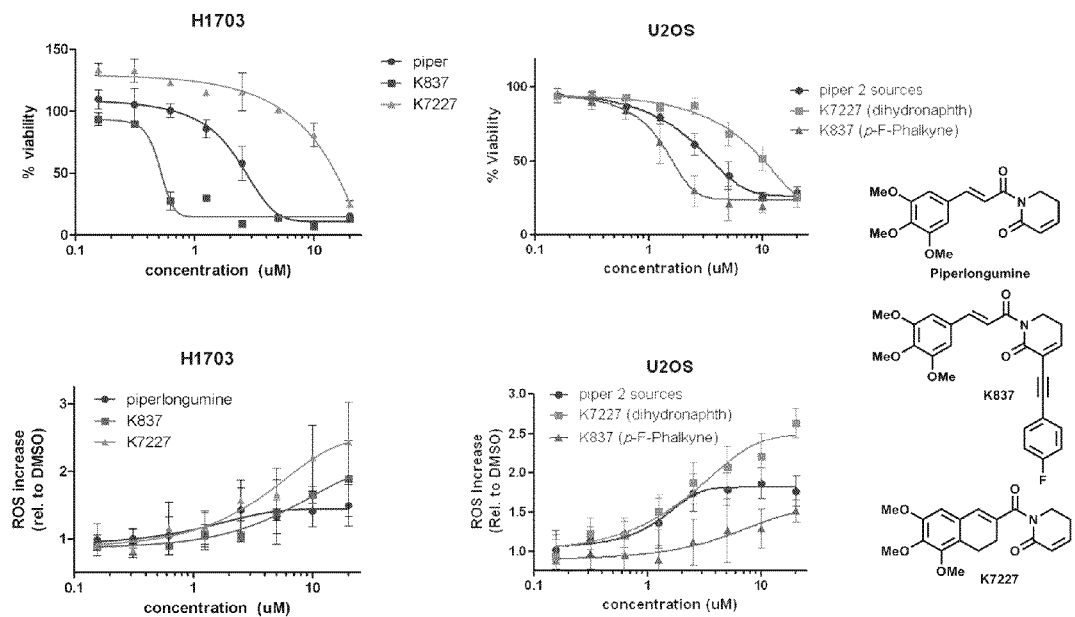
FIG. 15 illustrates the identification of probe compounds that decouple ROS elevation and toxicity.
Figure 16A:
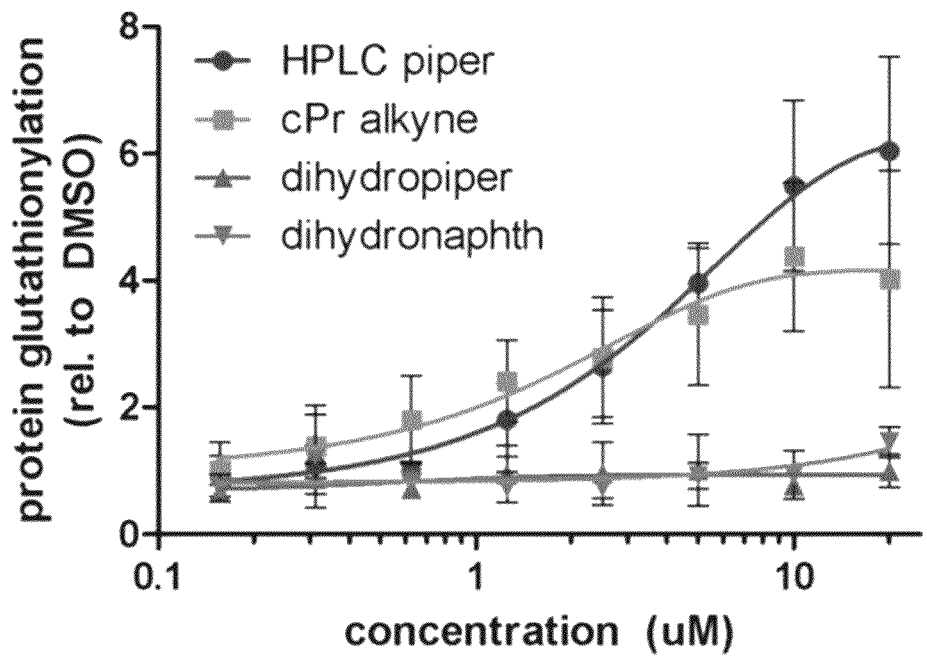
FIG. 16A, B, C, D illustrate compounds that relate the observed toxicity to protein glutathionylation.
Figure 16B:
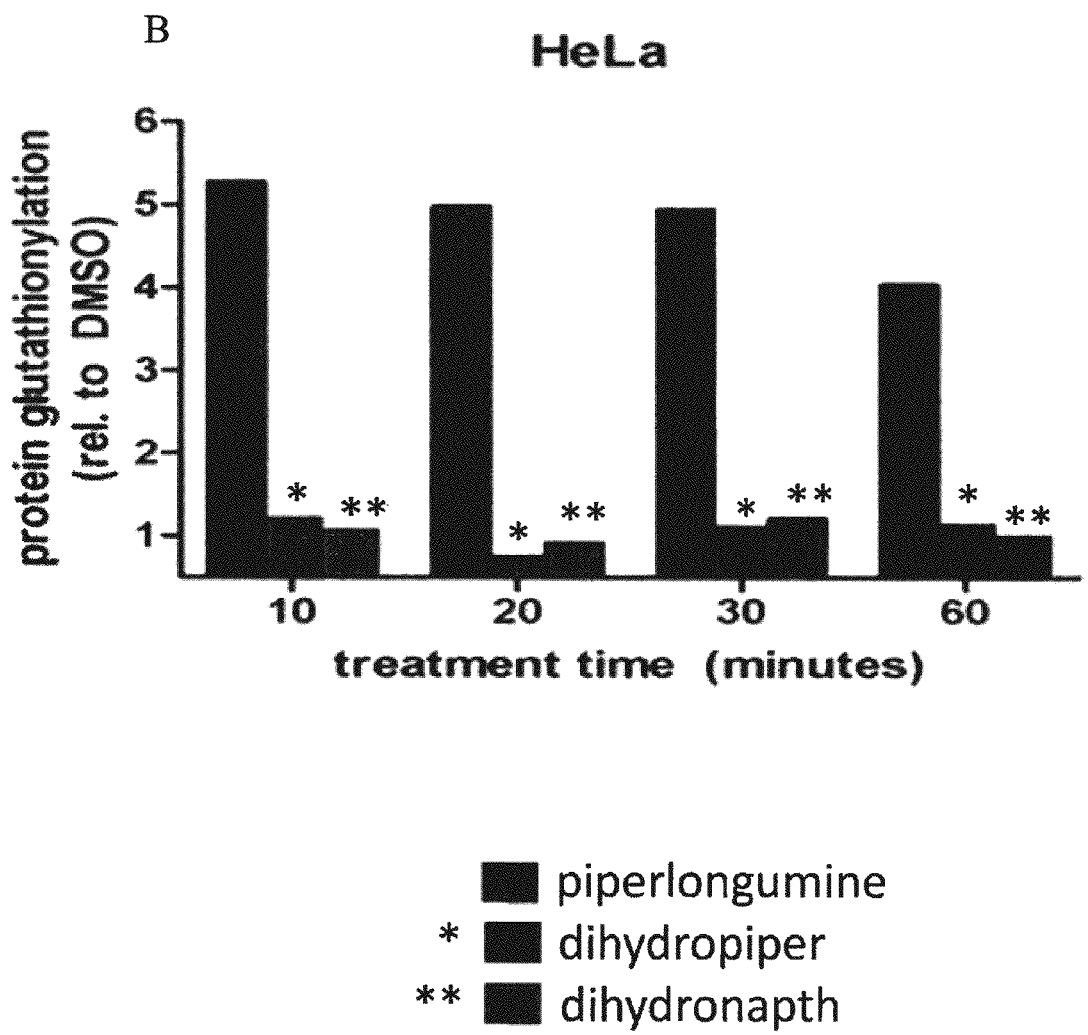
Figure 16C:
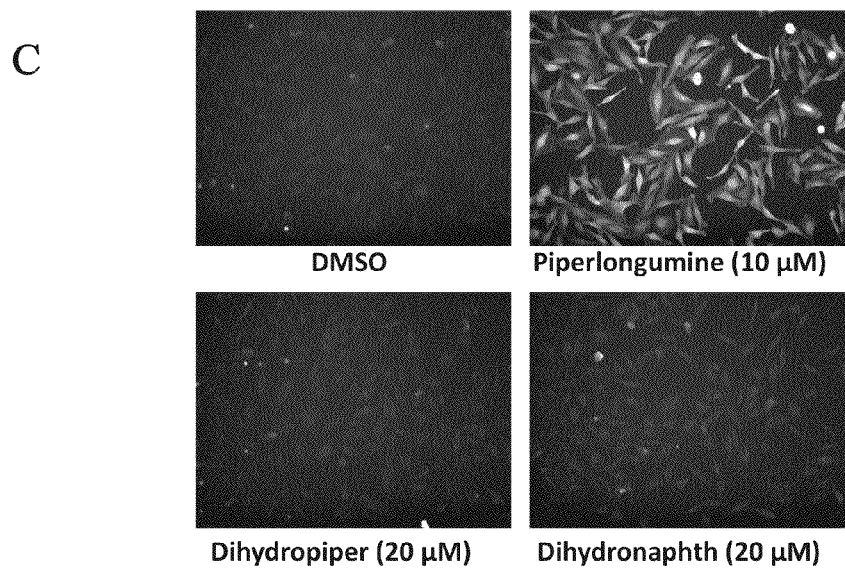
Figure 16D:
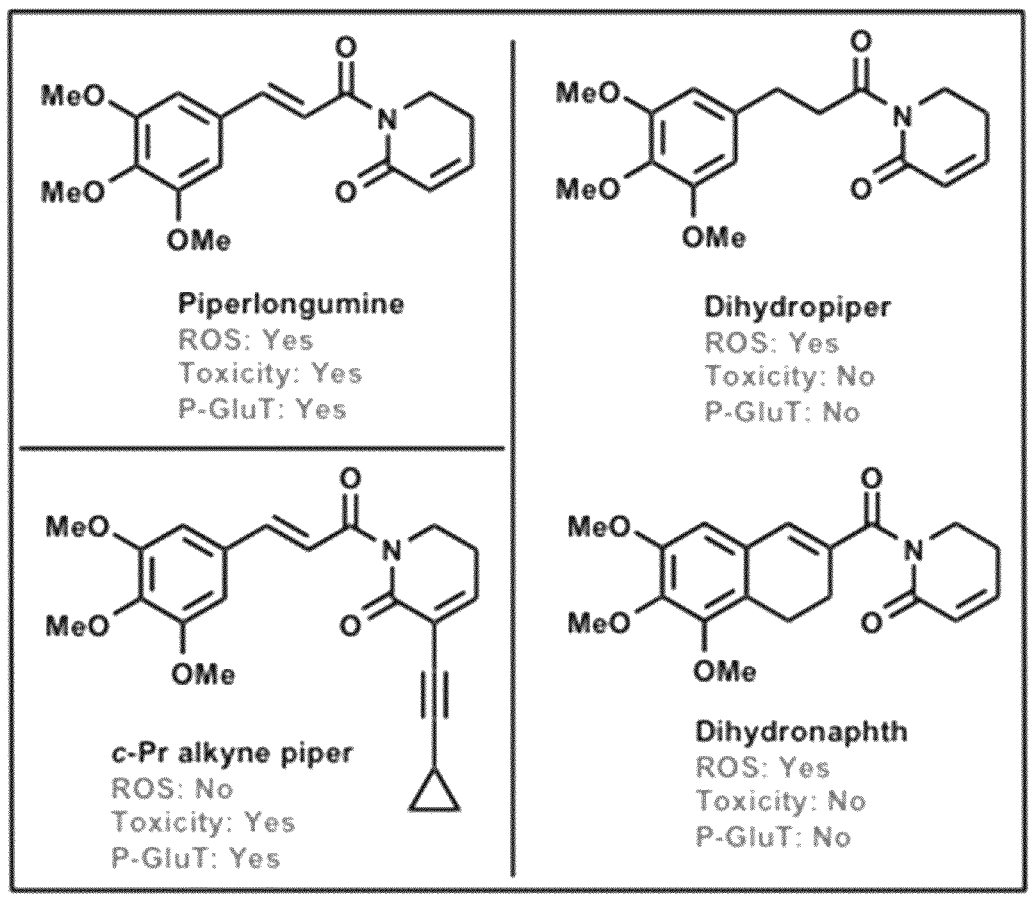
Figure 17:
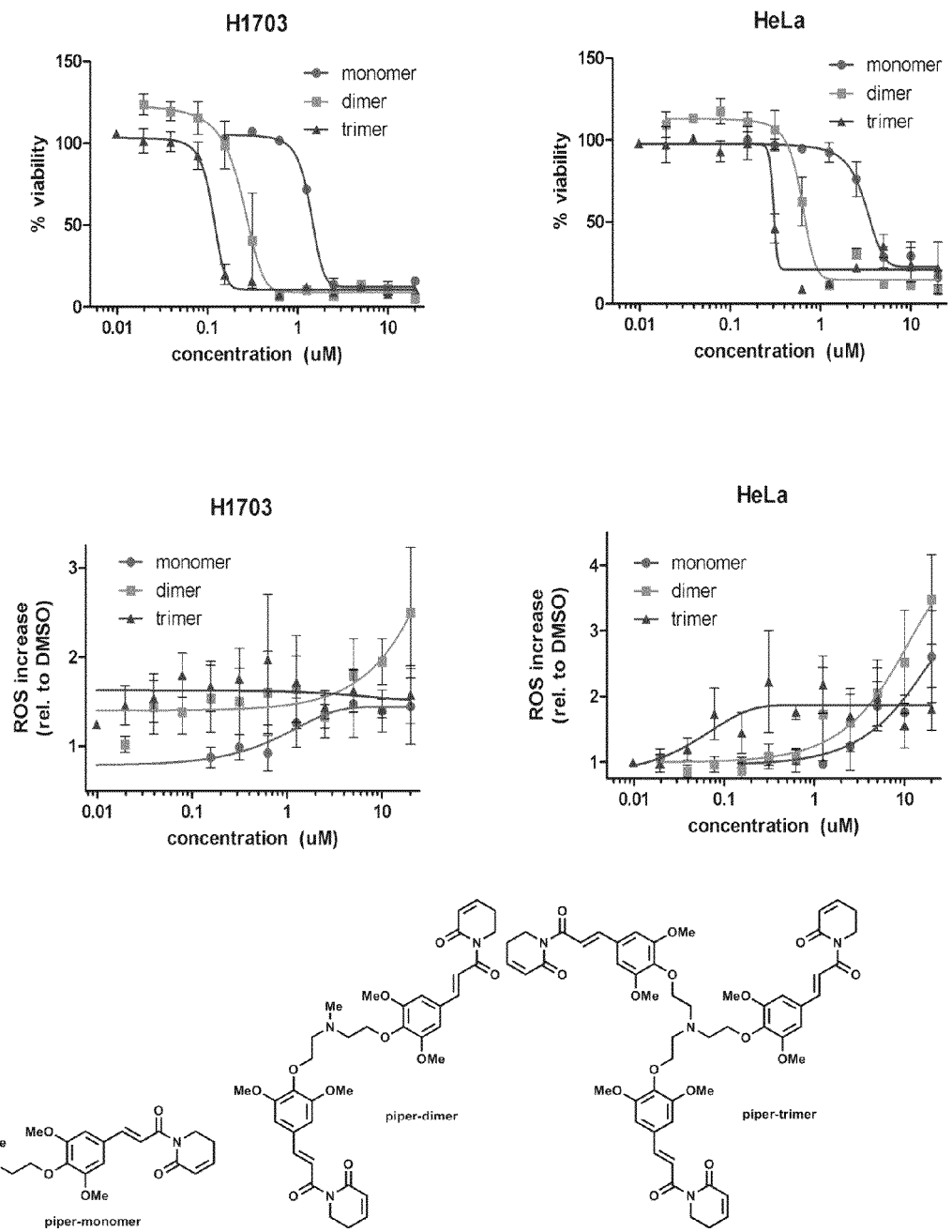
FIG. 17 illustrates that oligomers of piperlongumine potently elevate ROS levels and decrease cell viability.

We evaluated whether our analogs, like PL, could selectively target cancer cells over nontransformed cells using an established isogenic model of tumorigenesis (5). Such models rely on serial transduction of primary human cell types with defined genetic factors to create an engineered cancer cell line. We compared BJ human fibroblasts with the BJ-ELR line, which is fully transformed by the addition of hTERT, large-T antigen, and an oncogenic HRAS-V12 allele (19). Eight representative analogs were evaluated by crystal violet staining for cell numbers. Phenethylisothiocyanate and parthenolide, two electrophilic small molecules previously shown to be selectively toxic to cancer cells by a mechanism involving ROS elevation (8, 12), also showed selectivity in this assay. Initial screening of the eight analogs established that most retained a degree of selective toxicity in this isogenic cell line pair, although some were inferior to PL (FIG. 13). Further testing confirmed that four analogs showed selectivity comparable to PL (PL-7, PL-DI, PL-TRI, and sulfonimide derivative PL-SO2), with the ring-expanded analog PL-7 being the most selective (FIG. 6, 14, 18).

Figure 18:
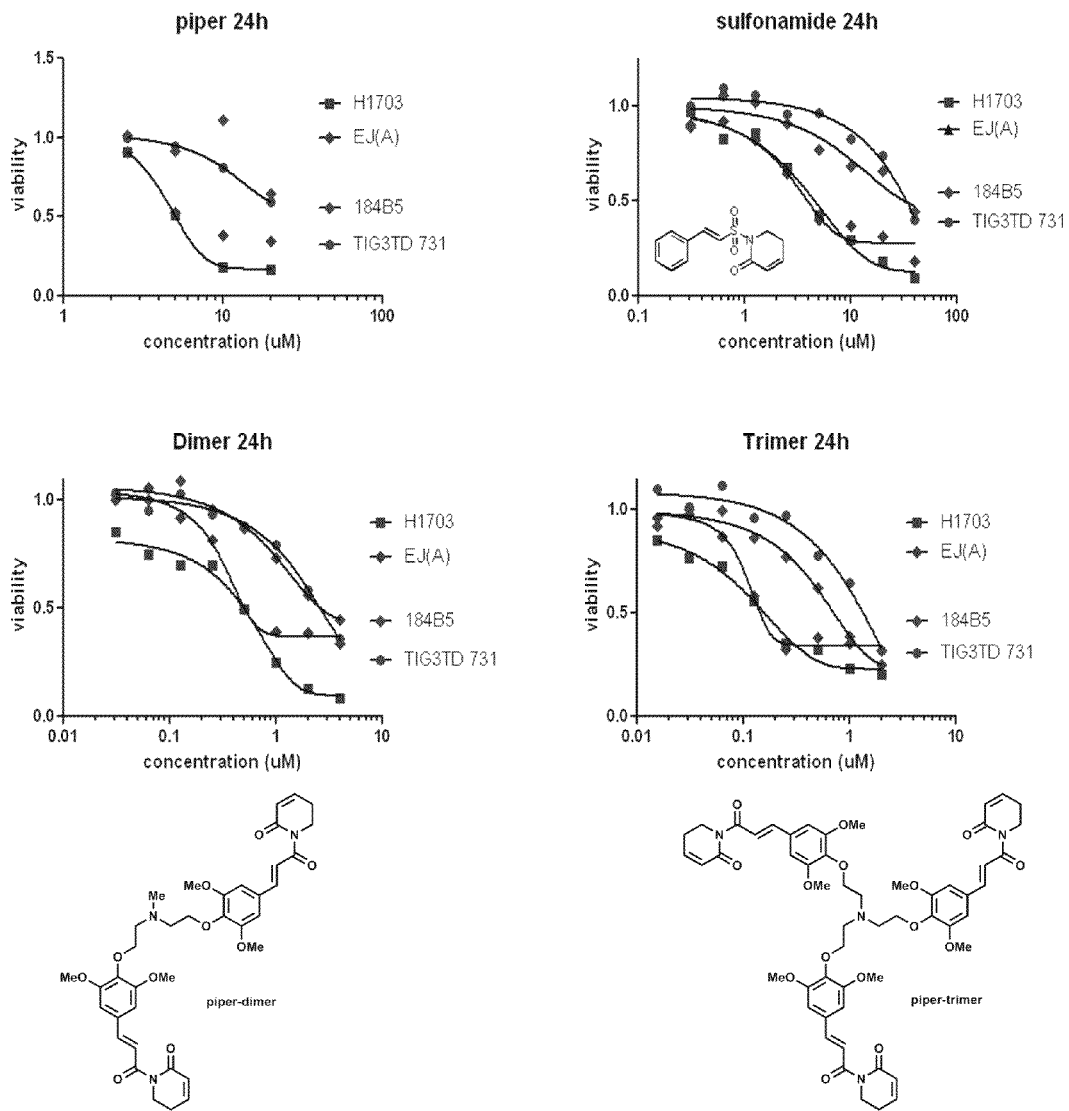
FIG. 18 illustrates selective cell death induced by improved piperlongumine analogs in cancer cells. Normal cell lines: 184B5, TIG3TD; Cancer cell lines: EJ, H1703, Hela; assays performed in a 12-well plate with crystal violet.

Similar experiments also indicated that certain iPLA analogs could exhibit improved selectivity towards certain transformed cells or cancer cells relative to non-transformed and non-cancer cells, respectively (see data for "Sul", "7 ring", "Dimer", and "Trimer" in FIGS. 18, and 19).

Example 8

Summary and References

By synthesizing and testing an array of PL analogs, we have identified the C2-C3 olefin as a key pharmacophore, with the C7-C8 olefin also playing a significant role in determining toxicity (FIG. 7A). Although a wide range of modifications at positions distal to these olefins is largely neutral, modifications expected to impair the reactivity of these olefins diminish analogs' effects on cells. The C2-C3 olefin reacts with a small-molecule thiol under neutral conditions in DMSO, but exposure of the resulting PL-thiol adduct to cells was largely without effect. Addition of a C2 methyl group ablates both chemical reactivity in vitro and all observed cellular phenotypes, further supporting the necessity of reactivity at C3 for actions in cells. Although addition of thiols at C8 was not observed using our neutral in vitro conditions, the presence of cellular thiolate nucleophiles or the enhanced effective molarity following addition of a cellular nucleophile at C3 may greatly enhance the rate of thiol addition at C8.

As both olefins appeared necessary for PL's toxicity to cells, we evaluated several oligomers of PL to explore further the role of multivalent electrophilicity in determining toxicity. Notably, a PL dimer resulted in a nearly ten-fold increase in toxicity. The ability to cross-link additional cellular nucleophiles may limit the reversibility of compound binding or cause more extensive disruption of the structure and function of targeted proteins relative to PL itself. A PL trimer was only two-fold more potent than the analogous dimer, suggesting diminishing returns for addition of further PL units. These highly potent oligomers, as well as several other analogs, also retained similar selectivity for transformed cells as observed for PL in an isogenic model of tumorigenesis.

As noted above, PL analogs with only a single electrophilic moiety showed diminished cell death but often gave rise to substantial increases in ROS, suggesting that ROS elevation may not be sufficient or even necessary for cell death in some cellular contexts. Although the specific ROS measured and their subcellular localization may vary between analogs, PL and its active analogs are likely capable of reaction with a variety of cellular protein thiols, including some that may contribute to cell death independent of elevation of ROS levels.

We also assessed the performance of our analogs in additional oxidative stress assays. Several analogs with varying degrees of toxicity showed a similar ability to deplete cellular glutathione. As previous reports have established that substantial reductions in glutathione (for example, as induced by the glutathione biosynthesis inhibitor BSO) need not result in cell death, the contribution of glutathione depletion to PL's cellular toxicity remains unclear (20-22). Additionally, we note that reported estimates of HeLa cell volume (2,600 $\mu m^3$) (23) and typical concentrations of cellular reduced glutathione (ca. 5 mM) (24) suggest that PL is present at quantities greatly in excess of cellular glutathione under our assay conditions (1,000 cells per well, 50 µl per well). As such, direct conjugation of PL with glutathione at C3 is a plausible explanation for the observed decrease in total glutathione.

Treatment with PL or analogs with two reactive electrophilic sites also gives rise to enhanced glutathionylation of cellular proteins, while analogs with a single Michael acceptor did not. We propose that formation of a covalent complex linking glutathione, PL, and a glutathione binding protein via both PL's electrophilic Michael acceptor functionalities can account for these observations (FIG. 7B). Without seeking to be limited by theory, we imagine a sequence involving first a Michael addition of glutathione to PL's more electrophilic C(2)-C(3) olefin followed by the formation of a noncovalent complex between the PL-glutathione adduct and a glutathione-binding protein, and finally a Michael addition of a nucleophilic residue of the glutathione-binding protein to the less electrophilic C(7)-C(8) olefin that is accelerated by the formation of the complex. Mechanistically analogous protein glutathionylation under conditions of electrophilic stress has been observed recently for the metabolic byproduct 4-oxononenal (25) and the chemotherapeutic busulfan (26), both of which are bivalent electrophiles. Such a model also provides a chemical rationale for the results of an unbiased quantitative proteomics analysis of proteins binding to PL, which identified numerous glutathione-binding proteins among the highest confidence interactions (5). We note that there exist other naturally occurring, biologically active small molecules with two sites of reactivity—one with greater and the other with lesser electrophilicity. Thus, it is possible that the proposed mechanism, where a small organic molecule is inserted between glutathione and a protein in the protein glutathionylation process, has generality beyond PL. Although not measured in this study, PL may also covalently modify additional cellular proteins. Notably, proteins that do not bind glutathione were also high-signal outliers in the reported quantitative proteomic analysis, including four proteins previously shown to be modified following treatment with electrophiles (PRDX1; RPS5; VIM; AHNAK) (5, 27-30). Taken together, our observations suggest that elevation of protein glutathionylation or other cellular cross-linking events may be a feature of cells treated with PL more closely associated with cellular toxicity than elevation of ROS or glutathione depletion. Further proteomic analyses will be required to identify specific protein glutathionylation events and proteins that interact with analogs of markedly enhanced (PL-DI, PL-TRI) or diminished (PL-H2) electrophilicity and toxicity (31). These studies establish a central role for multivalent electrophilicity in the chemical biology of PL and related compounds, and indicate that both electrophilic and oxidative stress phenotypes can contribute to PL's promising cancer-selective toxicity.

References

1. Lee A C, et al. (1999) Ras proteins induce senescence by altering the intracellular levels of reactive oxygen species. *J Biol Chem* 274(12):7936-7940.
2. Szatrowski T P & Nathan C F (1991) Production of large amounts of hydrogen peroxide by human tumor cells. *Cancer Res* 51(3):794-798.
3. Luo J, Solimini N L, & Elledge S J (2009) Principles of cancer therapy: oncogene and non-oncogene addiction. *Cell* 136(5):823-837.
4. Fruehauf J P & Meyskens F L, Jr. (2007) Reactive oxygen species: a breath of life or death? *Clin Cancer Res* 13(3): 789-794.
5. Raj L, et al. (2011) Selective killing of cancer cells by a small molecule targeting the stress response to ROS. *Nature* 475(7355):231-234.
6. Wondrak G T (2009) Redox-directed cancer therpeutics: molecular mechanisms and opportunities. *Antioxid Redox Signal* 11(12):3013-3069.
7. Trachootham D, Alexandre J, & Huang P (2009) Targeting cancer cells by ROSmediated mechanisms: a radical therapeutic approach? *Nat Rev Drug Discov* 8(7):579-591.
8. Trachootham D, et al. (2006) Selective killing of oncogenically transformed cells through a ROS-mediated mechanism by beta-phenylethyl isothiocyanate. *Cancer Cell* 10(3):241-252.
9. Huang P, Feng L, Oldham E A, Keating M J, & Plunkett W (2000) Superoxide dismutase as a target for the selective killing of cancer cells. *Nature* 407(6802):390-395.
10. Shaw A T, et al. (2011) Selective killing of K-ras mutant cancer cells by small molecule inducers of oxidative stress. *Proc Natl Acad Sci USA* 108(21):8773-8778.
11. Dolma S, Lessnick S L, Hahn W C, & Stockwell B R (2003) Identification of genotypeselective antitumor agents using synthetic lethal chemical screening in engineered human tumor cells. *Cancer Cell* 3(3):285-296.
12. Guzman M L, et al. (2007) An orally bioavailable parthenolide analog selectively eradicates acute myelogenous leukemia stem and progenitor cells. *Blood* 110(13):4427-4435.
13. Corson T W, Aberle N, & Crews C M (2008) Design and Applications of Bifunctional Small Molecules Why Two Heads Are Better Than One. *ACS Chem Biol* 3(11):677-692.
14. Dinkova-Kostova A T, et al. (2005) Extremely potent triterpenoid inducers of the phase 2 response: correlations of protection against oxidant and inflammatory stress. *Proc Natl Acad Sci USA* 102(12):4584-4589.
15. Wissner A, et al. (2003) Synthesis and structure-activity relationships of 6,7-disubstituted 4-anilinoquinoline-3-carbonitriles. The design of an orally active, irreversible inhibitor of the tyrosine kinase activity of the epidermal growth factor receptor (EGFR) and the human epidermal growth factor receptor-2 (HER-2). *J Med Chem* 46(1):49-63.
16. West J D, Stamm C E, Brown H A, Justice S L, & Morano K A (2011) Enhanced toxicity of the protein cross-linkers divinyl sulfone and diethyl acetylenedicarboxylate in comparison to related monofunctional electrophiles. *Chem Res Toxicol* 24(9):1457-1459.
17. Dalle-Donne I, et al. (2008) Molecular mechanisms and potential clinical significance of S-glutathionylation. *Antioxid Redox Signal* 10(3):445-473.
18. Klatt P & Lamas S (2000) Regulation of protein function by S-glutathiolation in response to oxidative and nitrosative stress. *Eur J Biochem* 267(16):4928-4944.
19. Hahn W C, et al. (1999) Creation of human tumour cells with defined genetic elements. *Nature* 400(6743):464-468.
20. Marengo B, et al. (2008) GSH loss per se does not affect neuroblastoma survival and is not genotoxic. *Int J Oncol* 32(1):121-127.
21. Goto H, Yanagimachi M, Kajiwara R, Kuroki F, & Yokota S (2007) Lack of mitochondrial depolarization by oxidative stress is associated with resistance to buthionine sulfoximine in acute lymphoblastic leukemia cells. *Leuk Res* 31(9):1293-1301.
22. Green R M, Graham M, O'Donovan M R, Chipman J K, & Hodges N J (2006) Subcellular compartmentalization of glutathione: correlations with parameters of oxidative stress related to genotoxicity. *Mutagenesis* 21(6):383-390.
23. Zhao L, et al. (2008) Intracellular water-specific MR of microbead-adherent cells: the HeLa cell intracellular water exchange lifetime. *NMR Biomed* 21(2):159-164.
24. Chakravarthi S, Jessop C E, & Bulleid N J (2006) The role of glutathione in disulphide bond formation and endoplasmic-reticulum-generated oxidative stress. *EMBO Rep* 7(3):271-275.
25. Zhu X, Gallogly M M, Mieyal J J, Anderson V E, & Sayre L M (2009) Covalent crosslinking of glutathione and carnosine to proteins by 4-oxo-2-nonenal. *Chem Res Toxicol* 22(6):1050-1059.
26. Cooper A J, Pinto J T, & Callery P S (2011) Reversible and irreversible protein glutathionylation: biological and clinical aspects. *Expert Opin Drug Metab Toxicol* 7(7):891-910.
27. Rabilloud T, et al. (2002) Proteomics analysis of cellular response to oxidative stress. Evidence for in vivo overoxidation of peroxiredoxins at their active site. *J Biol Chem* 277(22):19396-19401.
28. Shenton D & Grant C M (2003) Protein S-thiolation targets glycolysis and protein synthesis in response to oxidative stress in the yeast *Saccharomyces cerevisiae*. *Biochem J* 374(Pt 2):513-519.
29. Huang B, Liao C L, Lin Y P, Chen S C, & Wang D L (2009) S-nitrosoproteome in endothelial cells revealed by a modified biotin switch approach coupled with Western blot-based two-dimensional gel electrophoresis. *J Proteome Res* 8(10):4835-4843.
30. Koshiyama A & Imai K (2010) Synthesis and evaluation of a fluorogenic reagent for proteomic studies: 7-fluoro-N-[2-(dimethylamino)ethyl]-2,1,3-benzoxadiazole-4-sulfonamide (DAABD-F). *Analyst* 135(8):2119-2124.
31. Liebler D C (2008) Protein damage by reactive electrophiles: targets and consequences. *Chem Res Toxicol* 21(1): 117-128.

Example 10

EC50 Values for Cell Viability for Select Analogs

The effects of compound treatments on ATP levels, a surrogate for cell viability, were measured after 48 hours essentially as described in Example 2. Assays were performed in 384-well plates on two human cancer cell lines, H1703 (lung) and HeLa (cervix).

TABLE 2

Effects on cellular ATP levels for PL and selected PL analogs in two cell lines.

| No. | Structure | $EC_{50}$ H1703 (μM) | $EC_{50}$ HeLa (μM) |
|---|---|---|---|
| 1 | PL | 2.8 | 7.1 |
| 2 | PL-2,3H$_2$ | n.t. | n.t. |
| 3 | 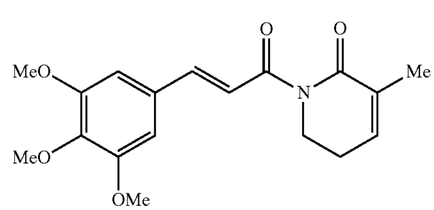 | n.t. | n.t. |

TABLE 2-continued

Effects on cellular ATP levels for PL and selected PL analogs in two cell lines.

| No. | Structure | EC$_{50}$ H1703 (μM) | EC$_{50}$ HeLa (μM) |
| --- | --- | --- | --- |
| 4 | PL-7 | 1.9 | 5.1 |
| 5 | PL-cPr | 0.7 | 1.3 |
| 6 | PL-H$_2$ | 17.5 | n.t. |
| 7 | 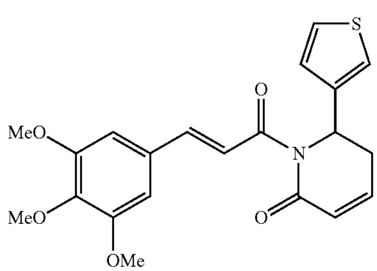 [SMILES: COc1cc(/C=C/C(=O)N2C(=O)C=CCC2c2ccsc2)cc(OC)c1OC] | 2 | 2 |
| 8 | 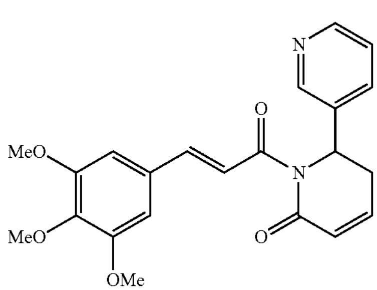 [SMILES: COc1cc(/C=C/C(=O)N2C(=O)C=CCC2c2cccnc2)cc(OC)c1OC] | 3 | 6 |

TABLE 2-continued

Effects on cellular ATP levels for PL and selected PL analogs in two cell lines.

| No. | Structure | EC$_{50}$ H1703 (μM) | EC$_{50}$ HeLa (μM) |
|---|---|---|---|
| 9 | 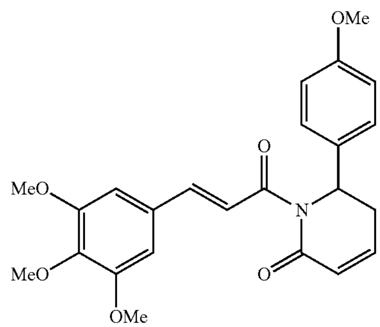 [SMILES: COc1ccc(C2CC=CC(=O)N2C(=O)/C=C/c2cc(OC)c(OC)c(OC)c2)cc1] | 4 | 7 |
| 10 | 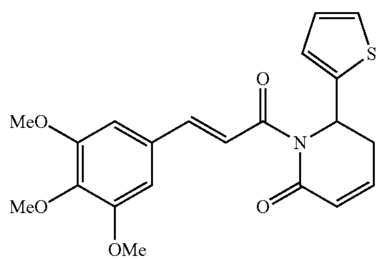 [SMILES: COc1cc(/C=C/C(=O)N2C(=O)C=CCC2c2cccs2)cc(OC)c1OC] | 2 | 4 |
| 11 | 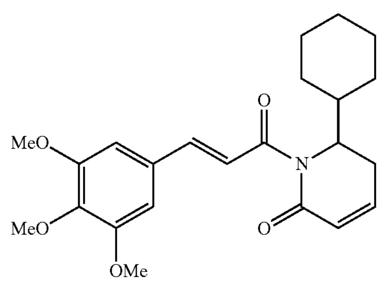 [SMILES: COc1cc(/C=C/C(=O)N2C(=O)C=CCC2C2CCCCC2)cc(OC)c1OC] | 6 | 7 |
| 12 | 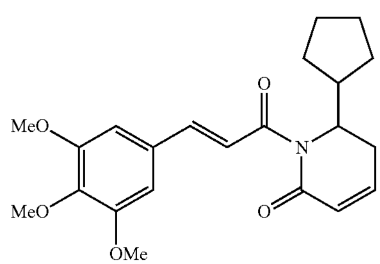 [SMILES: COc1cc(/C=C/C(=O)N2C(=O)C=CCC2C2CCCC2)cc(OC)c1OC] | 6 | 6 |
| 13 | 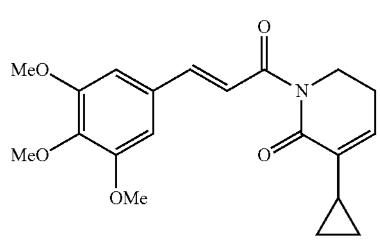 [SMILES: COc1cc(/C=C/C(=O)N2CCC=C(C3CC3)C2=O)cc(OC)c1OC] | n.t | n.t |

TABLE 2-continued

Effects on cellular ATP levels for PL and selected PL analogs in two cell lines.

| No. | Structure | EC$_{50}$ H1703 (μM) | EC$_{50}$ HeLa (μM) |
|---|---|---|---|
| 14 | 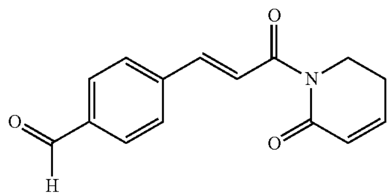 [SMILES: O=Cc1ccc(/C=C/C(=O)N2CCC=CC2=O)cc1] | 5 | 8 |
| 15 | 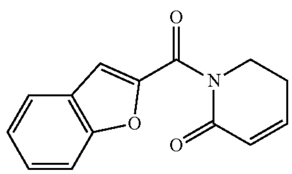 [SMILES: O=C1C=CCCN1C(=O)c1cc2ccccc2o1] | 10 | 20 |
| 16 | 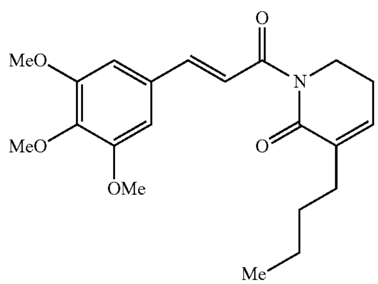 [SMILES: CCCCC1=CCCN(C(=O)/C=C/c2cc(OC)c(OC)c(OC)c2)C1=O] | n.t | n.t |
| 17 | 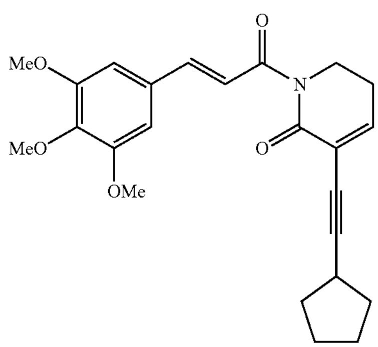 [SMILES: COc1cc(/C=C/C(=O)N2CCC=C(C#CC3CCCC3)C2=O)cc(OC)c1OC] | 1 | 3 |
| 18 | 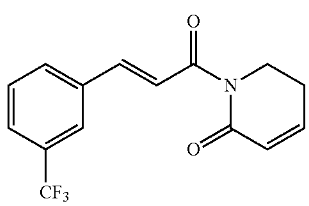 [SMILES: O=C1C=CCCN1C(=O)/C=C/c1cccc(C(F)(F)F)c1] | 5 | 6 |
| 19 | 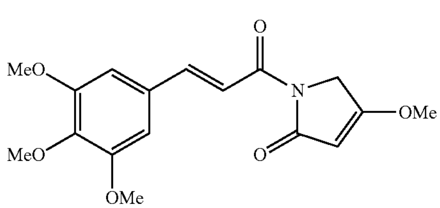 [SMILES: COC1=CC(=O)N(C(=O)/C=C/c2cc(OC)c(OC)c(OC)c2)C1] | n.t | n.t |

TABLE 2-continued

Effects on cellular ATP levels for PL and selected PL analogs in two cell lines.

| No. | Structure | EC$_{50}$ H1703 (μM) | EC$_{50}$ HeLa (μM) |
|---|---|---|---|
| 20 | 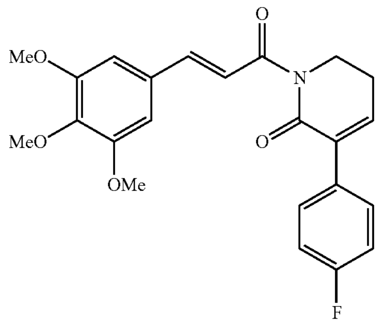 [SMILES: COc1cc(/C=C/C(=O)N2CCC=C(c3ccc(F)cc3)C2=O)cc(OC)c1OC] | >20 | n.t. |
| 21 | 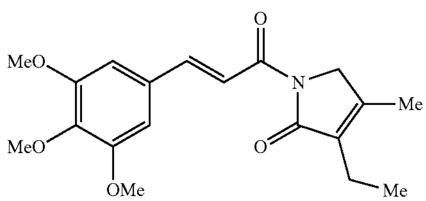 [SMILES: CCC1=C(C)CN(C(=O)/C=C/c2cc(OC)c(OC)c(OC)c2)C1=O] | n.t. | n.t. |
| 22 | 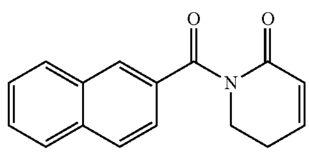 [SMILES: O=C1C=CCCN1C(=O)c1ccc2ccccc2c1] | 9 | 20 |
| 23 | 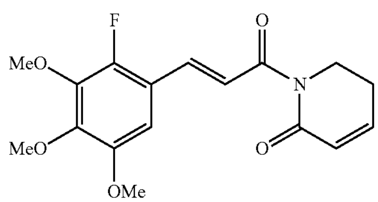 [SMILES: COc1cc(/C=C/C(=O)N2CCC=CC2=O)c(F)c(OC)c1OC] | 0.8 | 3 |
| 24 | 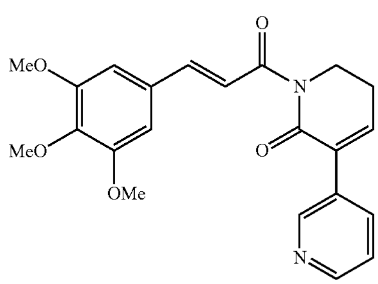 [SMILES: COc1cc(/C=C/C(=O)N2CCC=C(c3cccnc3)C2=O)cc(OC)c1OC] | >20 | n.t. |
| 25 | 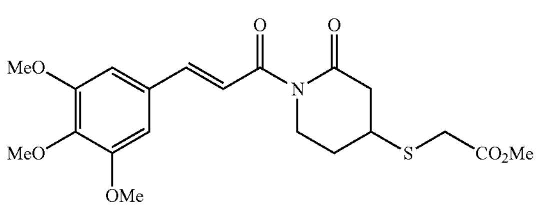 [SMILES: COC(=O)CSC1CCN(C(=O)/C=C/c2cc(OC)c(OC)c(OC)c2)C(=O)C1] | 7.9 | >20 |

TABLE 2-continued

Effects on cellular ATP levels for PL and selected PL analogs in two cell lines.

| No. | Structure | EC$_{50}$ H1703 (μM) | EC$_{50}$ HeLa (μM) |
|---|---|---|---|
| 26 | 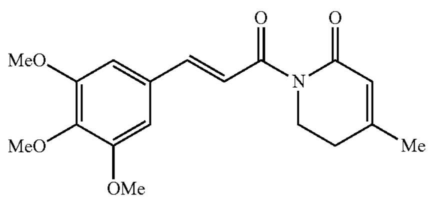 [SMILES: COc1cc(/C=C/C(=O)N2CCC(C)=CC2=O)cc(OC)c1OC] | n.t. | n.t. |
| 27 | 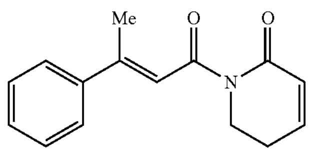 [SMILES: C/C(=C\C(=O)N1CCC=CC1=O)c1ccccc1] | 14 | >20 |
| 28 | 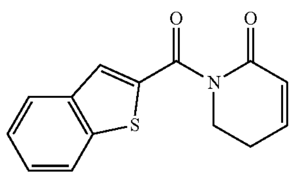 [SMILES: O=C1C=CCCN1C(=O)c1cc2ccccc2s1] | 18 | >20 |
| 29 | PL-DHN | 14 | n.t. |
| 30 | 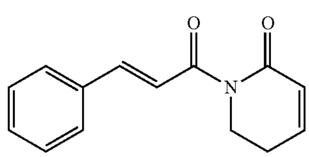 [SMILES: O=C1C=CCCN1C(=O)/C=C/c1ccccc1] | 3.5 | 7.1 |
| 31 | 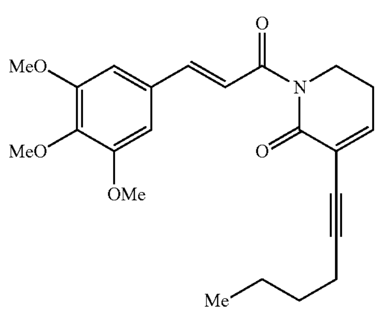 [SMILES: CCCCC#CC1=CCCN(C(=O)/C=C/c2cc(OC)c(OC)c(OC)c2)C1=O] | 0.9 | 2 |
| 32 | 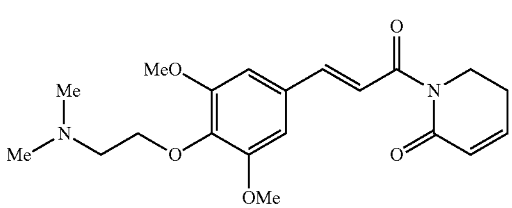 [SMILES: COc1cc(/C=C/C(=O)N2CCC=CC2=O)cc(OC)c1OCCN(C)C] | 1.5 | 4 |

TABLE 2-continued

Effects on cellular ATP levels for PL and selected PL analogs in two cell lines.

| No. | Structure | EC$_{50}$ H1703 (μM) | EC$_{50}$ HeLa (μM) |
|---|---|---|---|
| 33 | 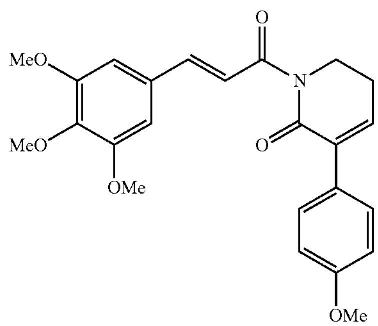 [SMILES: COc1ccc(C2=CCCN(C(=O)/C=C/c3cc(OC)c(OC)c(OC)c3)C2=O)cc1] | n.t | n.t |
| 34 | 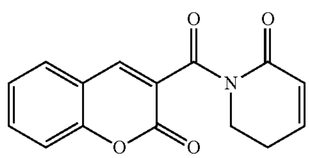 [SMILES: O=C1C=CCCN1C(=O)c1cc2ccccc2oc1=O] | 5 | 15 |
| 35 | 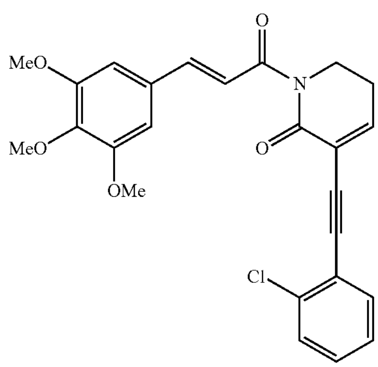 [SMILES: COc1cc(/C=C/C(=O)N2CCC=C(C#Cc3ccccc3Cl)C2=O)cc(OC)c1OC] | 0.6 | 1.5 |
| 36 | 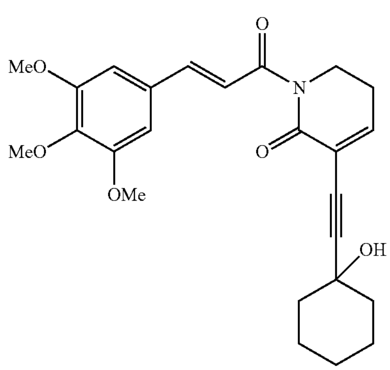 [SMILES: COc1cc(/C=C/C(=O)N2CCC=C(C#CC3(O)CCCCC3)C2=O)cc(OC)c1OC] | 0.5 | 1.5 |
| 37 | 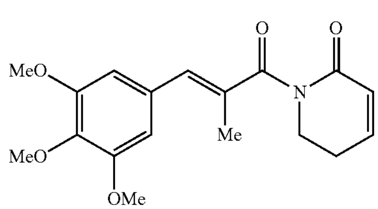 [SMILES: COc1cc(/C=C(\C)C(=O)N2CCC=CC2=O)cc(OC)c1OC] | 4 | 18 |

TABLE 2-continued

Effects on cellular ATP levels for PL and selected PL analogs in two cell lines.

| No. | Structure | EC$_{50}$ H1703 (μM) | EC$_{50}$ HeLa (μM) |
| --- | --- | --- | --- |
| 38 | 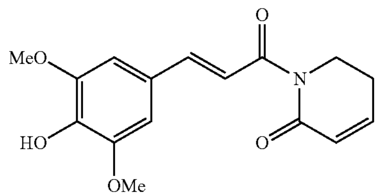 [SMILES: COc1cc(/C=C/C(=O)N2CCC=CC2=O)cc(OC)c1O] | 3 | 8 |
| 39 | 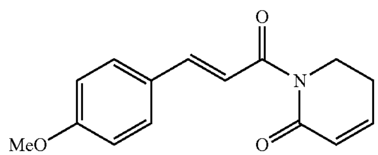 [SMILES: COc1ccc(/C=C/C(=O)N2CCC=CC2=O)cc1] | 5 | 18 |
| 40 | 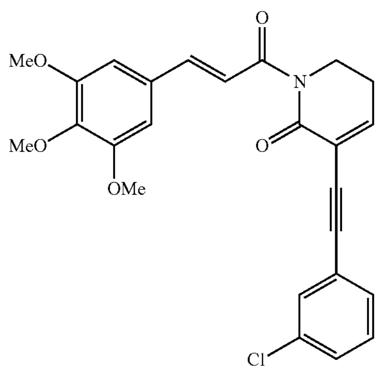 [SMILES: COc1cc(/C=C/C(=O)N2CCC=C(C#Cc3cccc(Cl)c3)C2=O)cc(OC)c1OC] | 1.5 | 5 |
| 41 | 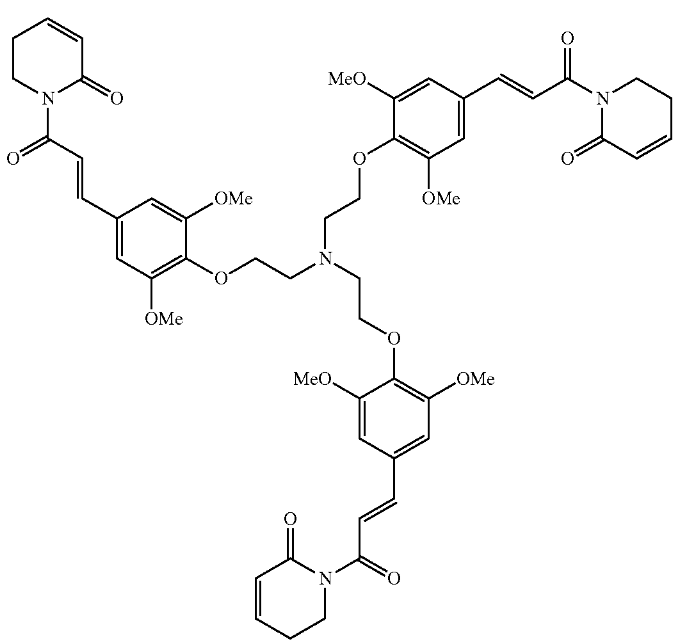 [SMILES: COc1cc(/C=C/C(=O)N2CCC=CC2=O)cc(OC)c1OCCN(CCOc1c(OC)cc(/C=C/C(=O)N2CCC=CC2=O)cc1OC)CCOc1c(OC)cc(/C=C/C(=O)N2CCC=CC2=O)cc1OC] | 0.1 | 0.3 |

TABLE 2-continued

Effects on cellular ATP levels for PL and selected PL analogs in two cell lines.

| No. | Structure | $EC_{50}$ H1703 (μM) | $EC_{50}$ HeLa (μM) |
|---|---|---|---|
| 42 | 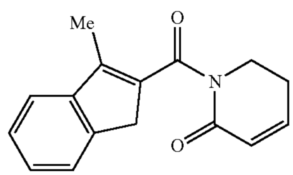 [SMILES: CC1=C(C(=O)N2CCC=CC2=O)Cc2ccccc21] | 12 | >20 |
| 43 | 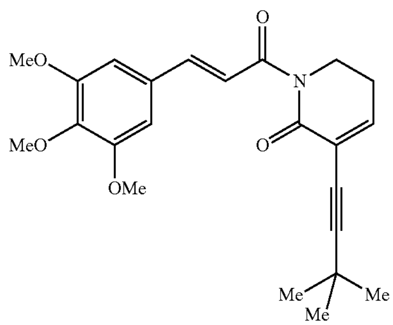 [SMILES: COc1cc(/C=C/C(=O)N2CCC=C(C#CC(C)(C)C)C2=O)cc(OC)c1OC] | 0.7 | 1.2 |
| 44 | 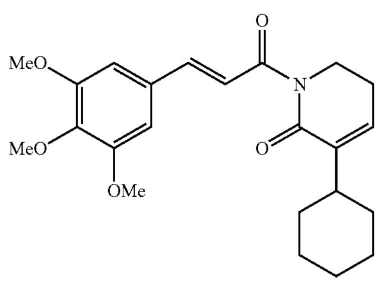 [SMILES: COc1cc(/C=C/C(=O)N2CCC=C(C3CCCCC3)C2=O)cc(OC)c1OC] | n.t. | n.t. |
| 45 | 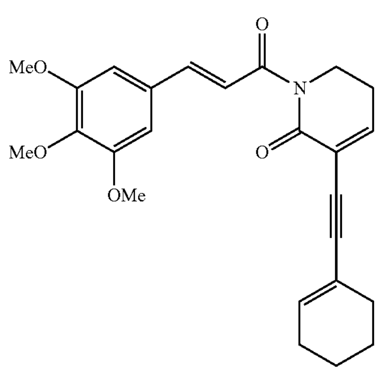 [SMILES: COc1cc(/C=C/C(=O)N2CCC=C(C#CC3=CCCCC3)C2=O)cc(OC)c1OC] | 3 | 5 |
| 46 | 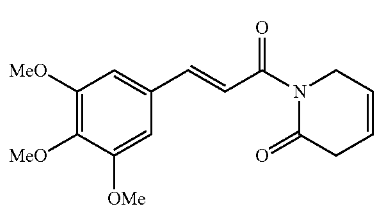 [SMILES: COc1cc(/C=C/C(=O)N2CC=CCC2=O)cc(OC)c1OC] | 13 | >20 |

TABLE 2-continued

Effects on cellular ATP levels for PL and selected PL analogs in two cell lines.

| No. | Structure | EC$_{50}$ H1703 (μM) | EC$_{50}$ HeLa (μM) |
| --- | --- | --- | --- |
| 47 | MeO, MeO, OMe — CH=CH—C(O)—N-(3,4-dimethyl-2-oxo-dihydropyridinyl) | n.t. | n.t. |
| 48 | MeO, MeO, OMe — CH=CH—C(O)—N-(2-oxo-3-(4-OCF$_3$-phenylethynyl)-dihydropyridinyl) | 0.7 | 3 |
| 49 | 2-Cl-C$_6$H$_4$—CH=CH—C(O)—N-(2-oxo-dihydropyridinyl) | 4.0 | 7.5 |
| 50 | MeO, MeO, OMe — CH=CH—C(O)—N-(6-Ph-2-oxo-dihydropyridinyl) | 3.6 | 6.8 |
| 51 | MeO, MeO, OMe — CH=CH—C(O)—N-(5-(2-thienyl)-2-oxo-dihydropyridinyl) | 6.5 | 15 |
| 52 | Ph—CH=CH—SO$_2$—N-(2-oxo-dihydropyridinyl) PL-SO$_2$ | 2.7 | 4.1 |

TABLE 2-continued

Effects on cellular ATP levels for PL and selected PL analogs in two cell lines.

| No. | Structure | EC$_{50}$ H1703 (μM) | EC$_{50}$ HeLa (μM) |
|---|---|---|---|
| 53 | PL-FPh | 0.4 | 1.0 |
| 54 | 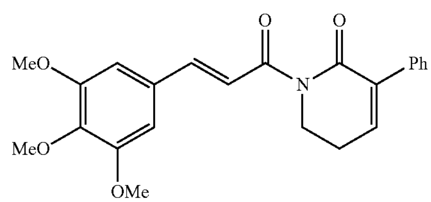 [SMILES: COc1cc(/C=C/C(=O)N2CCC=C(c3ccccc3)C2=O)cc(OC)c1OC] | n.t. | n.t. |
| 55 | 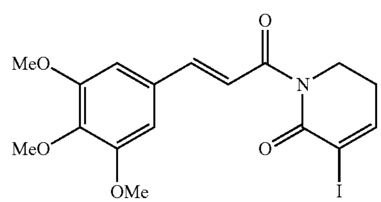 [SMILES: COc1cc(/C=C/C(=O)N2CCC=C(I)C2=O)cc(OC)c1OC] | 3 | >20 |
| 56 | 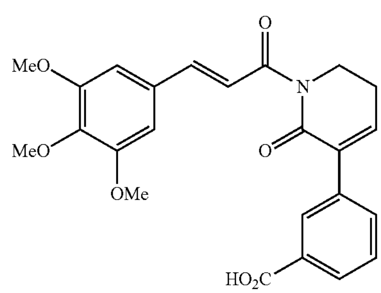 [SMILES: COc1cc(/C=C/C(=O)N2CCC=C(c3cccc(C(=O)O)c3)C2=O)cc(OC)c1OC] | n.t | n.t |
| 57 | 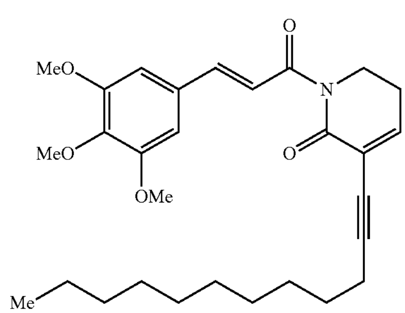 [SMILES: CCCCCCCCCCC#CC1=CCCN(C(=O)/C=C/c2cc(OC)c(OC)c(OC)c2)C1=O] | 4 | 9 |
| 58 | 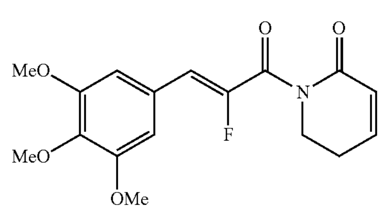 [SMILES: COc1cc(/C=C(\F)C(=O)N2CCC=CC2=O)cc(OC)c1OC] | 8 | 11 |

TABLE 2-continued

Effects on cellular ATP levels for PL and selected PL analogs in two cell lines.

| No. | Structure | EC$_{50}$ H1703 (μM) | EC$_{50}$ HeLa (μM) |
|---|---|---|---|
| 59 | 3,4,5-trimethoxycinnamoyl-3-(cyclohexylethynyl)-5,6-dihydropyridin-2(1H)-one | 1.5 | 3 |
| 60 | 2-methoxycinnamoyl-5,6-dihydropyridin-2(1H)-one | 2 | 4 |
| 61 | 3,4,5-trimethoxycinnamoyl-3-(phenylethynyl)-5,6-dihydropyridin-2(1H)-one | 0.5 | 1.5 |
| 62 | 3-bromocinnamoyl-5,6-dihydropyridin-2(1H)-one | 5 | 7 |
| 63 | 3,4,5-trimethoxycinnamoyl-3-(benzylethynyl)-5,6-dihydropyridin-2(1H)-one | 2 | 10 |

TABLE 2-continued

Effects on cellular ATP levels for PL and selected PL analogs in two cell lines.

| No. | Structure | EC$_{50}$ H1703 (µM) | EC$_{50}$ HeLa (µM) |
|---|---|---|---|
| 64 | 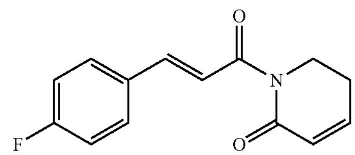 [SMILES: O=C1C=CCCN1C(=O)/C=C/c1ccc(F)cc1] | 7 | 10 |
| 65 | 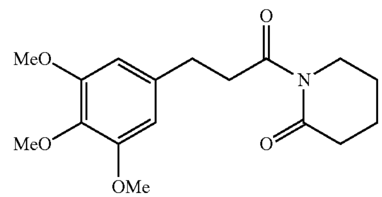 [SMILES: COc1cc(CCC(=O)N2CCCCC2=O)cc(OC)c1OC] | n.t | n.t. |
| 66 | 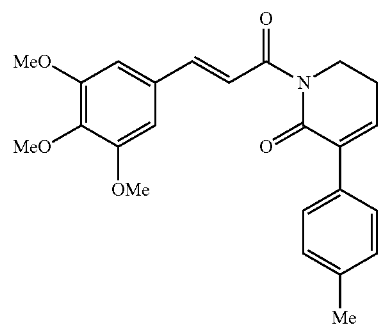 [SMILES: COc1cc(/C=C/C(=O)N2CCC=C(c3ccc(C)cc3)C2=O)cc(OC)c1OC] | n.t | n.t. |
| 67 | 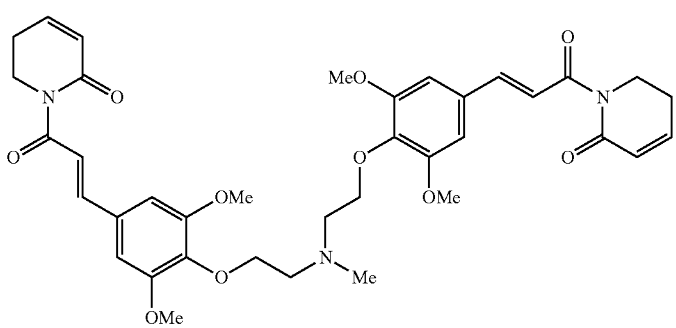 [SMILES: COc1cc(/C=C/C(=O)N2CCC=CC2=O)cc(OC)c1OCCN(C)CCOc1c(OC)cc(/C=C/C(=O)N2CCC=CC2=O)cc1OC] | 0.2 | 0.5 |
| 68 | 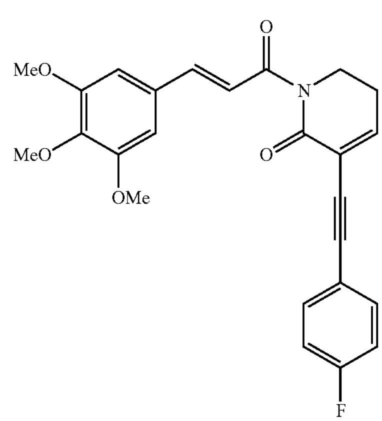 [SMILES: COc1cc(/C=C/C(=O)N2CCC=C(C#Cc3ccc(F)cc3)C2=O)cc(OC)c1OC] | 0.4 | 0.9 |

TABLE 2-continued

Effects on cellular ATP levels for PL and selected PL analogs in two cell lines.

| No. | Structure | EC$_{50}$ H1703 (μM) | EC$_{50}$ HeLa (μM) |
| --- | --- | --- | --- |
| 69 | 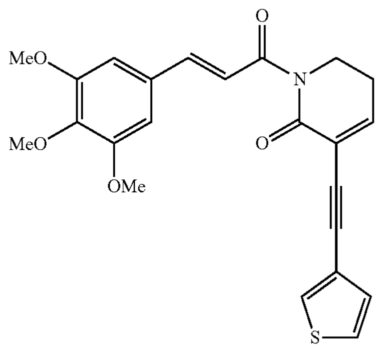 [SMILES: COc1cc(/C=C/C(=O)N2CCC=C(C#Cc3ccsc3)C2=O)cc(OC)c1OC] | 1 | 2 |
| 70 | 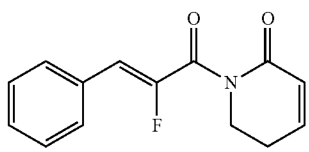 [SMILES: O=C1C=CCCN1C(=O)/C(F)=C/c1ccccc1] | 10 | >20 |
| 71 | 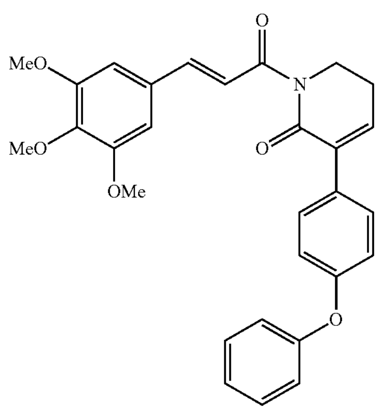 [SMILES: COc1cc(/C=C/C(=O)N2CCC=C(c3ccc(Oc4ccccc4)cc3)C2=O)cc(OC)c1OC] | n.t. | n.t. |
| 72 | 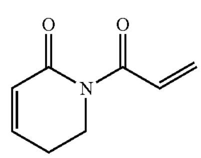 | 2.2 | 8.1 |
| 73 | 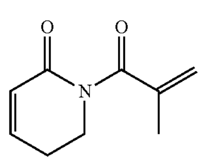 | 4.7 | 19 |
| 74 | 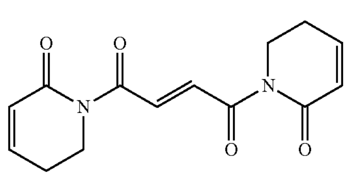 [SMILES: O=C1C=CCCN1C(=O)/C=C/C(=O)N1CCC=CC1=O] | 2.3 | 11 |

TABLE 2-continued

Effects on cellular ATP levels for PL and selected PL analogs in two cell lines.

| No. | Structure | EC$_{50}$ H1703 (μM) | EC$_{50}$ HeLa (μM) |
|---|---|---|---|
| 75 | 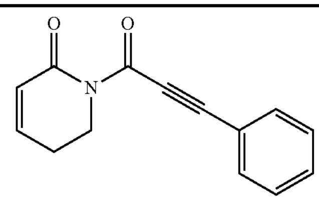 | 0.91 | 4.1 |
| 76 | 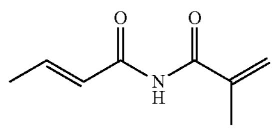 | 8.0 | >20 |
| 77 | 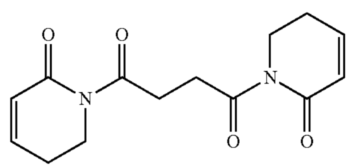 [SMILES: O=C1C=CCCN1C(=O)CCC(=O)N1CCC=CC1=O] | 5.5 | 15 |
| 78 | 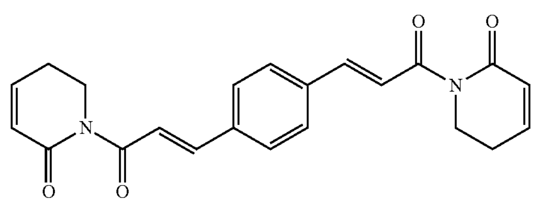 [SMILES: O=C1C=CCCN1C(=O)/C=C/c1ccc(/C=C/C(=O)N2CCC=CC2=O)cc1] | 0.30 | 0.78 |

Effects on cellular ATP levels for selected PL analogs in two cell lines (H1073 and HeLa).
n.t. indicates no loss of viability at 20 μM;
>20 μM indicates less than 50% decrease in viability observed at 20 μM.

What is claimed is:

1. A compound having the formula:

(II)

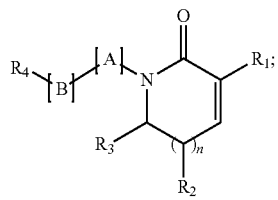

wherein A is C(O) or S(O)$_2$;
wherein B is alkenyl or alkynyl;
wherein n=0, 1, 2, or 3;
wherein R$_1$ is selected from the group consisting of a hydrogen, C≡C-alkyl, C≡C-cycloalkyl, C≡C-cycloalkyl halide, C≡C-phenyl, C≡C-thienyl, and a C≡C-phenyl halide wherein the halide is substituted ortho to the phenyl ring carbon that is bound to the alkynyl carbon;
wherein R$_2$ is selected from the group consisting of hydrogen, alkyl, alkenyl, and an aryl group;
wherein R$_3$ is selected from the group consisting of hydrogen, alkyl, alkenyl, and an aryl group; and,
wherein R$_4$ is selected from the group consisting of:
(i) substituted phenyl when B is alkynyl and R$_1$ is hydrogen,
(ii) a moiety of the formula:

(III)

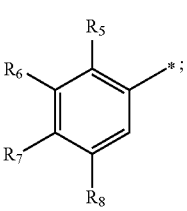

wherein, R$_5$ is selected from the group consisting of hydrogen, halogen, and methoxy, and wherein each of R$_6$, R$_7$, and R$_8$ are independently selected from the group consisting of hydrogen, bromine, chlorine, fluorine, keto, hydroxyl, alkyl, alkenyl, alkoxy, an aminoalkenyl, and an aminoalkoxy group with the proviso that R4 is (III) only when R1 is not hydrogen, (iii) a moiety of the formula:

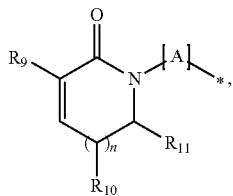

(IV)

and
(iv) a moiety of the formula (V):

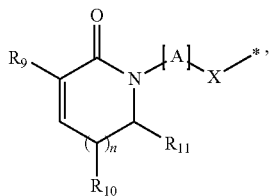

(V)

wherein A is C(O) or S(O)$_2$, wherein X, when present in (V), is an alkenyl, aryl, or combination thereof;
wherein n=0, 1, 2, or 3;
wherein R$_9$ is selected from the group consisting of a hydrogen, C≡C-alkyl, C≡C-cycloalkyl, C≡C-cycloalkyl halide, C≡C-phenyl, C≡C-thienyl, and a C≡C-phenyl halide wherein the halide is substituted ortho to the phenyl ring carbon that is bound to the alkynyl carbon;
wherein R$_{10}$ is selected from the group consisting of hydrogen, alkyl, alkenyl, and an aryl group; and,
wherein R$_{11}$ is selected from the group consisting of hydrogen, alkyl, alkenyl, and an aryl group.

2. The compound of claim 1,
wherein R4 is selected from the group consisting of a moiety of the formula:

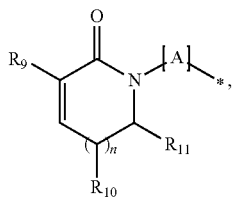

(IV)

and a moiety of the formula:

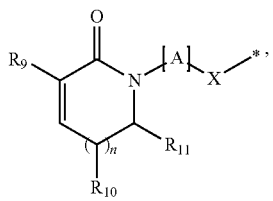

(V)

wherein A is C(O) or S(O)$_2$,
wherein X, when present in (V), is an alkyl, alkenyl, alkynyl, aryl, or combination thereof;
wherein n=0, 1, 2, or 3;
wherein R$_9$ is selected from the group consisting of a hydrogen, C≡C-alkyl, C≡C-cycloalkyl, C≡C-cycloalkyl halide, C≡C-phenyl, C≡C-thienyl, and a C≡C-phenyl halide wherein the halide is substituted ortho to the phenyl ring carbon that is bound to the alkynyl carbon;
wherein R$_{10}$ is selected from the group consisting of hydrogen, alkyl, alkenyl, and an aryl group; and,
wherein R$_{11}$ is selected from the group consisting of hydrogen, alkyl, alkenyl, and an aryl group.

3. The compound of claim 1, wherein R$_1$ is a C≡C-cycloalkyl group wherein said cycloalkyl is a C3 to C6 ring and/or wherein R$_3$ is hydrogen or a thienyl group.

4. The compound of claim 3, wherein R$_1$ is a C≡C-cycloalkyl, wherein said cycloalkyl is substituted at the ring carbon that is bound to the alkynyl carbon with a hydroxyl group and/or wherein R$_3$ is hydrogen or a thienyl group.

5. The compound of claim 1, wherein R$_1$ is a C≡C-phenyl or a C≡C-phenyl halide wherein the halide is substituted ortho to the phenyl ring carbon that is bound to the alkynyl carbon and/or wherein R$_3$ is hydrogen or a thienyl group.

6. The compound of claim 2, wherein R$_1$ and R$_9$ are independently selected from a group consisting of hydrogen, a halogen, and a C≡C-cycloalkyl group wherein said cycloalkyl is a C3 to C6 ring and/or wherein R$_3$ and R11 are independently selected from a group consisting of hydrogen and a thienyl group.

7. The compound of claim 6, wherein R$_1$ and R$_9$ are independently selected from the group consisting of hydrogen, a halogen, and a C≡C-cycloalkyl group, wherein said cycloalkyl is substituted at the ring carbon that is bound to the alkynyl carbon with a hydroxyl group and/or wherein R$_3$ is hydrogen or a thienyl group.

8. The compound of claim 2, wherein R$_1$ and R$_9$ are independently selected from the group consisting of hydrogen, a halogen, and is a C≡C-phenyl or a C≡C-phenyl halide wherein the halide is substituted ortho or para to the phenyl ring carbon that is bound to the alkynyl carbon and/or wherein R$_3$ is hydrogen or a thienyl group.

9. The compound of claim 1, wherein said compound has a formula selected from the group consisting of:

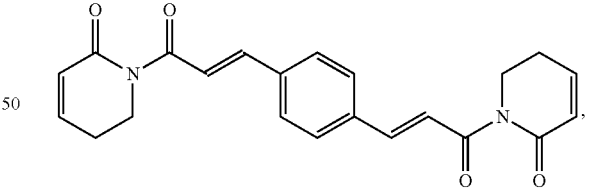

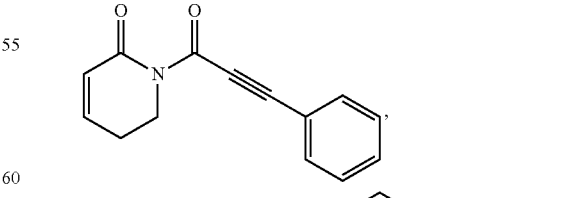

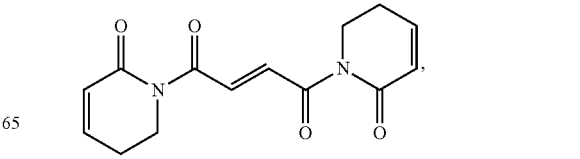

119

-continued

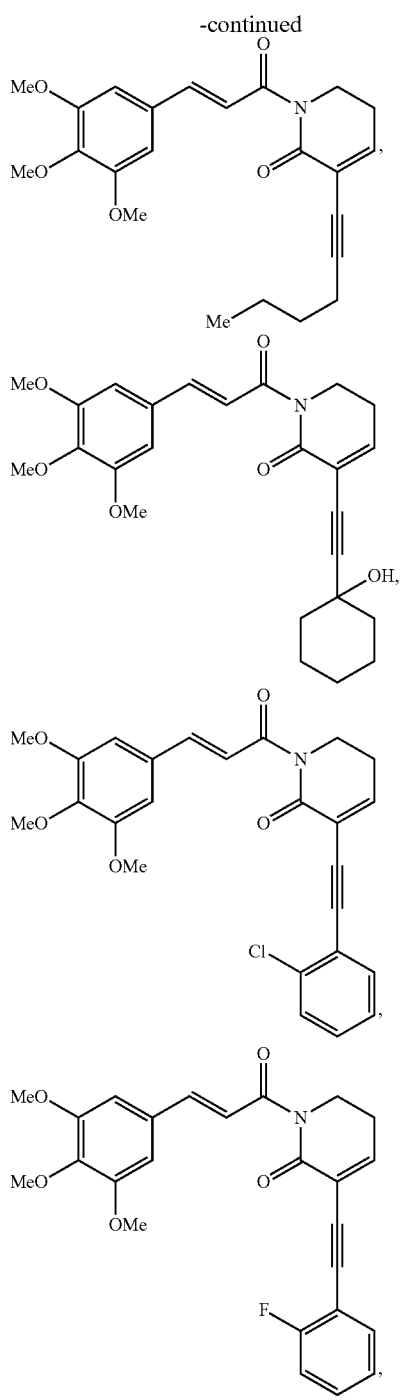

120

-continued

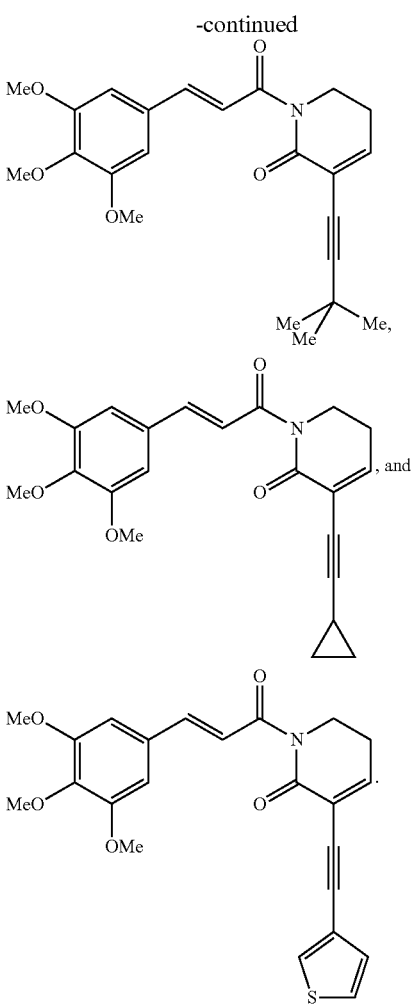

10. A composition comprising the compound of claim 1 and a pharmaceutically acceptable excipient.

11. The composition of claim 10, wherein said composition further comprises an additional chemotherapeutic agent.

12. A method of treating cancer comprising administration of a therapeutically effective amount of the compostion of claim 10 to a subject in need thereof, wherein the cancer is a cancer of the lung or cervix.

13. The method of claim 12, where said method further comprises administration of an additional chemotherapeutic agent.

* * * * *